US012648351B2

(12) United States Patent
Kim et al.

(10) Patent No.: US 12,648,351 B2

(45) Date of Patent: Jun. 2, 2026

(54) LIGHT EMITTING ELEMENT AND AMINE COMPOUND FOR THE SAME

(71) Applicant: Samsung Display Co., Ltd., Yongin-si (KR)

(72) Inventors: Dongjun Kim, Suwon-si (KR); Chaeyeong Kim, Yongin-si (KR); Hankyu Pak, Suwon-si (KR); Byeongwook Yoo, Hwaseong-si (KR); Seowon Cho, Anyang-si (KR); Sohee Jo, Cheonan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1000 days.

(21) Appl. No.: 17/811,269

(22) Filed: Jul. 7, 2022

(65) Prior Publication Data

US 2023/0165137 A1 May 25, 2023

(30) Foreign Application Priority Data

Nov. 19, 2021 (KR) ........................ 10-2021-0160326

(51) Int. Cl.

*H10K 85/60* (2023.01)

*C07D 221/18* (2006.01)

(Continued)

(52) U.S. Cl.

CPC ......... *H10K 85/636* (2023.02); *C07D 221/18* (2013.01); *C07D 401/12* (2013.01); (Continued)

(58) Field of Classification Search

CPC . H10K 85/636; H10K 85/6572; C07D 221/18

See application file for complete search history.

(56) References Cited

U.S. PATENT DOCUMENTS

| | | |
|---|---|---|
| 4,720,432 A | 1/1988 | VanSlyke et al. |
| 5,061,569 A | 10/1991 | VanSlyke et al. |

(Continued)

FOREIGN PATENT DOCUMENTS

| | | |
|---|---|---|
| CN | 111848514 A | 10/2020 |
| JP | H 11-144873 A | 5/1999 |

(Continued)

OTHER PUBLICATIONS

Machine-generated English-language translation of JP-2021109878-A.*

*Primary Examiner* — Vu A Nguyen

(74) *Attorney, Agent, or Firm* — Womble Bond Dickinson (US) LLP

(57) ABSTRACT

Provided is a light emitting element including a first electrode, a second electrode on the first electrode, and at least one functional layer between the first electrode and the second electrode. The at least one functional layer may include an amine compound represented by Formula 1 below.

Formula 1

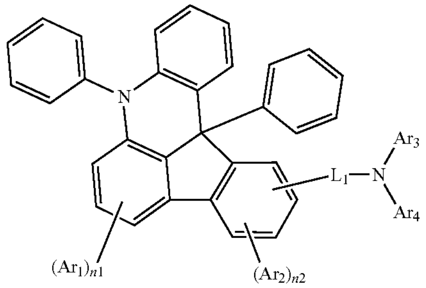

13 Claims, 8 Drawing Sheets

(51) Int. Cl.

| | |
|---|---|
| ***C07D 401/12*** | (2006.01) |
| ***C07D 409/12*** | (2006.01) |
| ***C09K 11/06*** | (2006.01) |
| ***H10K 50/15*** | (2023.01) |

(52) U.S. Cl.

CPC ............ *C07D 409/12* (2013.01); *C09K 11/06* (2013.01); *H10K 85/633* (2023.02); *C09K 2211/1018* (2013.01); *H10K 50/15* (2023.02); *H10K 85/615* (2023.02); *H10K 85/624* (2023.02); *H10K 85/626* (2023.02); *H10K 85/6572* (2023.02); *H10K 85/6576* (2023.02)

(56) References Cited

U.S. PATENT DOCUMENTS

| | | | |
|---|---|---|---|
| 6,242,115 | B1 | 6/2001 | Thomson et al. |
| 9,893,295 | B2 | 2/2018 | Kim et al. |

FOREIGN PATENT DOCUMENTS

| | | | | |
|---|---|---|---|---|
| JP | 2003-133075 | A | | 5/2003 |
| JP | 4103493 | B2 | | 6/2008 |
| JP | 4573923 | B2 | | 11/2010 |
| JP | 4589223 | B2 | | 12/2010 |
| JP | 2021109878 | A | * | 8/2021 |
| KR | 10-1984787 | B1 | | 6/2019 |
| KR | 10-2304723 | B1 | | 9/2021 |

* cited by examiner

LIGHT EMITTING ELEMENT AND AMINE COMPOUND FOR THE SAME

CROSS-REFERENCE TO RELATED APPLICATION

This application claims priority to and the benefit of Korean Patent Application No. 10-2021-0160326, filed on Nov. 19, 2021, the entire contents of which are hereby incorporated by reference.

BACKGROUND

Embodiments of the present disclosure herein relate to a light emitting element and an amine compound used therein.

Recently, the development of an organic electroluminescence display device as an image display device is being actively conducted. The organic electroluminescence display device includes a so-called self-luminescent light emitting element in which holes and electrons injected from a first electrode and a second electrode, respectively, recombine in an emission layer, and thus, a luminescent material of the emission layer emits light to implement display.

In the application of a light emitting element to a display device, there is a demand for a light emitting element having high luminous efficiency and a long service life, and development of materials for a light emitting element capable of stably attaining such a characteristic is being continuously researched.

SUMMARY

Embodiments of the present disclosure provide a light emitting element having excellent service life, efficiency, and brightness and having a decrease in driving voltage.

Embodiments of the present disclosure also provide an amine compound which is a material for a light emitting element having characteristics of reduced driving voltage, a long service life, high efficiency, and high brightness.

An embodiment of the present disclosure provides a light emitting element including: a first electrode; a second electrode on the first electrode; and at least one functional layer which is between the first electrode and the second electrode and includes an amine compound represented by Formula 1 below:

Formula 1

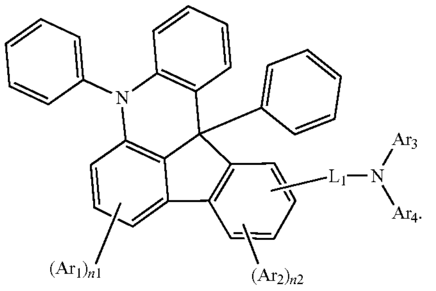

In Formula 1 above, $L_1$ is a direct linkage, a substituted or unsubstituted arylene group having 6 to 30 ring-forming carbon atoms, or a substituted or unsubstituted heteroarylene group having 2 to 30 ring-forming carbon atoms, n1 and n2 are each independently an integer of 0 to 3, $Ar_1$ and $Ar_2$ are each independently a hydrogen atom, a deuterium atom, a substituted or unsubstituted aryl group having 6 to 30 ring-forming carbon atoms, or a substituted or unsubstituted heteroaryl group having 2 to 30 ring-forming carbon atoms, and $Ar_3$ and $Ar_4$ are each independently a substituted or unsubstituted aryl group having 6 to 30 ring-forming carbon atoms, or a substituted or unsubstituted heteroaryl group having 2 to 30 ring-forming carbon atoms.

In Formula 1 above, $Ar_3$ and $Ar_4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

In an embodiment, in Formula 1 above, $Ar_3$ and $Ar_4$ may be each independently represented by any one selected from among A-1 to A-7 below:

A-1

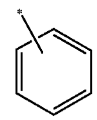

A-2

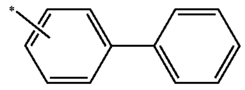

A-3

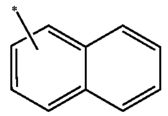

A-4

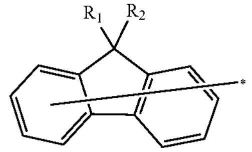

A-5

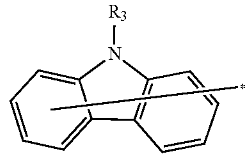

A-6

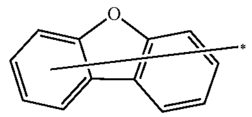

A-7

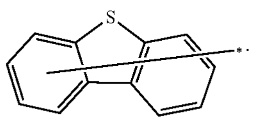

In A-4 above, $R_1$ and $R_2$ are each independently a substituted or unsubstituted alkyl group having 1 to 10 carbon atoms, or a substituted or unsubstituted aryl group having 6 to 30 ring-forming carbon atoms, or are bonded to an adjacent group to form a ring, and in A-5 above, $R_3$ is a substituted or unsubstituted aryl group having 6 to 30 ring-forming carbon atoms.

In an embodiment, Formula 1 above may be represented by Formula 1-1 below:

Formula 1-1

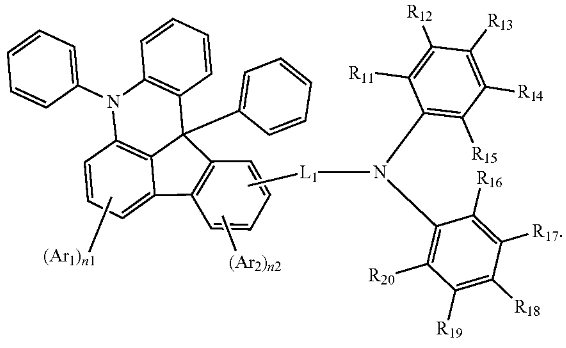

In Formula 1-1 above, $R_{11}$ to $R_{20}$ are each independently a hydrogen atom, a deuterium atom, a substituted or unsubstituted amine group, a substituted or unsubstituted oxy group, a substituted or unsubstituted thio group, a substituted or unsubstituted alkyl group having 1 to 10 carbon atoms, a substituted or unsubstituted alkenyl group having 2 to 10 carbon atoms, or a substituted or unsubstituted aryl group having 6 to 30 ring-forming carbon atoms, or may be bonded to an adjacent group to form a ring.

In an embodiment, Formula 1 above may be represented by Formula 1-A1 or Formula 1-A2 below:

Formula 1-A1

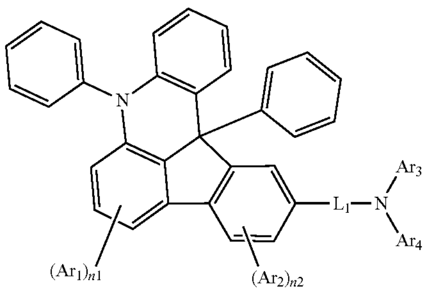

Formula 1-A2

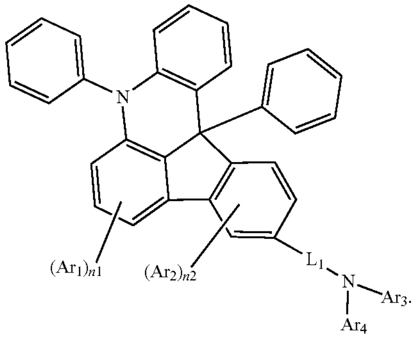

In Formula 1-A1 and Formula 1-A2 above, $L_1$, n1, n2, and $Ar_1$ to $Ar_4$ are the same as defined with respect to Formula 1 above.

In an embodiment, in Formula 1-A1 and Formula 1-A2 above, $L_1$ may be a direct linkage or a phenylene group.

In an embodiment, Formula 1 above may be represented by Formula 1-B1 or Formula 1-B2 below:

Formula 1-B1

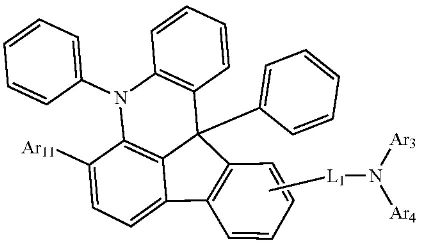

Formula 1-B2

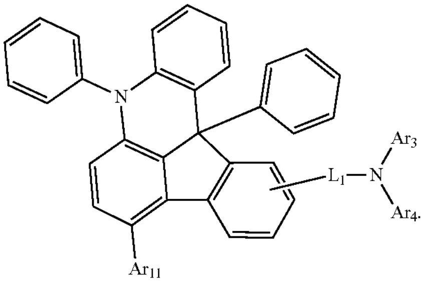

In Formula 1-B1 and Formula 1-B2, $Ar_{11}$ is a substituted or unsubstituted aryl group having 6 to 30 ring-forming carbon atoms, and $L_1$, $Ar_3$, and $Ar_4$ are the same as defined with respect to Formula 1 above.

In an embodiment, Formula 1 above may be represented by Formula 1-C1 or Formula 1-C2 below:

Formula 1-C1

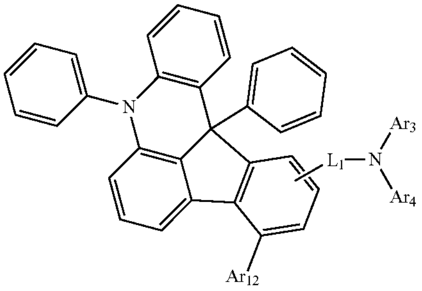

Formula 1-C2

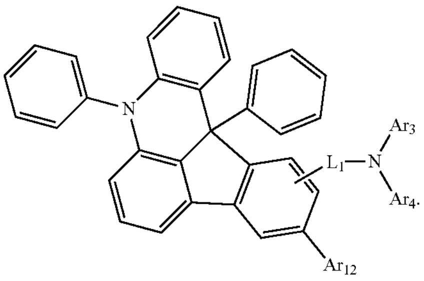

In Formula 1-C1 and Formula 1-C2 above, $Ar_{12}$ is a substituted or unsubstituted aryl group having 6 to 30 ring-forming carbon atoms, and $L_1$, $Ar_3$, and $Ar_4$ are the same as defined with respect to Formula 1 above.

In an embodiment, the at least one functional layer may include an emission layer, a hole transport region between the first electrode and the emission layer, and an electron transport region between the emission layer and the second electrode, and the hole transport region may include the amine compound.

In an embodiment, the hole transport region may include a hole injection layer on the first electrode, a hole transport layer on the hole injection layer, and an electron blocking layer on the hole transport layer, and at least one of the hole injection layer, the hole transport layer, or the electron blocking layer may include the amine compound.

In an embodiment, the emission layer may include a compound represented by Formula E-1 below:

Formula E-1

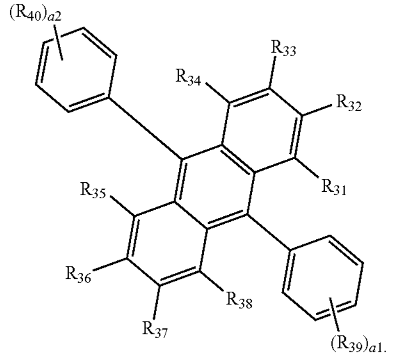

In Formula E-1 above, a1 and a2 are each independently an integer of 0 to 5, and $R_{31}$ to $R_{40}$ are each independently a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

In an embodiment of the present disclosure, an amine compound is represented by Formula 1 above.

BRIEF DESCRIPTION OF THE FIGURES

The accompanying drawings are included to provide a further understanding of embodiments of the present disclosure, and are incorporated in and constitute a part of this specification. The drawings illustrate example embodiments of the present disclosure and, together with the description, serve to explain principles of the subject matter of the present disclosure. In the drawings.

DETAILED DESCRIPTION

Figure 1:
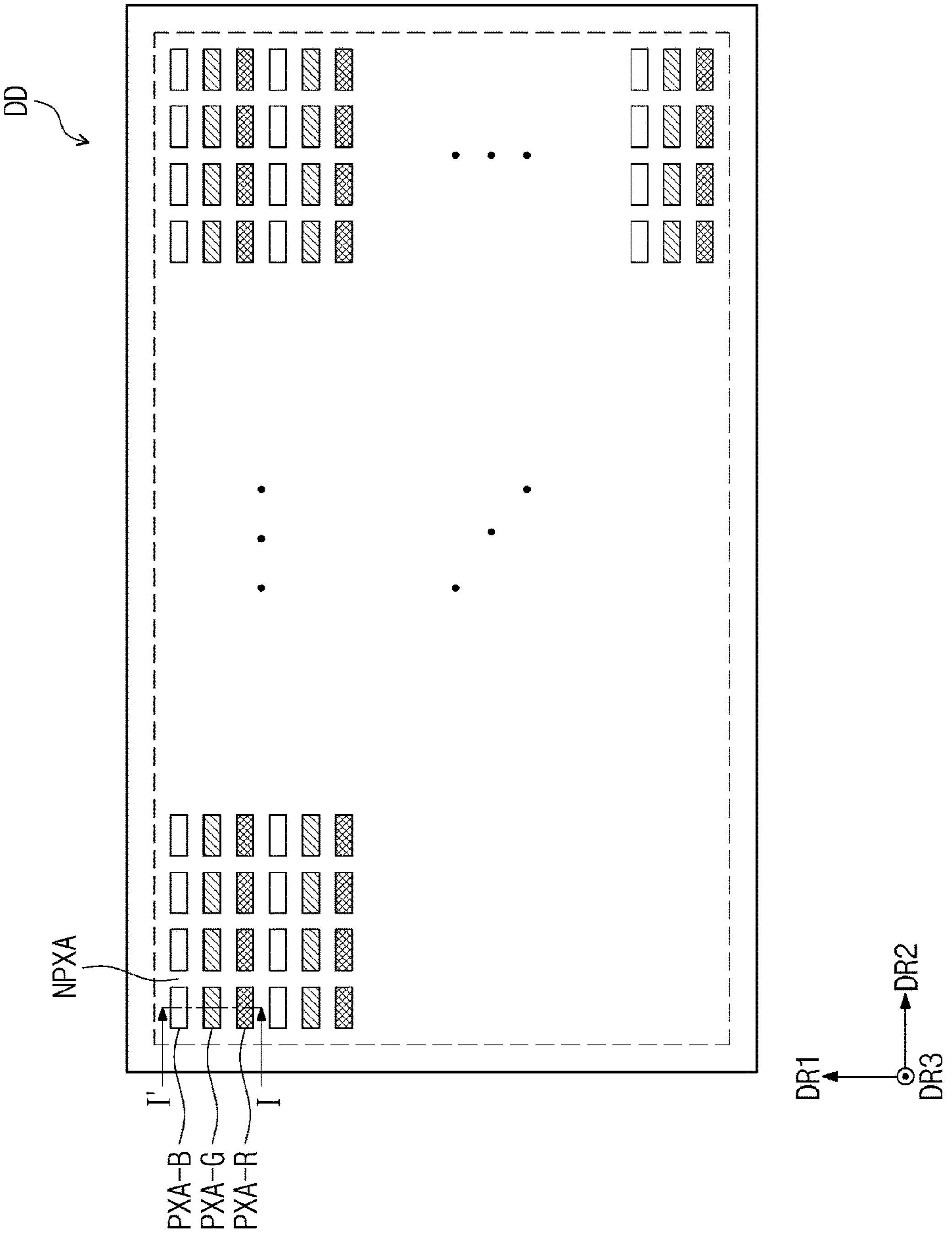
FIG. 1 is a plan view illustrating a display device according to an embodiment of the present disclosure.

The subject matter of the present disclosure may be modified in many alternate forms, and thus, example embodiments will be illustrated in the drawings and described in more detail. It should be understood, however, that it is not intended to limit the present disclosure to the particular forms disclosed, but rather, is intended to cover all modifications, equivalents, and alternatives falling within the spirit and scope of the present disclosure.

In the present specification, when a component (or a region, a layer, a portion, etc.) is referred to as being "on," "connected to," or "coupled to" another component, it means that the component may be directly on/connected to/coupled to the other component, or that a third component may be therebetween.

Like reference numerals refer to like components throughout. Also, in the drawings, the thickness, the ratio, and the dimensions of components may be exaggerated for an effective description of technical contents. The term "and/or" includes all combinations of one or more of which associated configurations may define.

It will be understood that, although the terms "first," "second," etc. may be used herein to describe various components, these components should not be limited by these terms. These terms are only used to distinguish one component from another. For example, a first component could be termed a second component, and, similarly, a second component could be termed a first component, without departing from the scope of the present disclosure. As used herein, the singular forms, "a," "an," and "the" are intended to include the plural forms as well, unless the context clearly indicates otherwise.

In addition, terms such as "below," "under," "on," and "above" may be used to describe the relationship between elements illustrated in the figures. The terms are used as a relative concept and are described with reference to the direction indicated in the drawings.

It should be understood that the terms "comprise," or "have" are intended to specify the presence of stated features, integers, steps, operations, components, parts, or combinations thereof in the disclosure, but do not preclude the presence or addition of one or more other features, integers, steps, operations, components, parts, or combinations thereof.

Unless otherwise defined, all terms (including technical and scientific terms) used herein have the same meaning as commonly understood by one of ordinary skill in the art to which the present disclosure belongs. In addition, it will be understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a light emitting element and an amine compound according to embodiments of the present disclosure will be described with reference to the drawings.

Figure 2:
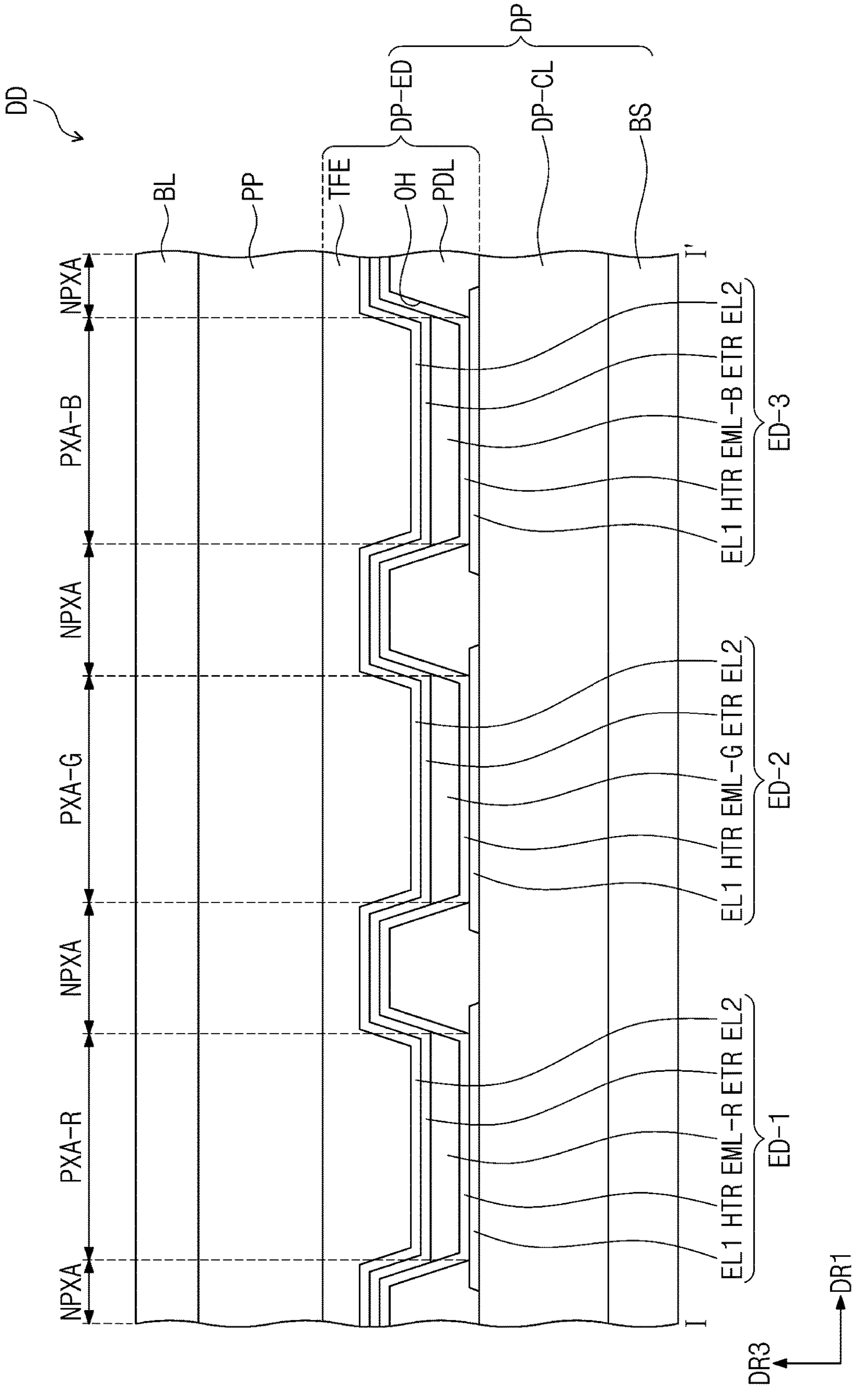
FIG. 2 is a cross-sectional view illustrating a portion taken along line I-I' of FIG. 1.

FIG. 1 is a plan view illustrating an embodiment of a display device DD. FIG. 2 is a cross-sectional view of the display device DD of the embodiment. FIG. 2 is a cross-sectional view illustrating a part taken along line I-I' of FIG. 1.

The display device DD may include a display panel DP and an optical layer PP on the display panel DP. The display panel DP may include light emitting elements ED-1, ED-2, and ED-3. The display device DD may include a plurality of light emitting elements ED-1, ED-2, and ED-3. The optical layer PP may be on the display panel DP and control reflected light in the display panel DP due to external light. The optical layer PP may include, for example, a polarization layer and/or a color filter layer. Unlike the configuration illustrated in the drawing, the optical layer PP may be omitted from the display device DD of an embodiment.

A base substrate BL may be on the optical layer PP. The base substrate BL may be a member which provides a base surface that the optical layer PP is on. The base substrate BL may be a glass substrate, a metal substrate, a plastic substrate, etc. However, embodiments of the present disclosure are not limited thereto, and the base substrate BL may be an inorganic layer, an organic layer, or a composite material layer. In addition, unlike the configuration illustrated, in an embodiment, the base substrate BL may be omitted.

The display device DD according to an embodiment may further include a filling layer. The filling layer may be between a display element layer DP-ED and the base substrate BL. The filling layer may be an organic material layer. The filling layer may include at least one of an acrylic-based resin, a silicone-based resin, or an epoxy-based resin.

The display panel DP may include a base layer BS, a circuit layer DP-CL provided on the base layer BS, and the display element layer DP-ED. The display element layer DP-ED may include a pixel defining film PDL, the light emitting elements ED-1, ED-2, and ED-3 between portions of the pixel defining film PDL, and an encapsulation layer TFE on the light emitting elements ED-1, ED-2, and ED-3.

The base layer BS may be a member which provides a base surface that the display element layer DP-ED is on. The base layer BS may be a glass substrate, a metal substrate, a plastic substrate, etc. However, embodiments of the present disclosure are not limited thereto, and the base layer BS may be an inorganic layer, an organic layer, or a composite material layer.

In an embodiment, the circuit layer DP-CL is on the base layer BS, and the circuit layer DP-CL may include a plurality of transistors. Each of the transistors may include a control electrode, an input electrode, and an output electrode. For example, the circuit layer DP-CL may include a switching transistor and a driving transistor in order to drive the light emitting elements ED-1, ED-2, and ED-3 of the display element layer DP-ED.

Each of the light emitting elements ED-1, ED-2, and ED-3 may have a structure of a light emitting element ED of an embodiment according to FIGS. 3 to 6, which will be further described herein below. Each of the light emitting elements ED-1, ED-2 and ED-3 may include a first electrode EL1, a hole transport region HTR, emission layers EML-R, EML-G and EML-B, an electron transport region ETR, and a second electrode EL2.

FIG. 2 illustrates an embodiment in which the emission layers EML-R, EML-G, and EML-B of the light emitting elements ED-1, ED-2, and ED-3 are in openings OH defined in the pixel defining film PDL, and the hole transport region HTR, the electron transport region ETR, and the second electrode EL2 are provided as a common layer in the entire light emitting elements ED-1, ED-2, and ED-3. However, embodiments of the present disclosure are not limited thereto, and unlike the configuration illustrated in FIG. 2, the hole transport region HTR and the electron transport region ETR in an embodiment may be provided by being patterned inside the opening OH defined in the pixel defining film PDL. For example, the hole transport region HTR, the emission layers EML-R, EML-G, and EML-B, and the electron transport region ETR of the light emitting elements ED-1, ED-2, and ED-3 in an embodiment may be provided by being patterned in an inkjet printing method.

The encapsulation layer TFE may cover the light emitting elements ED-1, ED-2 and ED-3. The encapsulation layer TFE may seal the display element layer DP-ED. The encapsulation layer TFE may be a thin film encapsulation layer. The encapsulation layer TFE may be formed by laminating one layer or a plurality of layers. The encapsulation layer TFE may include at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film may protect the display element layer DP-ED from moisture/oxygen, and the encapsulation-organic film may protect the display element layer DP-ED from foreign substances such as dust particles. The encapsulation-inorganic film may include silicon nitride, silicon oxynitride, silicon oxide, titanium oxide, aluminum oxide, and/or the like, but embodiments of the present disclosure are not particularly limited thereto. The encapsulation-organic film may include an acrylic-based compound, an epoxy-based compound, or the like. The encapsulation-organic film may include a photopolymerizable organic material, but embodiments of the present disclosure are not particularly limited thereto.

The encapsulation layer TFE may be on the second electrode EL2 and may fill the opening OH.

Referring to FIGS. 1 and 2, the display device DD may include a non-light emitting region NPXA and light emitting regions PXA-R, PXA-G and PXA-B. The light emitting regions PXA-R, PXA-G and PXA-B may be regions in which light generated by the respective light emitting elements ED-1, ED-2, and ED-3 is emitted. The light emitting regions PXA-R, PXA-G, and PXA-B may be spaced apart from each other on a plane.

Each of the light emitting regions PXA-R, PXA-G, and PXA-B may be a region divided by the pixel defining film PDL. The non-light emitting regions NPXA may be regions between the adjacent light emitting regions PXA-R, PXA-G, and PXA-B, which correspond to portions of the pixel defining film PDL. In the specification, the light emitting regions PXA-R, PXA-G, and PXA-B may respectively correspond to pixels. The pixel defining film PDL may divide the light emitting elements ED-1, ED-2, and ED-3. The emission layers EML-R, EML-G and EML-B of the light emitting elements ED-1, ED-2, and ED-3 may be in openings OH defined in the pixel defining film PDL and spaced apart from each other.

The light emitting regions PXA-R, PXA-G and PXA-B may be divided into a plurality of groups according to the color of light generated from the light emitting elements ED-1, ED-2 and ED-3. In the display device DD of an embodiment shown in FIGS. 1 and 2, three light emitting regions PXA-R, PXA-G, and PXA-B which emit red light, green light, and blue light, respectively are illustrated as example embodiments. For example, the display device DD of an embodiment may include the red light emitting region PXA-R, the green light emitting region PXA-G, and the blue light emitting region PXA-B that are spaced apart from each other.

In the display device DD according to an embodiment, the plurality of light emitting elements ED-1, ED-2, and ED-3 may emit light beams having wavelengths different from each other. For example, in an embodiment, the display device DD may include a first light emitting element ED-1 that emits red light, a second light emitting element ED-2 that emits green light, and a third light emitting element ED-3 that emits blue light. In some embodiments, the red light emitting region PXA-R, the green light emitting region PXA-G, and the blue light emitting region PXA-B of the display device DD may correspond to the first light emitting element ED-1, the second light emitting element ED-2, and the third light emitting element ED-3, respectively.

However, embodiments of the present disclosure are not limited thereto, and the first to third light emitting elements ED-1, ED-2, and ED-3 may emit light beams in the same wavelength range or at least one light emitting element may emit a light beam in a wavelength range different from the others. For example, the first to third light emitting elements ED-1, ED-2, and ED-3 may all emit blue light.

The light emitting regions PXA-R, PXA-G, and PXA-B in the display device DD according to an embodiment may be arranged in a stripe form. Referring to FIG. 1, the plurality of red light emitting regions PXA-R, the plurality of green light emitting regions PXA-G, and the plurality of blue light emitting regions PXA-B each may be arranged along a second directional axis DR2. In addition, the red light emitting region PXA-R, the green light emitting region PXA-G, and the blue light emitting region PXA-B may be alternately arranged in this order along a first directional axis DR1.

FIGS. 1 and 2 illustrate that all the light emitting regions PXA-R, PXA-G, and PXA-B have similar area, but embodiments of the present disclosure are not limited thereto. Thus, the light emitting regions PXA-R, PXA-G, and PXA-B may have different areas from each other according to the wavelength range of the emitted light. In this case, the areas of the light emitting regions PXA-R, PXA-G, and PXA-B may mean areas when viewed on a plane defined by the first directional axis DR1 and the second directional axis DR2.

An arrangement form of the light emitting regions PXA-R, PXA-G, and PXA-B is not limited to the configuration illustrated in FIG. 1, and the order in which the red light emitting region PXA-R, the green light emitting region PXA-G, and the blue light emitting region PXA-B are arranged may be provided in various combinations according to the characteristics of display quality required in the display device DD. For example, the arrangement form of the light emitting regions PXA-R, PXA-G, and PXA-B may be a PENTILE® arrangement structure (e.g., an RGBG matrix, RGBG structure, or RGBG matrix structure) or a Diamond Pixel™ arrangement form. PENTILE® is a duly registered trademark of Samsung Display Co., Ltd.

In addition, the areas of the light emitting regions PXA-R, PXA-G, and PXA-B may be different from each other. For example, in an embodiment, the area of the green light emitting region PXA-G may be smaller than that of the blue light emitting region PXA-B, but embodiments of the present disclosure are not limited thereto.

Hereinafter, FIGS. 3 to 6 are cross-sectional views schematically illustrating light emitting elements according to embodiments. Each of the light emitting elements ED according to embodiments may include a first electrode EL1, a hole transport region HTR, an emission layer EML, an electron transport region ETR, and a second electrode EL2 that are sequentially stacked.

Figure 3:
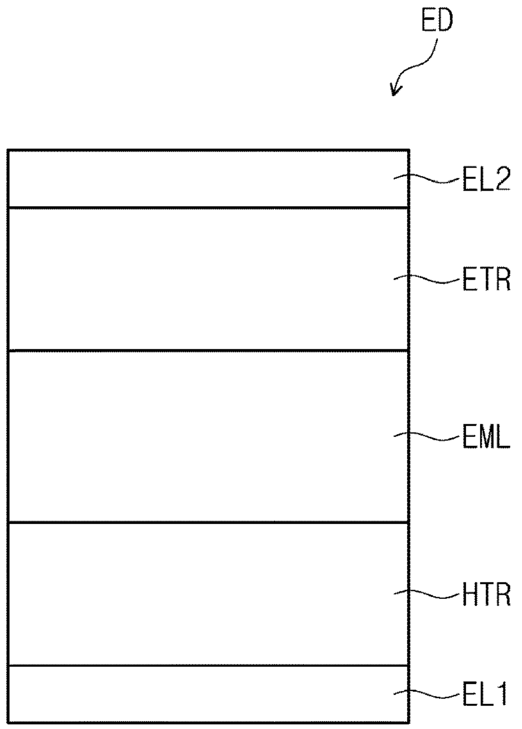
FIG. 3 is a cross-sectional view schematically illustrating a light emitting element of an embodiment of the present disclosure.
Figure 4:
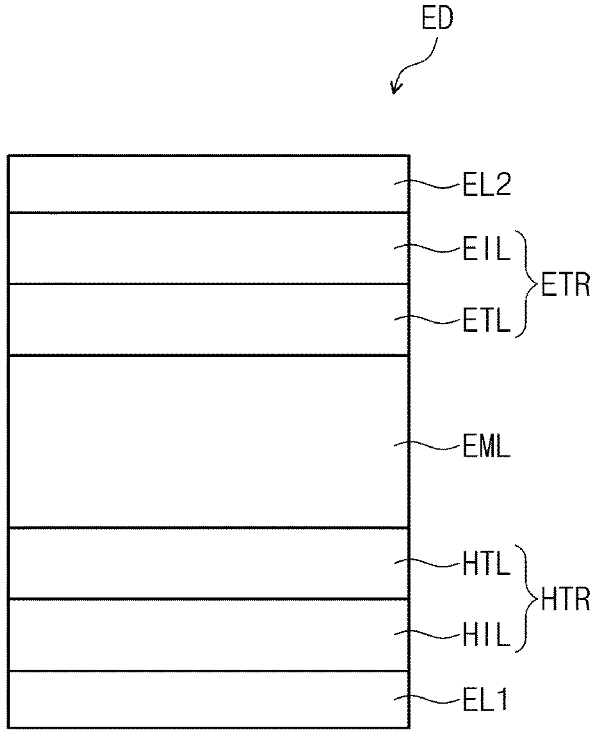
FIG. 4 is a cross-sectional view schematically illustrating a light emitting element of an embodiment of the present disclosure.
Figure 5:
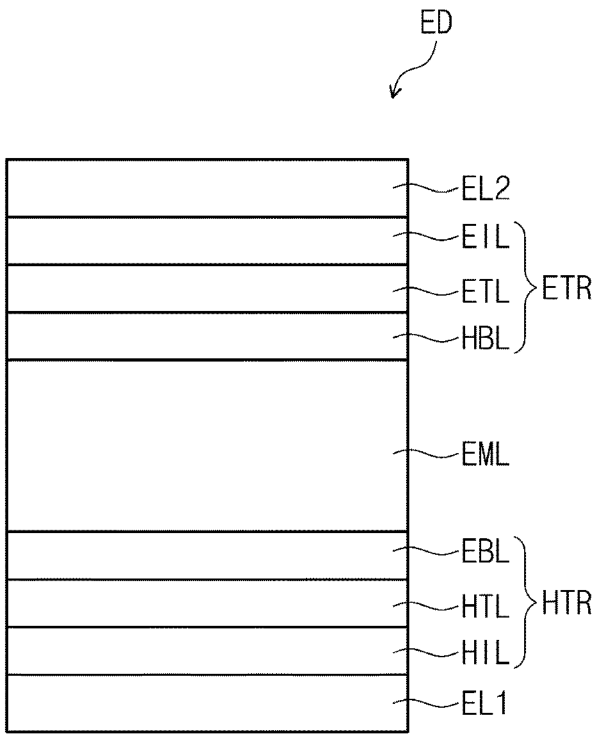
FIG. 5 is a cross-sectional view schematically illustrating a light emitting element of an embodiment of the present disclosure.
Figure 6:
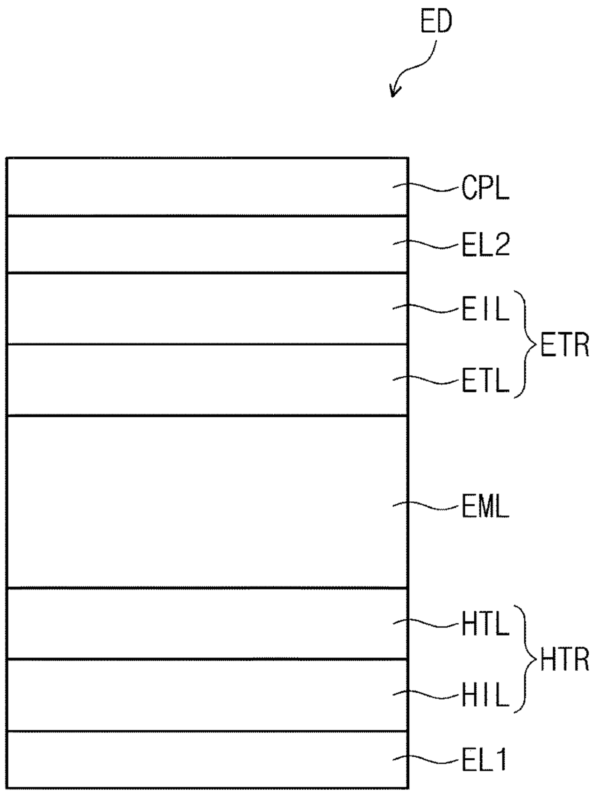
FIG. 6 is a cross-sectional view schematically illustrating a light emitting element of an embodiment of the present disclosure.

Compared to FIG. 3, FIG. 4 illustrates a cross-sectional view of a light emitting element ED of an embodiment, in which a hole transport region HTR includes a hole injection layer HIL and a hole transport layer HTL, and an electron transport region ETR includes an electron injection layer EIL and an electron transport layer ETL. In addition, compared to FIG. 3, FIG. 5 illustrates a cross-sectional view of a light emitting element ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 4, FIG. 6 illustrates a cross-sectional view of a light emitting element ED of an embodiment including a capping layer CPL on a second electrode EL2.

In an embodiment, the light emitting element ED may include an amine compound in at least one functional layer between the first electrode EL1 and the second electrode EL2. The at least one functional layer may include a hole transport region HTR, an emission layer EML, and/or an electron transport region ETR. The amine compound may include an amine group directly or indirectly bonded to a pentacyclic fused ring containing an acridine moiety.

In the specification, the term "substituted or unsubstituted" may mean unsubstituted or substituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the substituents identified above may be substituted or unsubstituted. For example, a biphenyl group may be interpreted as an aryl group or a phenyl group substituted with a phenyl group.

In the specification, the phrase "bonded to an adjacent group to form a ring" may indicate that one is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In addition, the rings formed by being bonded to each other may be connected to another ring to form a spiro structure.

In the specification, the term "adjacent group" may mean a substituent substituted for an atom which is directly linked to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other. In addition, two methyl groups in 4,5-dimethylphenanthrene may be interpreted as "adjacent groups" to each other.

In the specification, examples of the halogen atom may include a fluorine atom, a chlorine atom, a bromine atom, or an iodine atom.

In the specification, the alkyl group may be a linear, branched or cyclic type (e.g., a linear alkyl group, a branched alkyl group, or a cyclic alkyl group). The number of carbons in the alkyl group is 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but embodiments of the present disclosure are not limited thereto.

In the specification, an alkenyl group means a hydrocarbon group including at least one carbon double bond at a main chain (e.g., in the middle) or at a terminal end of an alkyl group having 2 or more carbon atoms. The alkenyl group may be linear or branched. The carbon number is not specifically limited, but is 2 to 30, 2 to 20 or 2 to 10. Examples of the alkenyl group include a vinyl group, a 1-butenyl group, a 1-pentenyl group, a 1,3-butadienyl aryl group, a styrenyl group, a styrylvinyl group, etc., without limitation.

The hydrocarbon ring group herein means any functional group or substituent derived from an aliphatic hydrocarbon ring. The hydrocarbon ring group may be a saturated hydrocarbon ring group having 5 to 20 ring-forming carbon atoms.

In the specification, an aryl group means any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but embodiments of the present disclosure are not limited thereto.

In the specification, the fluorenyl group may be substituted, and two substituents may be bonded to each other to form a spiro structure. Examples of cases where the fluorenyl group is substituted are as follows. However, embodiments of the present disclosure are not limited thereto.

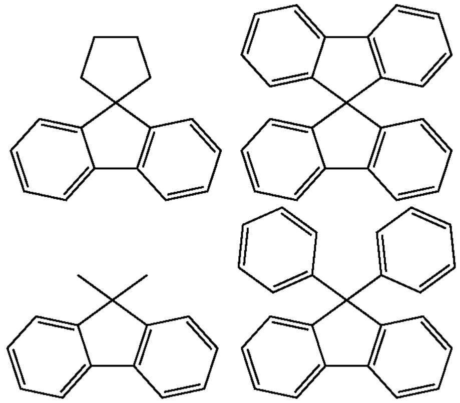

The term "heterocyclic group," as used herein, means any functional group or substituent derived from a ring including at least one of B, O, N, P, Si, or Se as a heteroatom. The heterocyclic group includes an aliphatic heterocyclic group and an aromatic heterocyclic group. The aromatic heterocyclic group may be a heteroaryl group. The aliphatic heterocycle and the aromatic heterocycle may be monocyclic or polycyclic. If the heterocyclic group includes two or more heteroatoms, the two or more heteroatoms may be the same as or different from each other. The heterocyclic group may be a monocyclic heterocyclic group or a polycyclic heterocyclic group and has the concept including a heteroaryl group. The number of ring-forming carbon atoms in the heterocyclic group may be 2 to 30, 2 to 20, or 2 to 10.

In the specification, the heteroaryl group may include at least one of B, O, N, P, Si, or S as a heteroatom. When the heteroaryl group contains two or more hetero atoms, the two or more hetero atoms may be the same as or different from each other. The heteroaryl group may be a monocyclic heteroaryl group or polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but embodiments of the present disclosure are not limited thereto.

In the specification, the above description of the aryl group may be applied to an arylene group except that the arylene group is a divalent group. The above description of the heteroaryl group may be applied to a heteroarylene group except that the heteroarylene group is a divalent group.

In the specification, a silyl group includes an alkylsilyl group and an arylsilyl group. Examples of the silyl group may include a trimethylsilyl group, a triethylsilyl group, a t-butyldimethylsilyl group, an ethyldimethylsilyl group, a propyldimethylsilyl group, a triphenylsilyl group, a diphenylsilyl group, a phenylsilyl group, etc., but embodiments of the present disclosure are not limited thereto.

In the specification, a thio group may include an alkylthio group and an arylthio group. The thio group may have a sulfur atom that is bonded to the alkyl group or the aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., but embodiments of the present disclosure are not limited thereto.

In the specification, an oxy group may have an oxygen atom that is bonded to the alkyl group or the aryl group as defined above. The oxy group may include an alkoxy group and an aryl oxy group. The alkoxy group may be a linear chain, a branched chain or a ring chain. The number of carbon atoms in the alkoxy group is not specifically limited, but may be, for example, 1 to 20 or 1 to 10. Examples of the oxy group include methoxy, ethoxy, n-propoxy, isopropoxy, butoxy, pentyloxy, hexyloxy, octyloxy, nonyloxy, decyloxy, benzyloxy, etc., but embodiments of the present disclosure are not limited thereto.

In the specification, a boryl group may have a boron atom that is bonded to the alkyl group or the aryl group as defined above. The boryl group includes an alkyl boryl group and an aryl boryl group. Examples of the boryl group may include a dimethylboryl group, a diethylboryl group, a t-butylmethylboryl group, a diphenylboryl group, a phenylboryl group, etc., but embodiments of the present disclosure are not limited thereto.

In the specification, an amine group may include —$NH_2$, an alkyl amine group, and an aryl amine group. The number of carbon atoms in the amine group is not specifically limited, but may be 1 to 30. Examples of the amine group may include a methylamine group, a dimethylamine group, a phenylamine group, a diphenylamine group, a naphthylamine group, a 9-methyl-anthracenylamine group, a triphenylamine group, etc., but embodiments of the present disclosure are not limited thereto.

In the specification, the alkyl group among an alkylthio group, an alkylsulfoxy group, an alkyl oxy group, an alkyl amino group, an alkyl boron group, an alkyl silyl group, and an alkyl amine group is the same as the examples of the alkyl group described above.

In the specification, the aryl group among an aryloxy group, an arylthio group, an arylsulfoxy group, an arylamino group, an arylboron group, an arylsilyl group, an arylamine group is the same as the examples of the aryl group described above.

In the specification, a direct linkage may be a single bond (e.g., a single covalent bond). In the specification,

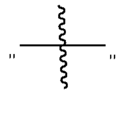

and

"——*"

mean a position to be linked.

The amine compound of an embodiment may be represented by Formula 1 below. The light emitting element ED may include an amine compound represented by Formula 1 below:

Formula 1

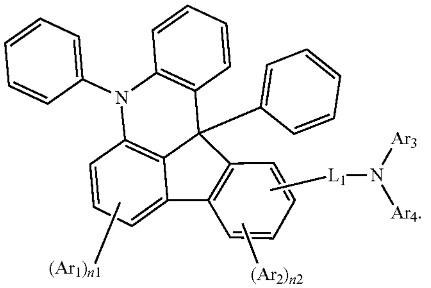

In Formula 1, $L_1$ may be a direct linkage, a substituted or unsubstituted arylene group having 6 to 30 ring-forming carbon atoms, or a substituted or unsubstituted heteroarylene group having 2 to 30 ring-forming carbon atoms. When $L_1$ is a direct linkage, the amine group may be directly bonded to the pentacyclic fused ring containing an acridine moiety. When $L_1$ is an arylene group or heteroarylene group, the amine group may be indirectly bonded to the pentacyclic fused ring containing an acridine moiety. For example, $L_1$ may be a phenyl group, a divalent naphthyl group, a divalent fluorenyl group, a divalent spiro fluorenyl group, a divalent phenanthrenyl group, a divalent dibenzofuranyl group, or a divalent dibenzothiophene group. When $L_1$ is a phenylene group, the amine group and the pentacyclic fused ring may be bonded at the para-position of the phenylene group. When $L_1$ is a phenylene group, $L_1$ may be represented by L-1 below:

L-1

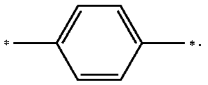

In Formula 1, n1 and n2 may be each independently an integer of 0 to 3. When n1 is an integer of 2 or more, a plurality of $Ar_1$'s may be the same as each other or at least one may be different from the others. When n2 is an integer of 2 or more, a plurality of $Ar_2$'s may be the same as each other or at least one may be different from the others.

$Ar_1$ and $Ar_2$ may be each independently a hydrogen atom, a deuterium atom, a substituted or unsubstituted aryl group having 6 to 30 ring-forming carbon atoms, or a substituted or unsubstituted heteroaryl group having 2 to 30 ring-forming carbon atoms. For example, n1 may be 1, n2 may be 0, and $Ar_1$ may be a substituted or unsubstituted phenyl group. In some embodiments, n1 may be 0, n2 may be 1, and $Ar_1$ may be a substituted or unsubstituted phenyl group.

$Ar_3$ and $Ar_4$ may be each independently a substituted or unsubstituted aryl group having 6 to 30 ring-forming carbon atoms, or a substituted or unsubstituted heteroaryl group having 2 to 30 ring-forming carbon atoms. For example, $Ar_3$ and $Ar_4$ may be each independently a heteroaryl group containing N, O, or S as a ring-forming atom. In some embodiments, $Ar_3$ and $Ar_4$ may be each independently a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

In an embodiment, $Ar_3$ and $Ar_4$ may be each independently represented by any one selected from among A-1 to A-7 below. A-1 represents an unsubstituted phenyl group, and A-2 represents an unsubstituted biphenyl group. A-3 represents an unsubstituted naphthyl group, and A-4 represents a substituted or unsubstituted fluorenyl group. A-5 represents a substituted carbazole group, A-6 represents an unsubstituted dibenzofuran group, and A-7 represents an unsubstituted dibenzothiophene group.

A-1

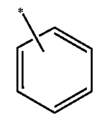

A-2

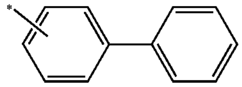

A-3

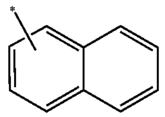

A-4

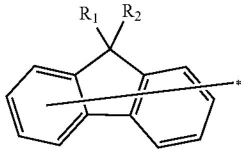

A-5

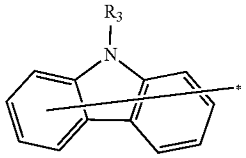

A-6

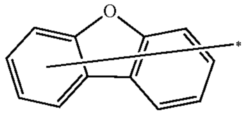

A-7

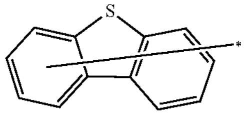

In A-4, $R_1$ and $R_2$ may be each independently a substituted or unsubstituted alkyl group having 1 to 10 carbon atoms, or a substituted or unsubstituted aryl group having 6 to 30 ring-forming carbon atoms, or may be bonded to an adjacent group to form a ring. For example, each of $R_1$ and $R_2$ may be a substituted or unsubstituted phenyl group, and $R_1$ and $R_2$ may be bonded to form a spiro fluorenyl group. In some embodiments, $R_1$ and $R_2$ may be each independently a methyl group or a phenyl group.

In A-5, $R_3$ may be a substituted or unsubstituted aryl group having 6 to 30 ring-forming carbon atoms. For example, $R_3$ may be a substituted or unsubstituted phenyl group.

In some embodiments, A-2 may be represented by any one selected from among A-21 to A-23 below, and A-21 to A-23 have a different position at which an amine group is bonded. A-3 may be represented by A-31 or A-32 below, and A-31 and A-32 have a different position at which an amine group is bonded. A-4 may be represented by any one selected from among A-41 to A-43 below, and A-41 to A-43 represent the case where $R_1$ and $R_2$ are methyl groups or phenyl groups. For A-43, $R_1$ and $R_2$ are phenyl groups, and $R_1$ and $R_2$ are bonded to form a spiro fluorenyl group.

A-21

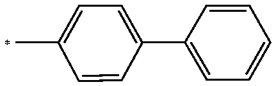

A-22

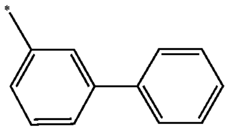

A-23

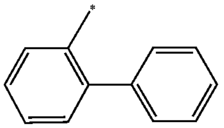

A-31

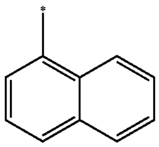

A-32

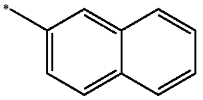

A-41

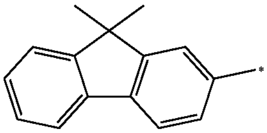

A-42

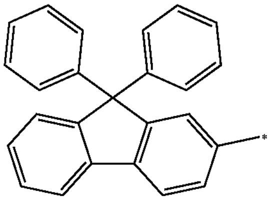

-continued

A-43

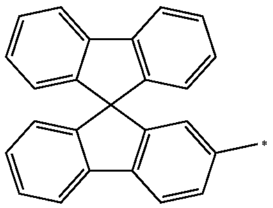

In addition, A-5 may be represented by A-51 or A-52 below, and A-51 and A-52 have a different position at which an amine group is bonded. A-51 and A-52 represent the case where $R_3$ is an unsubstituted phenyl group. A-6 may be represented by any one selected from among A-61 to A-64 below, and A-61 to A-64 have a different position at which an amine group is bonded. A-7 may be represented by any one selected from among A-71 to A-74 below, and A-71 to A-74 have a different position at which an amine group is bonded.

A-51

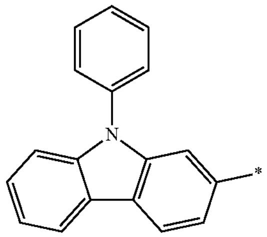

A-52

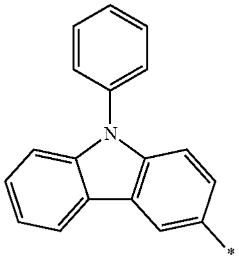

A-61

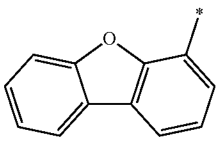

A-62

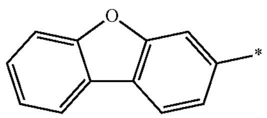

A-63

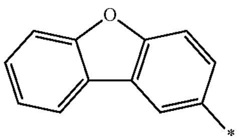

-continued

A-64

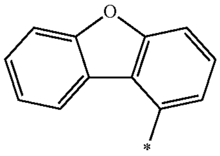

A-71

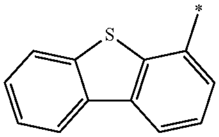

A-72

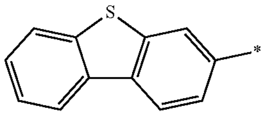

A-73

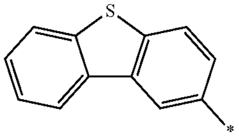

A-74

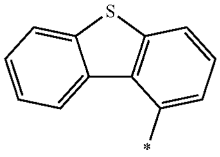

In an embodiment, Formula 1 may be represented by Formula 1-1 below: Formula 1-1 represents the case where $Ar_3$ and $Ar_4$ are each independently a substituted or unsubstituted phenyl group in Formula 1.

Formula 1-1

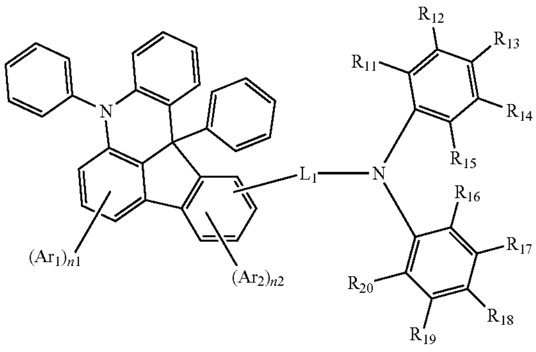

In Formula 1-1, $R_{11}$ to $R_{20}$ are each independently a hydrogen atom, a deuterium atom, a substituted or unsubstituted amine group, a substituted or unsubstituted oxy group, a substituted or unsubstituted thio group, a substituted or unsubstituted alkyl group having 1 to 10 carbon atoms, a substituted or unsubstituted alkenyl group having 2 to 10 carbon atoms, or a substituted or unsubstituted aryl group having 6 to 30 ring-forming carbon atoms, or may be bonded to an adjacent group to form a ring. For example, any one selected from among $R_{11}$ to $R_{15}$ may be an unsubstituted phenyl group.

In Formula 1-1, $R_{13}$ and $R_{14}$ may be vinyl groups, and $R_{13}$ and $R_{14}$ may be bonded to form a naphthyl group. $R_{13}$ may be an aryloxy group, and $R_{13}$ and $R_{14}$ may be bonded to form a dibenzofuran group. $R_{13}$ may be an arylthio group, and $R_{13}$ and $R_{14}$ may be bonded to form a dibenzothiophene group. $R_{17}$ may be an isopropyl group, $R_{18}$ may be a phenyl group, and $R_{17}$ and $R_{18}$ may be bonded to form a dimethylfluorenyl group. $R_{18}$ may be a phenyl group, $R_{19}$ may be an arylamine group, and $R_{18}$ and $R_{19}$ may be bonded to form a carbazole group. However, this is an example, and embodiments of the present disclosure are not limited thereto.

Formula 1 may be represented by Formula 1-A1 or Formula 1-A2 below. Formula 1-A1 and Formula 1-A2 represent examples of the bonding position of $L_1$ in Formula 1.

Formula 1-A1

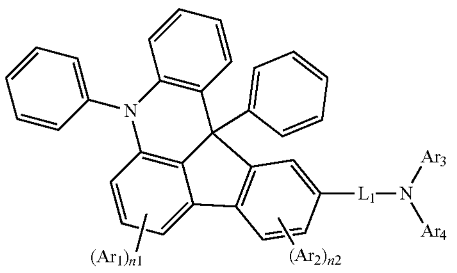

Formula 1-A2

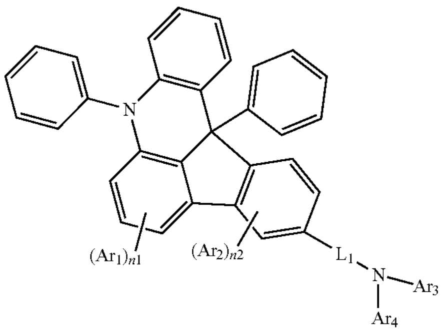

In Formula 1-A1 and Formula 1-A2, the same as described with respect to Formula 1 may be applied to $L_1$, n1, n2, and $Ar_1$ to $Ar_4$. For example, in Formula 1-A1 and Formula 1-A2, $L_1$ may be a direct linkage or a phenylene group.

Formula 1 may be represented by Formula 1-B1 or Formula 1-B2. Formula 1-B1 and Formula 1-B2 represent examples of the position and kind of $Ar_1$ when n1 is 1 in Formula 1.

Formula 1-B1

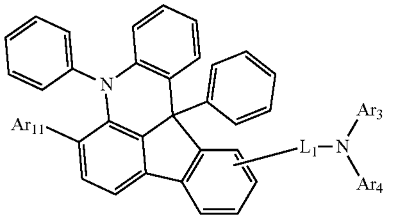

-continued

Formula 1-B2

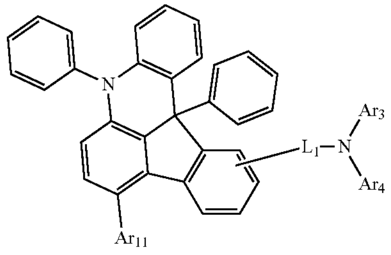

In Formula 1-B1 and Formula 1-B2, the same as described with respect to Formula 1 may be applied to $L_1$, $Ar_3$, and $Ar_4$. $Ar_{11}$ may be a substituted or unsubstituted aryl group having 6 to 30 ring-forming carbon atoms. $Ar_{11}$ may correspond to $Ar_1$ in Formula 1. For example, $Ar_{11}$ may be a substituted or unsubstituted phenyl group.

Formula 1-B1 may be represented by Formula 1-B11 below, and Formula 1-B2 may be represented by Formula 1-B21 below. Formula 1-B11 represent examples of the bonding position of $L_1$ in Formula 1-B1. Formula 1-B21 represent examples of the bonding position of $L_1$ in Formula 1-B2.

Formula 1-B11

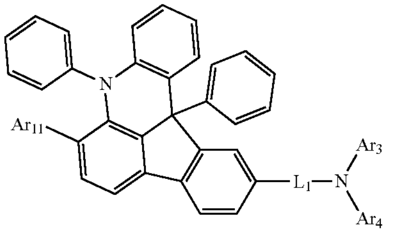

Formula 1-B21

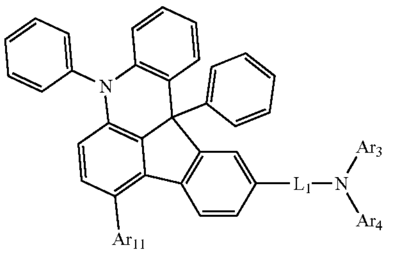

In Formula 1-B11, the same as described with respect to Formula 1-B1 may be applied to $Ar_{11}$, $L_1$, $Ar_3$, and $Ar_4$. In Formula 1-B21, the same as described with respect to Formula 1-B2 may be applied to $Ar_{11}$, $L_1$, $Ar_3$, and $Ar_4$.

Formula 1 may be represented by Formula 1-C1 or Formula 1-C2 below. Formula 1-C1 and Formula 1-C2 represent examples of the position and kind of Are when n2 is 1 in Formula 1.

Formula 1-C1

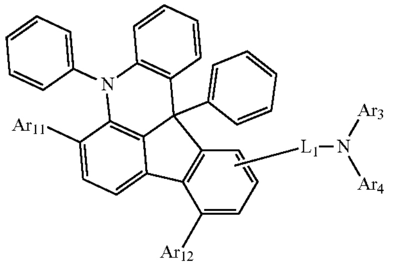

Formula 1-C2

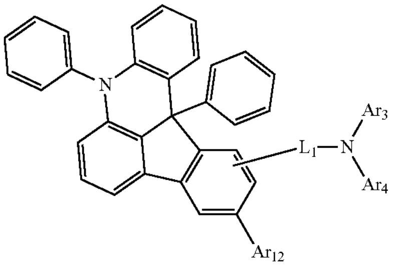

In Formula 1-C1 and in Formula 1-C2, $Ar_{12}$ may be a substituted or unsubstituted aryl group having 6 to 30 ring-forming carbon atoms. For example, $Ar_{12}$ may be a substituted or unsubstituted phenyl group. In Formula 1-C1 and Formula 1-C2, the same as described with respect to Formula 1 may be applied to $L_1$, $Ar_3$, and $Ar_4$.

Formula 1-C1 may be represented by Formula 1-C11 below, and Formula 1-C2 may be represented by Formula 1-C21 below. Formula 1-C11 represent examples of the bonding position of $L_1$ in Formula 1-C1. Formula 1-C21 represent examples of the bonding position of $L_1$ in Formula 1-C2.

Formula 1-C11

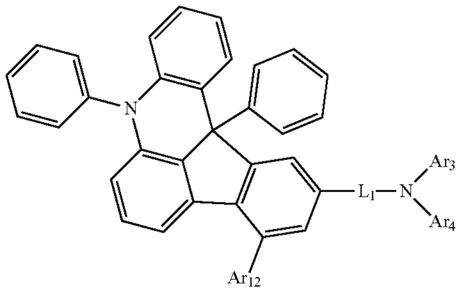

Formula 1-C21

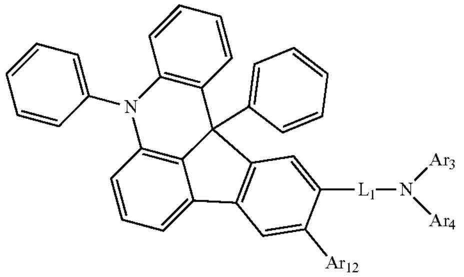

In Formula 1-C11, the same as described with respect to Formula 1-C1 may be applied to $Ar_{12}$, $L_1$, $Ar_3$, and $Ar_4$. In Formula 1-C21, the same as described with respect to Formula 1-C2 may be applied to $Ar_{12}$, $L_1$, $Ar_3$, and $Ar_4$.

The amine compound of an embodiment may be represented by any one selected from among compounds in Compound Group 1 below. The light emitting element ED of an embodiment may include any one selected from among the compounds of Compound Group 1 below:

Compound Group 1

1

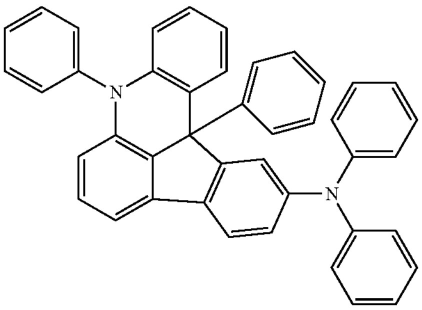

2

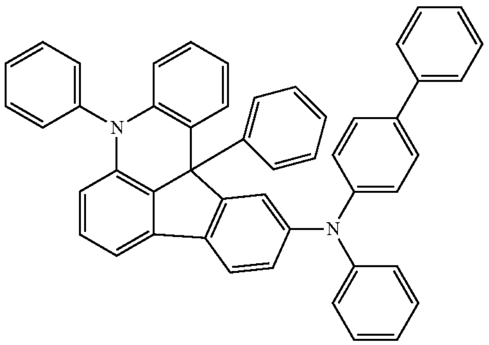

3

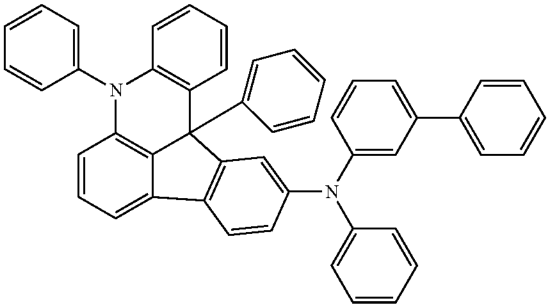

4

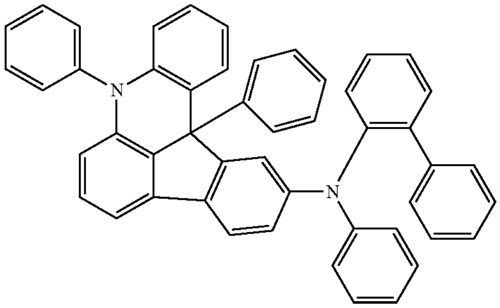

-continued
5
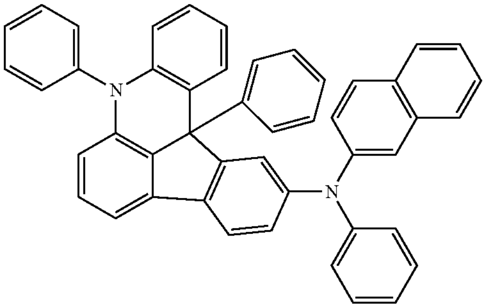
6
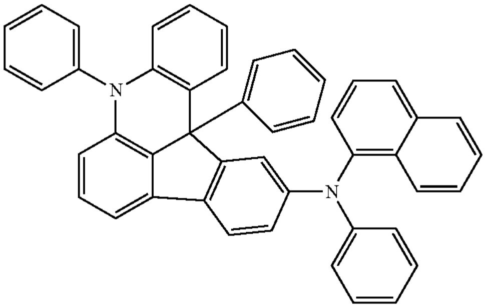
7
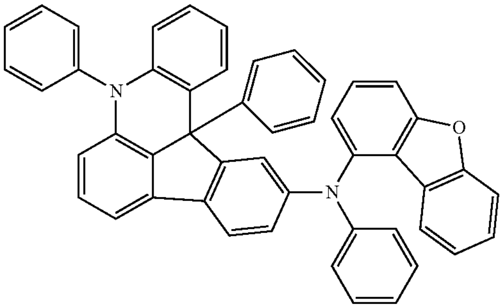
8
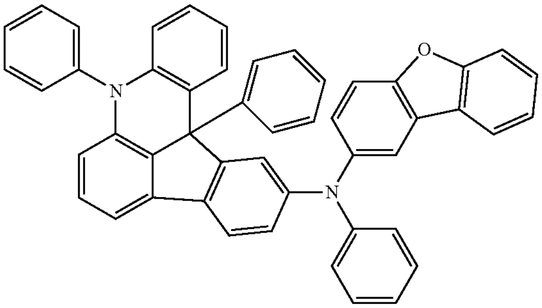
9
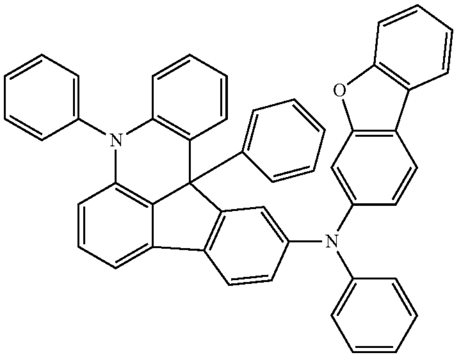
10
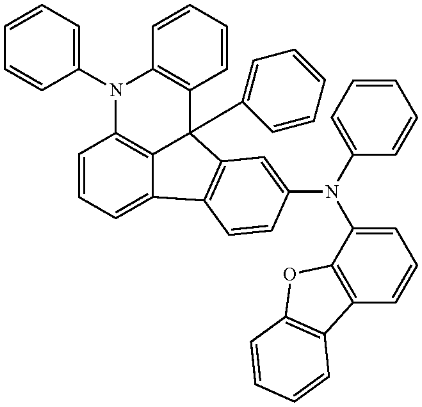
11
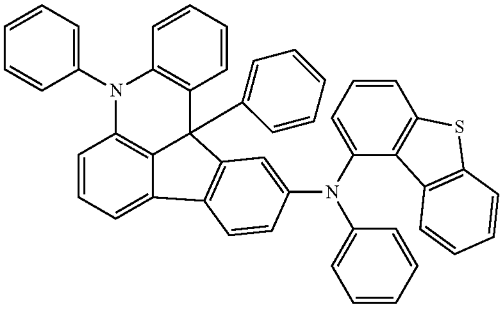
12
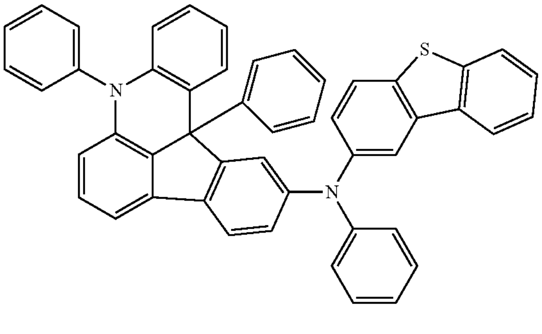

-continued
13
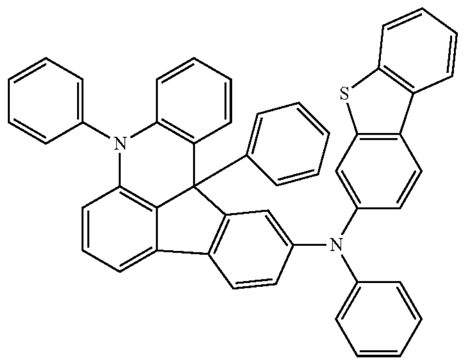
14
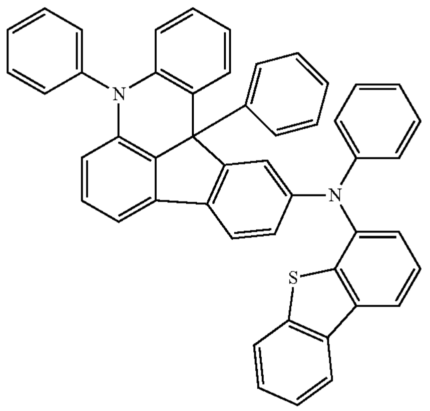
15
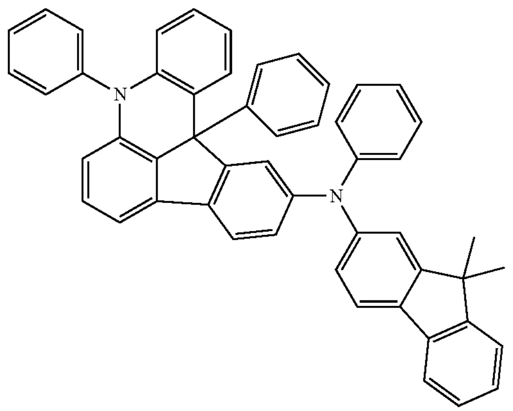
16
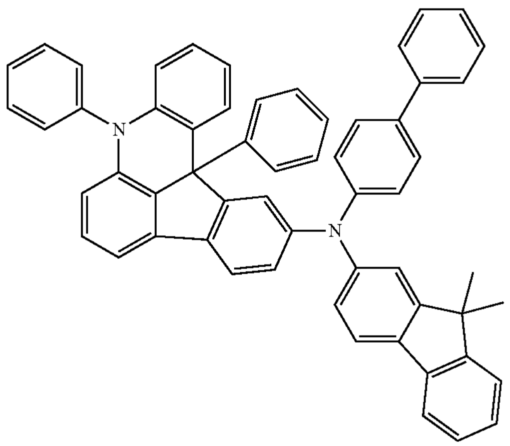
17
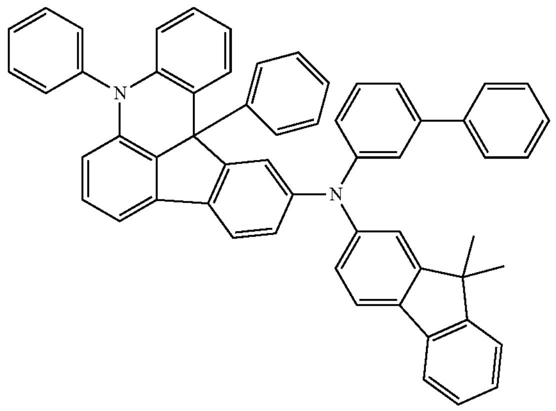
18
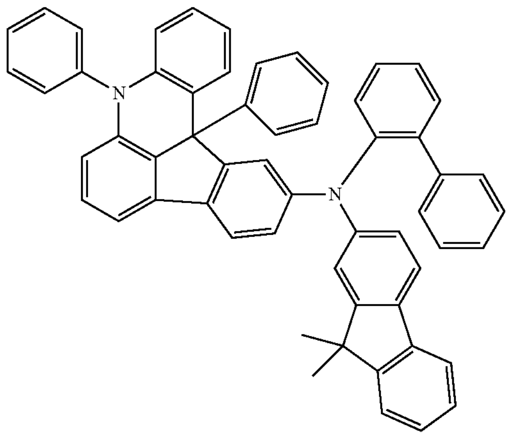

-continued
19
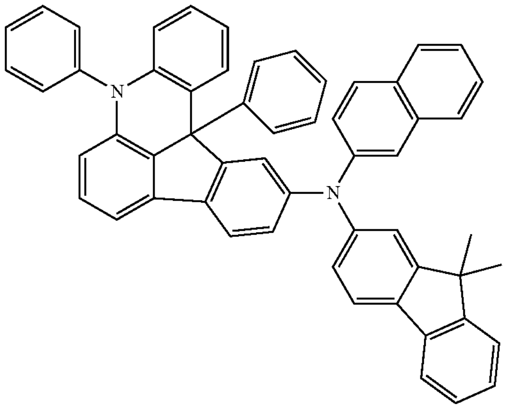
20
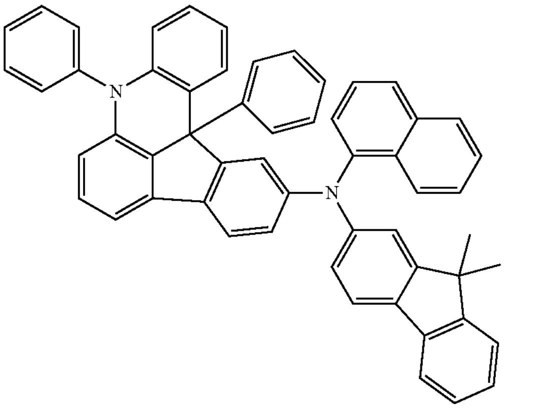
21
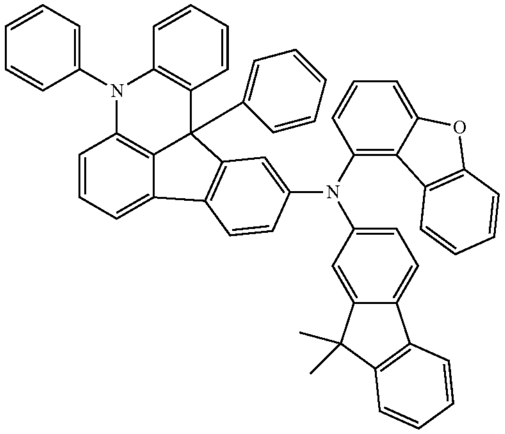
22
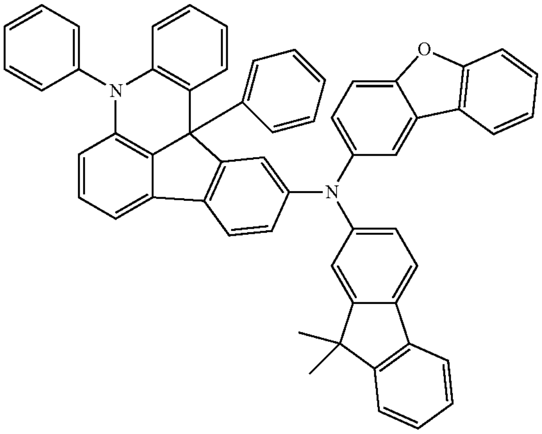
23
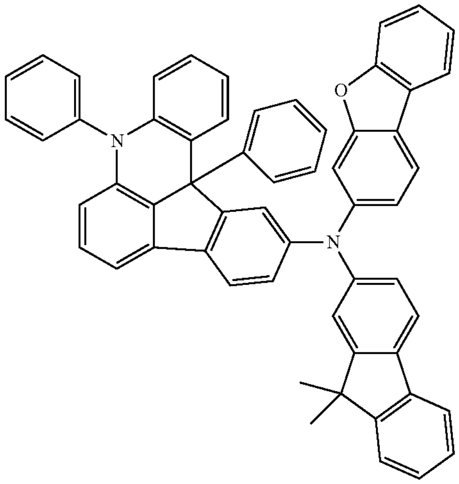
24
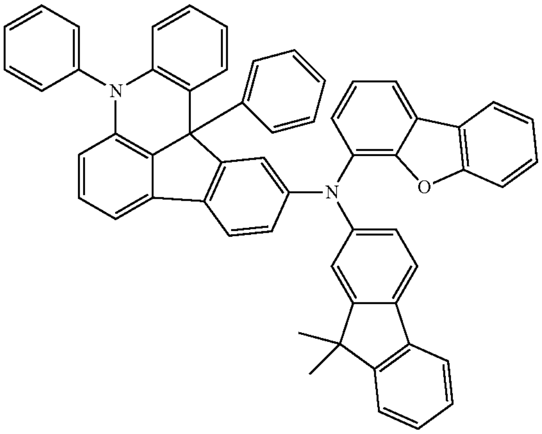

-continued
25
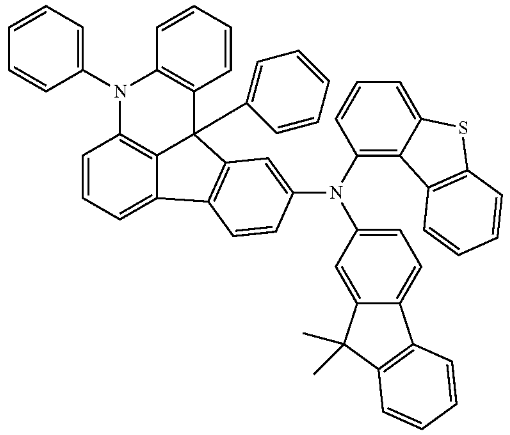
26
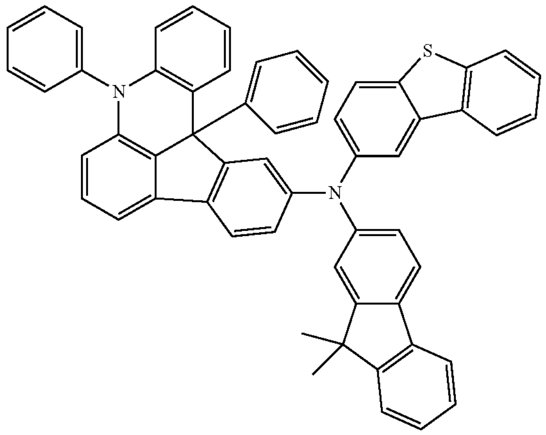
27
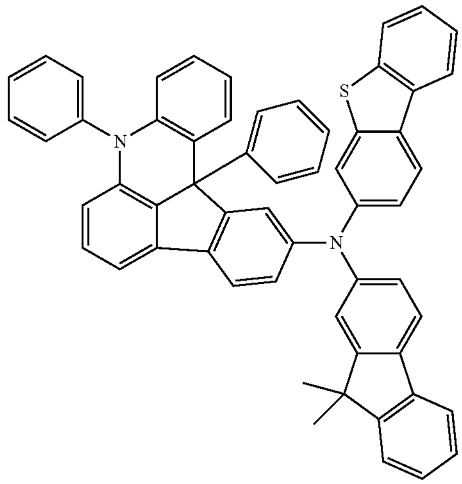
28
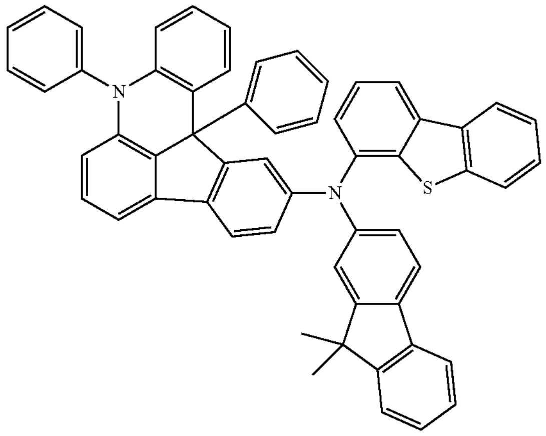
29
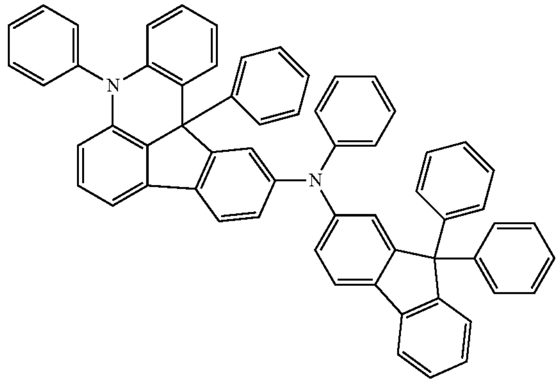
30
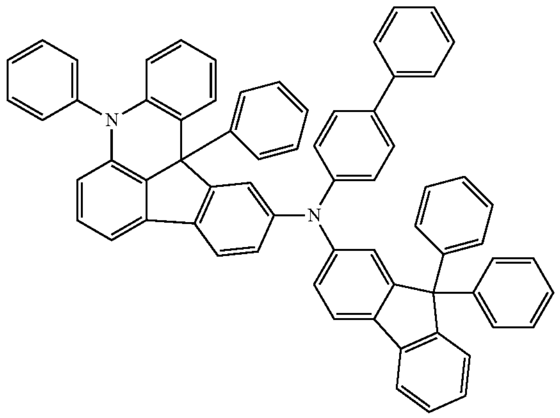

-continued
31
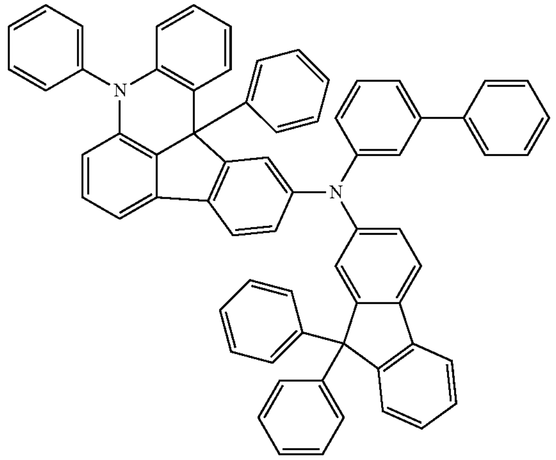
32
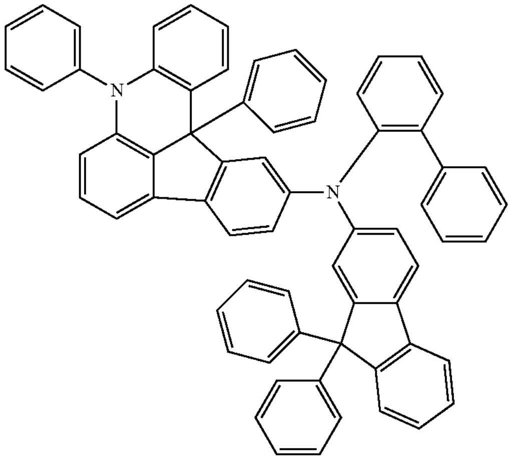
33
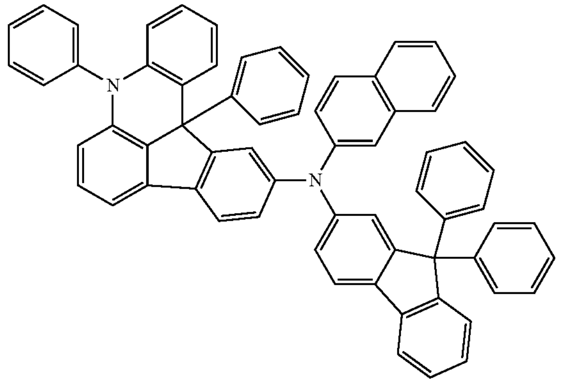
34
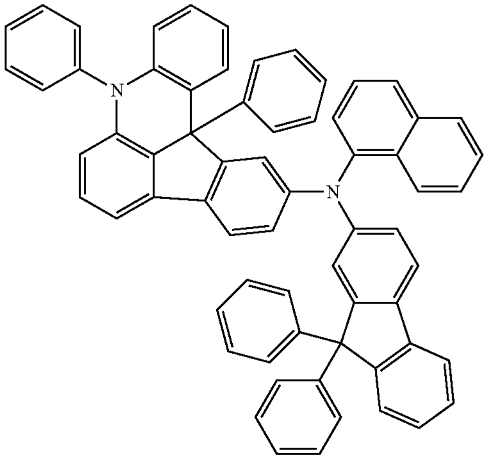
35
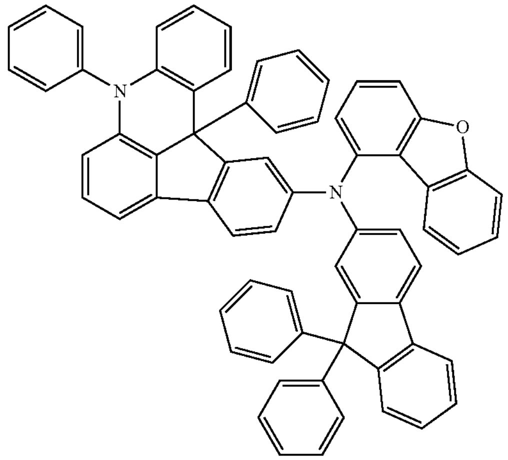
36
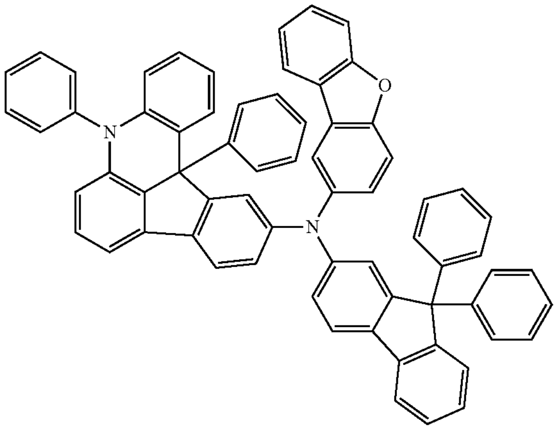

-continued
37
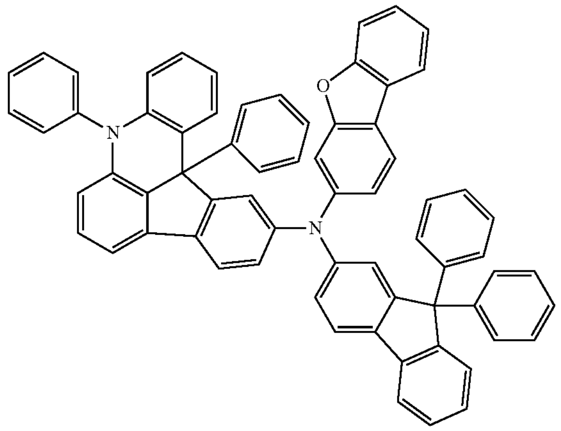
38
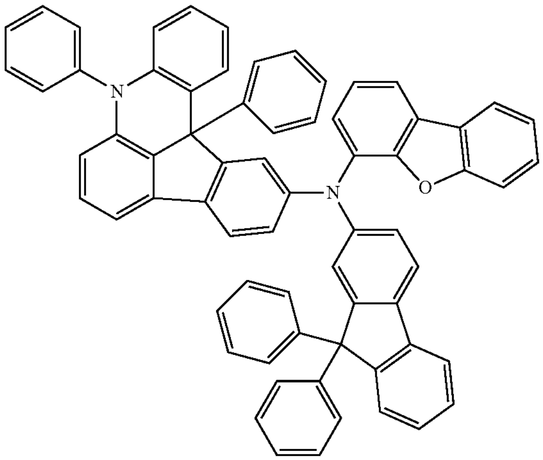
39
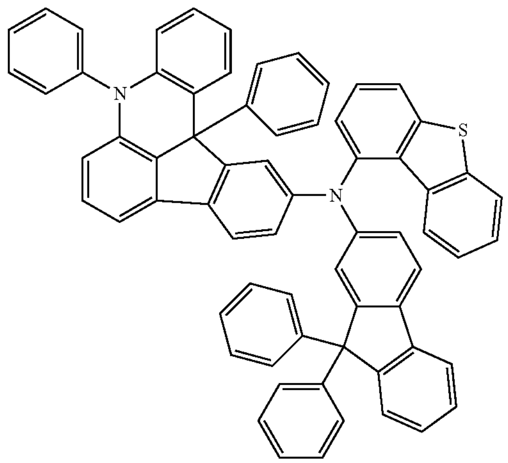
40
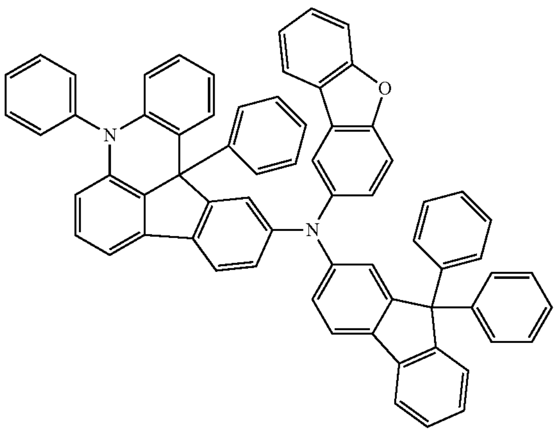
41
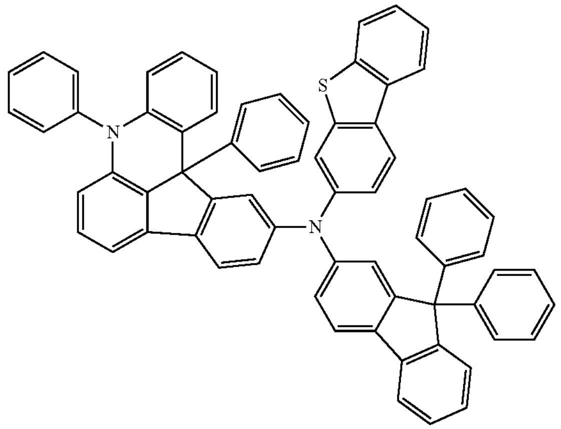
42
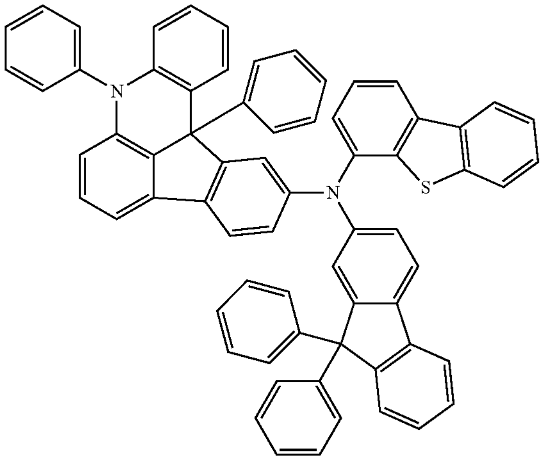

-continued
43
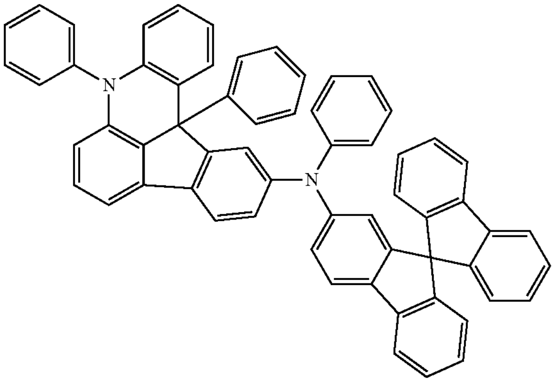
44
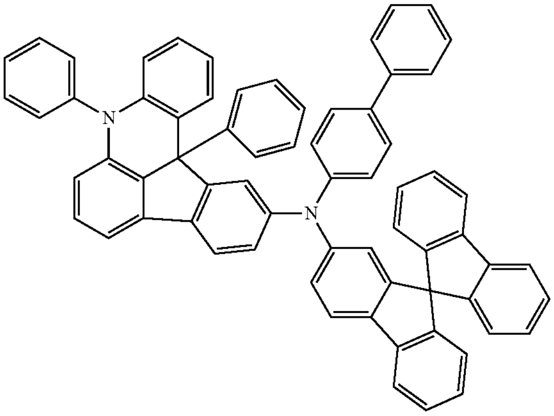
45
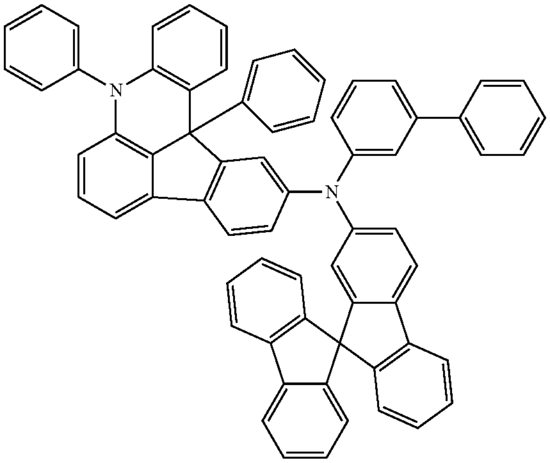
46
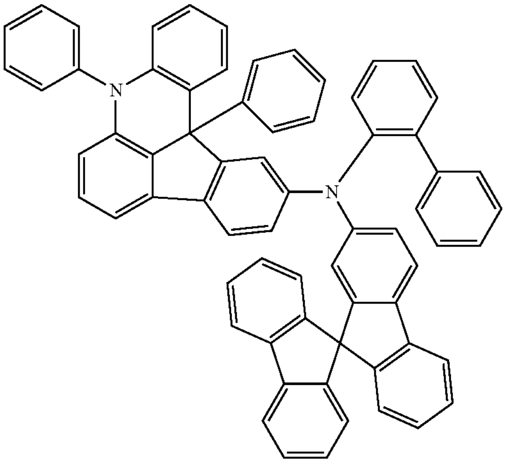
47
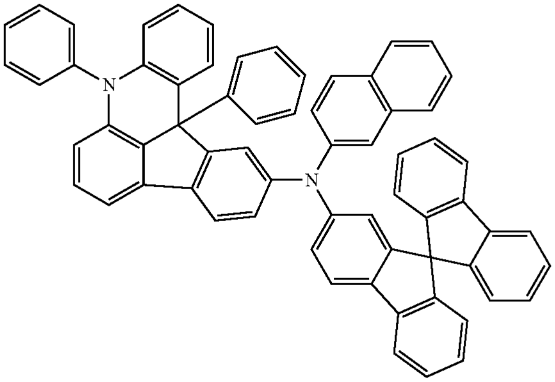
48
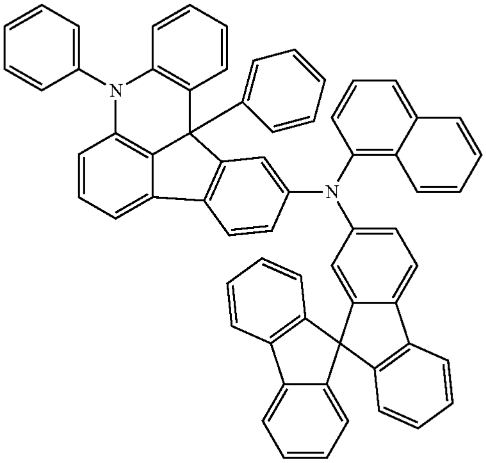

-continued
49
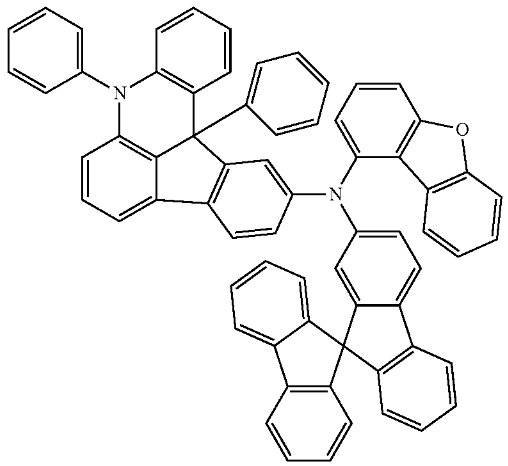
50
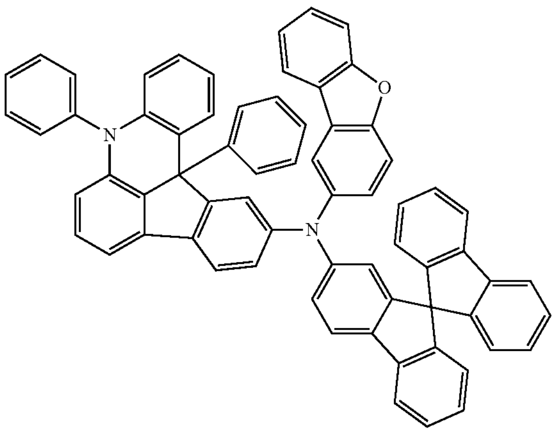
51
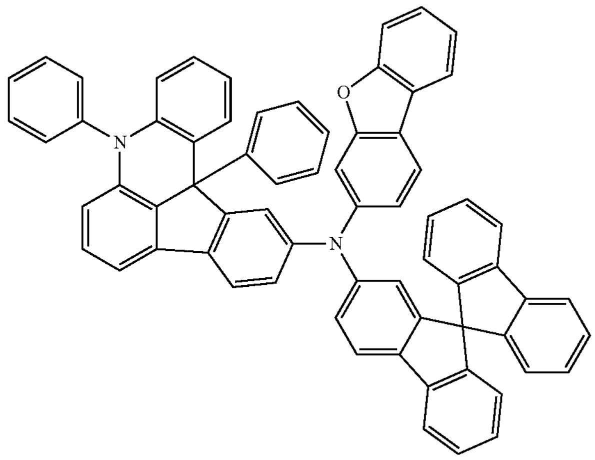
52
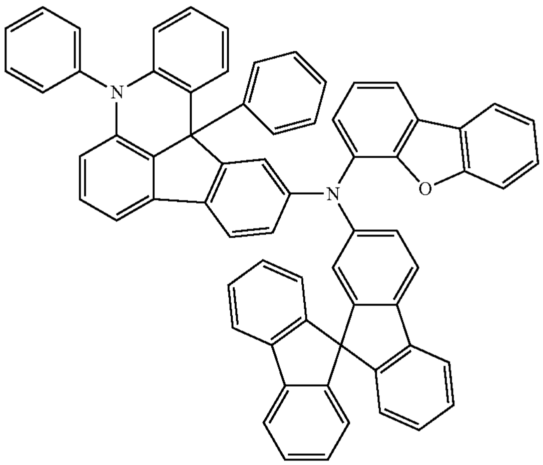
53
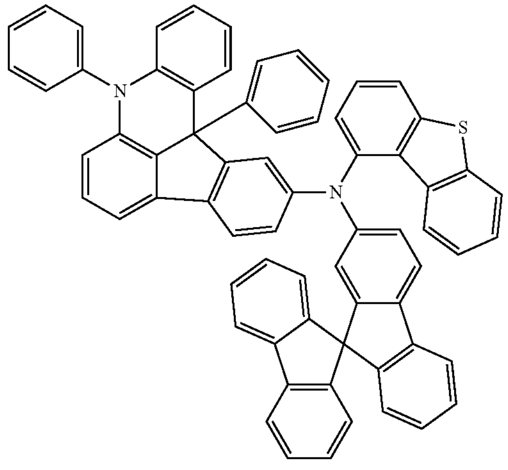
54
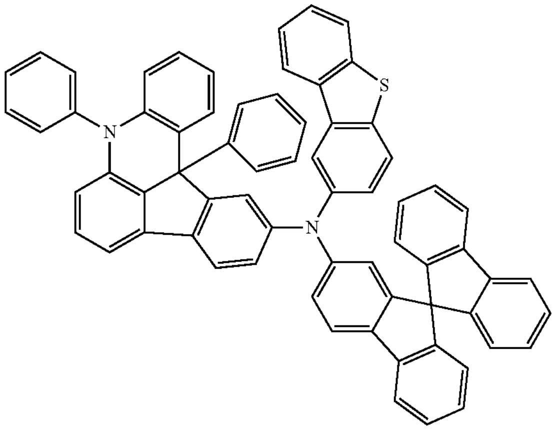

-continued
55
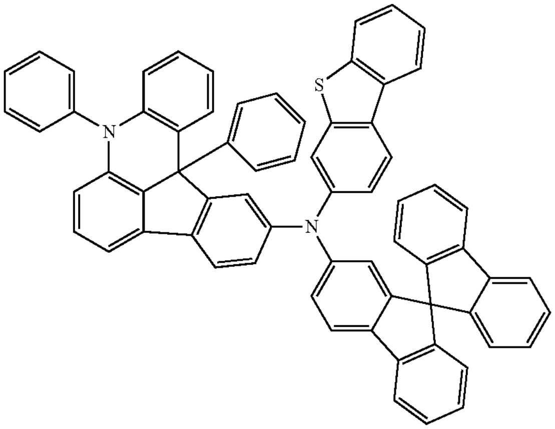
56
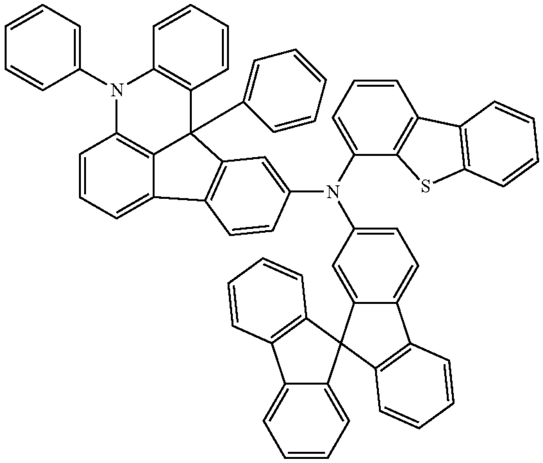
57
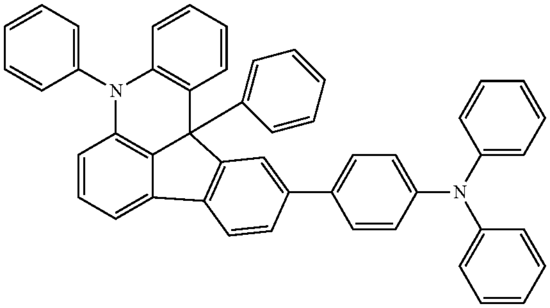
58
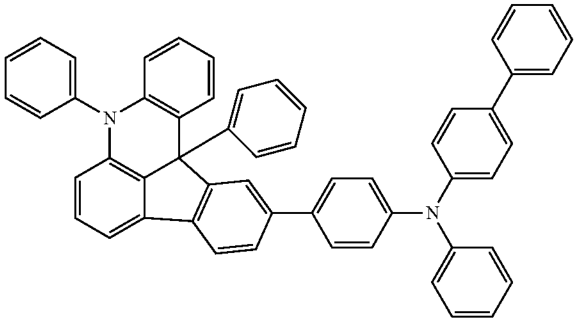
59
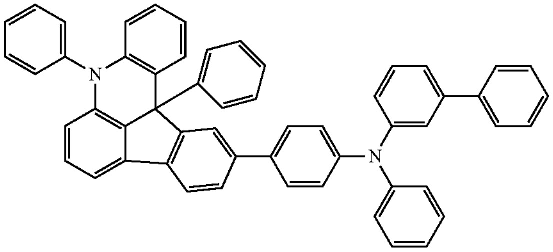
60
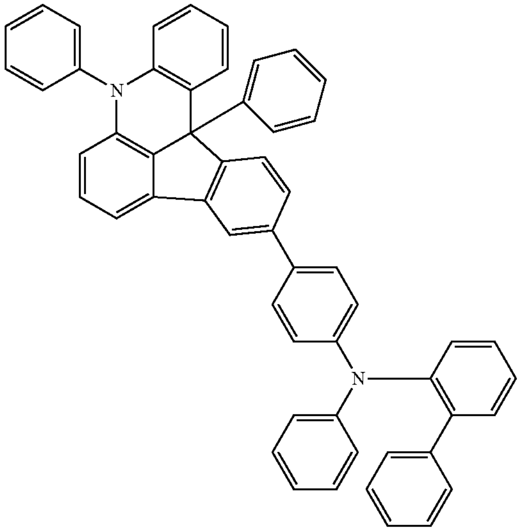
61
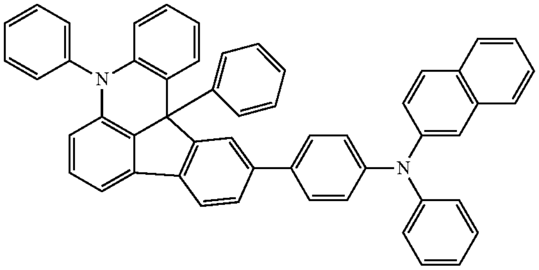
62
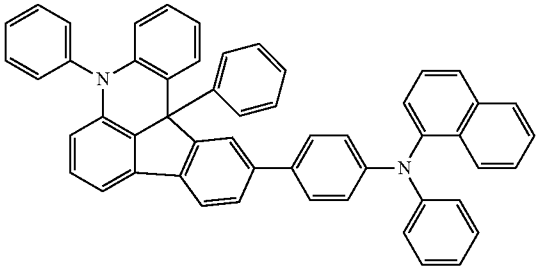

-continued
63
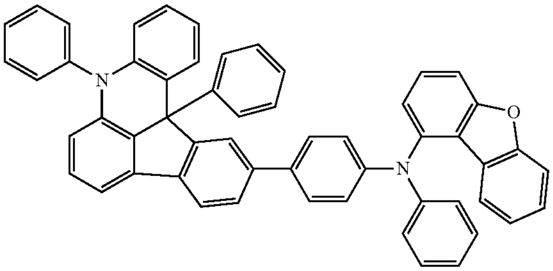
64
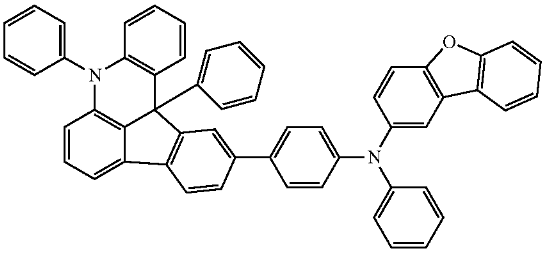
65
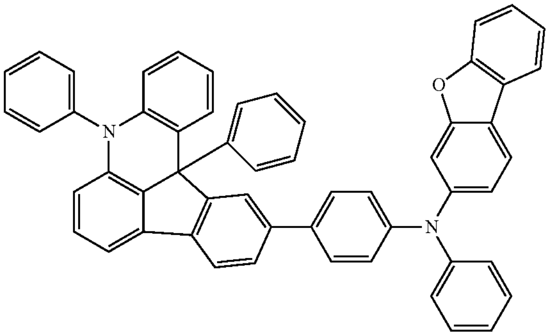
66
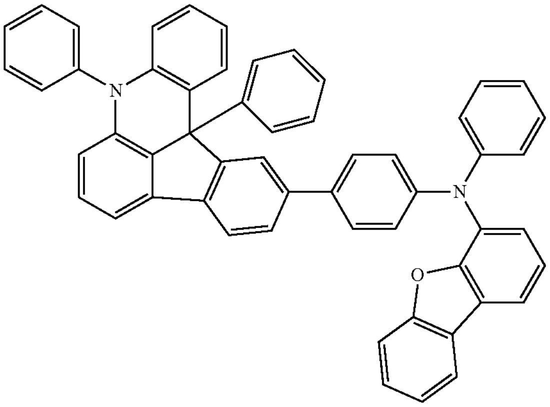
67
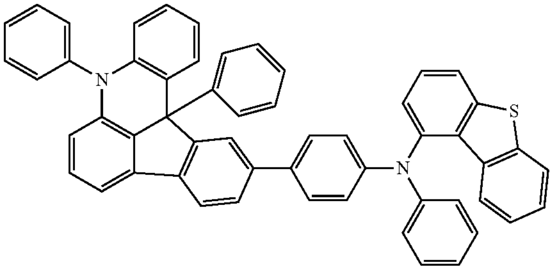
68
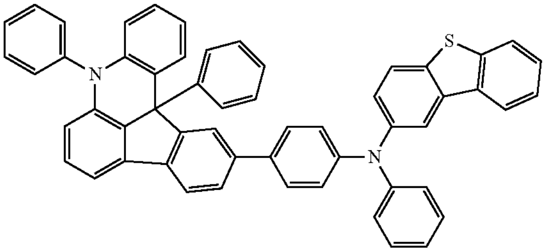
69
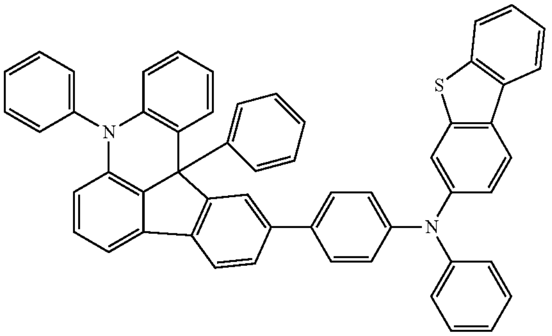
70
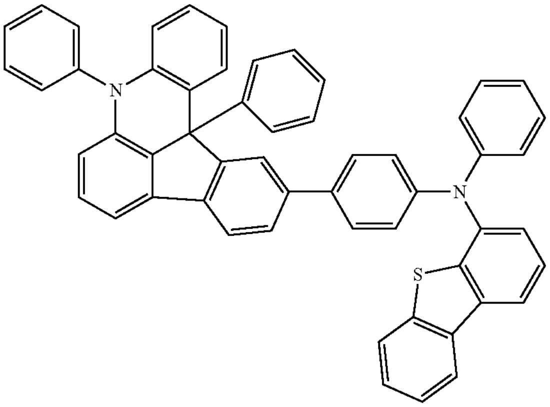

-continued
71
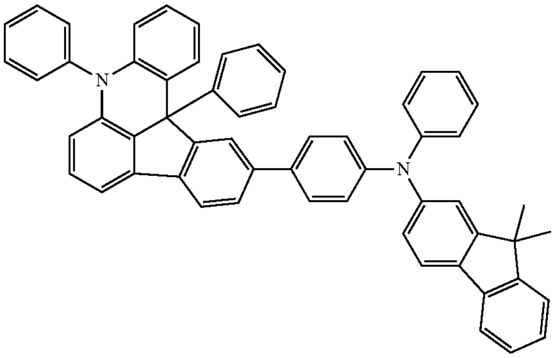
72
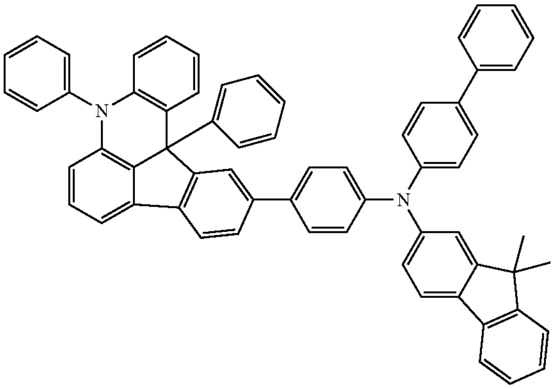
73
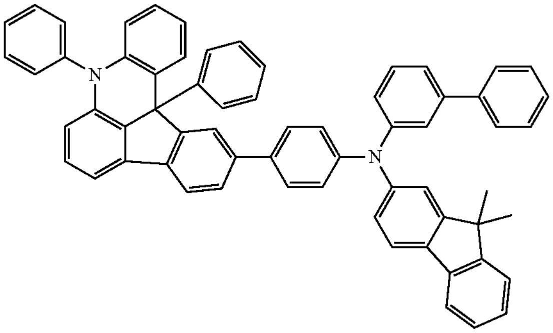
74
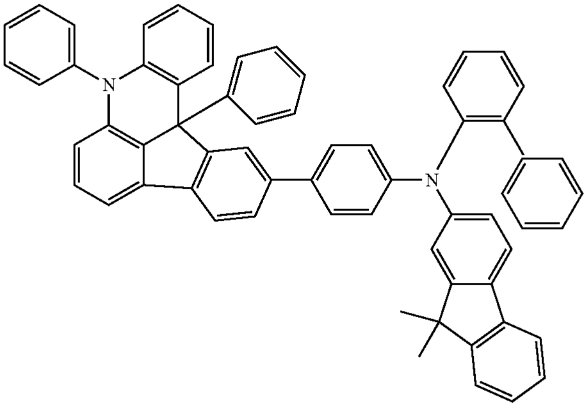
75
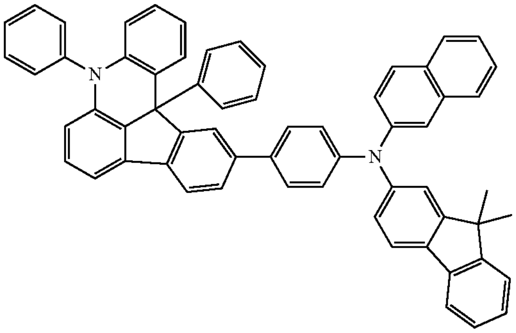
76
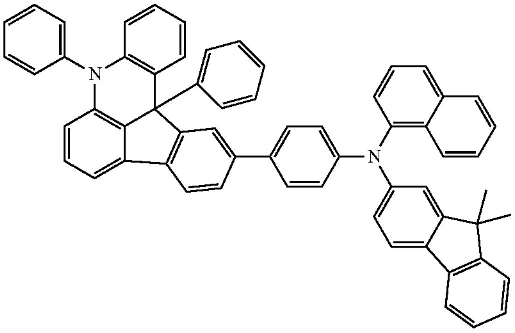
77
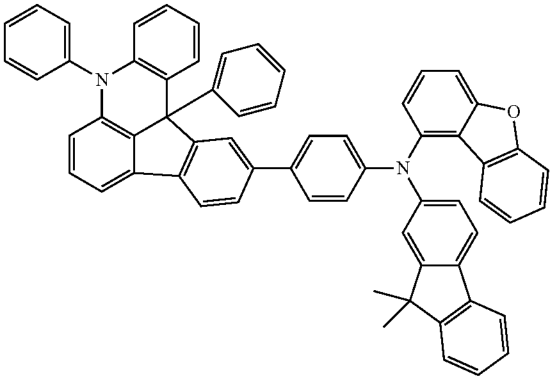
78
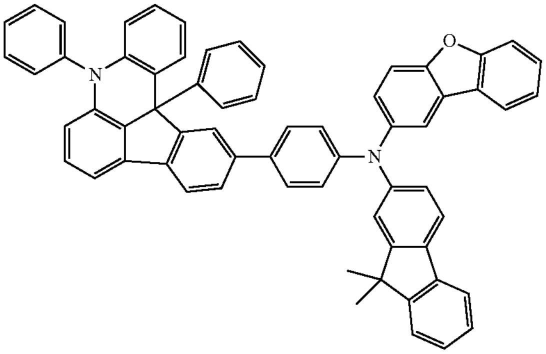

-continued
79
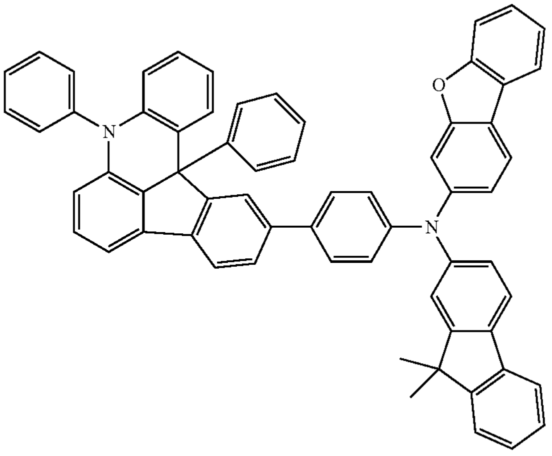
80
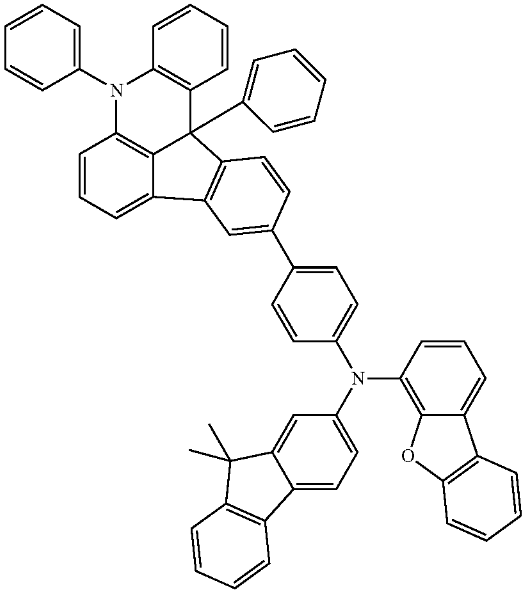
81
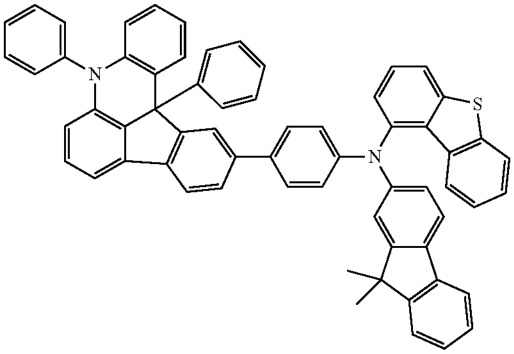
82
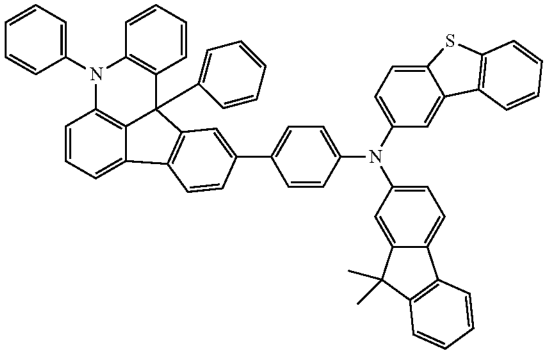
83
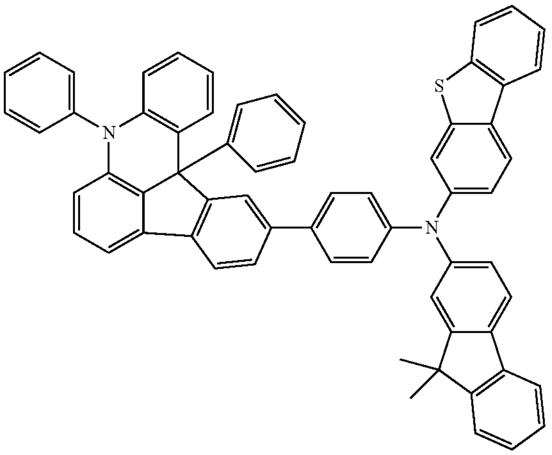
84
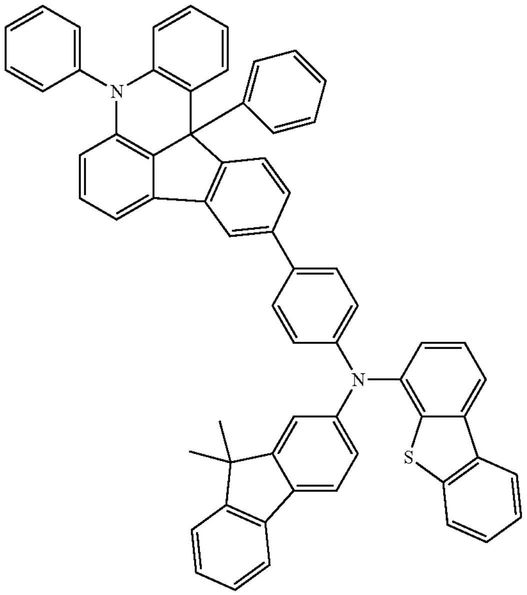

-continued
85
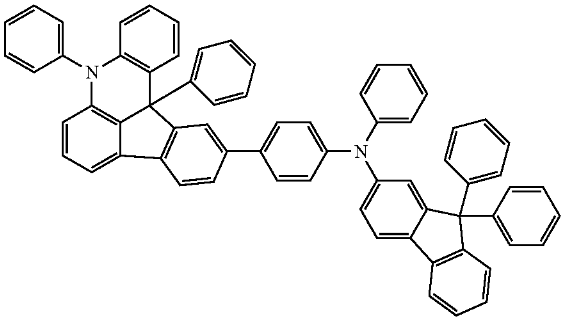
86
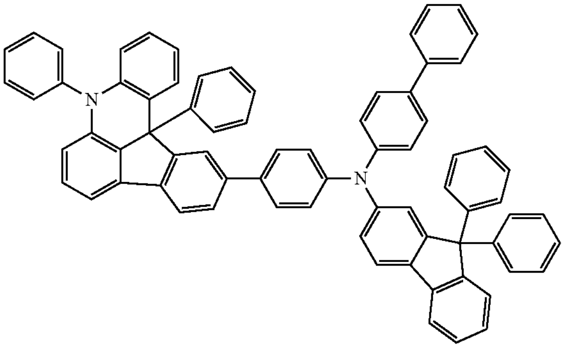
87
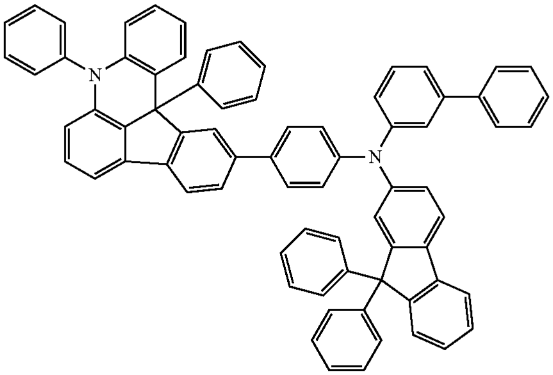
88
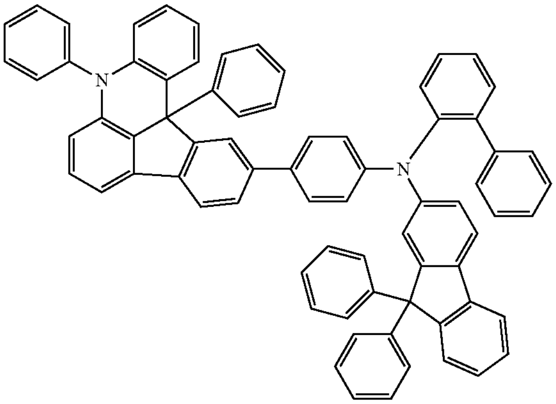
89
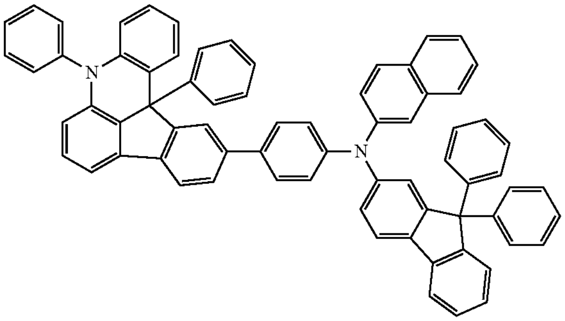
90
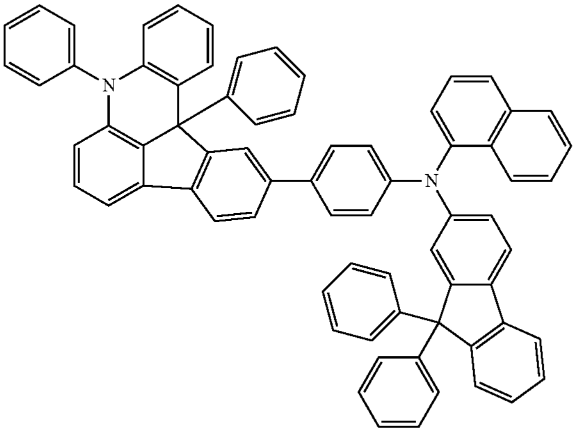
91
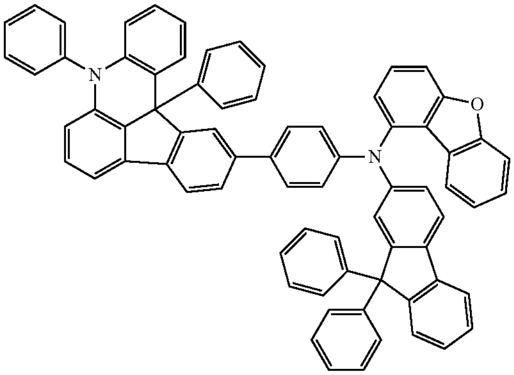
92
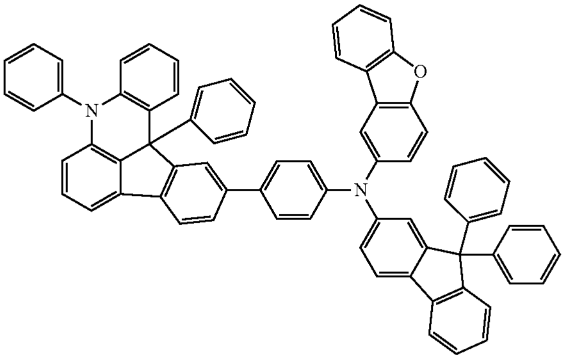

-continued
93
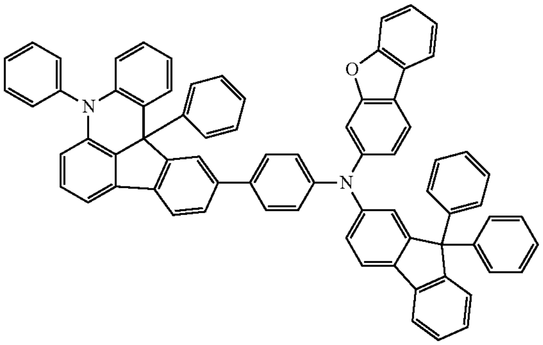
94
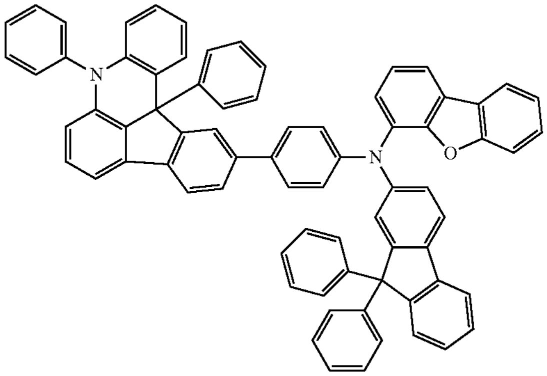
95
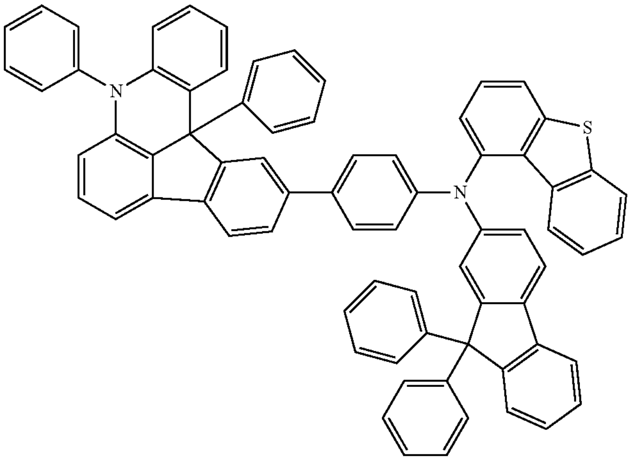
96
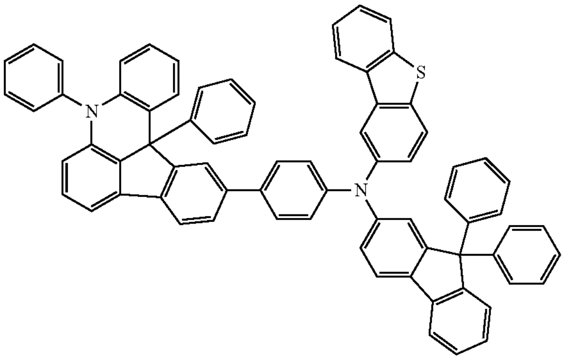
97
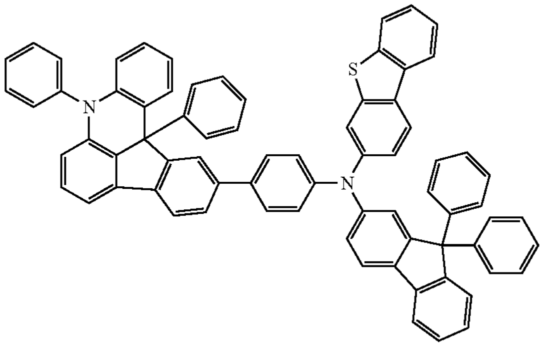
98
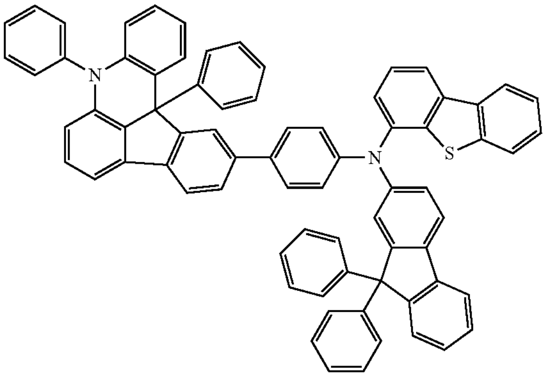
99
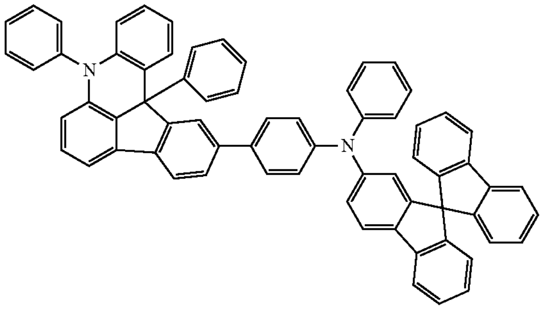

-continued
100
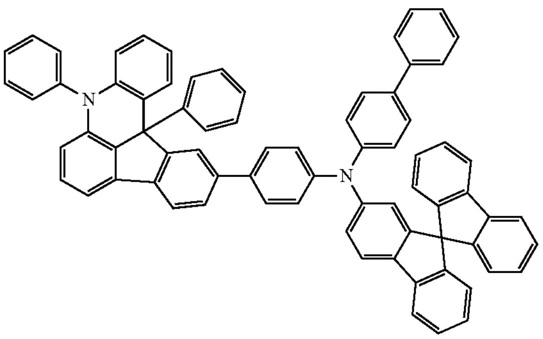
101
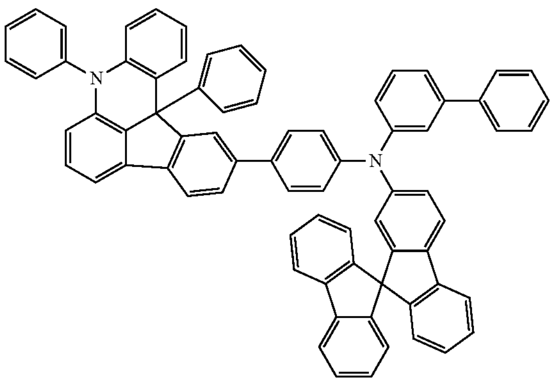
102
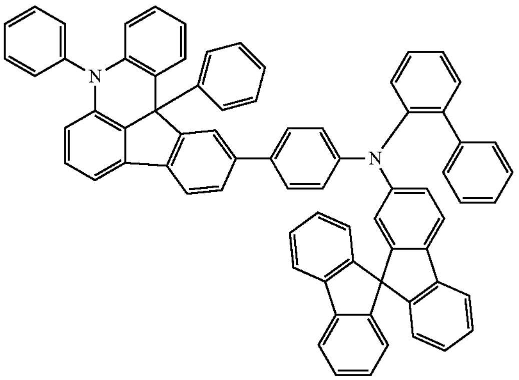
103
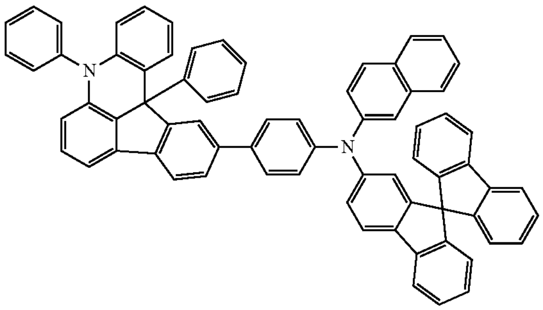
104
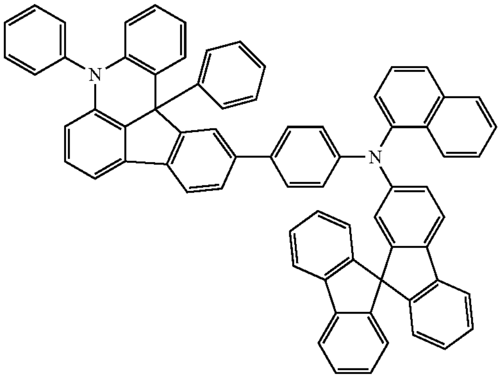
105
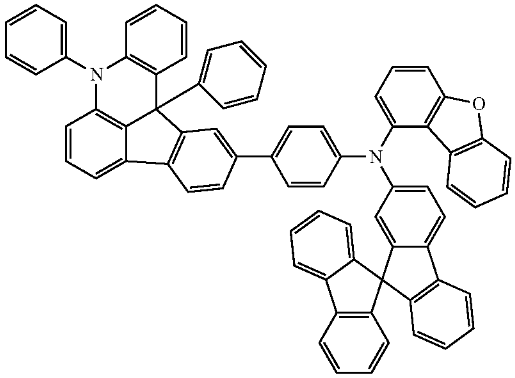
106
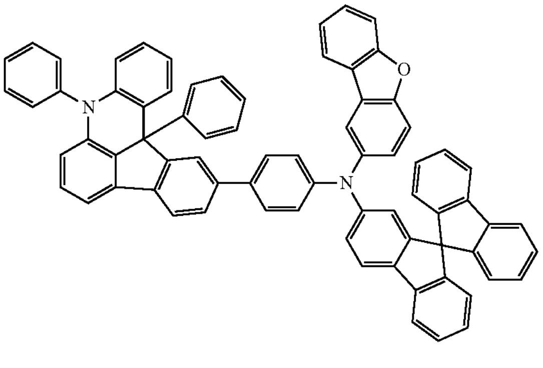
107
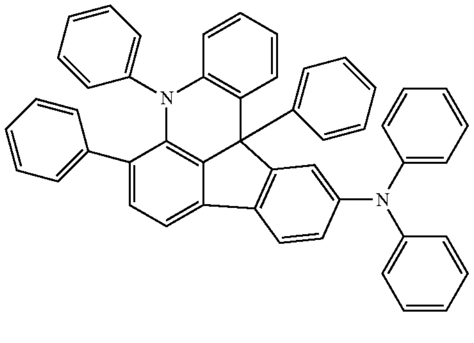

-continued
108
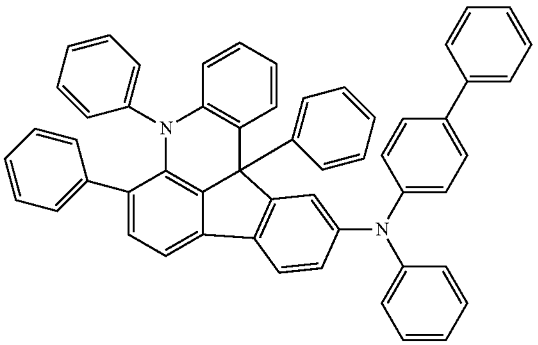
109
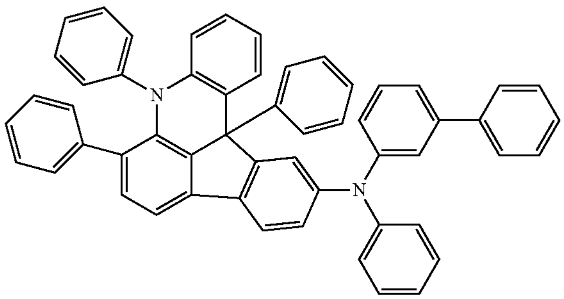
110
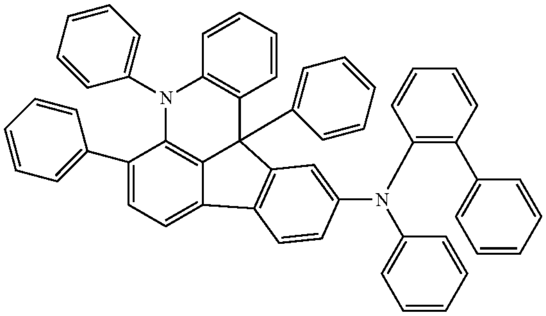
111
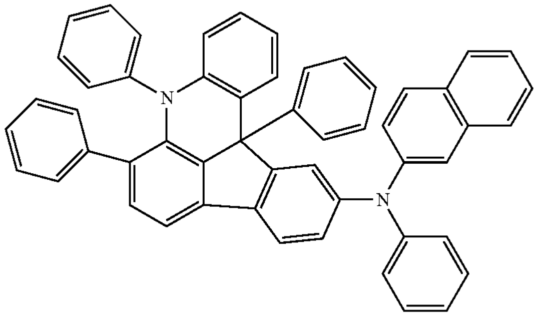
112
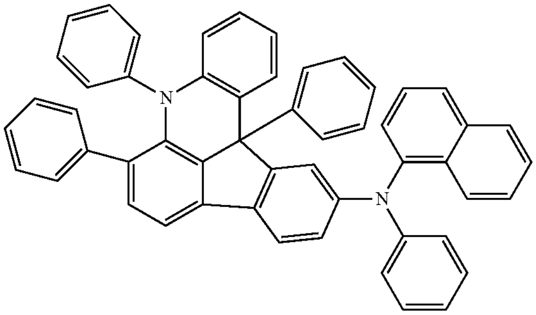
113
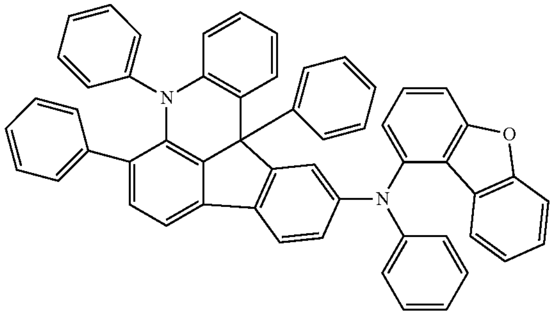
114
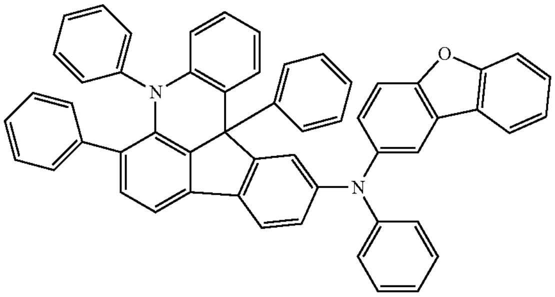
115
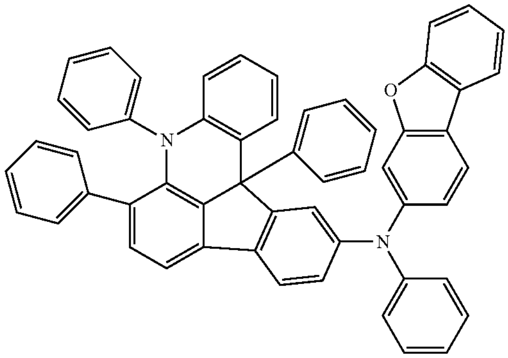

-continued
116
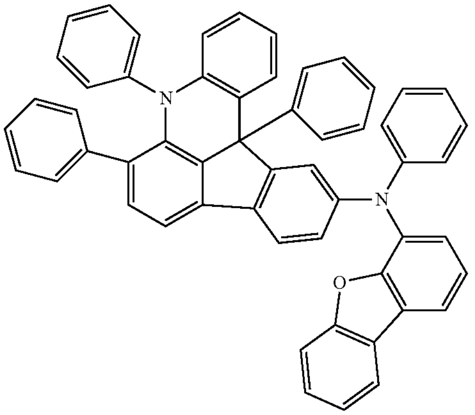
117
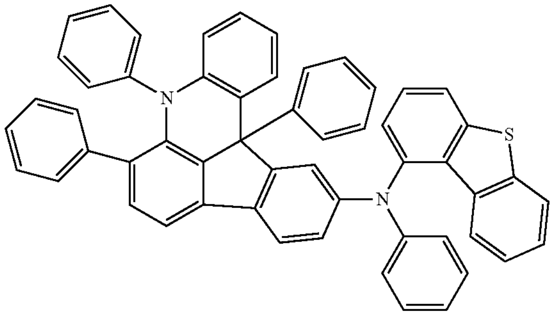
118
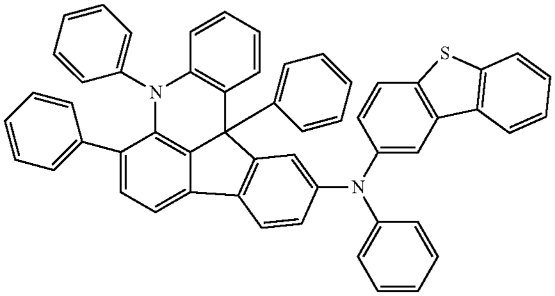
119
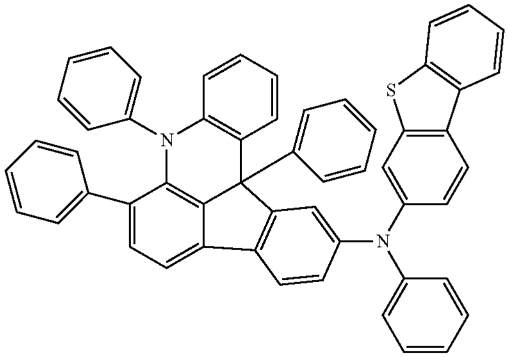
120
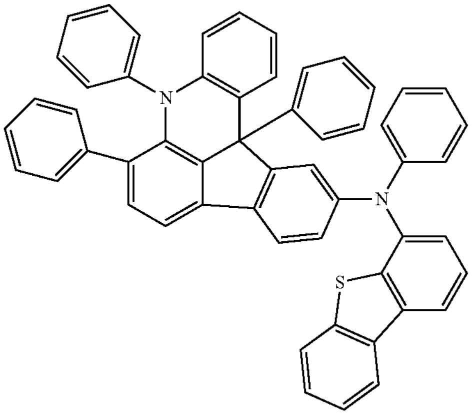
121
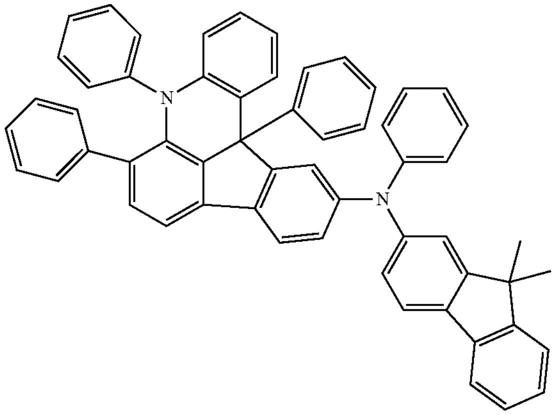

-continued
122
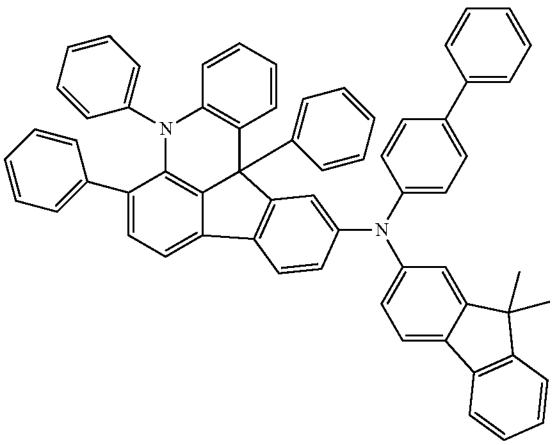
123
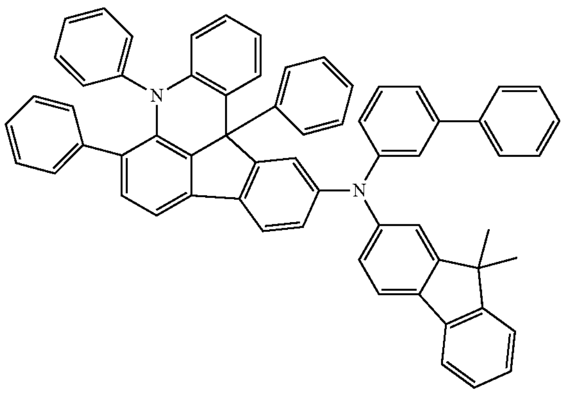
124
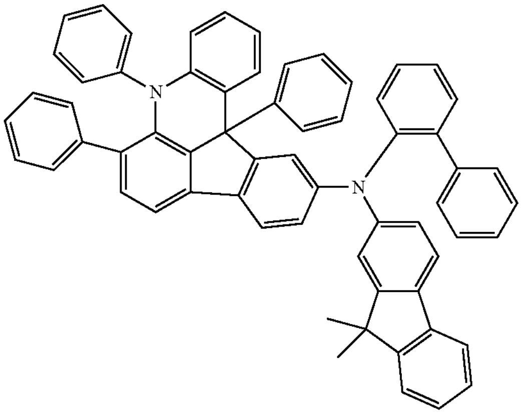
125
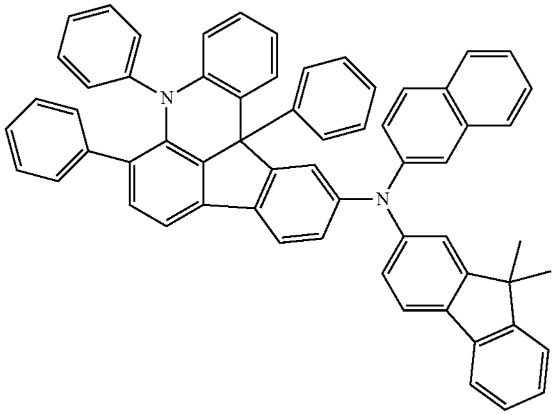
126
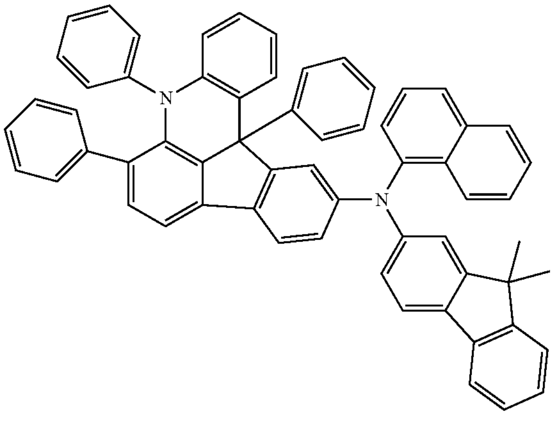
127
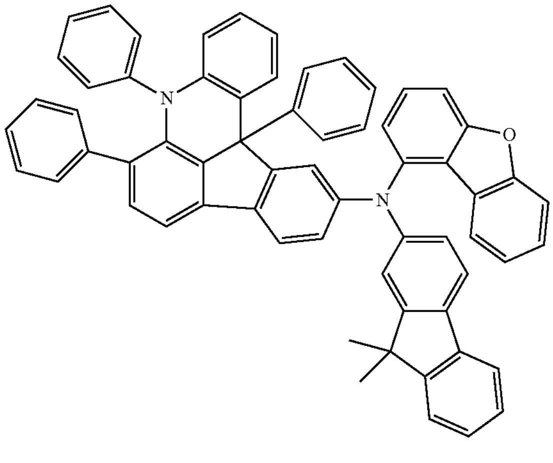

-continued
128
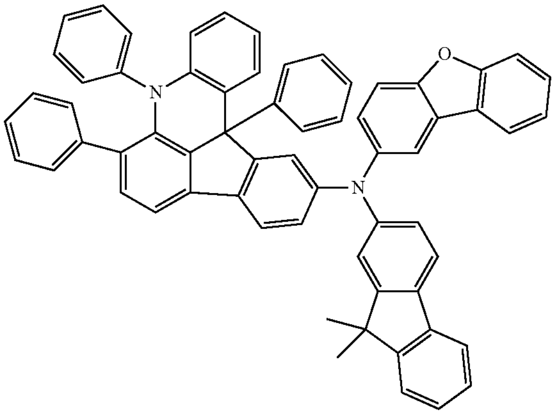
129
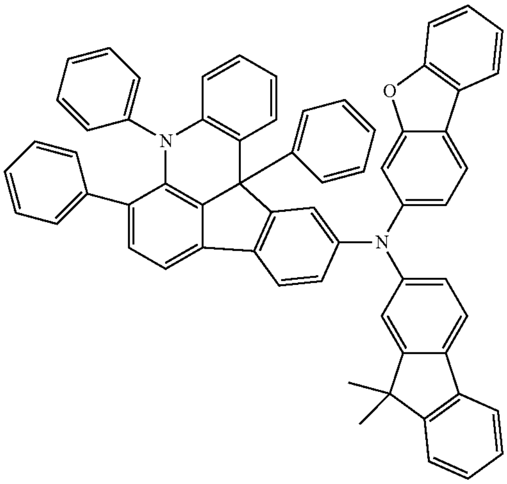
130
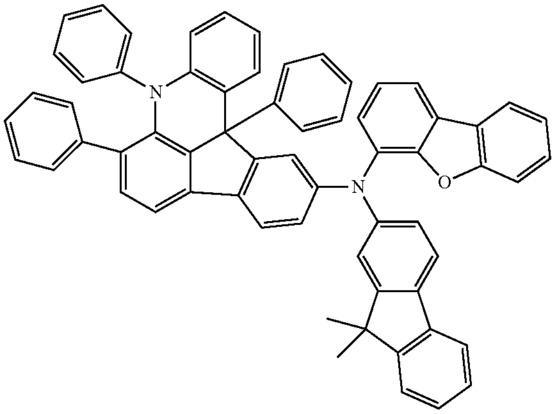
131
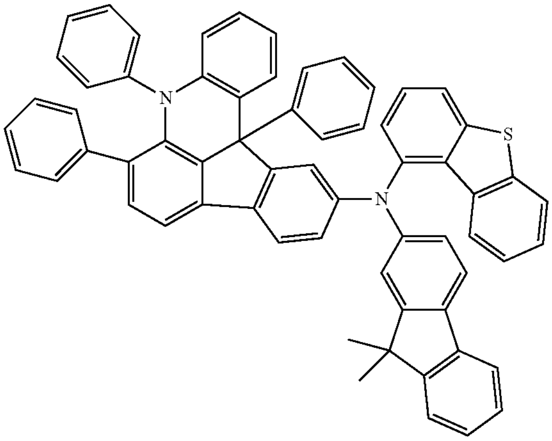
132
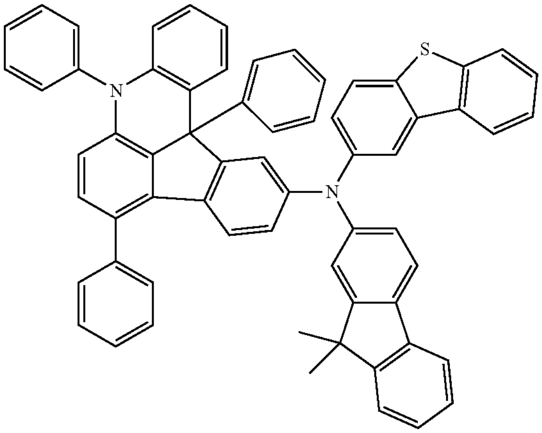
133
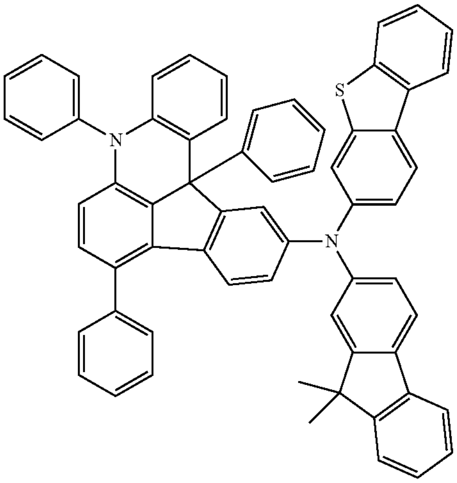

-continued
134
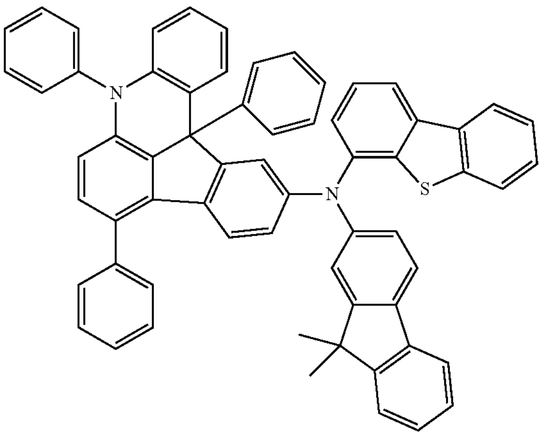
135
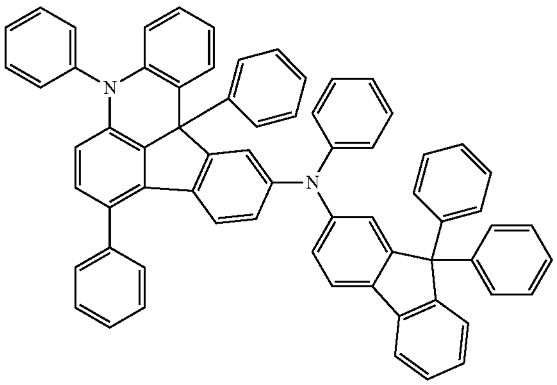
136
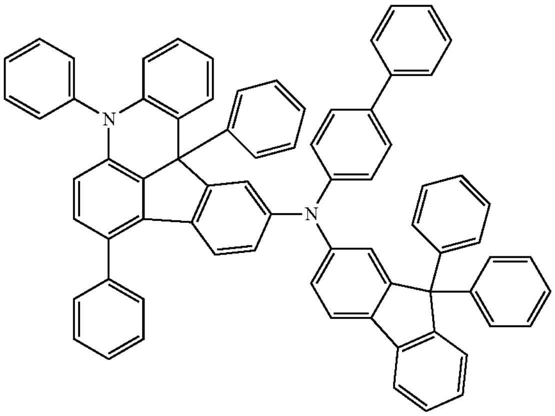
137
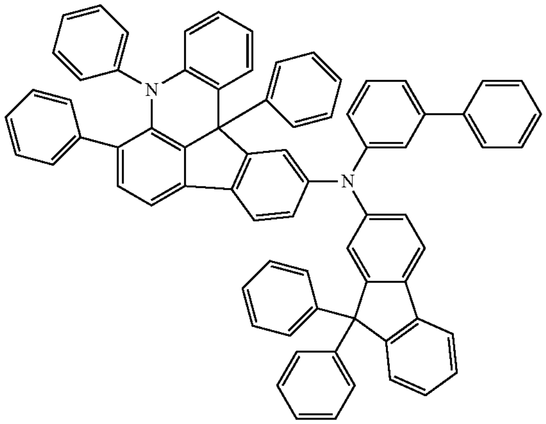
138
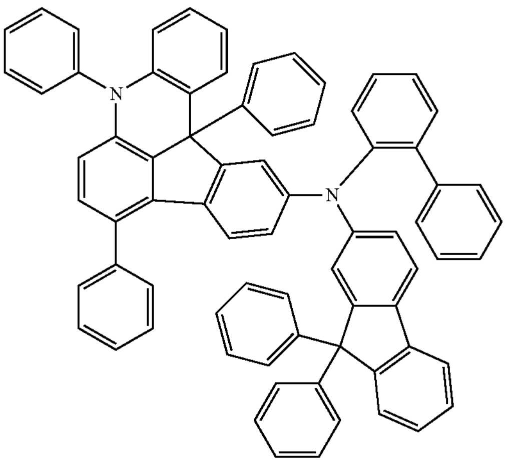
139
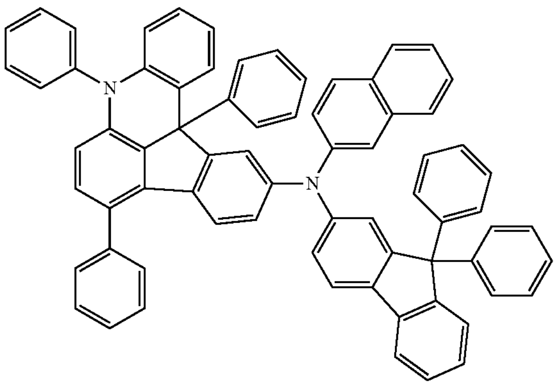

-continued
140
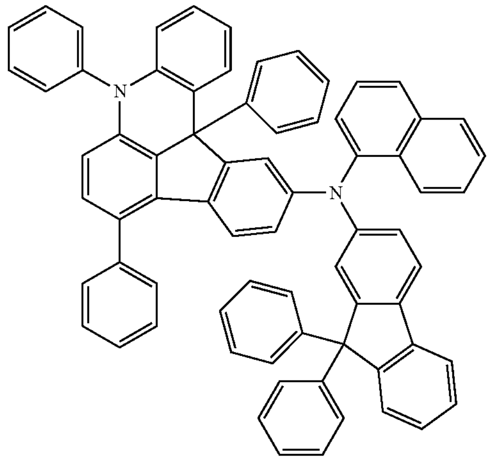
141
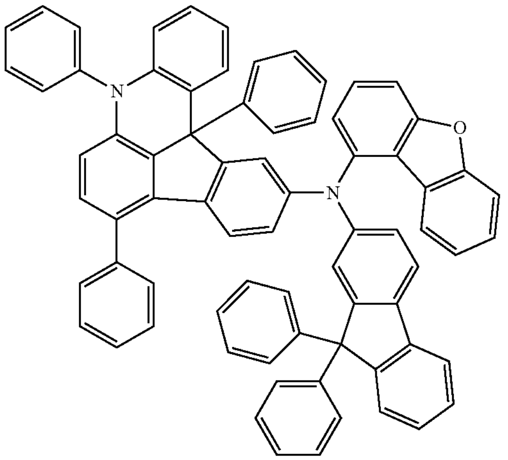
142
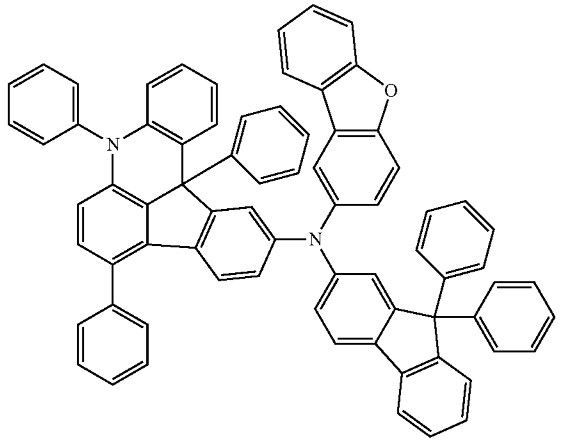
143
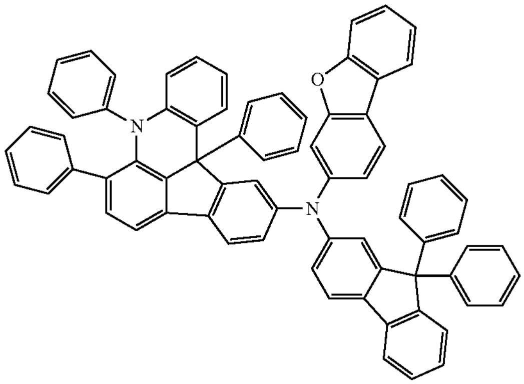
144
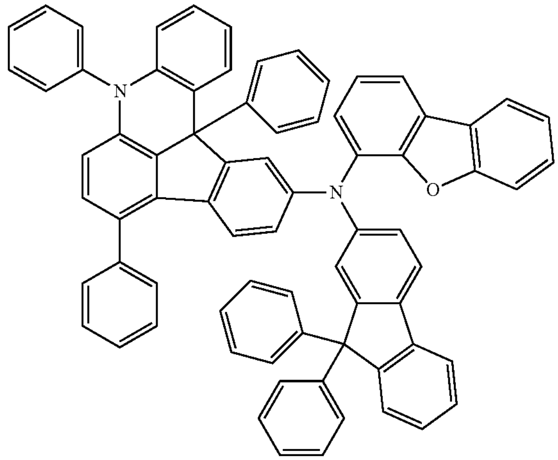
145
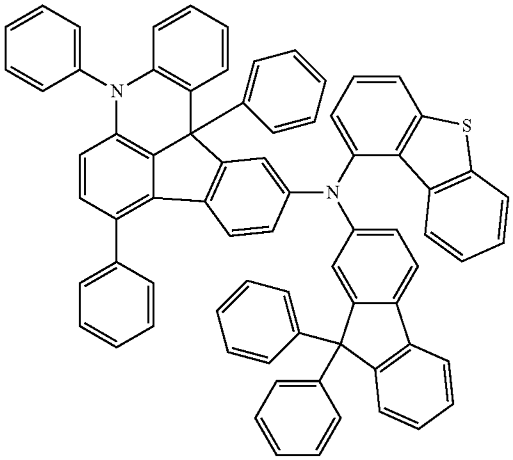

-continued
146
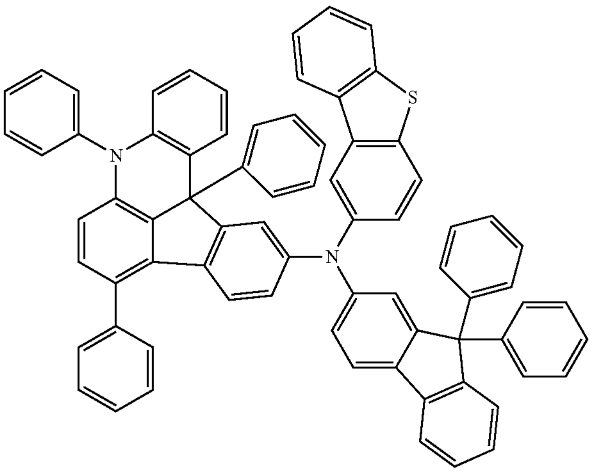
147
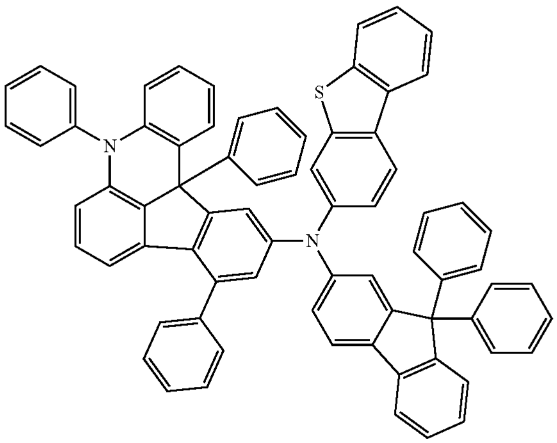
148
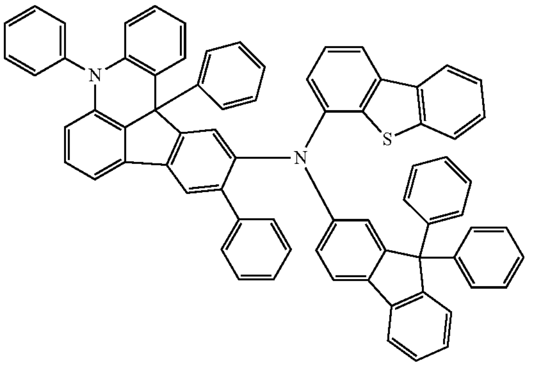
149
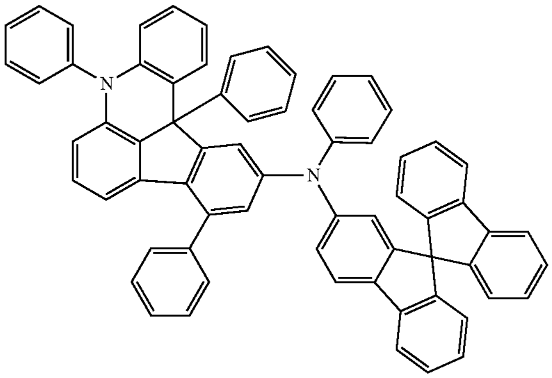
150
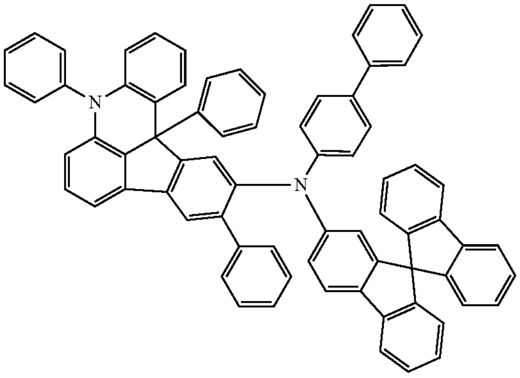
151
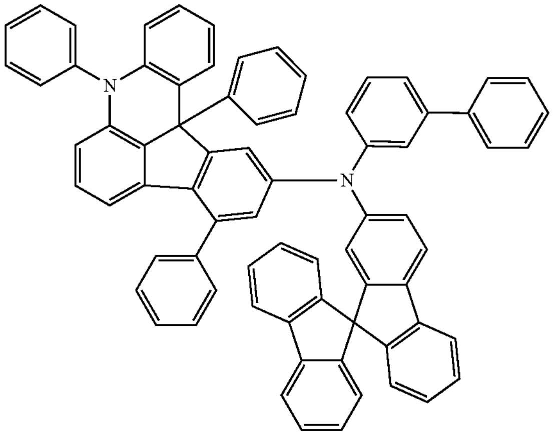

-continued
152
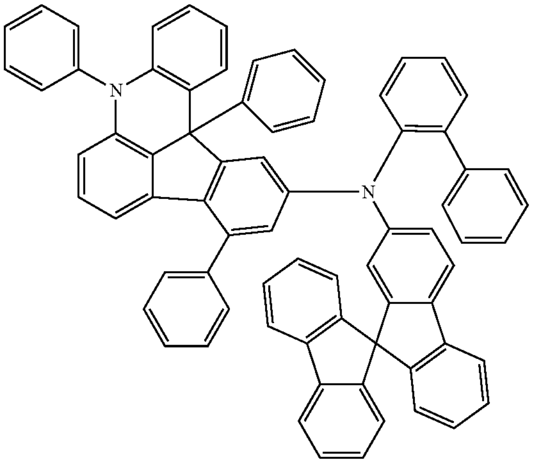
153
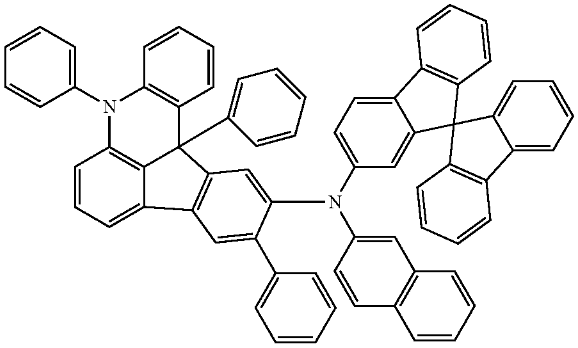
154
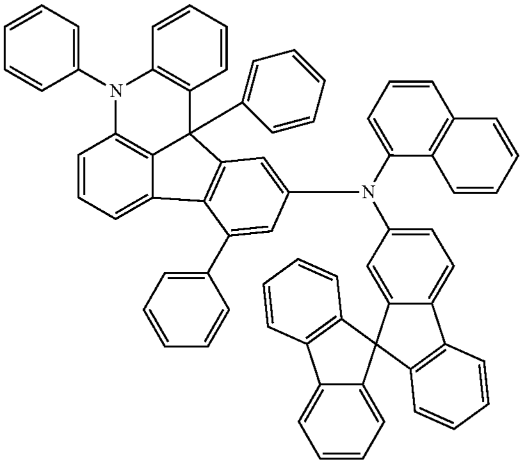
155
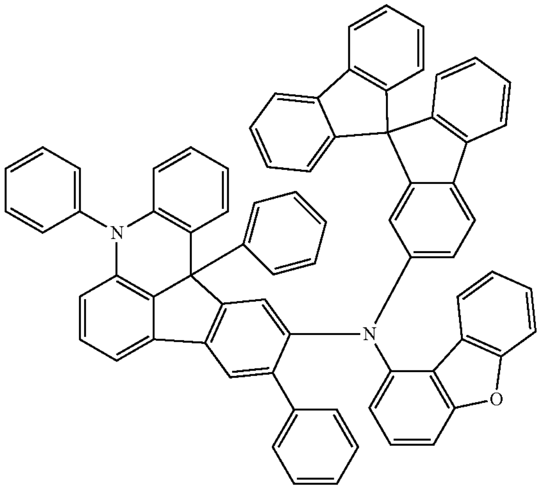
156
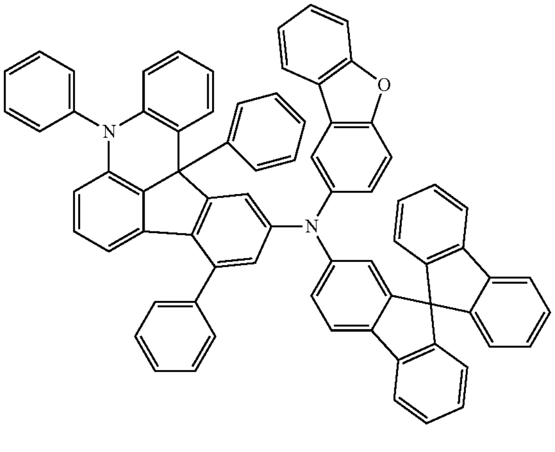
157
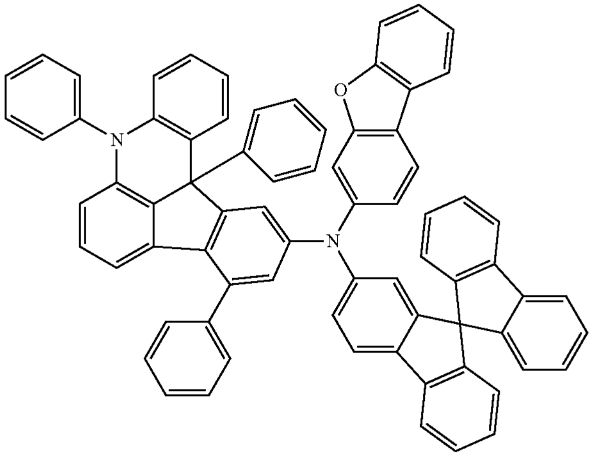

-continued
158
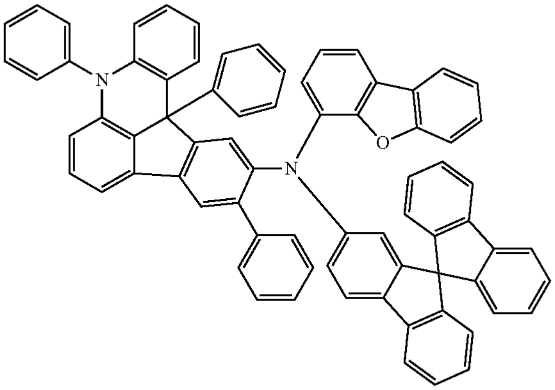
159
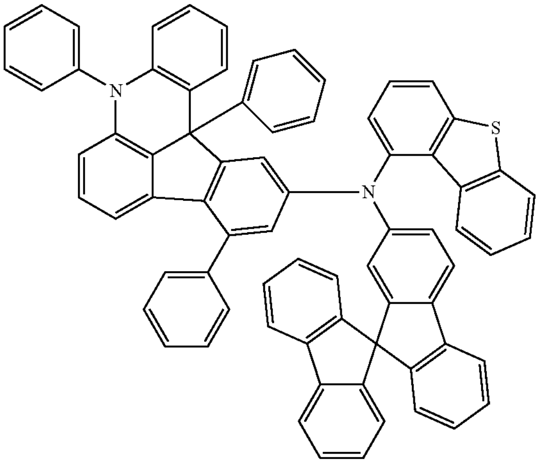
160
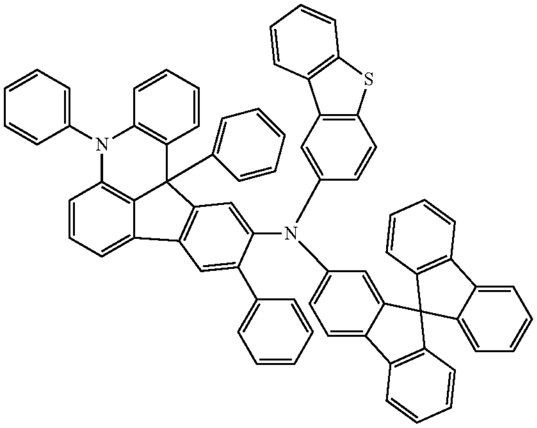
161
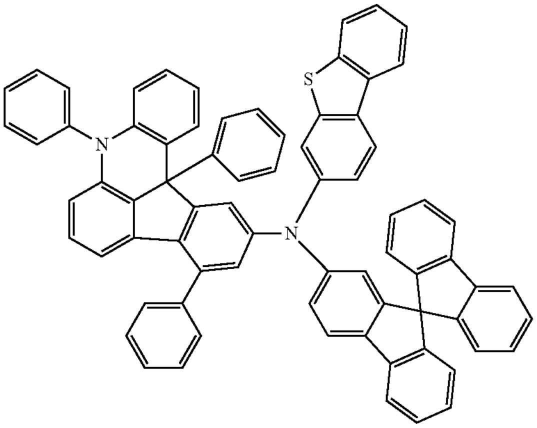
162
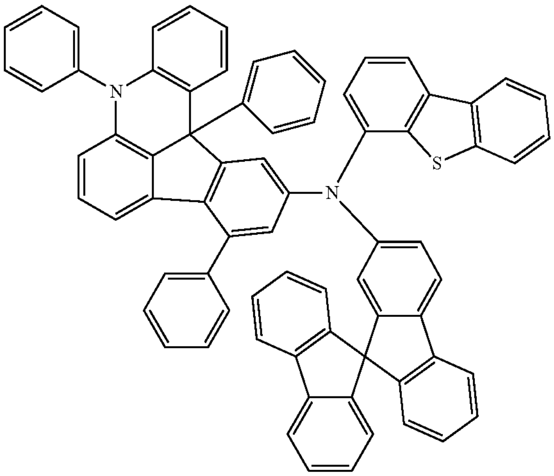
163
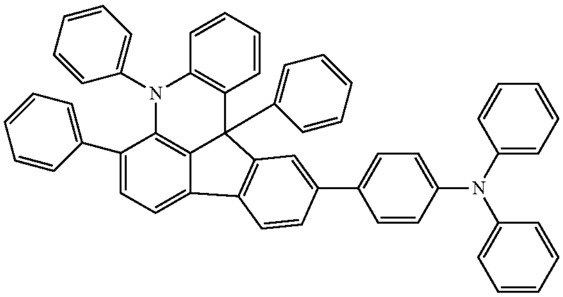

-continued
164
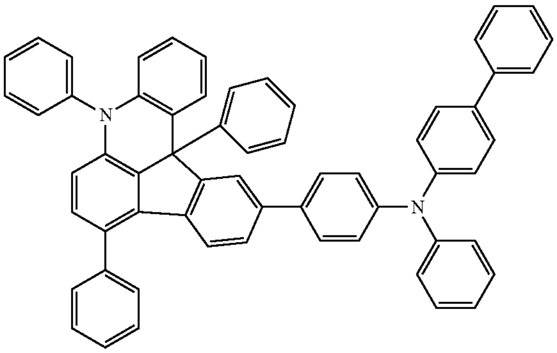
165
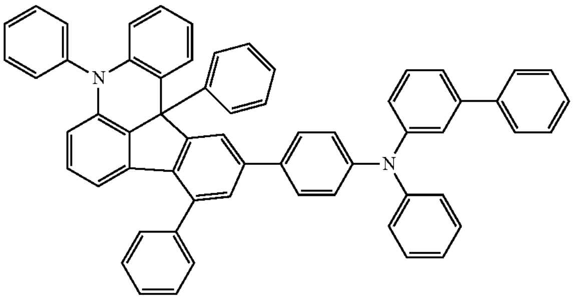
166
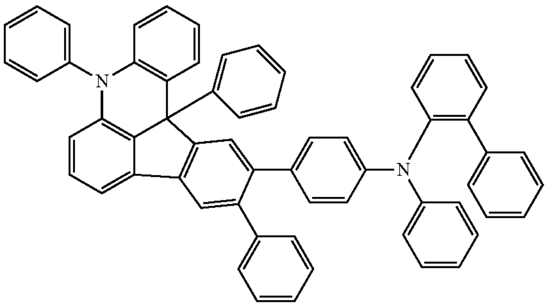
167
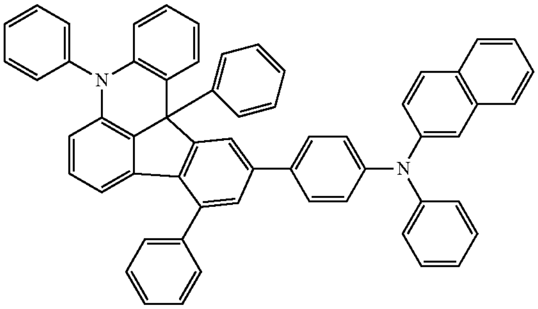
168
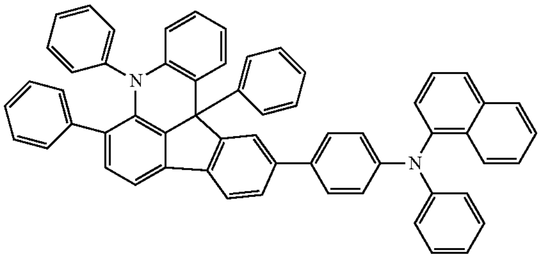
169
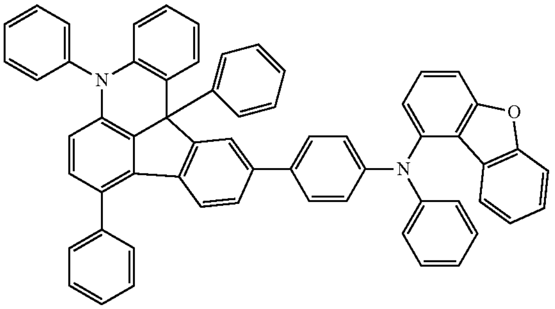
170
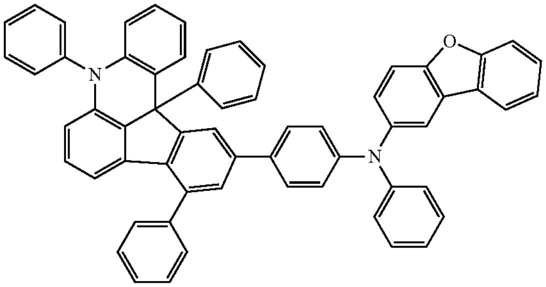
171
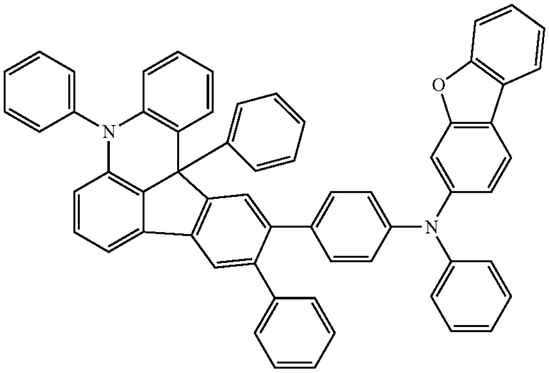

-continued
172
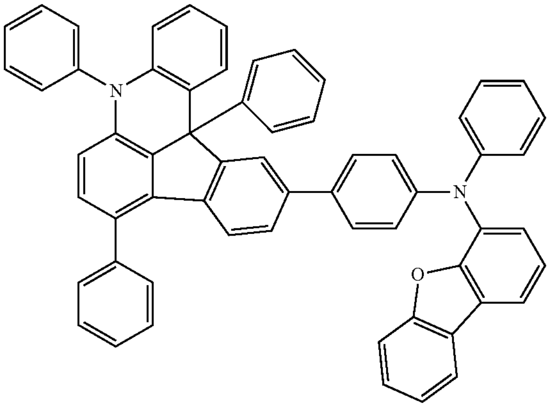
173
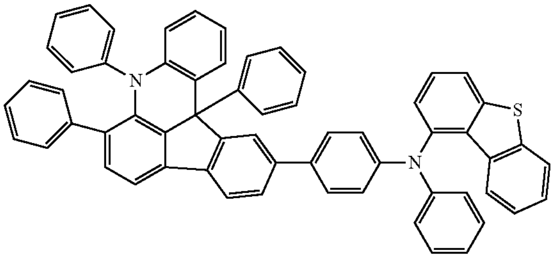
174
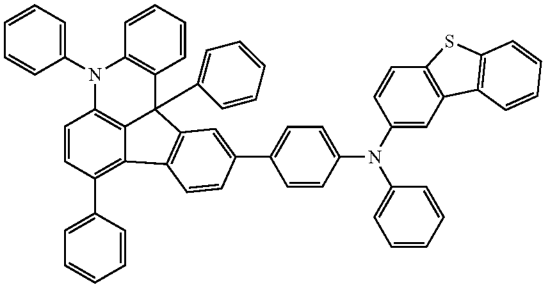
175
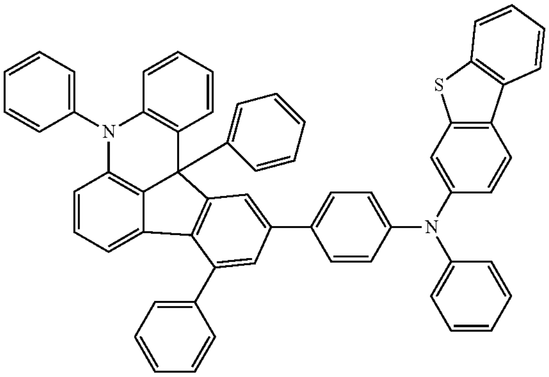
176
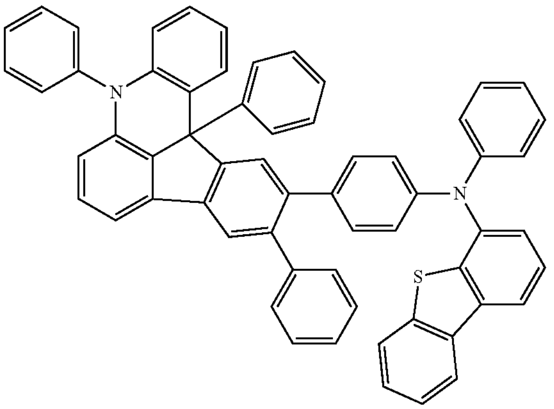
177
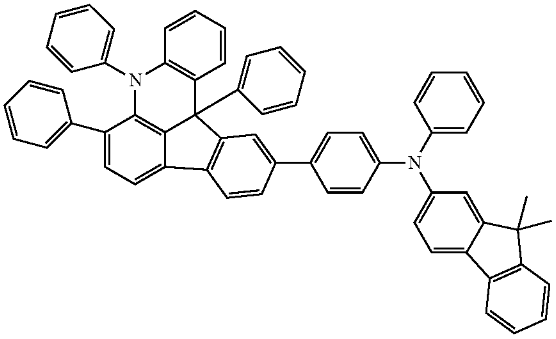
178
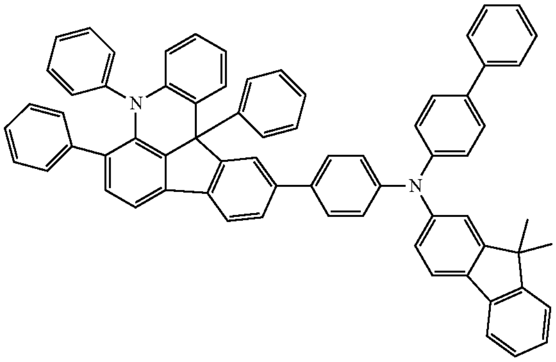
179
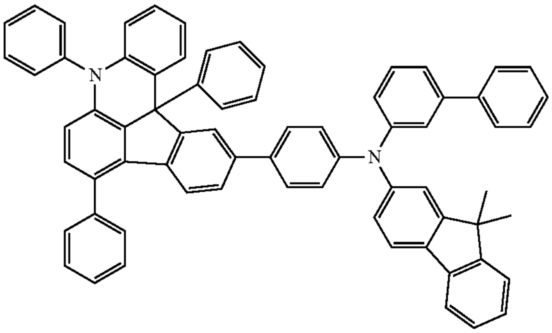

-continued
180
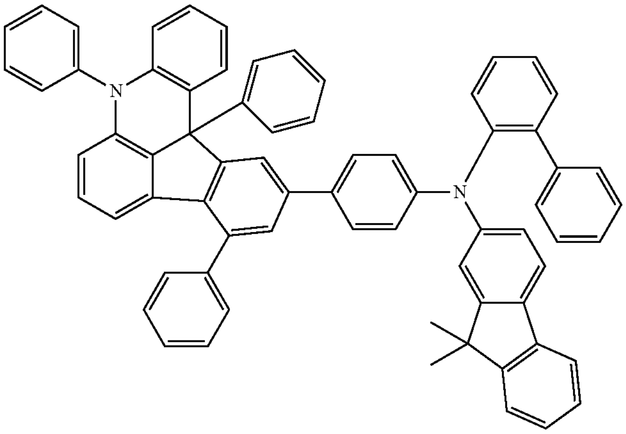
181
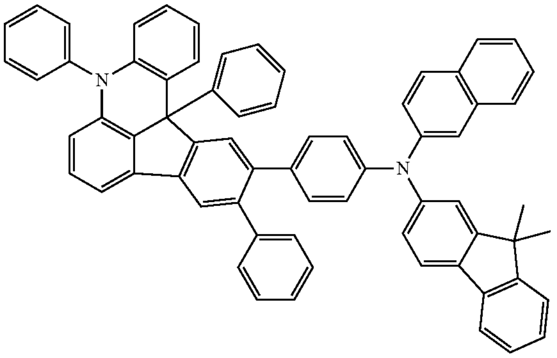
182
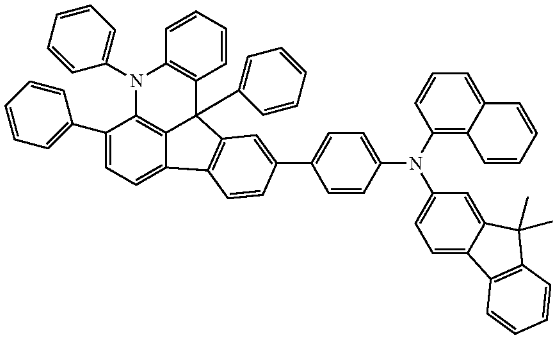
183
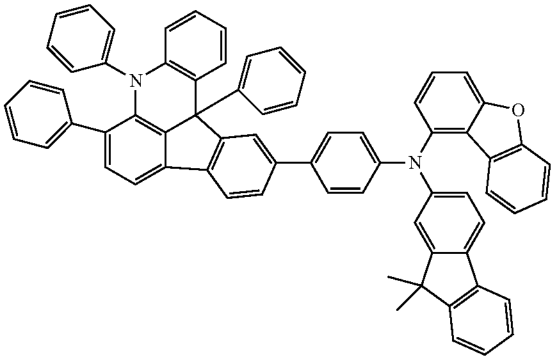
184
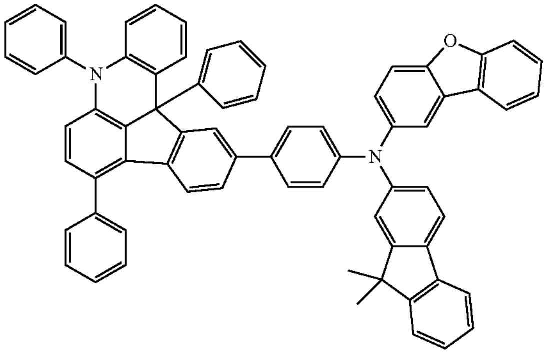
185
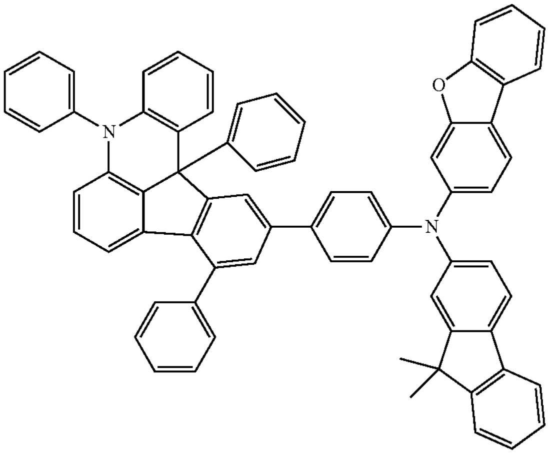
186
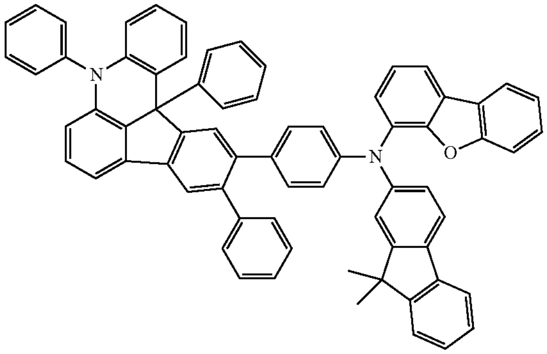

-continued
187
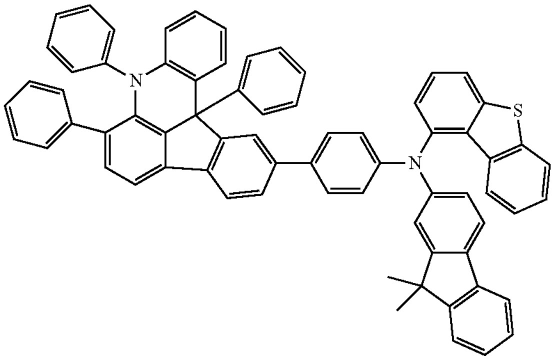
188
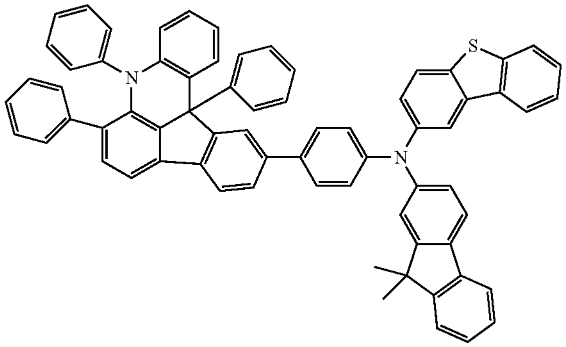
189
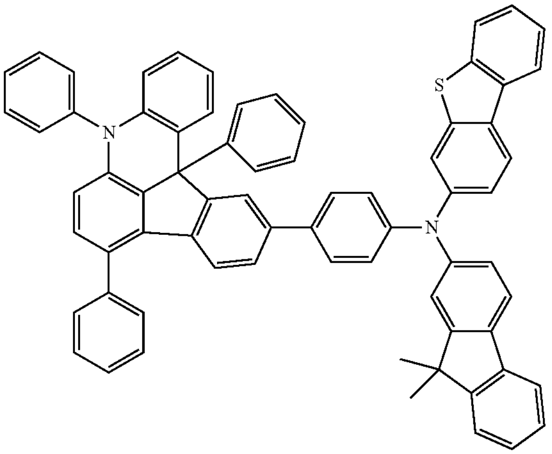
190
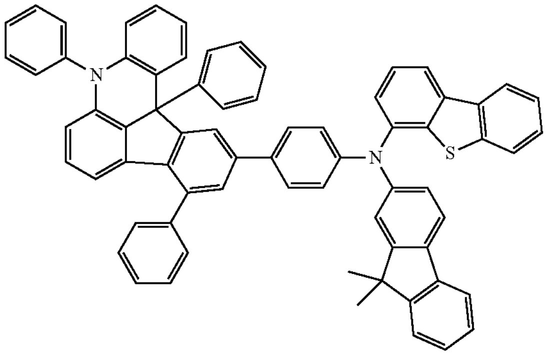
191
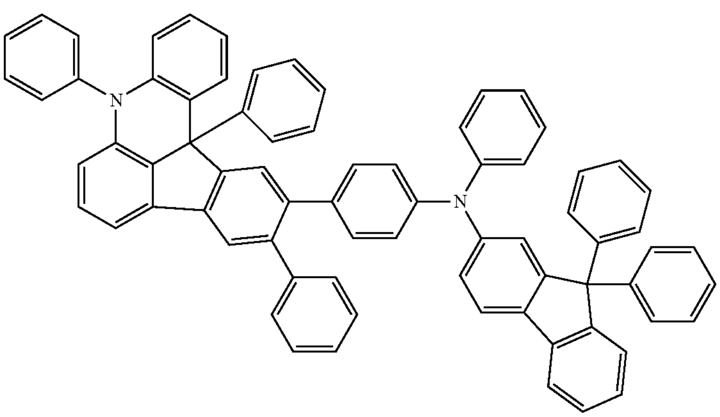

-continued
192
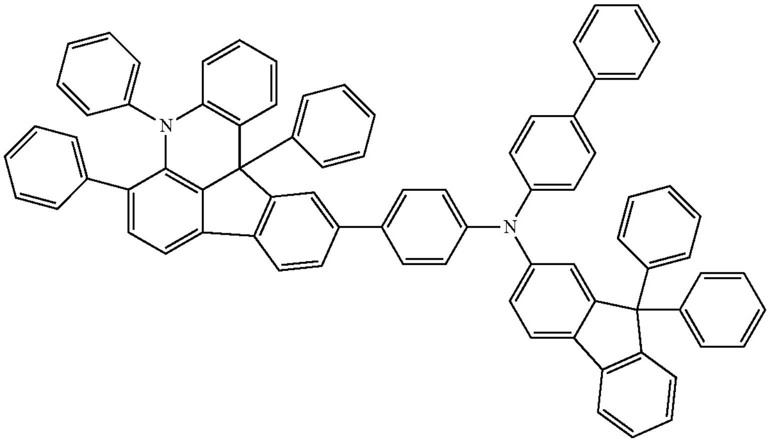
193
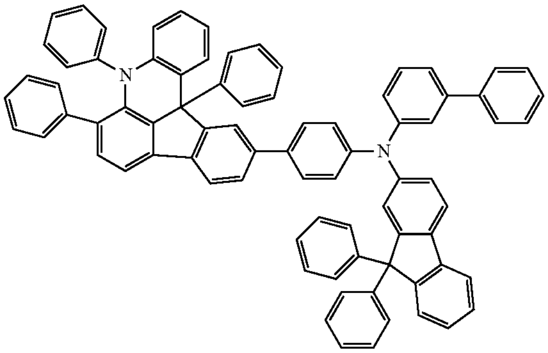
194
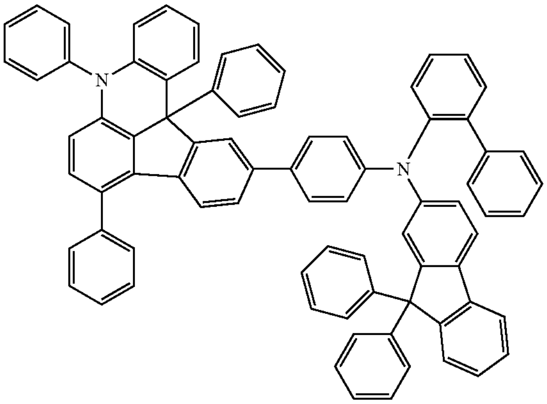
195
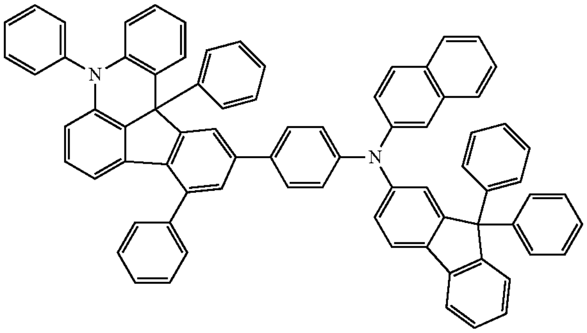
196
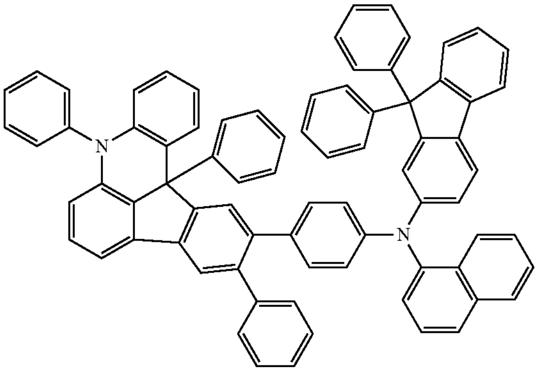

-continued
197
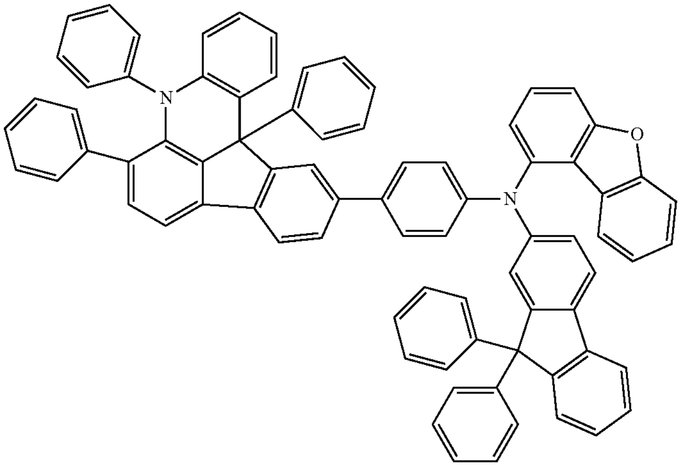
198
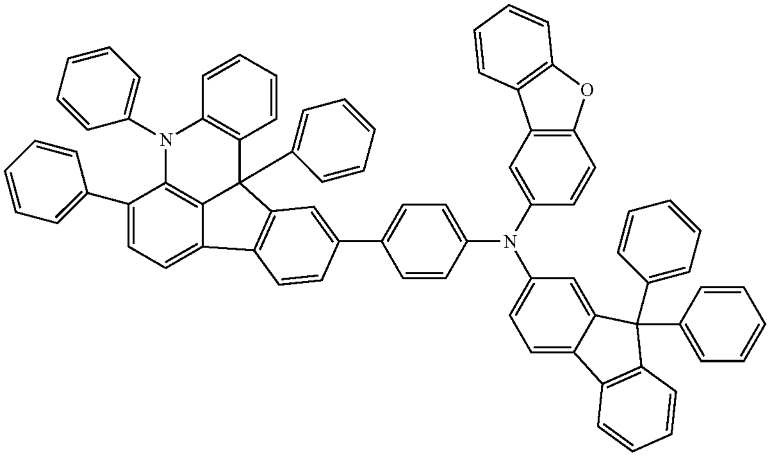
199
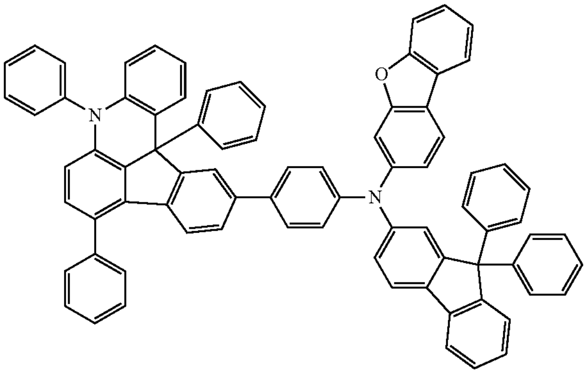
200
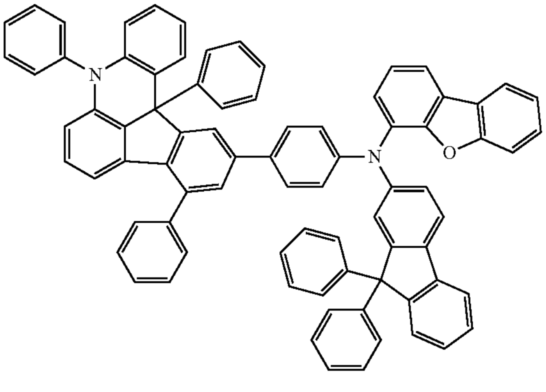

-continued
201
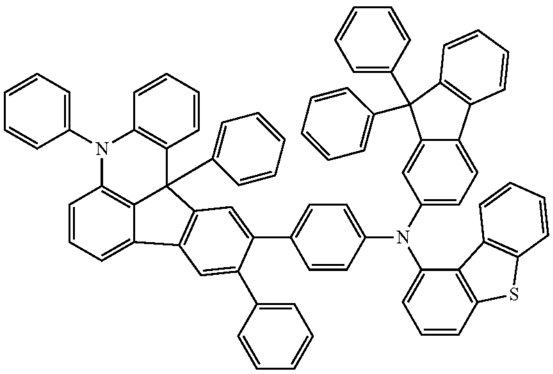
202
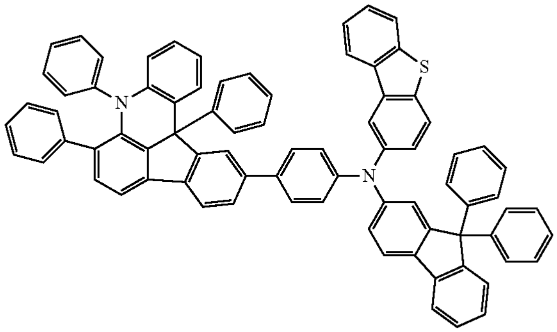
203
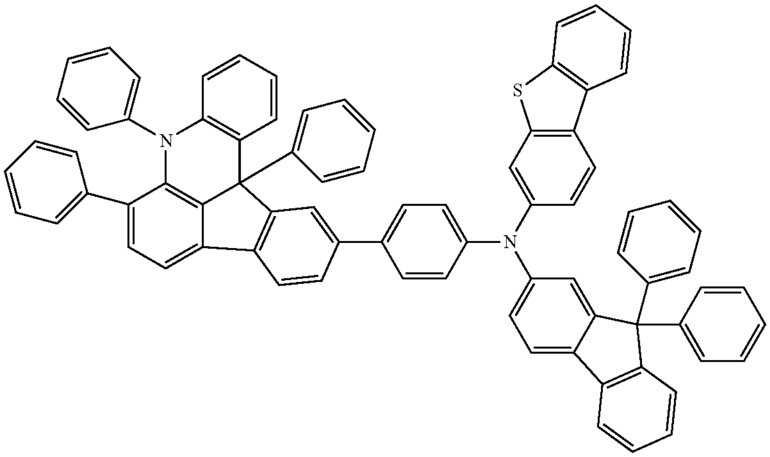
204
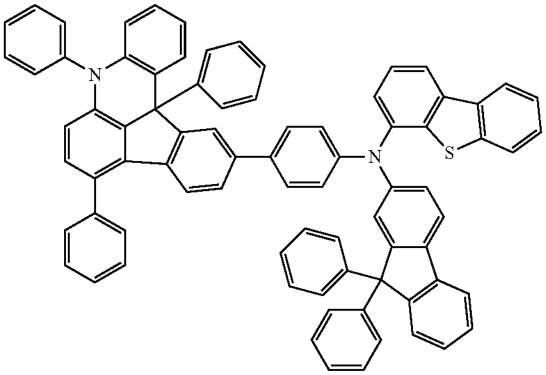
205
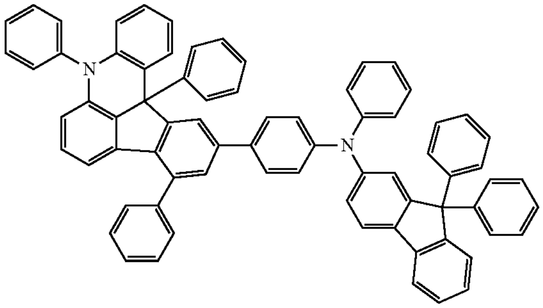
206
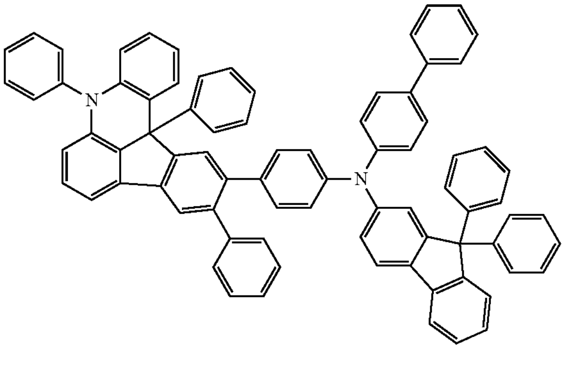
207
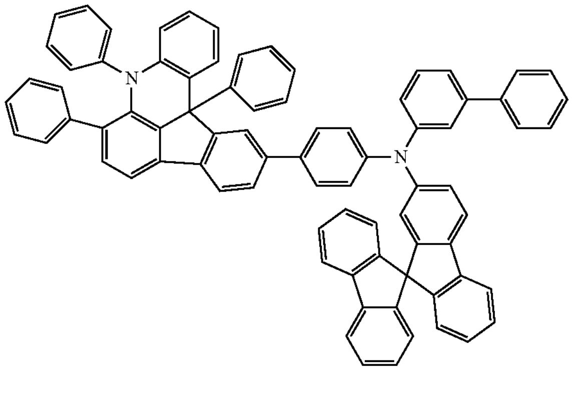

-continued
208
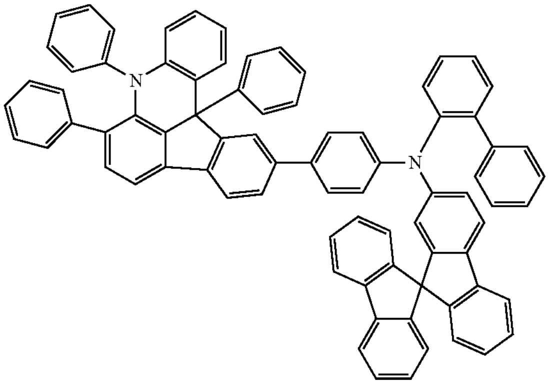
209
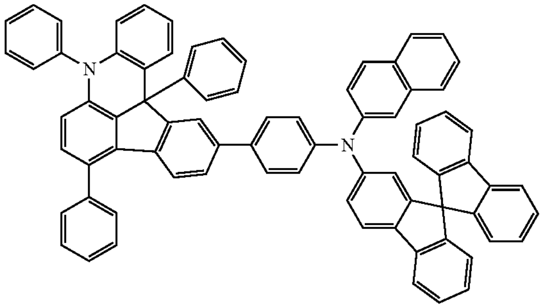
210
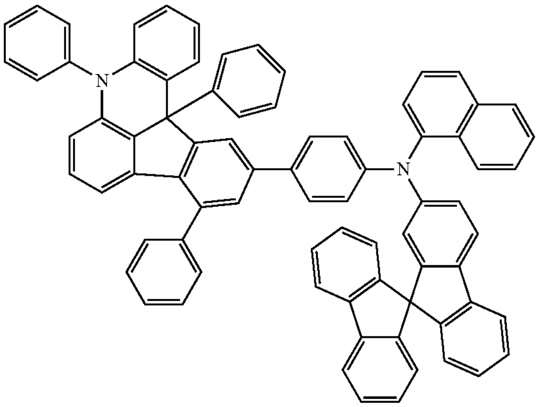
211
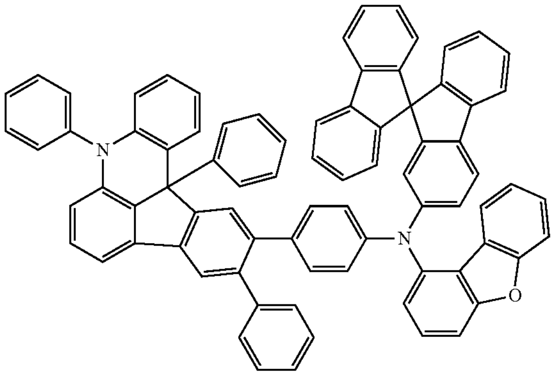
212
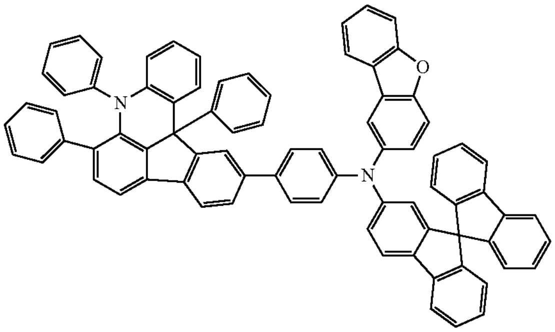
213
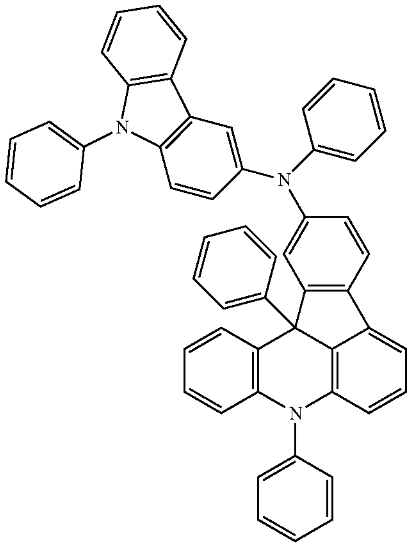

-continued
214
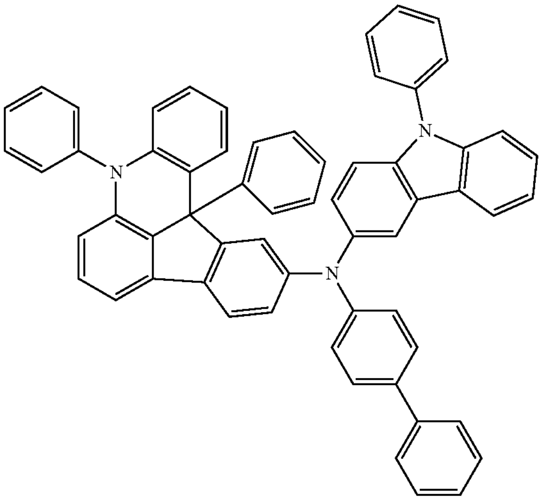
215
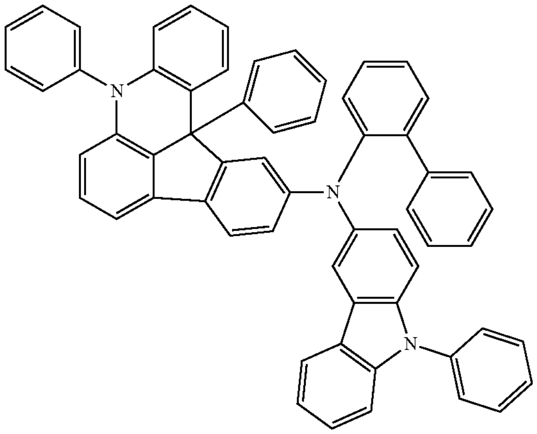
216
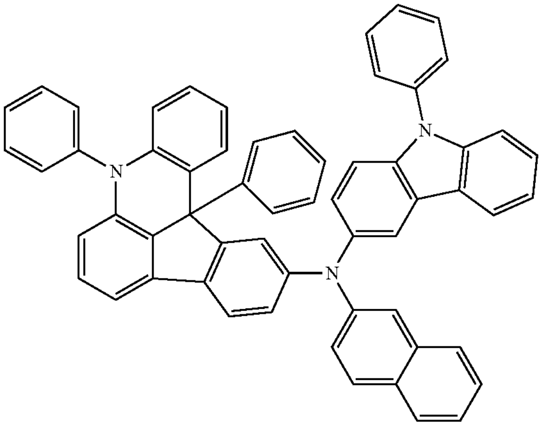
217
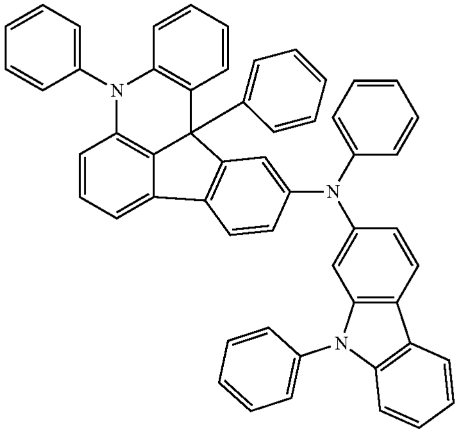
218
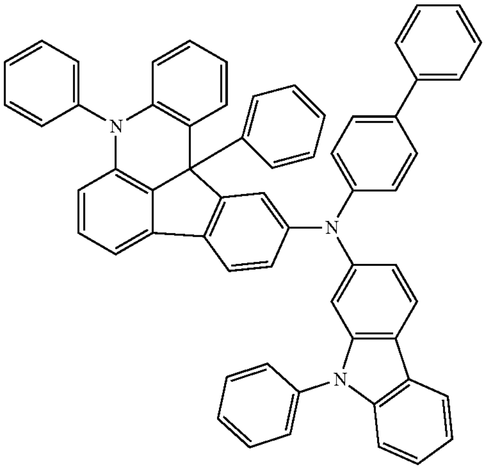
219
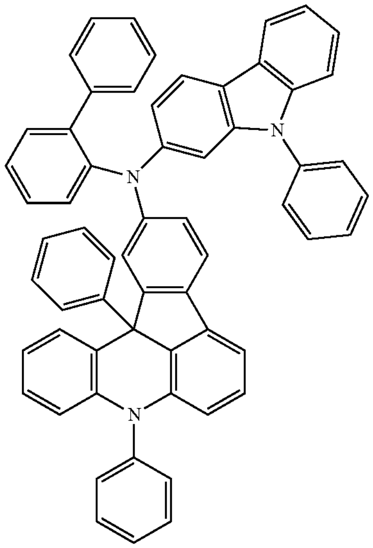

-continued
220
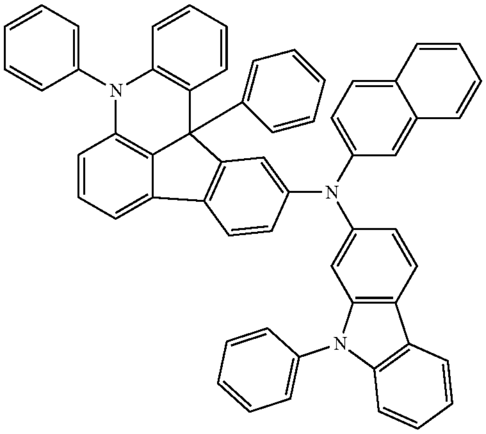
221
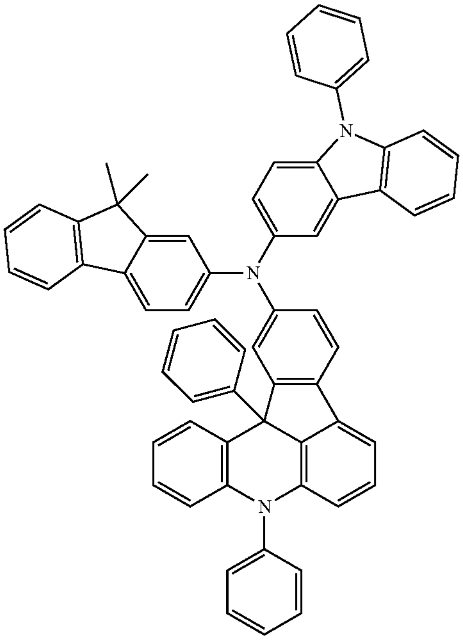
222
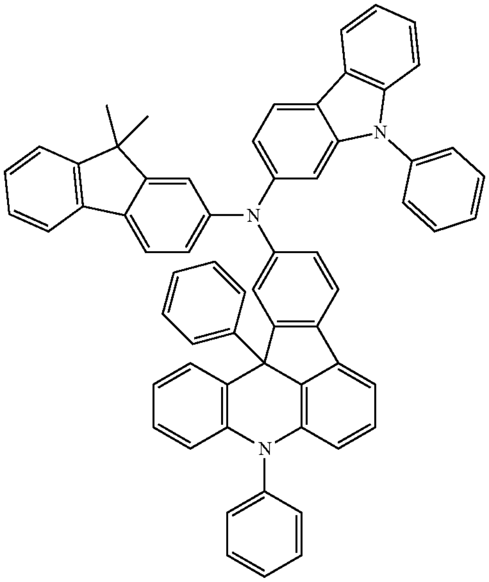
223
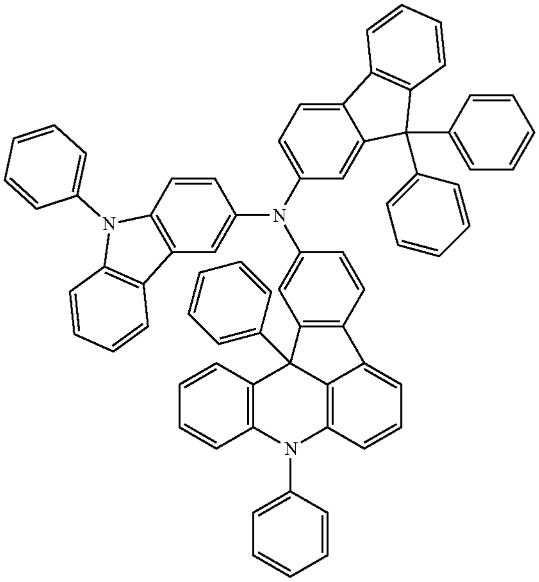

-continued
224
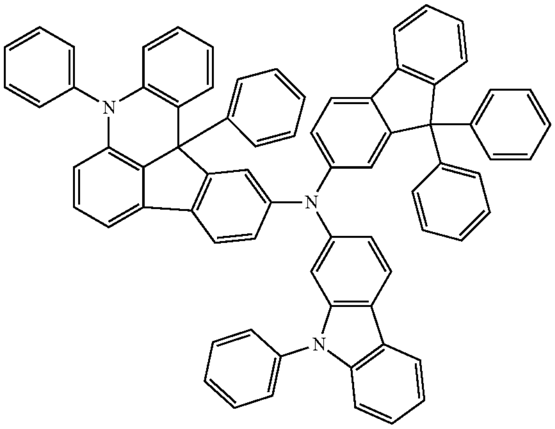
225
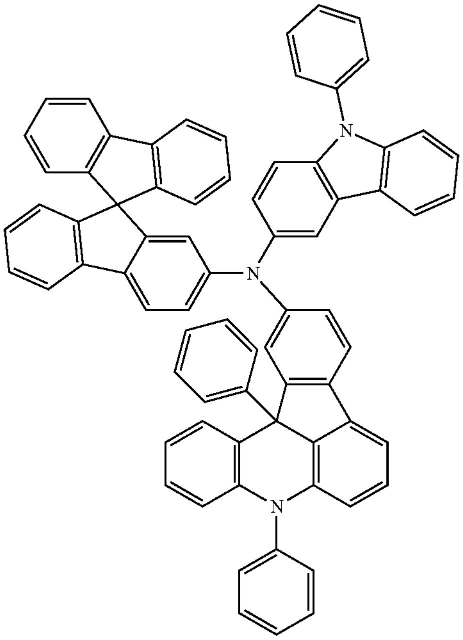
226
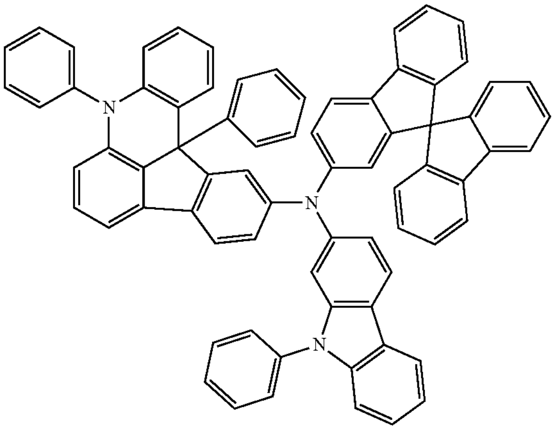
227
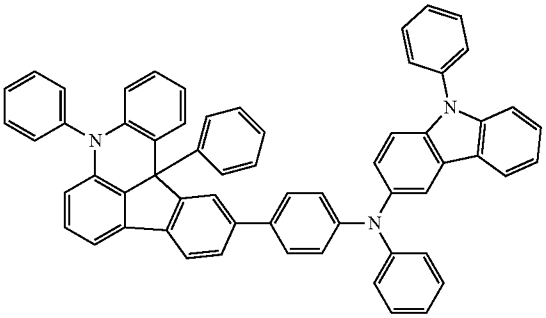
228
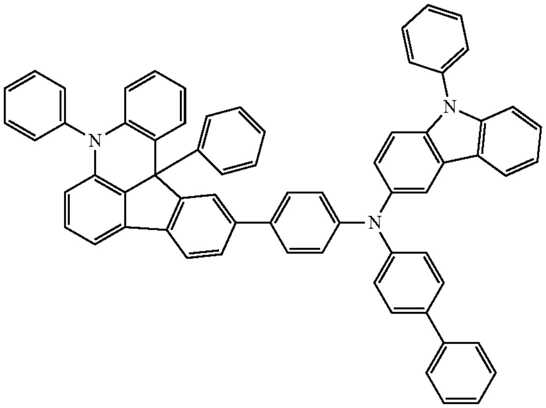
229
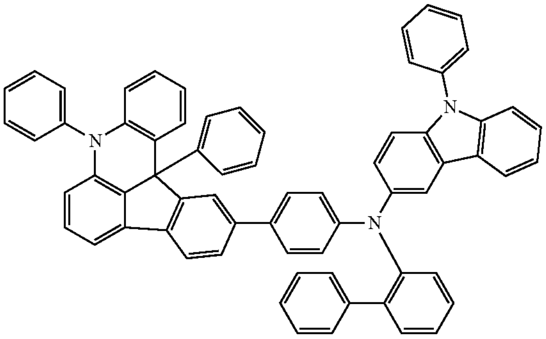

-continued
230
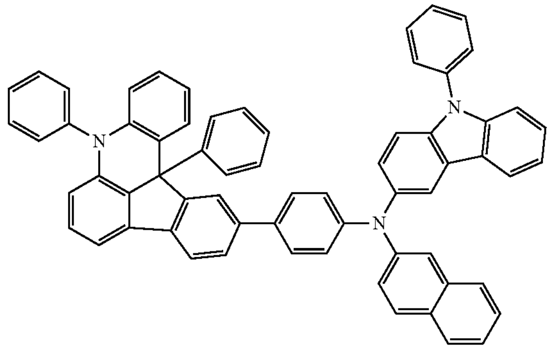
231
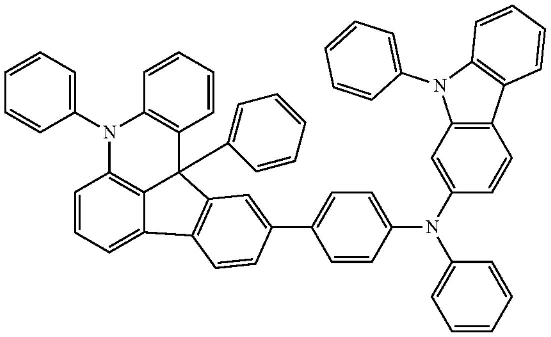
232
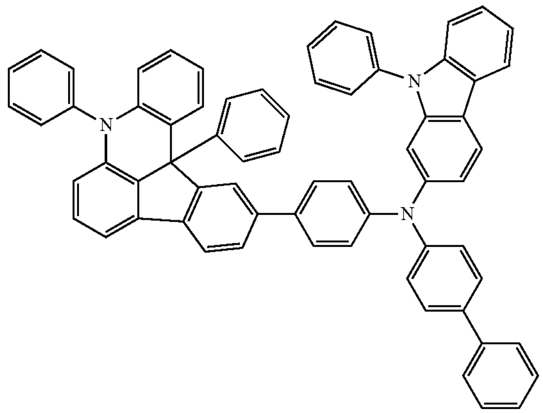
233
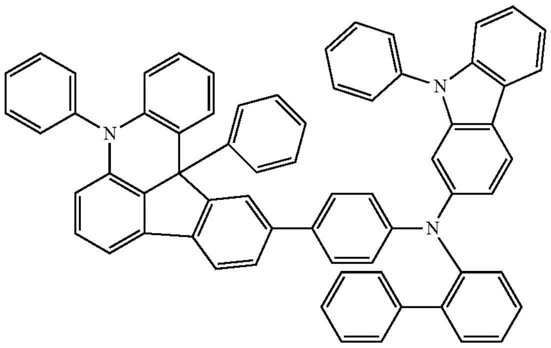
234
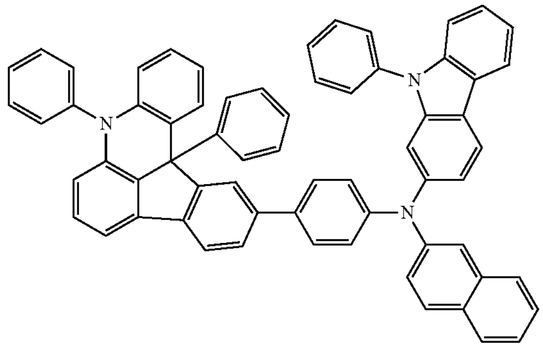
235
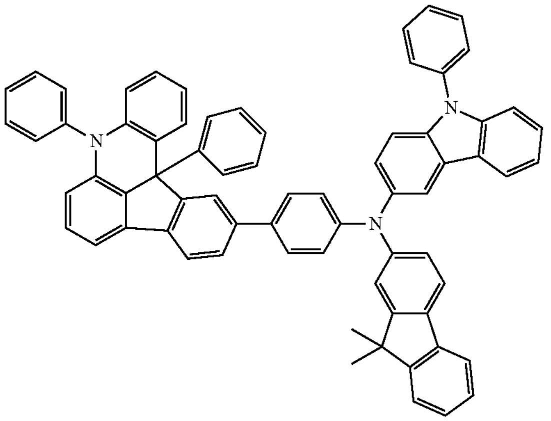
236
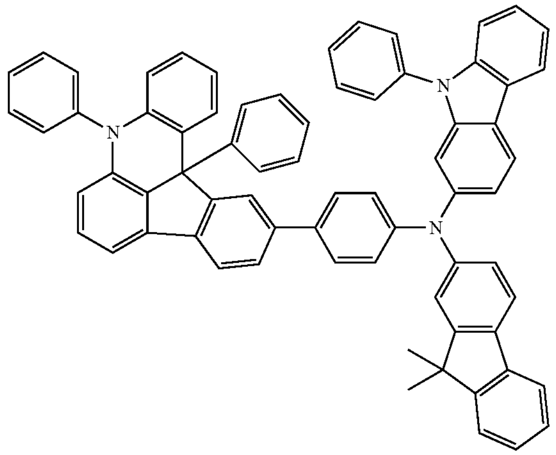
237
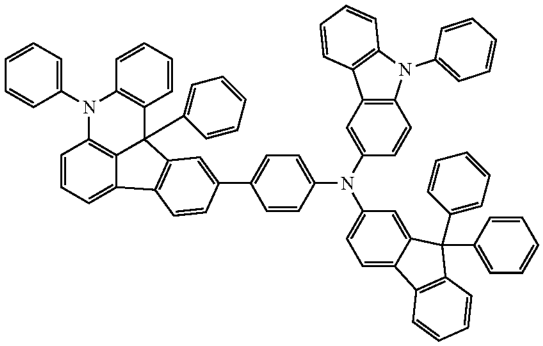

-continued
238
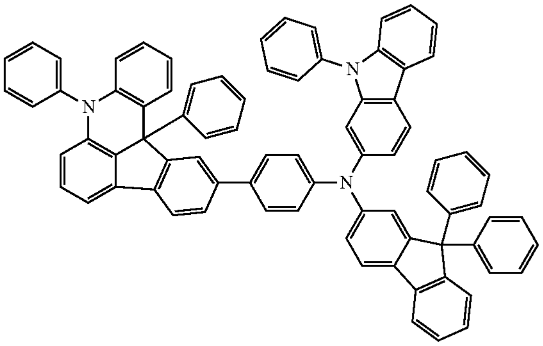
239
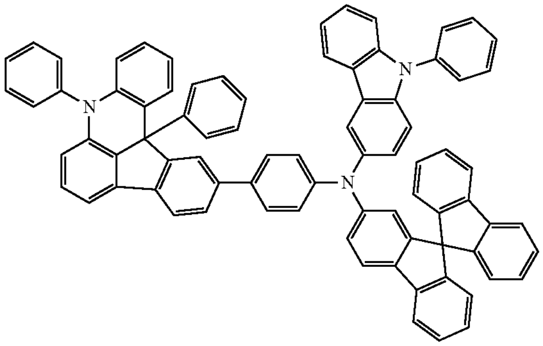
240
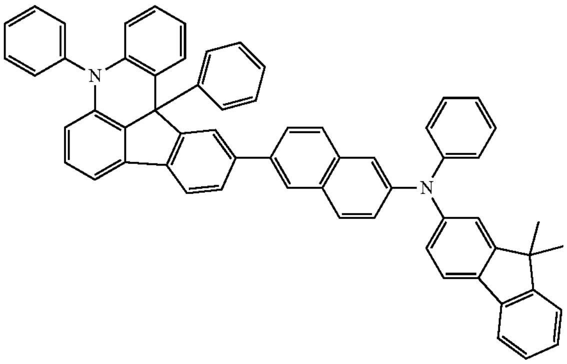
241
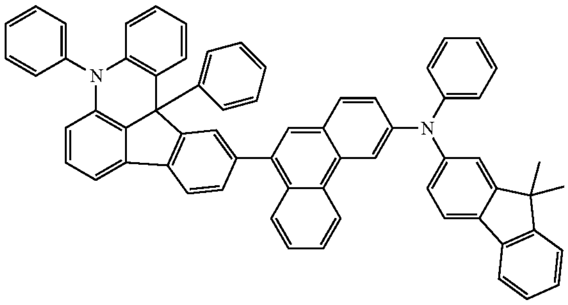
242
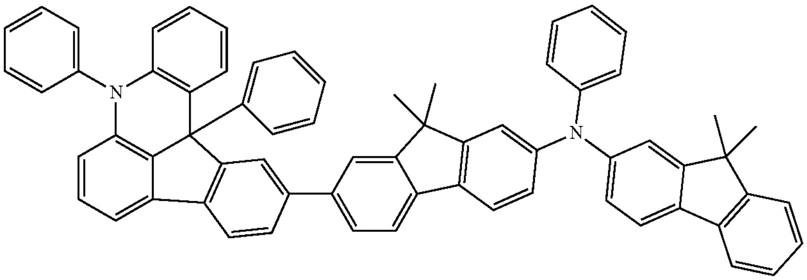
243
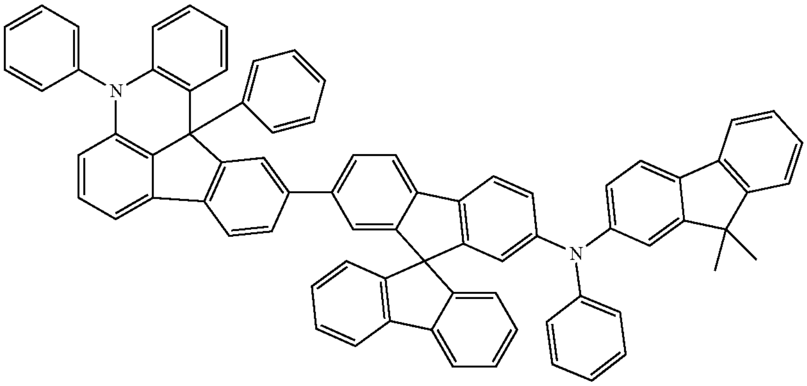

-continued

244

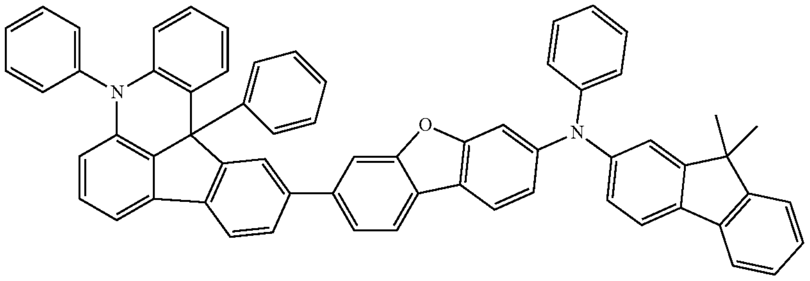

245

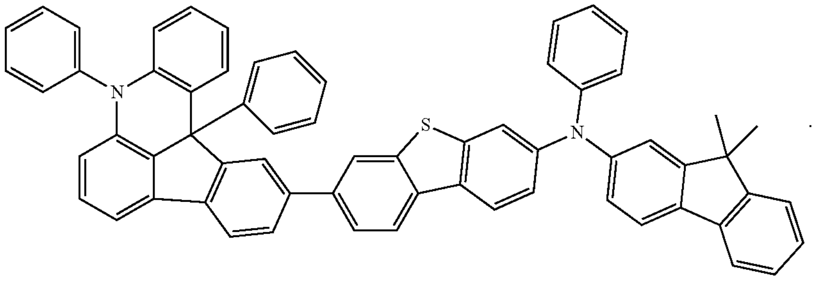

The amine compound of an embodiment may have an amine group is bonded to a pentacyclic fused ring containing an acridine moiety. The amine compound may include a structure represented by Formula Z1 below:

Formula Z1

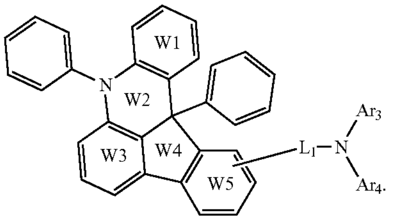

In Formula Z1, W1 to W5 are expressed to refer to ring groups that form the pentacyclic fused ring. In Formula Z1, the same as described with respect to Formula 1 may be applied to $L_1$, $Ar_3$, and $Ar_4$. In Formula Z1, a fused ring composed of ring groups of W1 to W3 may correspond to the acridine moiety.

The amine compound of an embodiment may include the pentacyclic fused ring containing a nitrogen atom as a ring-forming atom, thereby exhibiting a high glass-transition temperature (Tg). The amine compound may have different kinds of $Ar_3$ and $Ar_4$, which are substituents of the amine group, thereby changing a highest occupied molecular orbital (HOMO) energy level of the amine compound. Accordingly, the amine compound may exhibit an improvement in hole transport properties.

The light emitting element ED may include the amine compound of an embodiment in the hole transport region HTR. The light emitting element ED including the amine compound of an embodiment may have an improvement in exciton generation efficiency in the emission layer EML. Therefore, the light emitting element ED including the amine compound of an embodiment may exhibit characteristics in which the driving voltage is reduced, and the brightness and efficiency are improved. In addition, the light emitting element including the amine compound of an embodiment may exhibit a long service life characteristic.

Referring to FIGS. 3 to 6 again, the first electrode EL1 has conductivity (e.g., electrical conductivity). The first electrode EL1 may be formed of a metal material, a metal alloy, and/or a conductive compound. The first electrode EL1 may be an anode or a cathode. However, embodiments of the present disclosure are not limited thereto. In addition, the first electrode EL1 may be a pixel electrode. The first electrode EL1 may be a transmissive electrode, a transflective electrode, or a reflective electrode. The first electrode EL1 may include at least one selected from among Ag, Mg, Cu, Al, Pt, Pd, Au, Ni, Nd, Ir, Cr, Li, Ca, LiF, Mo, Ti, W, In, Sn, Zn, a compound of two or more thereof, a mixture of two or more thereof, and an oxide thereof.

When the first electrode EL1 is a transmissive electrode, the first electrode EL1 may include a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca (a stacked structure of LiF and Ca), LiF/Al (a stacked structure of LiF and Al), Mo, Ti, W, or a compound or mixture thereof (e.g., a mixture of Ag and Mg). In some embodiments, the first electrode EL1 may have a multilayer structure including a reflective film or a transflective film formed of the above-described materials, and a transparent conductive film formed of ITO, IZO, ZnO, ITZO, etc. For example, the first electrode EL1 may have a three-layer structure of ITO/Ag/ITO, but embodiments of the present disclosure are not limited thereto. In some embodiments, the first electrode EL1 may include the above-described metal materials, combinations of at least two metal materials of the above-described metal materials, oxides of the above-described metal materials, and/or the like. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. The thickness of the hole transport region HTR may be, for example, from about 50 Å to about 15,000 Å.

The hole transport region HTR may include at least one of a hole injection layer HIL, a hole transport layer HTL, a buffer layer or an emission-auxiliary layer, or an electron blocking layer EBL. As described above, the hole transport region HTR may include the amine compound of an embodiment. At least one of the hole injection layer HIL, the hole transport layer HTL, or the electron blocking layer EBL may include the amine compound of an embodiment.

The hole transport region HTR may be formed using various suitable methods such as a vacuum deposition method, a spin coating method, a cast method, a Langmuir-Blodgett (LB) method, an inkjet printing method, a laser printing method, and/or a laser induced thermal imaging (LITI) method. The hole transport region HTR may have a single layer formed of a single material, a single layer formed of a plurality of different materials, or a multilayer structure including a plurality of layers formed of a plurality of different materials.

For example, the hole transport region HTR may have a single layer structure of the hole injection layer HIL or the hole transport layer HTL, or may have a single layer structure formed of a hole injection material and a hole transport material. In addition, the hole transport region HTR may have a single layer structure formed of a plurality of different materials, or a structure in which a hole injection layer HIL/hole transport layer HTL, a hole injection layer HIL/hole transport layer HTL/buffer layer, a hole injection layer HIL/buffer layer, a hole transport layer HTL/buffer layer, or a hole injection layer HIL/hole transport layer HTL/electron blocking layer EBL are stacked in order from the first electrode EL1, but embodiments of the present disclosure are not limited thereto.

The hole transport region HTR may further include compounds which will be further described below. The hole transport region HTR may include a compound represented by Formula H-1 below:

Formula H-1

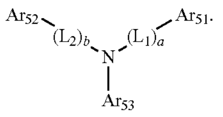

In Formula H-1 above, $L_1$ and $L_2$ may be each independently a direct linkage, a substituted or unsubstituted arylene group having 6 to 30 ring-forming carbon atoms, or a substituted or unsubstituted heteroarylene group having 2 to 30 ring-forming carbon atoms. In Formula H-1, a and b may be each independently an integer of 0 to 10. When a or b is an integer of 2 or greater, a plurality of $L_1$'s and $L_2$'s may be each independently a substituted or unsubstituted arylene group having 6 to 30 ring-forming carbon atoms, or a substituted or unsubstituted heteroarylene group having 2 to 30 ring-forming carbon atoms.

In Formula H-1, $Ar_{51}$ and $Ar_{52}$ may be each independently a substituted or unsubstituted aryl group having 6 to 30 ring-forming carbon atoms, or a substituted or unsubstituted heteroaryl group having 2 to 30 ring-forming carbon atoms. In addition, in Formula H-1, $Ar_{53}$ may be a substituted or unsubstituted aryl group having 6 to 30 ring-forming carbon atoms.

The compound represented by Formula H-1 may be a monoamine compound. In some embodiments, the compound represented by Formula H-1 may be a diamine compound in which at least one among $Ar_{51}$ to $Ar_{53}$ includes the amine group as a substituent. In addition, the compound represented by Formula H-1 may be a carbazole-based compound containing a substituted or unsubstituted carbazole group in at least one of $Ar_{51}$ or $Ar_{52}$, or a fluorene-based compound containing a substituted or unsubstituted fluorene group in at least one of $Ar_{51}$ or $Ar_{52}$.

The compound represented by Formula H-1 may be represented by any one selected from among the compounds of Compound Group H below. However, the compounds listed in Compound Group H below are examples, and the compounds represented by Formula H-1 are not limited to those represented by Compound Group H below:

Compound Group H

H-1-1

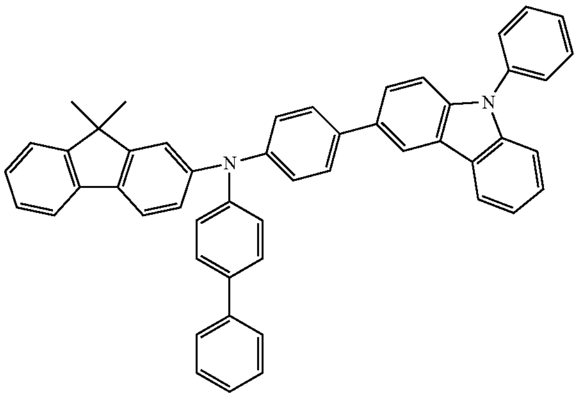

H-1-2

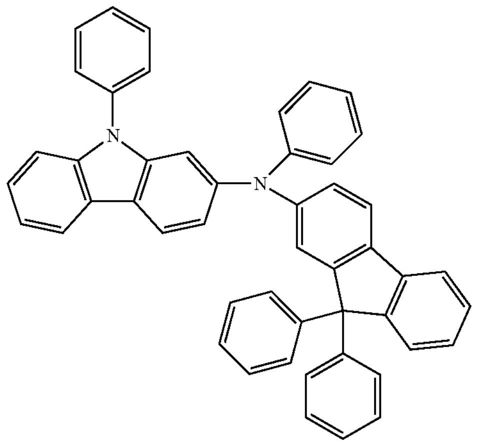

H-1-3
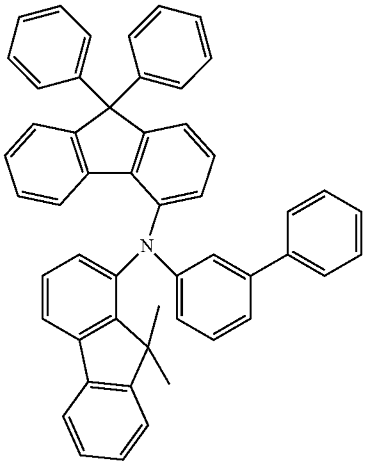
H-1-4
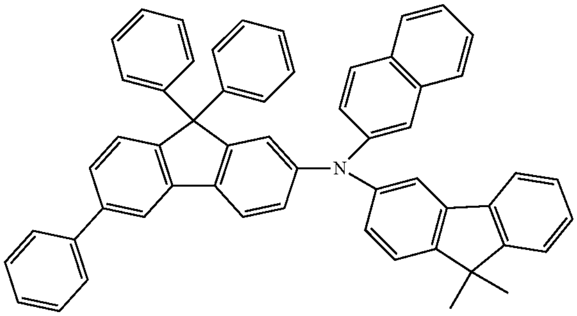
H-1-5
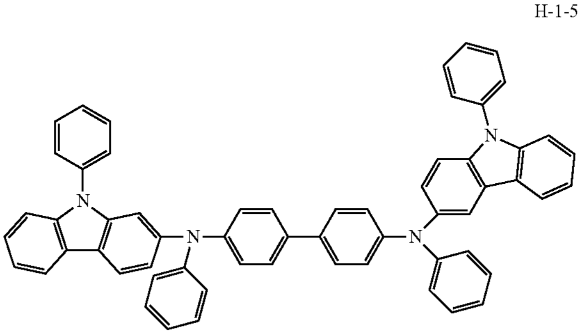
H-1-6
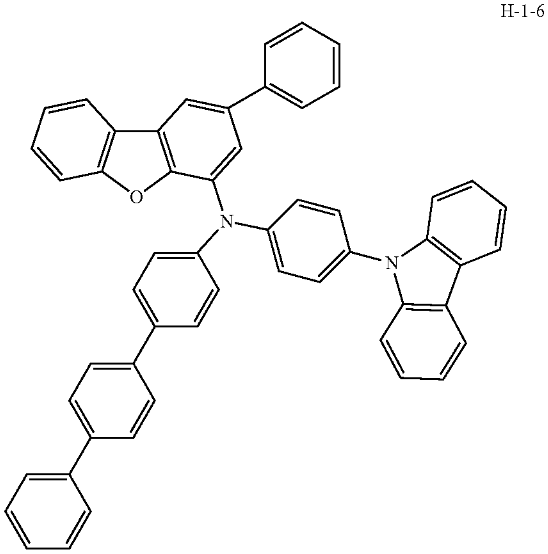
H-1-7
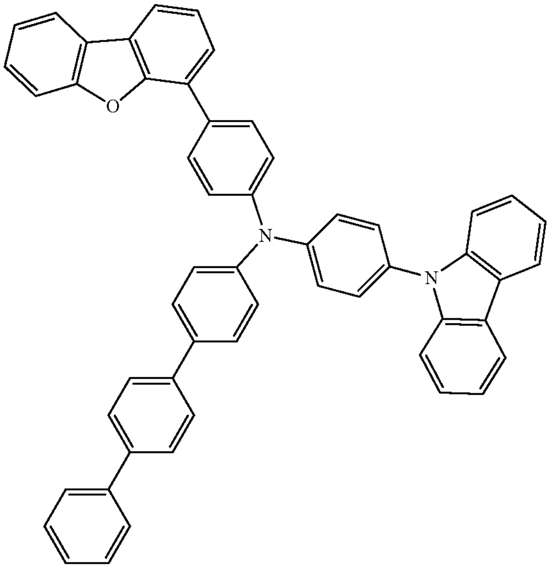
H-1-8
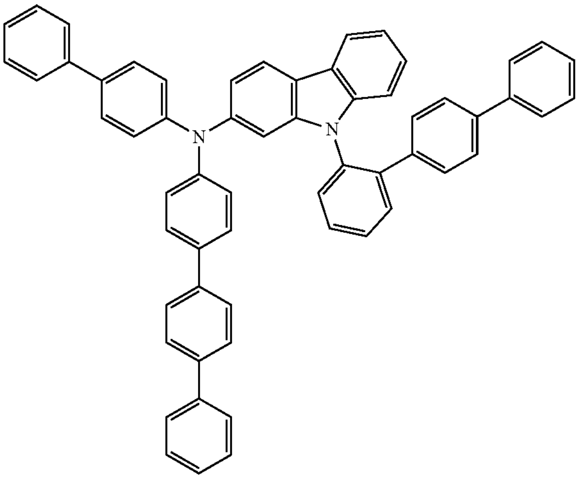

H-1-9
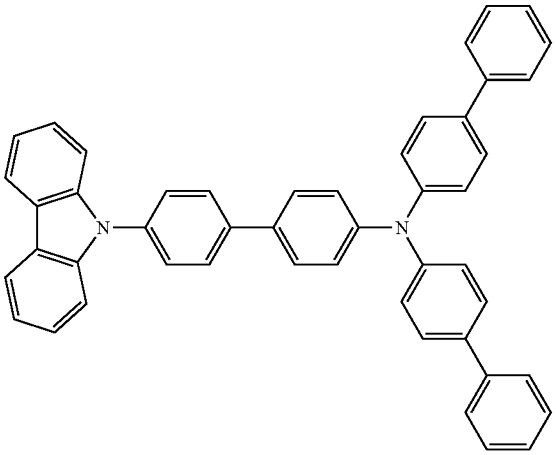
H-1-10
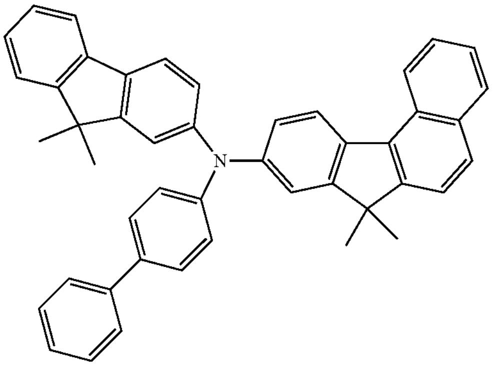
H-1-11
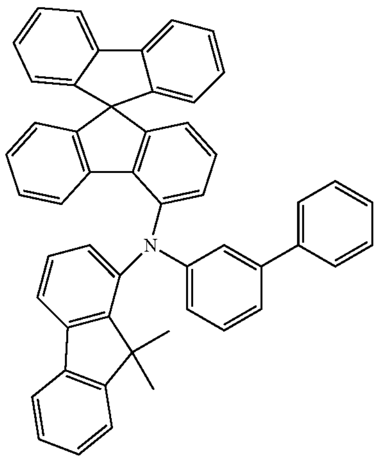
H-1-12
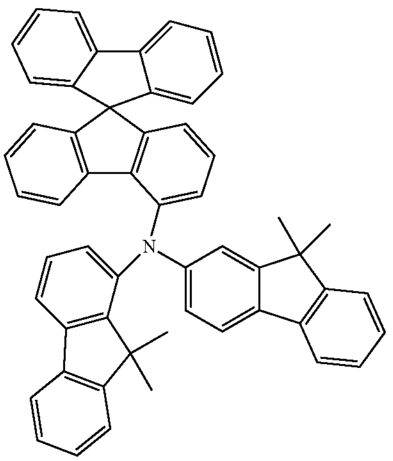
H-1-13
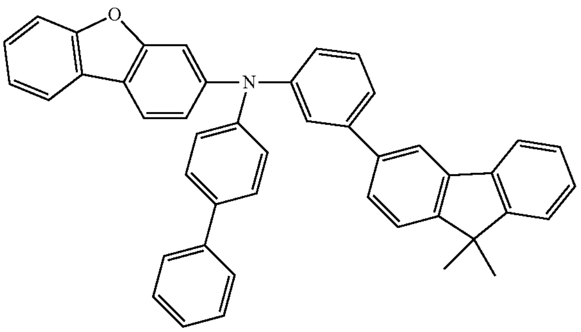
H-1-14
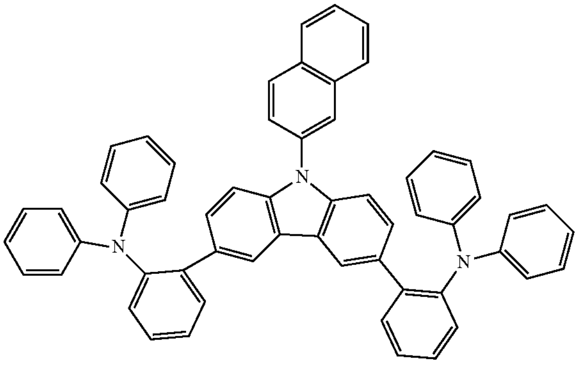

-continued

H-1-15

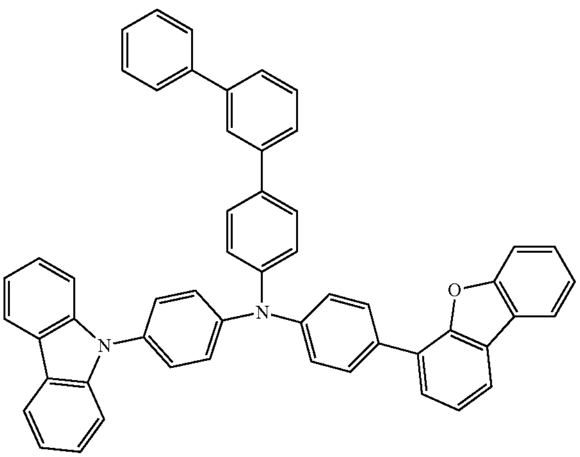

H-1-16

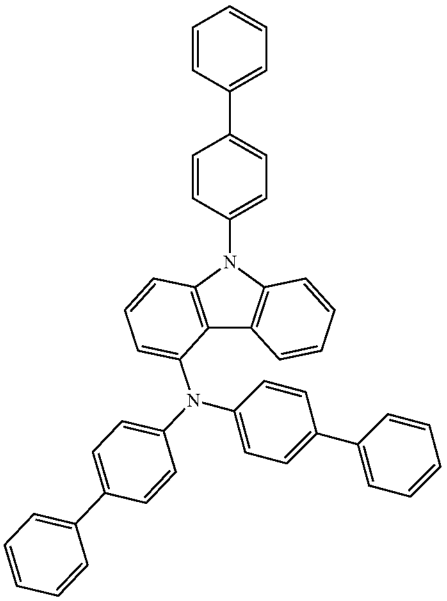

H-1-17

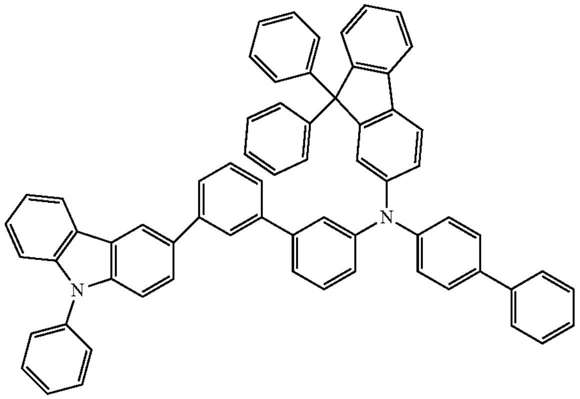

-continued

H-1-18

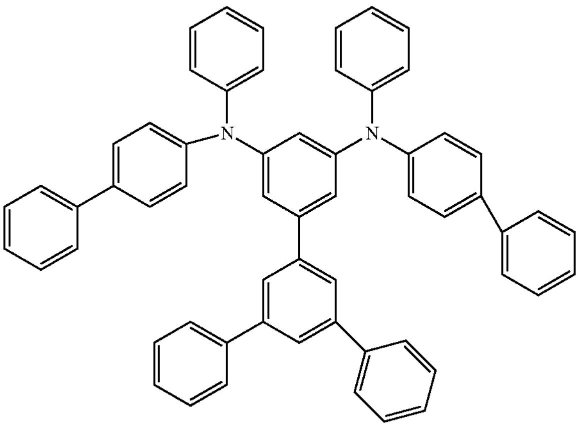

H-1-19

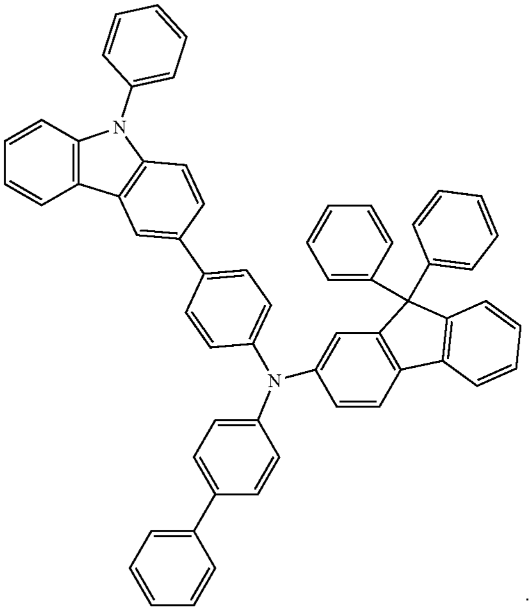

The hole transport region HTR may further include a phthalocyanine compound such as copper phthalocyanine; $N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino] triphenylamine (m-MTDATA), 4,4',4"-Tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-l-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], dipyrazino[2,3-f: 2',3'-h]quinoxaline-2,3,6,7,10,11-hexacarbonitrile (HATCN), and/or the like.

In addition, the hole transport region HTR may include carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)

triphenylamine (TCTA), N,N'-di(naphthalene-l-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl) benzene (mCP), 1,3-bis(1,8-dimethyl-9H-carbazol-9-yl) benzene (mDCP), etc. The hole transport region HTR may include the above-described compounds of the hole transport region in at least one of a hole injection layer HIL, a hole transport layer HTL, or an electron blocking layer EBL.

The thickness of the hole transport region HTR may be from about 100 Å to about 10,000 Å, for example, from about 100 Å to about 5,000 Å. When the hole transport region HTR includes the hole injection layer HIL, the hole injection layer HIL may have, for example, a thickness of about 30 Å to about 1,000 Å. When the hole transport region HTR includes the hole transport layer HTL, the hole transport layer HTL may have a thickness of about 30 Å to about 1,000 Å. For example, when the hole transport region HTR includes the electron blocking layer EBL, the electron blocking layer EBL may have a thickness of about 10 Å to about 1,000 Å. If the thicknesses of the hole transport region HTR, the hole injection layer HIL, the hole transport layer HTL and the electron blocking layer EBL satisfy the above-described ranges, suitable or satisfactory hole transport properties may be achieved without a substantial increase in driving voltage.

The hole transport region HTR may further include a charge generating material to increase conductivity (e.g., electrical conductivity) in addition to the above-described materials. The charge generating material may be dispersed uniformly or non-uniformly in the hole transport region HTR. The charge generating material may be, for example, a p-dopant. The p-dopant may include at least one of a halogenated metal compound, a quinone derivative, a metal oxide, or a cyano group-containing compound, but embodiments of the present disclosure are not limited thereto. For example, the p-dopant may include a metal halide compound such as CuI and RbI, a quinone derivative such as tetracyanoquinodimethane (TCNQ) and/or 2,3,5,6-tetrafluoro-7,7'8,8-tetracyanoquinodimethane (F4-TCNQ), a metal oxide such as tungsten oxide and/or molybdenum oxide, a cyano group-containing compound such as dipyrazino[2,3-f: 2',3'-h] quinoxaline-2,3,6,7,10,11-hexacarbonitrile (HATCN), 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), etc., but embodiments of the present disclosure are not limited thereto.

As described above, the hole transport region HTR may further include at least one of the buffer layer or the electron blocking layer EBL in addition to the hole injection layer HIL and the hole transport layer HTL. The buffer layer may compensate for a resonance distance according to the wavelength of light emitted from the emission layer EML and may thus increase light emission efficiency. A material that may be contained in the hole transport region HTR may be used as a material to be contained in the buffer layer. The electron blocking layer EBL is a layer that serves to prevent or reduce injection of electrons from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed of a single material, a single layer formed of a plurality of different materials, or a multilayer structure having a plurality of layers formed of a plurality of different materials.

In the light emitting element ED of an embodiment, the emission layer EML may include an anthracene derivative, a pyrene derivative, a fluoranthene derivative, a chrysene derivative, a dehydrobenzanthracene derivative, and/or a triphenylene derivative. In some embodiments, the emission layer EML may include the anthracene derivative and/or the pyrene derivative.

In the light emitting elements ED of embodiments illustrated in FIGS. 3 to 6, the emission layer EML may include a host and a dopant. For example, the emission layer EML may include a single host and a single dopant. In some embodiments, the emission layer EML may include at least two hosts, a sensitizer, and a dopant. In some embodiments, the emission layer EML may include a hole transport host and an electron transport host. The emission layer EML may include a phosphorescent sensitizer or a thermally activated delayed fluorescence (TADF) sensitizer as a sensitizer. When the emission layer EML includes a hole transport host, an electron transport host, a sensitizer, and a dopant, the hole transport host and the electron transport host may form an exciplex, and the energy may be transferred from the exciplex to the sensitizer and from the sensitizer to the dopant, and thus, light may be emitted. However, this is an example, and materials included in the emission layer EML are not limited thereto.

The emission layer EML may include a compound represented by Formula E-1 below. The compound represented by Formula E-1 below may be used as a fluorescent host material.

Formula E-1

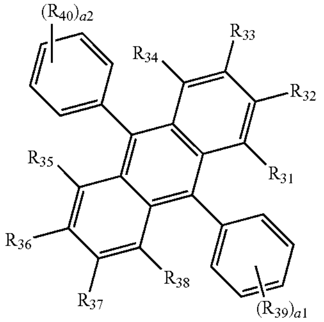

In Formula E-1, a1 and a2 may be each independently an integer of 0 to 5. When a1 is an integer of 2 or more, a plurality of $R_{39}$'s may be the same as each other or at least one may be different from the others. When a2 is an integer of 2 or more, a plurality of $R_{40}$'s may be the same as each other or at least one may be different from the others.

$R_{31}$ to $R_{40}$ may be each independently a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. For example, $R_{31}$ to $R_{40}$ may be bonded to an adjacent group to form a saturated hydrocarbon ring or an unsaturated hydrocarbon ring, a saturated heterocycle, or an unsaturated heterocycle. Formula E-1 may be represented by any one selected from among Compound E1 to Compound E19 below:
E1
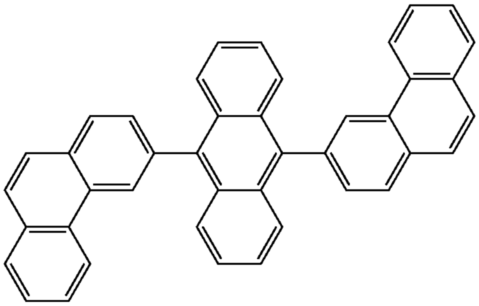
E2
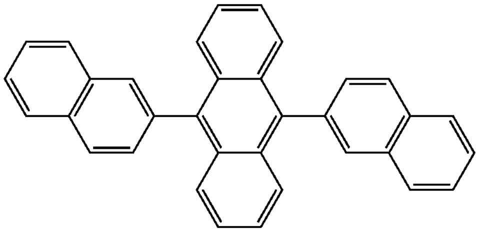
E3
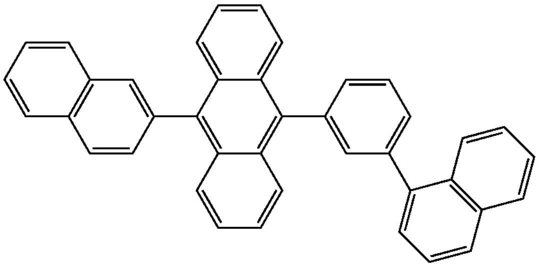
E4
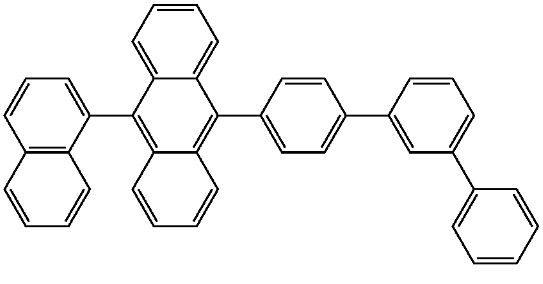
E5
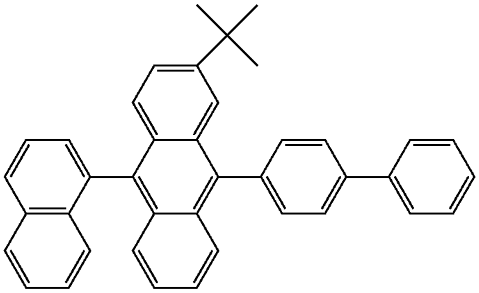
-continued
E6
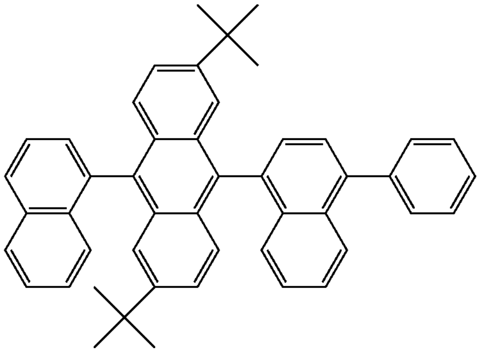
E7
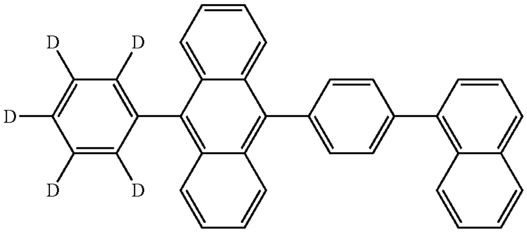
E8
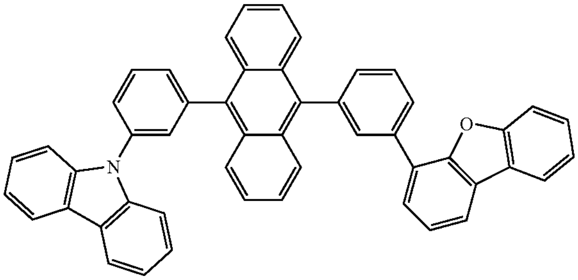
E9
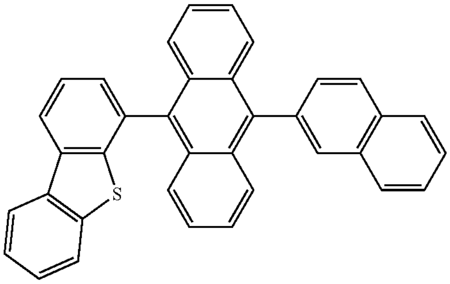
E10
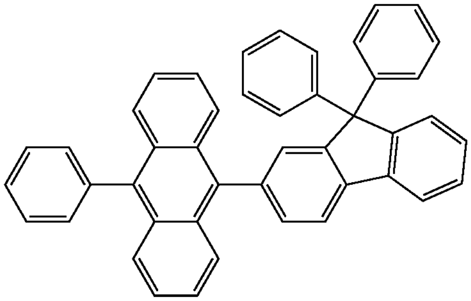

-continued
E11
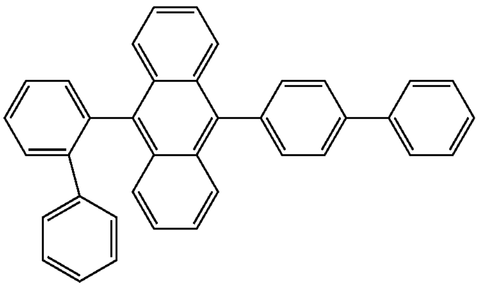
E12
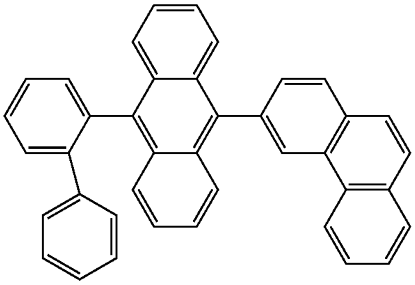
E13
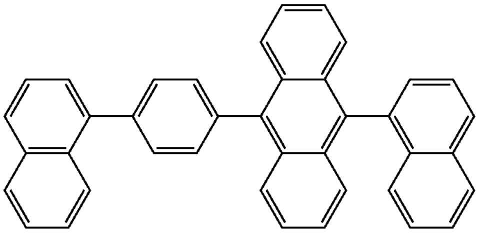
E14
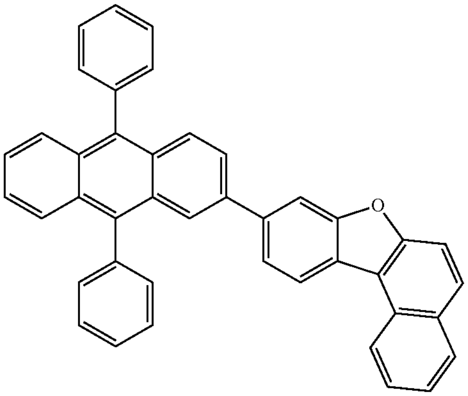
-continued
E15
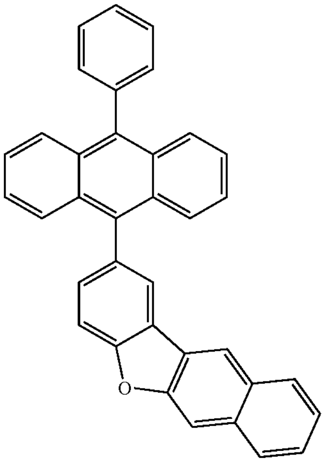
E16
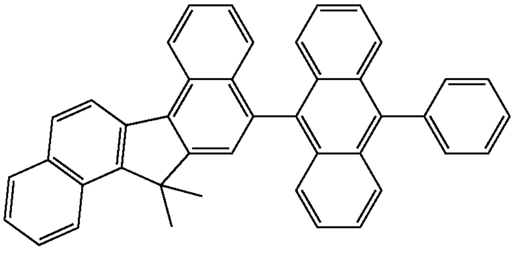
E17
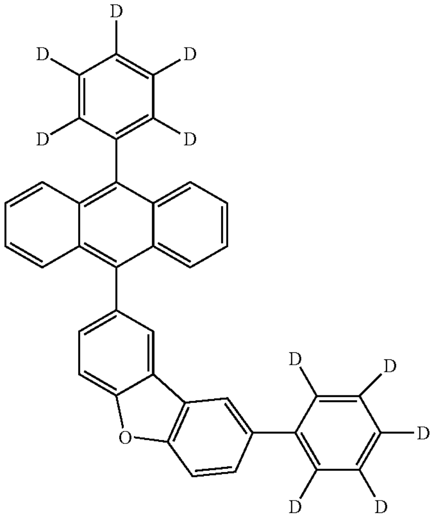
E18
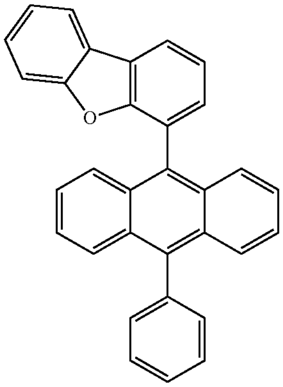

-continued

E19

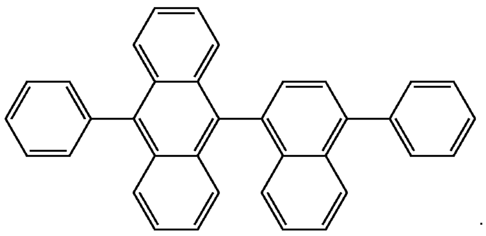

In an embodiment, the emission layer EML may include a compound represented by Formula E-2a or Formula E-2b below. The compound represented by Formula E-2a or Formula E-2b below may be used as a phosphorescent host material.

Formula E-2a

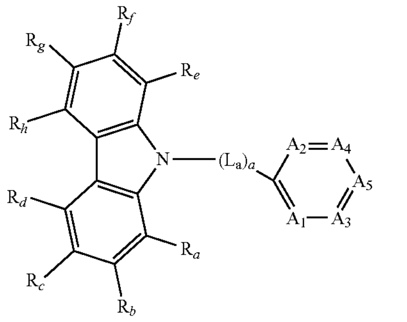

In Formula E-2a, and a may be an integer of 0 to 10, $L_a$ may be a direct linkage, a substituted or unsubstituted arylene group having 6 to 30 ring-forming carbon atoms, or a substituted or unsubstituted heteroarylene group having 2 to 30 ring-forming carbon atoms. When a is an integer of 2 or more, a plurality of $L_a$'s may be each independently a substituted or unsubstituted arylene group having 6 to 30 ring-forming carbon atoms, or a substituted or unsubstituted heteroarylene group having 2 to 30 ring-forming carbon atoms.

In addition, in Formula E-2a, $A_1$ to $A_5$ may be each independently N or $CR_i$. $R_a$ to $R_i$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $R_a$ to $R_i$ may be bonded to an adjacent group to form a hydrocarbon ring or a heterocycle containing N, O, S, etc. as a ring-forming atom.

In Formula E-2a, two or three selected from among $A_1$ to $A_5$ may be N, and the rest may be $CR_i$.

Formula E-2b $$(\mathrm{Cbz1})\!-\!(L_b)_b\!-\!(\mathrm{Cbz2})$$

In Formula E-2b, Cbz1 and Cbz2 may be each independently an unsubstituted carbazole group, or a carbazole group substituted with an aryl group having 6 to 30 ring-forming carbon atoms. $L_b$ is a direct linkage, a substituted or unsubstituted arylene group having 6 to 30 ring-forming carbon atoms, or a substituted or unsubstituted heteroarylene group having 2 to 30 ring-forming carbon atoms. In Formula E-2b, b is an integer of 0 to 10, and when b is an integer of 2 or more, a plurality of $L_b$'s may be each independently a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be represented by any one selected from among the compounds of Compound Group E-2 below. However, the compounds listed in Compound Group E-2 below are examples, and the compound represented by Formula E-2a or Formula E-2b is not limited to those represented in Compound Group E-2 below.

Compound Group E-2

E-2-1

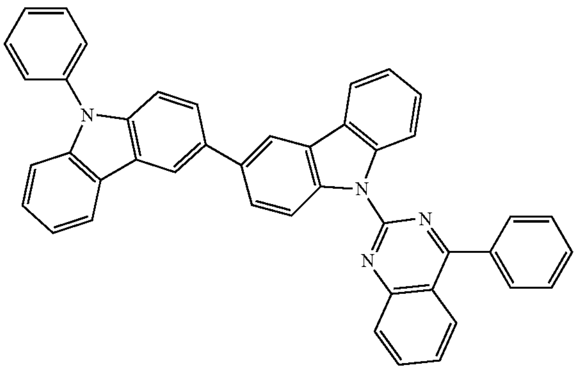

E-2-2

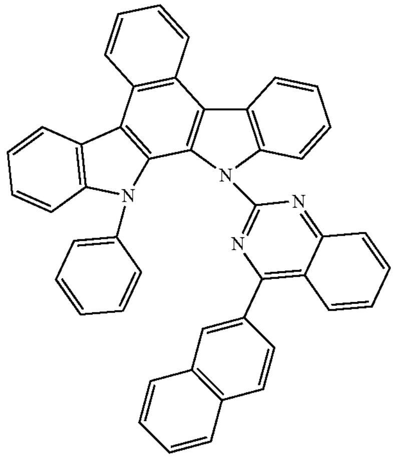

-continued
E-2-3
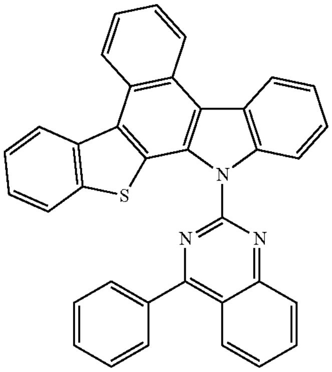
E-2-4
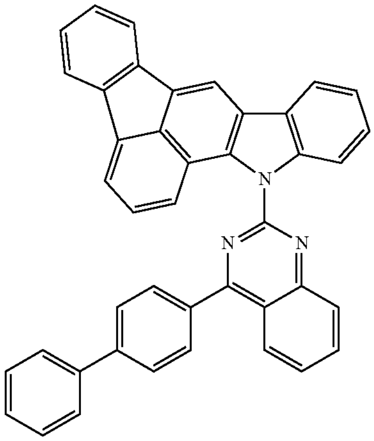
E-2-5
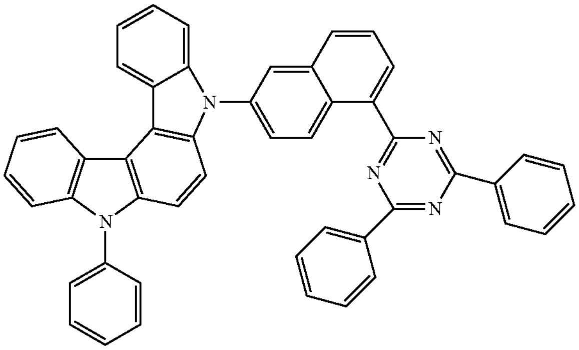
E-2-6
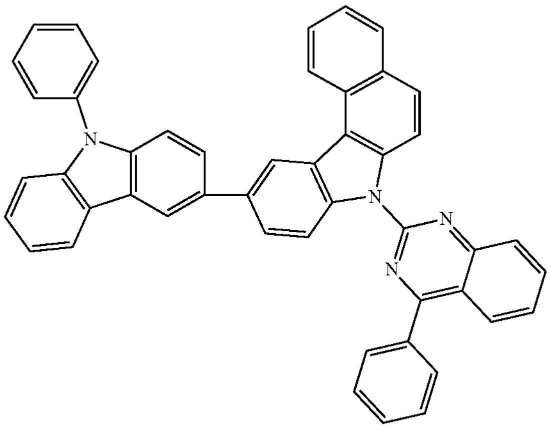
-continued
E-2-7
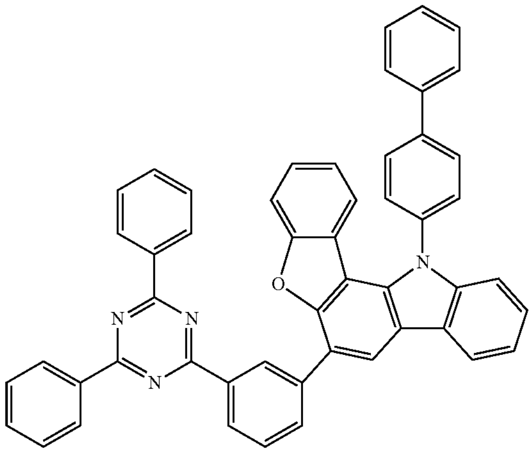
E-2-8
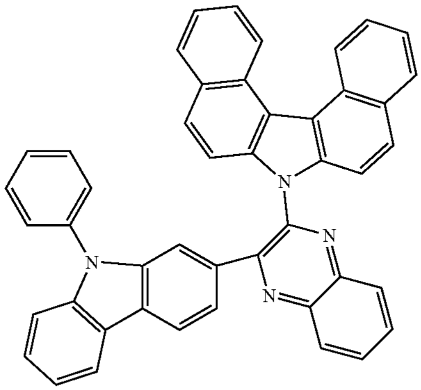
E-2-9
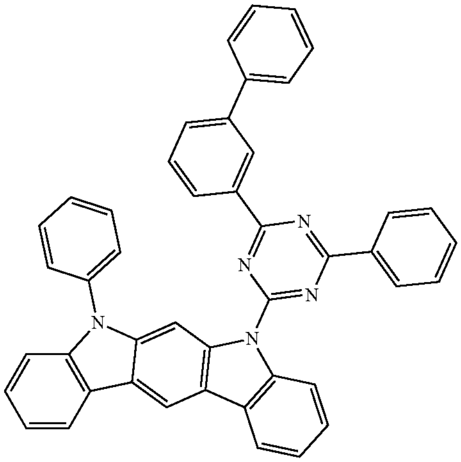

-continued
E-2-10
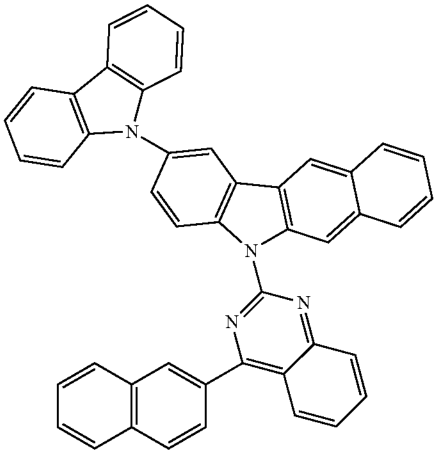
E-2-11
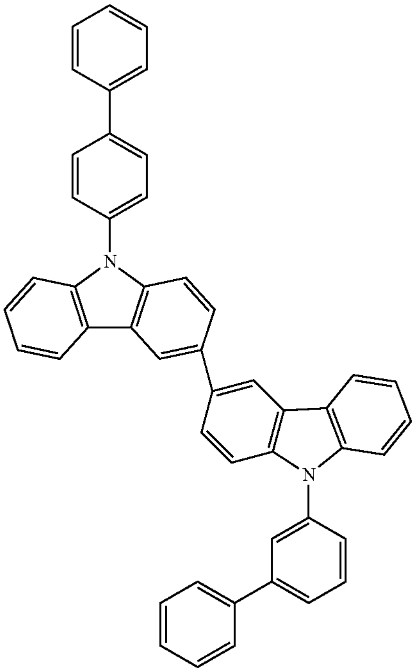
E-2-12
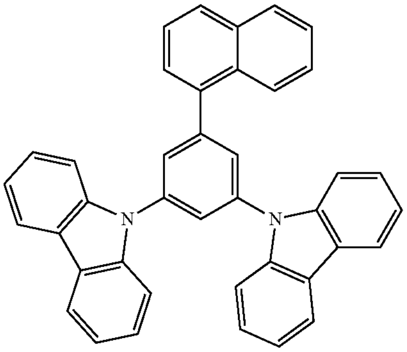
-continued
E-2-13
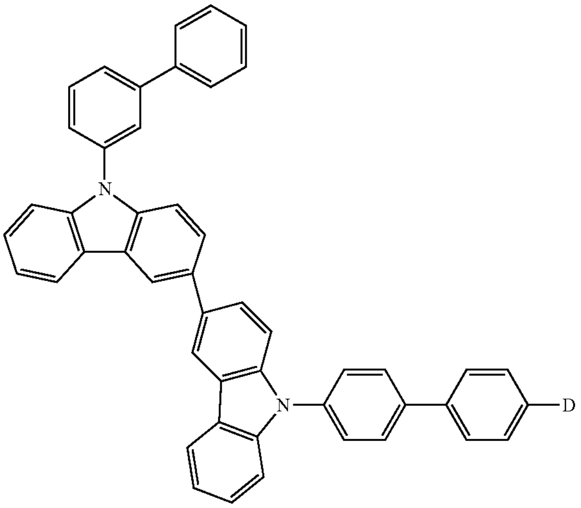
E-2-14
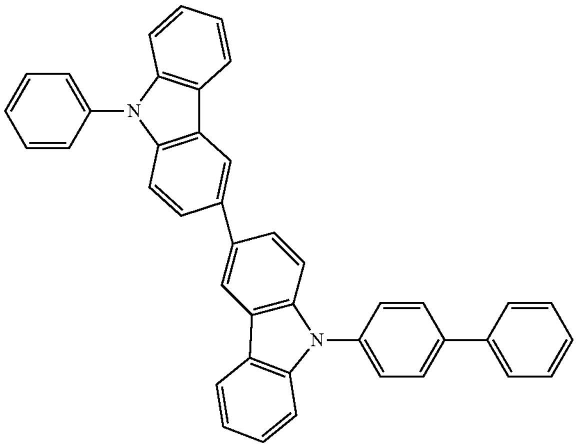
E-2-15
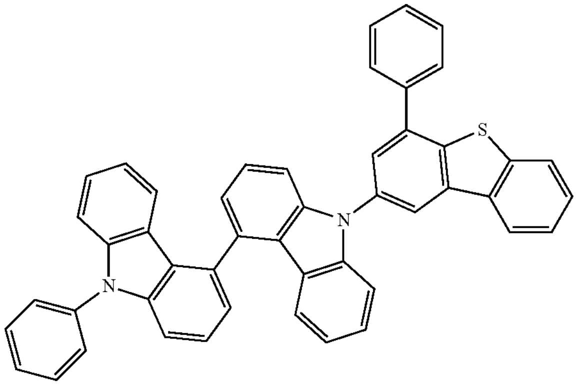

-continued
E-2-16
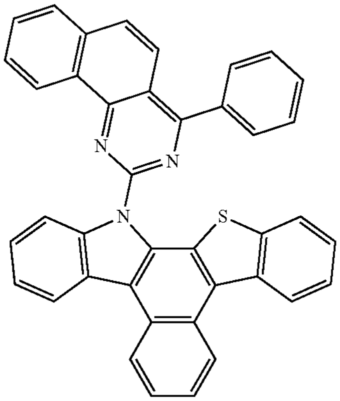
E-2-17
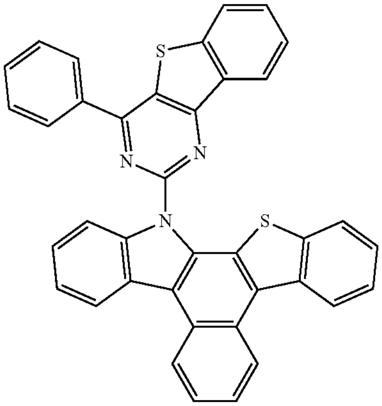
E-2-18
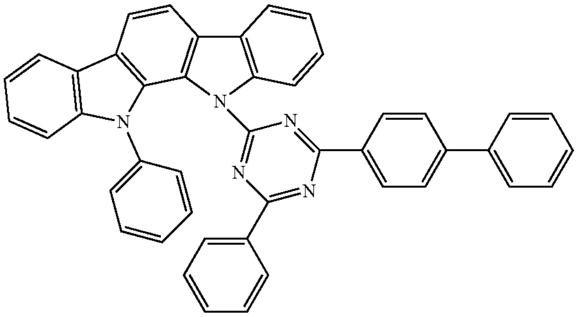
E-2-19
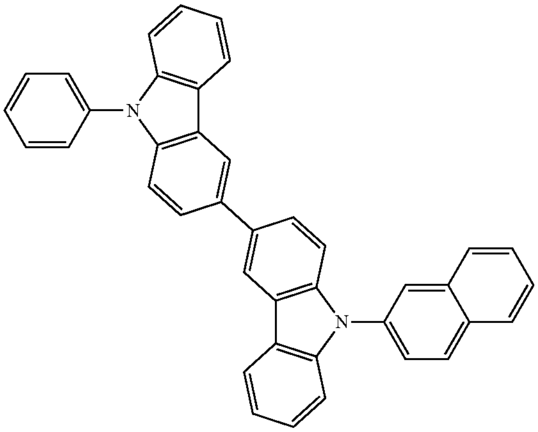
-continued
E-2-20
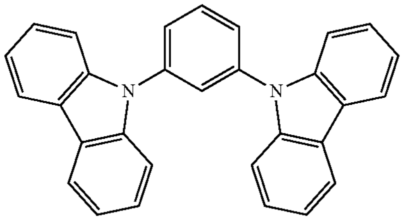
E-2-21
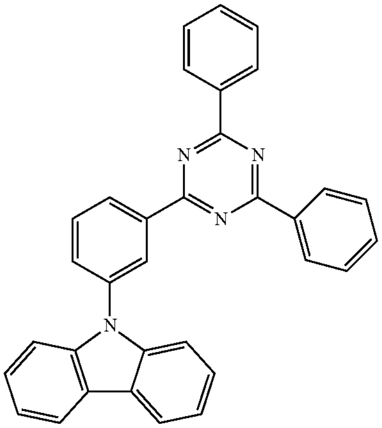
E-2-22
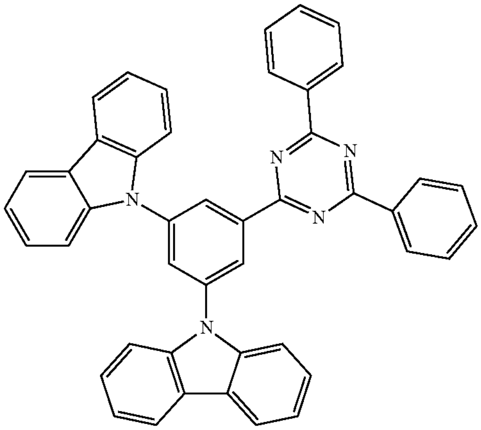
E-2-23
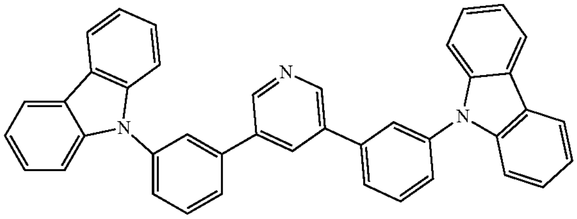

-continued

E-2-24

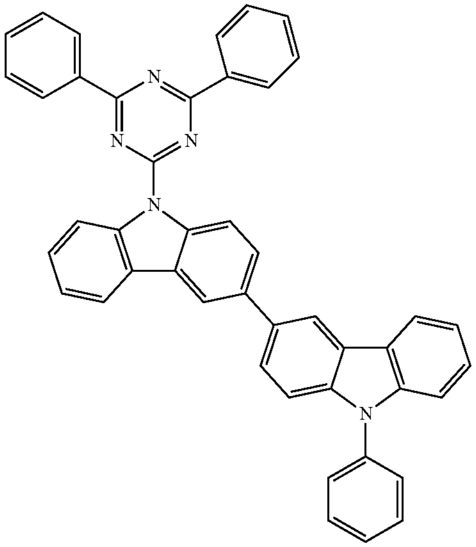

The emission layer EML may further include any suitable material generally used in the art as a host material. For example, the emission layer EML may include, as a host material, at least one of bis(4-(9H-carbazol-9-yl)phenyl) diphenylsilane (BCPDS), (4-(1-(4-(diphenylamino)phenyl) cyclohexyl)phenyl)diphenyl-phosphine oxide (POPCPA), bis[2-(diphenylphosphino)phenyl]ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl) dibenzo[b,d]furan (PPF), 4,4',4"-tris(carbazol-9-yl)-triphenylamine (TCTA), or 1,3,5-tris(1-phenyl-1H-benzo[d] imidazole-2-yl)benzene (TPBi).

However, embodiments of the present disclosure are not limited thereto, for example, tris(8-hydroxyquinolino)aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be used as a host material.

The emission layer EML may include a compound represented by Formula M-a or Formula M-b below. The compound represented by Formula M-a or Formula M-b below may be used as a phosphorescence dopant material.

Formula M-a

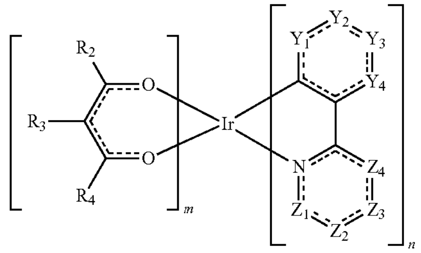

In Formula M-a above, $Y_1$ to $Y_4$ and $Z_1$ to $Z_4$ may be each independently $CR_1$ or N, $R_1$ to $R_4$ may be each independently a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m is 0 or 1, and n is 2 or 3. In Formula M-a, when m is 0, n is 3, and when m is 1, n is 2.

The compound represented by Formula M-a may be used as a phosphorescent dopant. The compound represented by Formula M-a may be represented by any one selected from among Compound M-a1 to Compound M-a25 below. However, Compounds M-a1 to M-a25 below are examples, and the compound represented by Formula M-a is not limited to those represented by Compounds M-a1 to M-a25 below.

M-a1

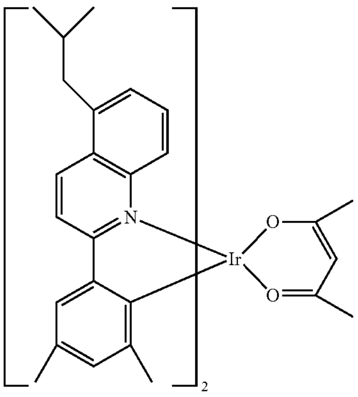

M-a2

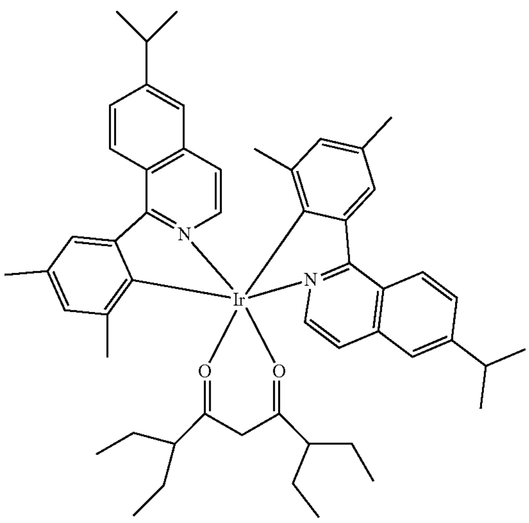

-continued
M-a3
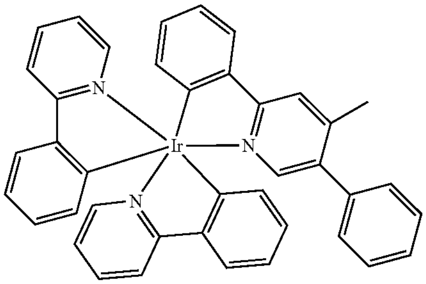
M-a4
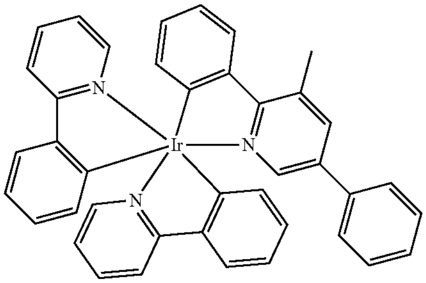
M-a5
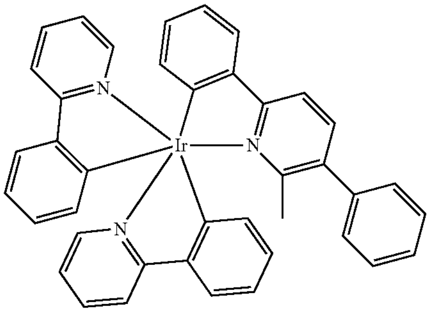
M-a6
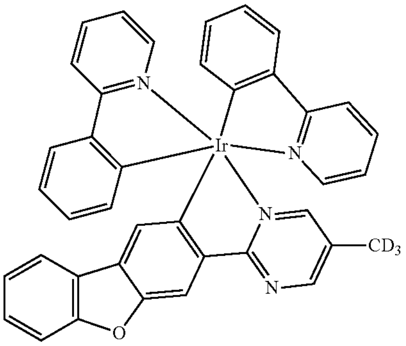
M-a7
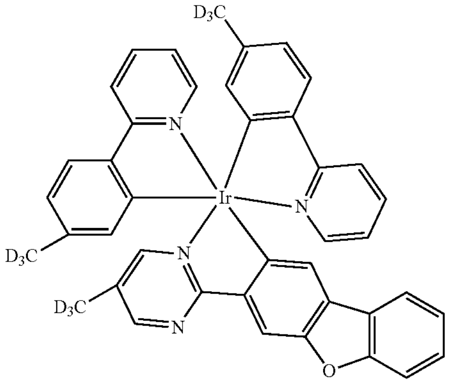
-continued
M-a8
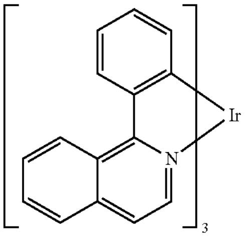
M-a9
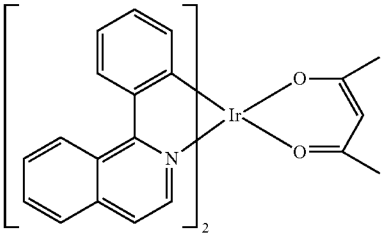
M-a10
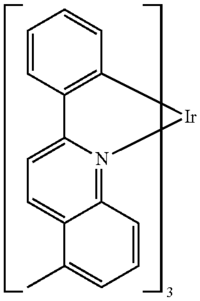
M-a11
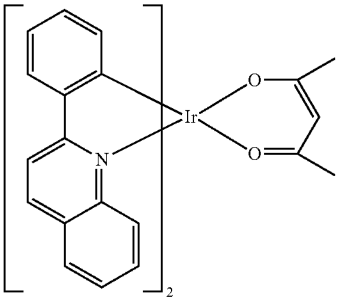
M-a12
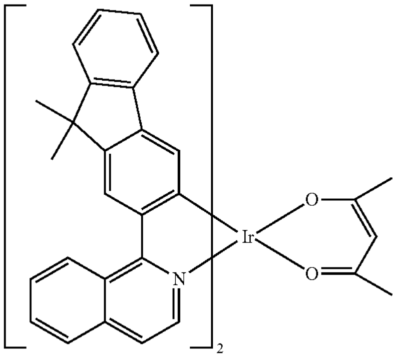

-continued
M-a13
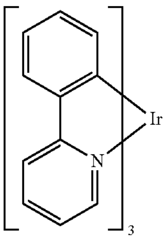
M-a14
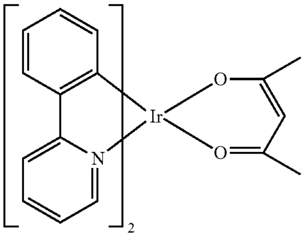
M-a15
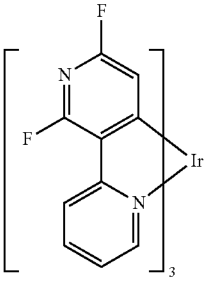
M-a16
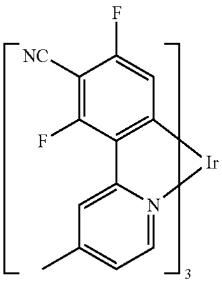
M-a17
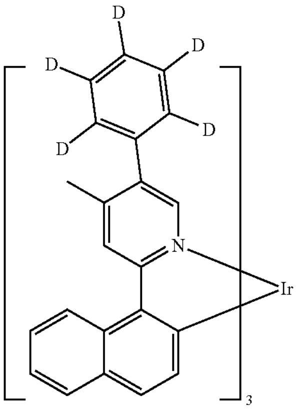
-continued
M-a18
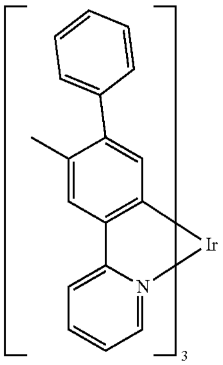
M-a19
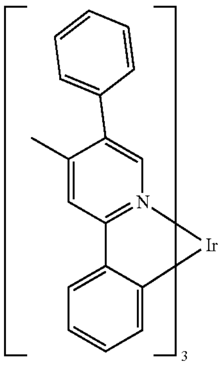
M-a20
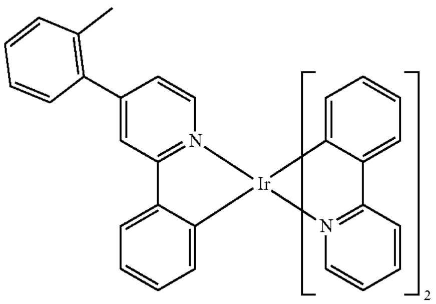
M-a21
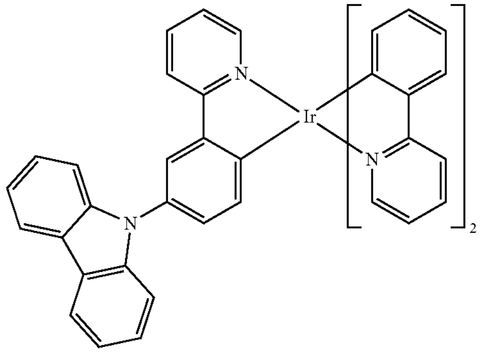

-continued

M-a22

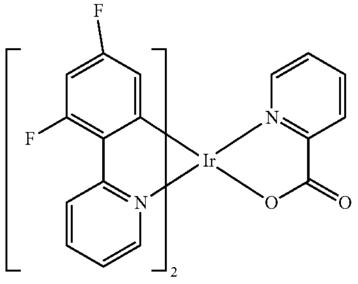

M-a23

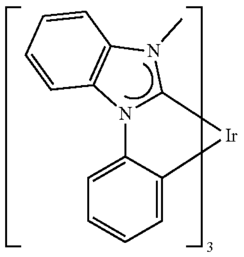

M-a24

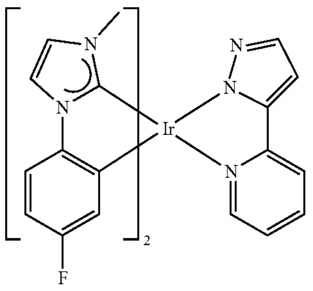

M-a25

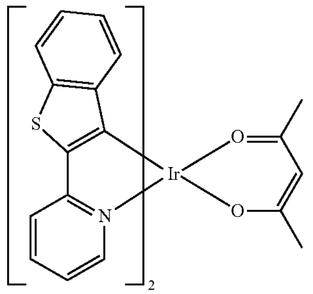

Formula M-a1 and Formula M-a2 may be used as a red dopant material. Formula M-a3 to Formula M-a7 may be used as a green dopant material.

Formula M-b

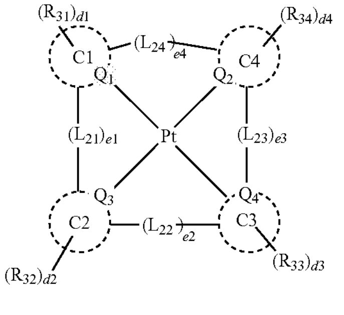

In Formula M-b, $Q_1$ to $Q_4$ may be each independently C or N, and C1 to C4 are each independently a substituted or unsubstituted hydrocarbon ring having 5 to 30 ring-forming carbon atoms, or a substituted or unsubstituted heterocycle having 2 to 30 ring-forming carbon atoms. e1 to e4 may be each independently 0 or 1. $L_{21}$ to $L_{24}$ may be each independently a direct linkage,

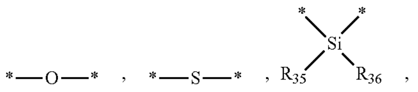

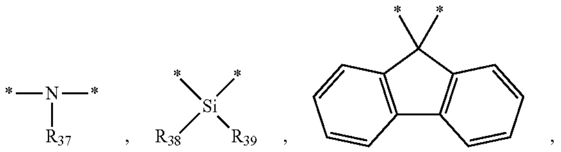

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms.

In Formula M-b, d1 to d4 may be each independently an integer of 0 to 4. $R_{31}$ to $R_{39}$ may be each independently a hydrogen atom, a deuterium atom, a halogen atom, a cyano group, a substituted or unsubstituted divalent alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be other bonded to an adjacent group to form a ring.

The compound represented by Formula M-b may be used as a blue phosphorescence dopant or a green phosphorescence dopant. The compound represented by Formula M-b may be represented by any one selected from among the compounds below. However, the compounds below are examples, and the compound represented by Formula M-b is not limited to those represented by the compounds below.

M-b-1

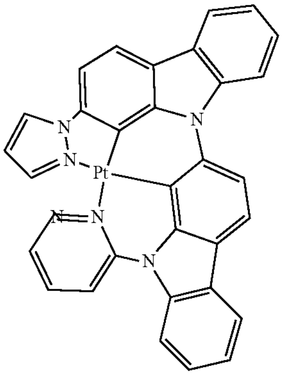

M-b-2
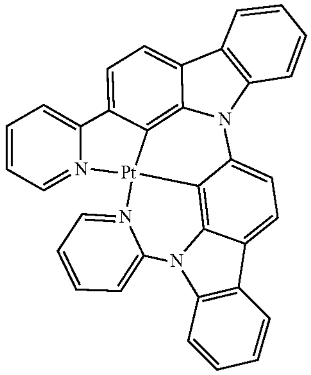
M-b-3
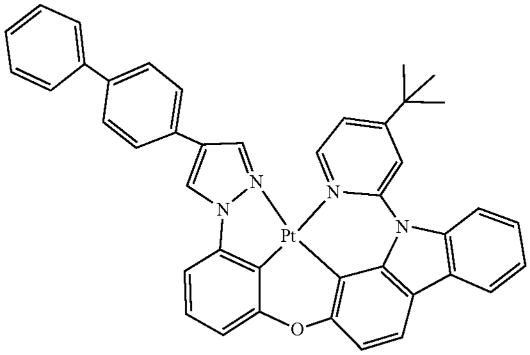
M-b-4
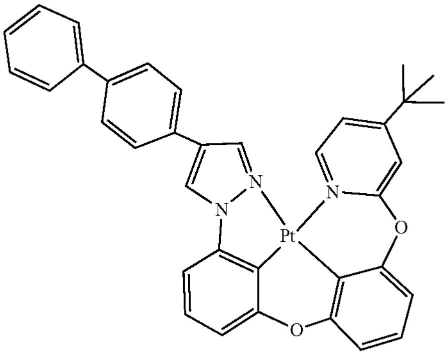
M-b-5
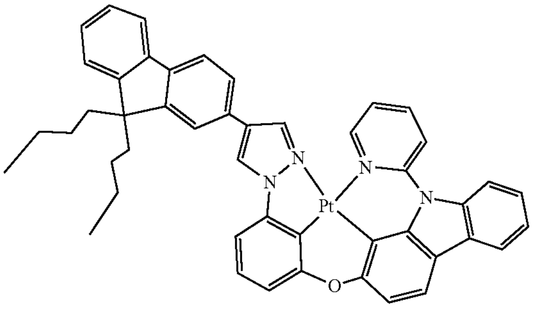
M-b-6
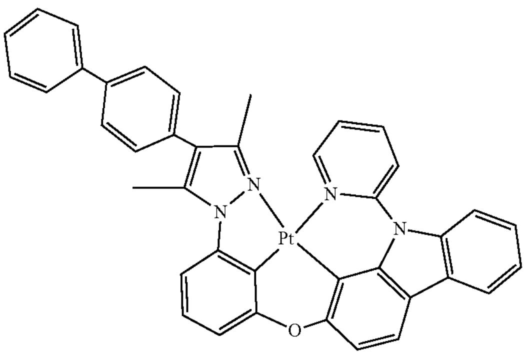
M-b-7
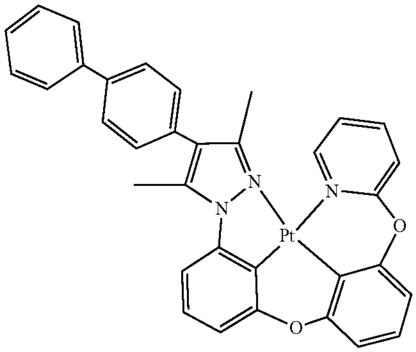
M-b-8
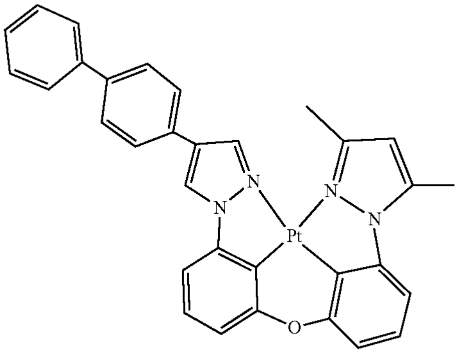
M-b-9
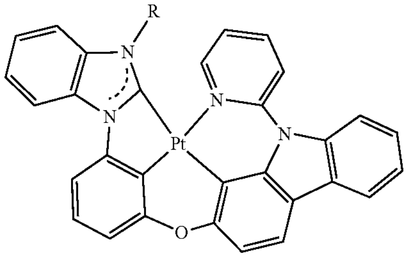
M-b-10
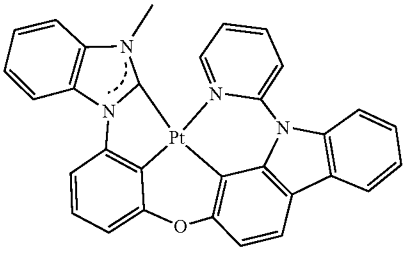

-continued

M-b-11

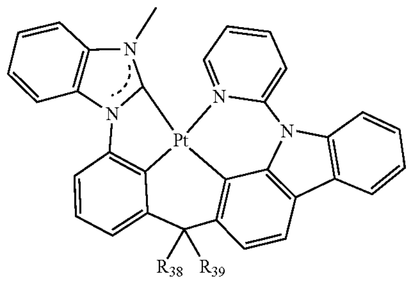

In the above compounds, R, $R_{38}$, and $R_{39}$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one selected from among Formula F-a to Formula F-c below. The compound represented by Formula F-a or Formula F-c below may be used as a fluorescence dopant material.

Formula F-a

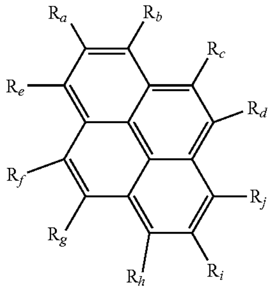

In Formula F-a above, two selected from among $R_a$ to $R_j$ may each independently be substituted with $$*—NAr_1Ar_2.$$

The others, which are not substituted with $$*—NAr_1Ar_2,$$

among $R_a$ to $R_j$ may be each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In $$*—NAr_1Ar_2,$$

$Ar_1$ and $Ar_2$ may be each independently a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

Formula F-b

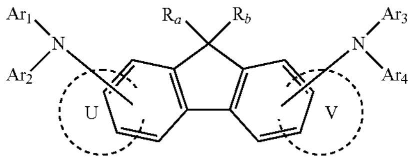

In Formula F-b above, $R_a$ and $R_b$ may be each independently a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $Ar_1$ to $Ar_4$ may be each independently a substituted or unsubstituted aryl group having 6 to 30 ring-forming carbon atoms, or a substituted or unsubstituted heteroaryl group having 2 to 30 ring-forming carbon atoms.

In Formula F-b, U and V may be each independently a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may be each independently 0 or 1. For example, in Formula F-b, when the number of U or V is 1, one ring constitutes a fused ring at a portion indicated by U or V, and when the number of U or V is 0, a ring indicated by U or V does not exist. In some embodiments, when the number of U is 0 and the number of V is 1, or when the number of U is 1 and the number of V is 0, the fused ring having a fluorene core in Formula F-b may be a cyclic compound having four rings. In addition, when each number of U and V is 0, the fused ring in Formula F-b may be a cyclic compound having three rings. In addition, when each number of U and V is 1, the fused ring having a fluorene core in Formula F-b may be a cyclic compound having five rings.

Formula F-c

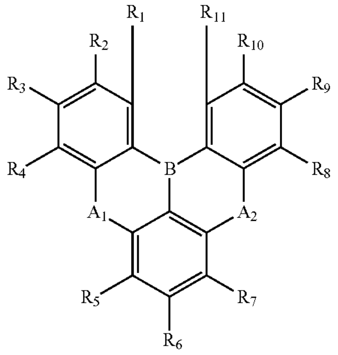

In Formula F-c, $A_1$ and $A_2$ may be each independently O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may be each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-c, $A_1$ and $A_2$ may each independently be bonded to substituents of an adjacent ring to form a condensed ring. For example, when $A_1$ and $A_2$ are each independently $NR_m$, $A_1$ may be bonded to $R_4$ or $R_5$ to form a ring. In addition, $A_2$ may be bonded to $R_7$ or $R_8$ to form a ring.

In an embodiment, the emission layer EML may include any suitable dopant material. In some embodiments, the emission layer EML may include styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl)phenyl)-N-phenylbenzenamine (N-BDAVBi), 4,4'-bis[2-(4-(N,N-diphenylamino)phenyl)vinyl]biphenyl(DPAVBi), perylene and/or derivatives thereof (e.g., 2,5,8,11-tetra-t-butylperylene (TBP)), pyrene and/or derivatives thereof (e.g., 1,1-dipyrene, 1,4-dipyrenylbenzene, 1,4-bis(N,N-diphenylamino)pyrene), etc.

The emission layer EML may include any suitable phosphorescent dopant material. For example, a metal complex containing iridium (Ir), platinum (Pt), osmium (Os), aurum (Au), titanium (Ti), zirconium (Zr), hafnium (Hf), europium (Eu), terbium (Tb), or thulium (Tm) may be used as a phosphorescent dopant. In some embodiments, iridium(III) bis(4,6-difluorophenylpyridinato-N,C2')picolinate (Flrpic), bis(2,4-difluorophenylpyridinato)-tetrakis(1-pyrazolyl)borate iridium(III) (Fir6), and/or platinum octaethyl porphyrin (PtOEP) may be used as a phosphorescence dopant. However, embodiments of the present disclosure are not limited thereto.

The emission layer EML may include a quantum dot material. The core of the quantum dot may be selected from among a Group II-VI compound, a Group III-VI compound, a Group I-III-IV compound, a Group III-V compound, a Group III-II-V compound, a Group IV-VI compound, a Group IV element, a Group IV compound, and a combination thereof.

The Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and/or $In_2Se_3$, a ternary compound such as $InGaS_3$ and/or $InGaSe_3$, or any combination thereof.

The Group I-III-VI compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, a mixture thereof, and a quaternary compound such as $AgInGaS_2$ and/or $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

In this case, a binary compound, a ternary compound, and/or a quaternary compound may be present in a particle having a uniform (e.g., substantially uniform) concentration distribution, or may be present in the same particle with a partially different concentration. In addition, a core/shell structure in which one quantum dot surrounds another quantum dot may also be possible. The core/shell structure may have a concentration gradient in which the concentration of elements present in the shell decreases along a direction toward the core.

In some embodiments, the quantum dot may have the above-described core/shell structure including a core containing nanocrystals and a shell surrounding the core. The shell of the quantum dot may serve as a protection layer to prevent or reduce the chemical deformation of the core so as to maintain semiconductor properties, and/or a charging layer to impart electrophoresis properties to the quantum dot. The shell may be a single layer or a multilayer. An example of the shell of the quantum dot may include a metal and/or non-metal oxide, a semiconductor compound, or a combination thereof.

For example, the metal and/or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO, and/or a ternary compound such as $MgAl_2O_4$, $CoFe_2O_4$, $NiFe_2O_4$, and/or $CoMn_2O_4$, but embodiments of the present disclosure are not limited thereto.

Also, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

The quantum dot may have a full width of half maximum (FWHM) of a light emission wavelength spectrum of about 45 nm or less, about 40 nm or less, or, for example, about 30 nm or less, and color purity and/or color reproducibility may be improved in the above range. In addition, light emitted through such a quantum dot is emitted in all directions (e.g., substantially all directions), and thus a wide viewing angle may be improved.

In addition, the form of the quantum dot is not particularly limited and may be any suitable form generally used in the art. In some embodiments, the quantum dot in the form of spherical, pyramidal, multi-arm, and/or cubic nanoparticles, nanotubes, nanowires, nanofibers, nanoplate particles, etc. may be used. The quantum dot may control the color of emitted light according to the particle size thereof, and accordingly, the quantum dot may have various suitable emission colors such as blue, red, or green.

In the light emitting element ED of an embodiment as illustrated, an electron transport region ETR is provided on the emission layer EML. The electron transport region ETR may include at least one of the hole blocking layer HBL, the electron transport layer ETL, or the electron injection layer EIL, but embodiments of the present disclosure are not limited thereto.

The electron transport region ETR may have a single layer formed of a single material, a single layer formed of a plurality of different materials, or a multilayer structure including a plurality of layers formed of a plurality of different materials. For example, the electron transport region ETR may have a single layer structure of the electron injection layer EIL or the electron transport layer ETL, and may have a single layer structure formed of an electron injection material and an electron transport material. In addition, the electron transport region ETR may have a single layer structure formed of a plurality of different materials, or may have a structure in which an electron transport layer ETL/electron injection layer EIL, a hole blocking layer HBL/electron transport layer ETL/electron injection layer EIL are stacked in order from the emission layer EML, but embodiments of the present disclosure are not limited thereto. The electron transport region ETR may have a thickness, for example, from about 1,000 Å to about 1,500 Å.

The electron transport region ETR may be formed by using various suitable methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1 below:

Formula ET-1

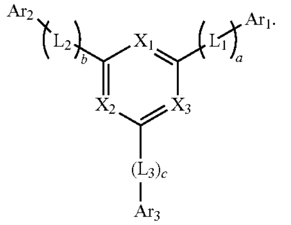

In Formula ET-1, at least one selected from among $X_1$ to $X_3$ may be N, and the rest may be $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_3$ may be each independently a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may be each independently an integer of 0 to 10. In Formula ET-1, $L_1$ to $L_3$ may be each independently a direct linkage, a substituted or unsubstituted arylene group having 6 to 30 ring-forming carbon atoms, or a substituted or unsubstituted heteroarylene group having 2 to 30 ring-forming carbon atoms. When a to c are an integer of 2 or more, $L_1$ to $L_3$ may be each independently a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl) phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate) ($Bebq_2$), 9,10-di(naphthalene-2-yl)anthracene (ADN), 1,3-Bis[3,5-di(pyridin-3-yl)phenyl]benzene (BmPyPhB), or a mixture thereof.

In addition, the electron transport regions ETR may include a metal halide such as LiF, NaCl, CsF, RbCl, RbI, CuI, and/or KI, a lanthanide metal such as Yb, and/or a co-deposited material of the metal halide and the lanthanide metal. For example, the electron transport region ETR may include KI:Yb, RbI:Yb, LiF:Yb, etc. as a co-deposited material. The electron transport region ETR may be formed using a metal oxide such as $Li_2O$ and/or BaO, and/or 8-hydroxyl-lithium quinolate (Liq), etc., but embodiments of the present disclosure are not limited thereto. The electron transport region ETR may also be formed of a mixture of an electron transport material and an insulating organometallic salt. The organometallic salt may be a material having an energy band gap of about 4 eV or more. In some embodiments, the organometallic salt may include, for example, a metal acetate, a metal benzoate, a metal acetoacetate, a metal acetylacetonate, and/or a metal stearate.

The electron transport region ETR may further include at least one of 2,9-dimethyl-4,7-diphenyl-1,10-phenanthroline (BCP), diphenyl(4-(triphenylsilyl)phenyl)phosphine oxide (TSPO1), or 4,7-diphenyl-1,10-phenanthroline (Bphen) in addition to the above-described materials, but embodiments of the present disclosure are not limited thereto. The electron transport region ETR may include the above-described compounds of the electron transport region in at least one of the electron injection layer EIL, the electron transport layer ETL, or the hole blocking layer HBL.

When the electron transport region ETR includes the electron transport layer ETL, the electron transport layer ETL may have a thickness of about 100 Å to about 1,000 Å, for example, about 150 Å to about 500 Å. If the thickness of the electron transport layer ETL satisfies the aforementioned range, suitable or satisfactory electron transport characteristics may be obtained without a substantial increase in driving voltage. When the electron transport region ETR includes the electron injection layer EIL, the electron injection layer EIL may have a thickness of about 1 Å to about 100 Å, for example, about 3 Å to about 90 Å. If the thickness of the electron injection layer EIL satisfies the above-described range, suitable or satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, when the first electrode EL1 is an anode, the second electrode EL2 may be a cathode, and when the first electrode EL1 is a cathode, the second electrode EL2 may be an anode. The second electrode EL2 may include at least one selected from among Ag, Mg, Cu, Al, Pt, Pd, Au, Ni, Nd, Ir, Cr, Li, Ca, LiF, Mo, Ti, W, In, Sn, Zn, a compound of two or more thereof, a mixture of two or more thereof, and an oxide thereof.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, a compound thereof, or mixture thereof (e.g., AgMg, AgYb, and/or MgAg). In some embodiments, the second electrode EL2 may have a multi-layer structure including a reflective film or a transflective film formed of the above-described materials, and a transparent conductive film formed of ITO, IZO, ZnO, ITZO, etc. For example, the second electrode EL2 may include the above-described metal materials, combinations of at least two metal materials of the above-described metal materials, oxides of the above-described metal materials, and/or the like.

In some embodiments, the second electrode EL2 may be connected with an auxiliary electrode. If the second electrode EL2 is connected with the auxiliary electrode, the resistance of the second electrode EL2 may decrease.

A capping layer CPL may further be on the second electrode EL2 of the light emitting element ED of an embodiment. The capping layer CPL may include a multi-layer or a single layer.

In an embodiment, the capping layer CPL may be an organic layer and/or an inorganic layer. For example, when the capping layer CPL contains an inorganic material, the inorganic material may include an alkaline metal compound (for example, LiF), an alkaline earth metal compound (for example, $MgF_2$), SiON, $SiN_x$, SiOy, etc.

For example, when the capping layer CPL includes an organic material, the organic material may include α-NPD, NPB, TPD, m-MTDATA, $Alq_3$, CuPc, N4,N4,N4',N4'-tetra (biphenyl-4-yl)biphenyl-4,4'-diamine (TPD15), 4,4',4"-tris (carbazol-9-yl)triphenylamine (TCTA), etc., an epoxy resin, and/or acrylate such as methacrylate. However, embodiments of the present disclosure are not limited thereto, and the capping layer CPL may include at least one selected from among Compounds P1 to P5 below:

P1

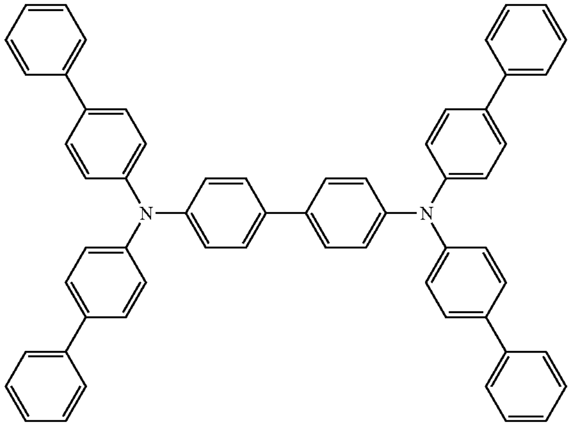

P2

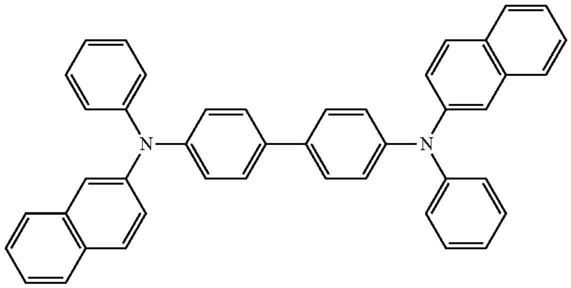

P3

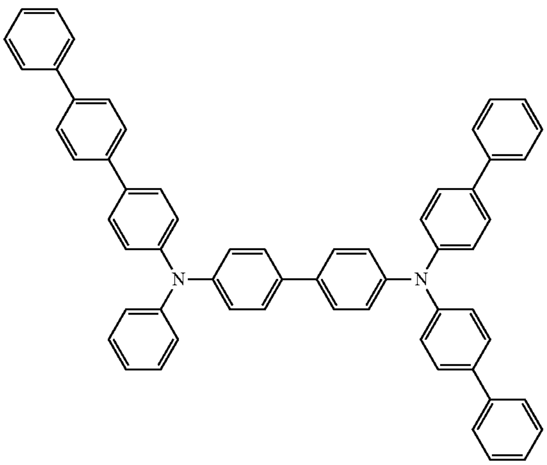

-continued

P4

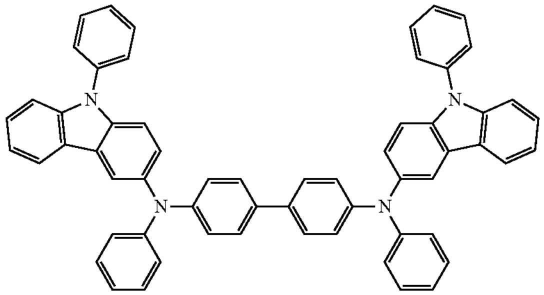

P5

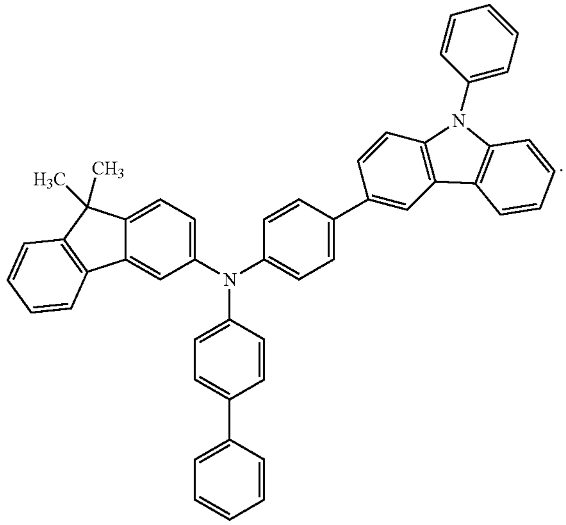

The refractive index of the capping layer CPL may be about 1.6 or more. In some embodiments, the refractive index of the capping layer CPL may be about 1.6 or more with respect to light in a wavelength range of about 550 nm to about 660 nm.

Each of FIGS. 7 to 10 is a cross-sectional view of a display device according to an embodiment of the present disclosure. Hereinafter, in describing the display devices of embodiments with reference to FIGS. 7 to 10, features that have been described with respect to FIGS. 1 to 6 may not be described again, but their differences will be mainly described.

Figure 7:
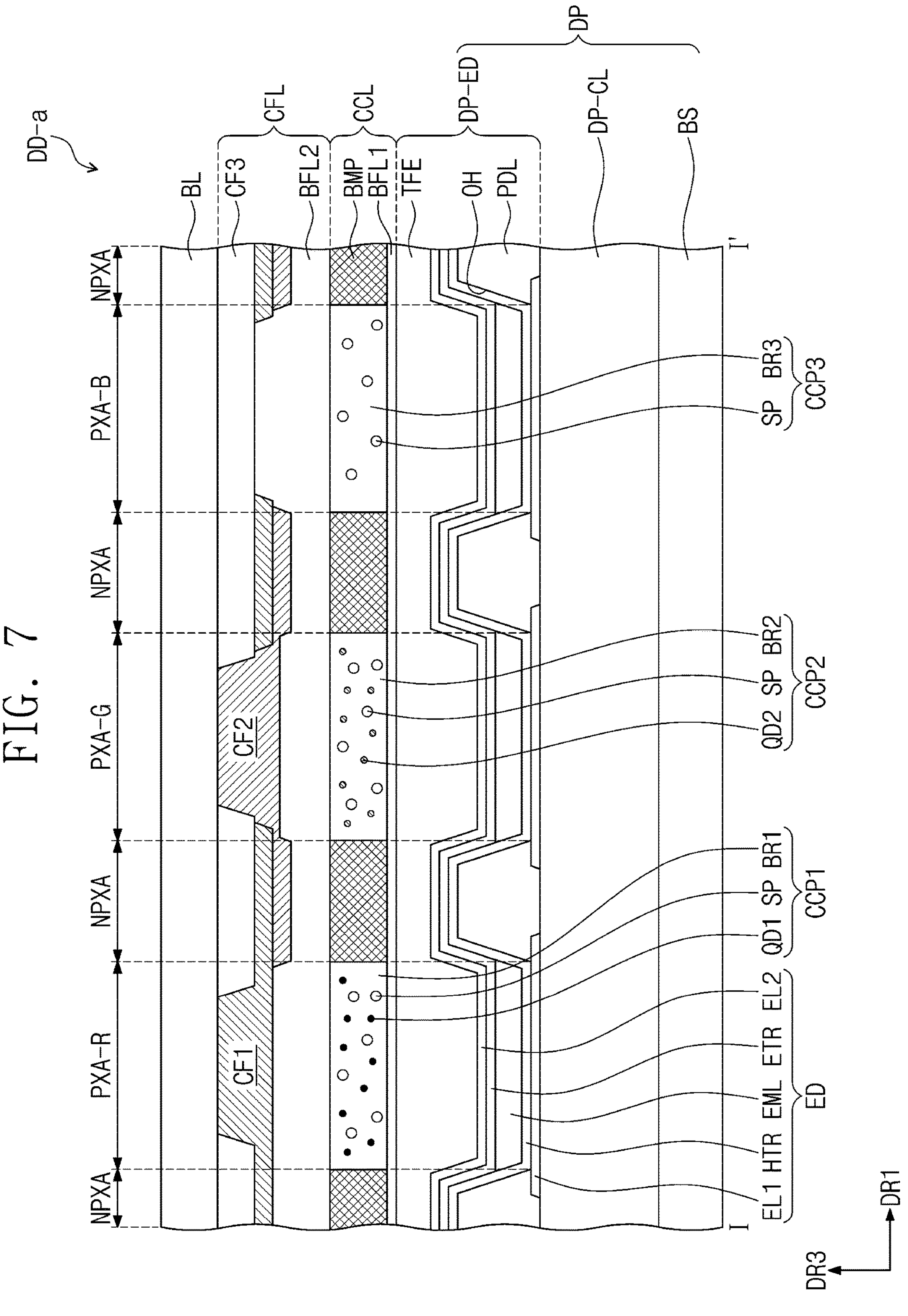
FIG. 7 is a cross-sectional view illustrating a display device according to an embodiment of the present disclosure.

Referring to FIG. 7, the display device DD according to an embodiment may include a display panel DP including a display element layer DP-ED, a light control layer CCL on the display panel DP, and a color filter layer CFL.

In an embodiment illustrated in FIG. 7, the display panel DP may include a base layer BS, a circuit layer DP-CL provided on the base layer BS, and the display element layer DP-ED, and the display element layer DP-ED may include a light emitting element ED.

The light emitting element ED may include a first electrode EL1, a hole transport region HTR on the first electrode EL1, an emission layer EML on the hole transport region HTR, an electron transport region ETR on the emission layer EML, and a second electrode EL2 on the electron transport region ETR. The structures of the light emitting elements of FIGS. 3 to 6 as described above may be equally applied to the structure of the light emitting element ED illustrated in FIG. 7.

Referring to FIG. 7, the light emission layer EML in the display device DD-a may be in an opening OH defined in a pixel defining film PDL. For example, the emission layer EML which is divided by the pixel defining film PDL and provided corresponding to each light emitting regions PXA-R, PXA-G, and PXA-B may emit light in the same wavelength range. In the display device DD of an embodiment, the emission layer EML may emit blue light. Unlike the configuration illustrated, in an embodiment, the emission layer EML may be provided as a common layer in the entire light emitting regions PXA-R, PXA-G, and PXA-B.

The light control layer CCL may be on the display panel DP. The light control layer CCL may include a light conversion body. The light conversion body may be a quantum dot, a phosphor, and/or the like. The light conversion body may emit provided light by converting the wavelength thereof. For example, the light control layer CCL may be a layer containing the quantum dot and/or a layer containing the phosphor.

The light control layer CCL may include a plurality of light control parts CCP1, CCP2, and CCP3. The light control parts CCP1, CCP2, and CCP3 may be spaced apart from each other.

Referring to FIG. 7, divided patterns BMP may be between the light control parts CCP1, CCP2, and CCP3, which are spaced apart from each other, but embodiments of the present disclosure are not limited thereto. FIG. 7 illustrates that the divided patterns BMP do not overlap the light control parts CCP1, CCP2, and CCP3, but at least a portion of the edges of the light control parts CCP1, CCP2, and CCP3 may overlap the divided patterns BMP.

The light control layer CCL may include a first light control part CCP1 containing a first quantum dot QD1 which converts a first color light provided from the light emitting element ED into a second color light, a second light control part CCP2 containing a second quantum dot QD2 which converts the first color light into a third color light, and a third light control part CCP3 which transmits the first color light.

In an embodiment, the first light control part CCP1 may provide red light that is the second color light, and the second light control part CCP2 may provide green light that is the third color light. The third light control part CCP3 may provide blue light by transmitting the blue light that is the first color light provided from the light emitting element ED. For example, the first quantum dot QD1 may be a red quantum dot, and the second quantum dot QD2 may be a green quantum dot. The same as described above may be applied with respect to the quantum dots QD1 and QD2.

In addition, the light control layer CCL may further include a scatterer SP (e.g., a light scatterer SP). The first light control part CCP1 may include the first quantum dot QD1 and the scatterer SP, the second light control part CCP2 may include the second quantum dot QD2 and the scatterer SP, and the third light control part CCP3 may not include any quantum dot but may include the scatterer SP.

The scatterer SP may be inorganic particles. For example, the scatterer SP may include at least one of $TiO_2$, ZnO, $Al_2O_3$, $SiO_2$, or hollow sphere silica. The scatterer SP may include any one selected from among $TiO_2$, ZnO, $Al_2O_3$, $SiO_2$, and hollow sphere silica, or may be a mixture of at least two materials selected from among $TiO_2$, ZnO, $Al_2O_3$, $SiO_2$, and hollow sphere silica.

The first light control part CCP1, the second light control part CCP2, and the third light control part CCP3 each may include base resins BR1, BR2, and BR3 in which the quantum dots QD1 and QD2 and the scatterer SP are dispersed. In an embodiment, the first light control part CCP1 may include the first quantum dot QD1 and the scatterer SP dispersed in a first base resin BR1, the second light control part CCP2 may include the second quantum dot QD2 and the scatterer SP dispersed in a second base resin BR2, and the third light control part CCP3 may include the scatterer SP dispersed in a third base resin BR3. The base resins BR1, BR2, and BR3 are media in which the quantum dots QD1 and QD2 and the scatterer SP are dispersed, and may be formed of various suitable resin compositions, which may be generally referred to as a binder. For example, the base resins BR1, BR2, and BR3 may be acrylic-based resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may be the same as or different from each other.

The light control layer CCL may include a barrier layer BFL1. The barrier layer BFL1 may serve to prevent or reduce the penetration of moisture and/or oxygen (hereinafter may be referred to as "moisture/oxygen"). The barrier layer BFL1 may block or reduce exposure of the light control parts CCP1, CCP2 and CCP3 to moisture/oxygen. The barrier layer BFL1 may cover the light control parts CCP1, CCP2, and CCP3. In addition, the barrier layer BFL2 may be provided between the light control parts CCP1, CCP2, and CCP3 and the color filter layer CFL.

The barrier layers BFL1 and BFL2 may include at least one inorganic layer. In some embodiments, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. The barrier layers BFL1 and BFL2 may further include an organic film. The barrier layers BFL1 and BFL2 may be formed of a single layer or a plurality of layers.

In the display device DD of an embodiment, the color filter layer CFL may be on the light control layer CCL. For example, the color filter layer CFL may be directly on the light control layer CCL. In this case, the barrier layer BFL2 may be omitted.

The color filter layer CFL may include filters CF1, CF2, and CF3. The color filter layer CFL may include a first filter CF1 configured to transmit the second color light, a second filter CF2 configured to transmit the third color light, and a third filter CF3 configured to transmit the first color light. For example, the first filter CF1 may be a red filter, the second filter CF2 may be a green filter, and the third filter CF3 may be a blue filter. The filters CF1, CF2, and CF3 each may include a polymeric photosensitive resin and a pigment and/or dye. The first filter CF1 may include a red pigment and/or dye, the second filter CF2 may include a green pigment and/or dye, and the third filter CF3 may include a blue pigment and/or dye.

Embodiments of the present disclosure are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

Furthermore, in an embodiment, the first filter CF1 and the second filter CF2 may be a yellow filter. The first filter CF1 and the second filter CF2 may not be separated but be provided as one filter. The first to third filters CF1, CF2, and CF3 may correspond to the red light emitting region PXA-R, the green light emitting region PXA-G, and the blue light emitting region PXA-B, respectively.

A base substrate BL may be on the color filter layer CFL. The base substrate BL may be a member which provides a base surface that the color filter layer CFL, the light control layer CCL, and the like are on. The base substrate BL may be a glass substrate, a metal substrate, a plastic substrate, etc. However, embodiments of the present disclosure are not limited thereto, and the base substrate BL may be an inorganic layer, an organic layer, or a composite material layer. In addition, unlike the configuration illustrated, in an embodiment, the base substrate BL may be omitted.

Figure 8:
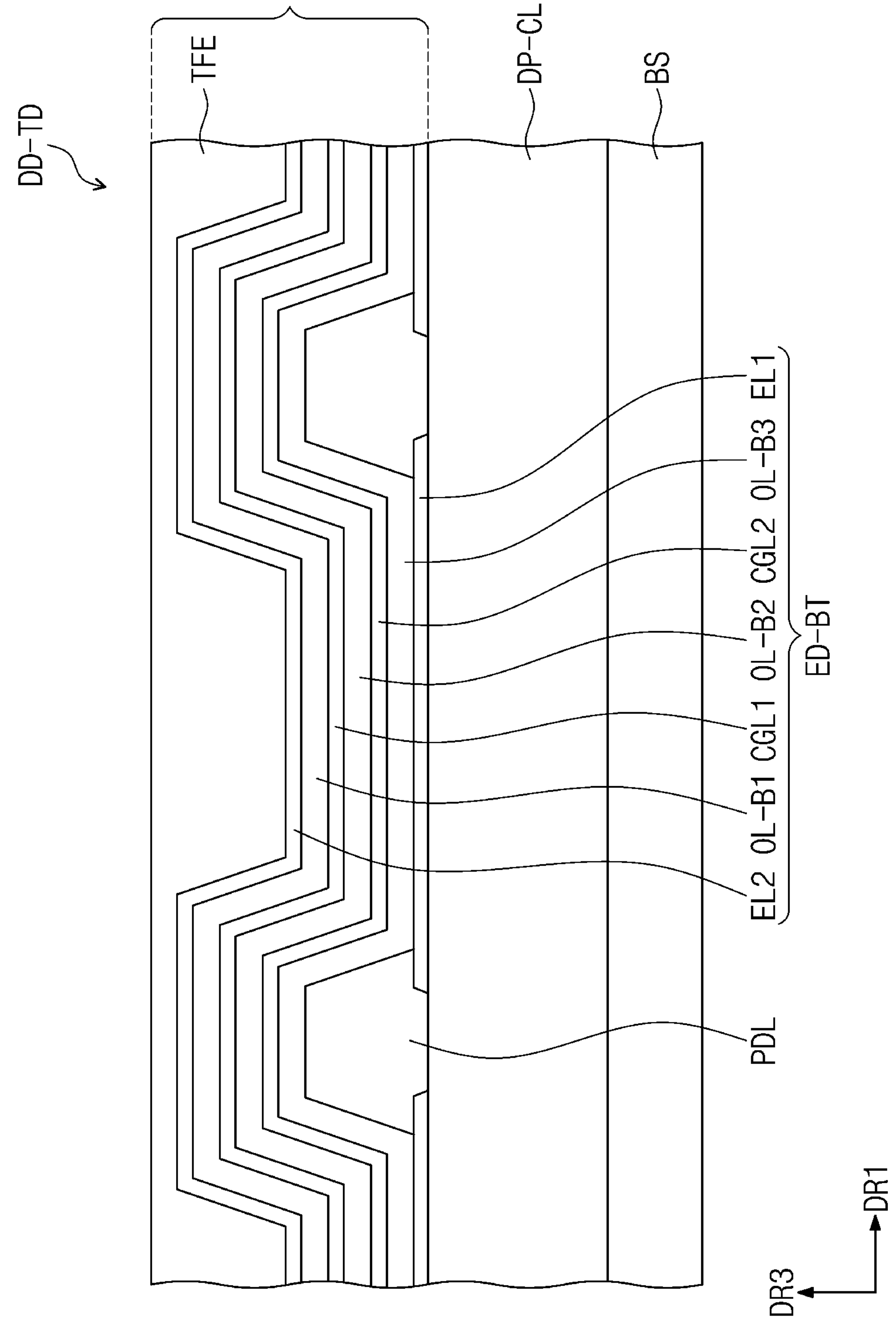
FIG. 8 is a cross-sectional view illustrating a display device according to an embodiment of the present disclosure.

FIG. 8 is a cross-sectional view illustrating a portion of a display device according to an embodiment of the present disclosure. FIG. 8 illustrates a cross-sectional view of a part corresponding to the display panel DP of FIG. 7. In the display device DD-TD of an embodiment, the light emitting element ED-BT may include a plurality of light emitting structures OL-B1, OL-B2, and OL-B3. The light emitting element ED-BT may include a first electrode EL1 and a second electrode EL2 which face each other, and the plurality of light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR with the emission layer EML (FIG. 7) therebetween. In some embodiments, the light emitting element ED-BT included in the display device DD-TD of an embodiment may be a light emitting element having a tandem structure and including a plurality of emission layers.

In an embodiment illustrated in FIG. 8, all light beams respectively emitted from the light emitting structures OL-B1, OL-B2, and OL-B3 may be blue light. However, embodiments of the present disclosure are not limited thereto, and the light beams respectively emitted from the light emitting structures OL-B1, OL-B2, and OL-3 may have wavelength ranges different from each other. For example, the light emitting element ED-BT including the plurality of light emitting structures OL-B1, OL-B2 and OL-B3 which emit light beams having wavelength ranges different from each other may emit white light.

A charge generation layers CGL1 and CGL2 may be between two of the neighboring light emitting structures OL-B1, OL-B2, and OL-B3. The charge generation layers CGL1 and CGL2 may include a p-type charge generation layer and/or an n-type charge generation layer.

Figure 9:
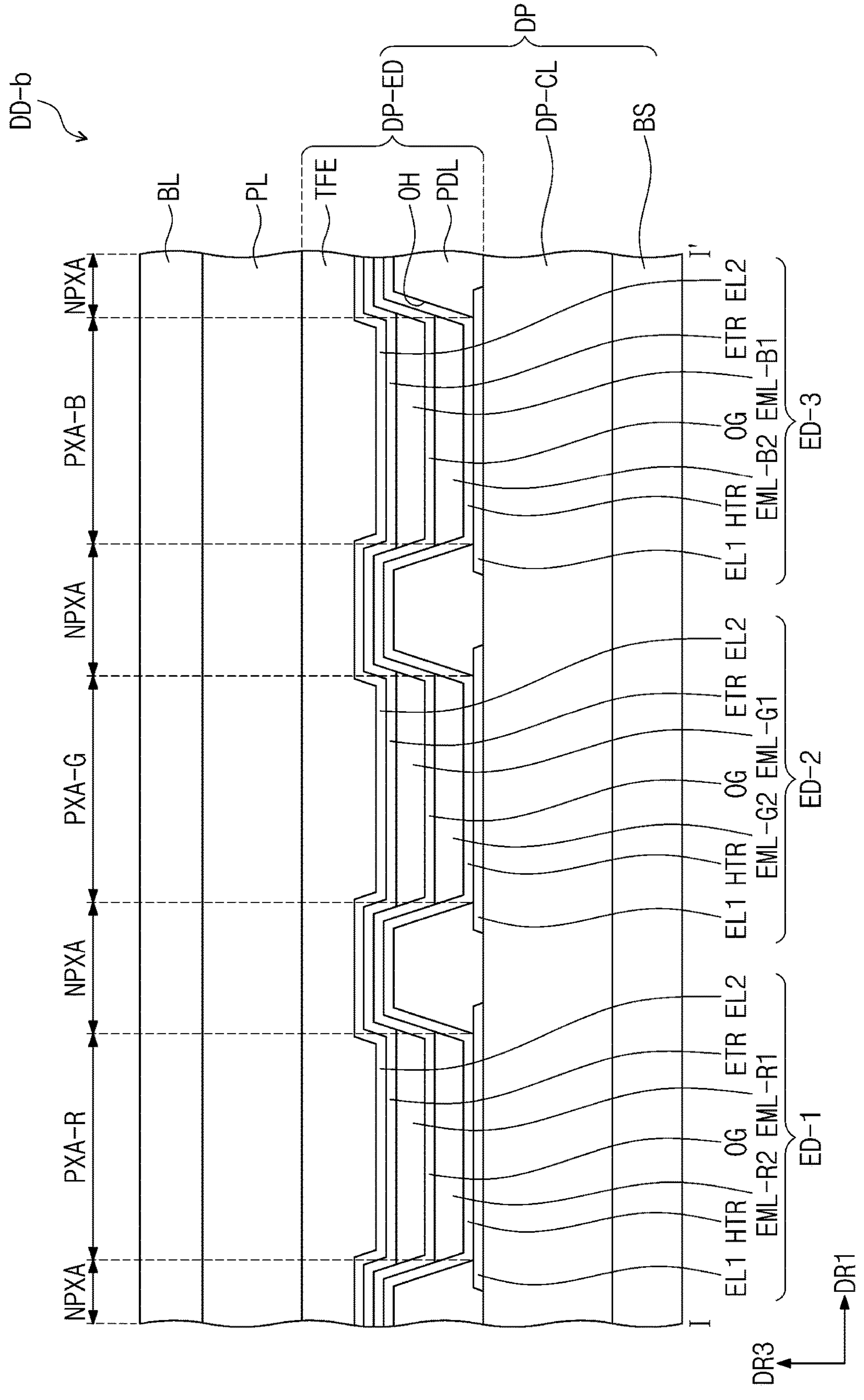
FIG. 9 is a cross-sectional view illustrating a display device according to an embodiment of the present disclosure.

Referring to FIG. 9, the display device DD-b according to an embodiment may include light emitting elements ED-1, ED-2, and ED-3 in which two emission layers are stacked. Compared to the display device DD of an embodiment illustrated in FIG. 2, an embodiment illustrated in FIG. 9 has a difference in that the first to third light emitting elements ED-1, ED-2, and ED-3 each include two emission layers stacked in the thickness direction. In each of the first to third light emitting elements ED-1, ED-2, and ED-3, the two emission layers may emit light in the same wavelength region.

The first light emitting element ED-1 may include a first red emission layer EML-R1 and a second red emission layer EML-R2. The second light emitting element ED-2 may include a first green emission layer EML-G1 and a second green emission layer EML-G2. The third light emitting element ED-3 may include a first blue emission layer EML-B1 and a second blue emission layer EML-B2. An emission auxiliary part OG may be between the first red emission layer EML-R1 and the second red emission layer EML-R2, between the first green emission layer EML-G1 and the second green emission layer EML-G2, and between the first blue emission layer EML-B1 and the second blue emission layer EML-B2.

The emission auxiliary part OG may include a single layer or a multilayer. The emission auxiliary part OG may include a charge generation layer. For example, the emission auxiliary part OG may include an electron transport region, a charge generation layer, and a hole transport region that are sequentially stacked. The emission auxiliary part OG may be provided as a common layer in the whole of the first to third light emitting elements ED-1, ED-2, and ED-3. However, embodiments of the present disclosure are not limited thereto, and the emission auxiliary part OG may be provided by being patterned within the openings OH defined in the pixel defining film PDL.

The first red emission layer EML-R1, the first green emission layer EML-G1, and the first blue emission layer EML-B1 may be between the hole transport region HTR and the emission auxiliary part OG. The second red emission layer EML-R2, the second green emission layer EML-G2, and the second blue emission layer EML-B2 may be between the emission auxiliary part OG and the electron transport region ETR.

In some embodiments, the first light emitting element ED-1 may include the first electrode EL1, the hole transport region HTR, the second red emission layer EML-R2, the emission auxiliary part OG, the first red emission layer EML-R1, the electron transport region ETR, and the second electrode EL2 that are sequentially stacked. The second light emitting element ED-2 may include the first electrode EL1, the hole transport region HTR, the second green emission layer EML-G2, the emission auxiliary part OG, the first green emission layer EML-G1, the electron transport region ETR, and the second electrode EL2 that are sequentially stacked. The third light emitting element ED-3 may include the first electrode EL1, the hole transport region HTR, the second blue emission layer EML-B2, the emission auxiliary part OG, the first blue emission layer EML-B1, the electron transport region ETR, and the second electrode EL2 that are sequentially stacked.

An optical auxiliary layer PL may be on the display element layer DP-ED. The optical auxiliary layer PL may include a polarizing layer. The optical auxiliary layer PL may be on the display panel DP and control reflected light in the display panel DP due to external light. Unlike the configuration illustrated, the optical auxiliary layer PL in the display device according to an embodiment may be omitted.

Figure 10:
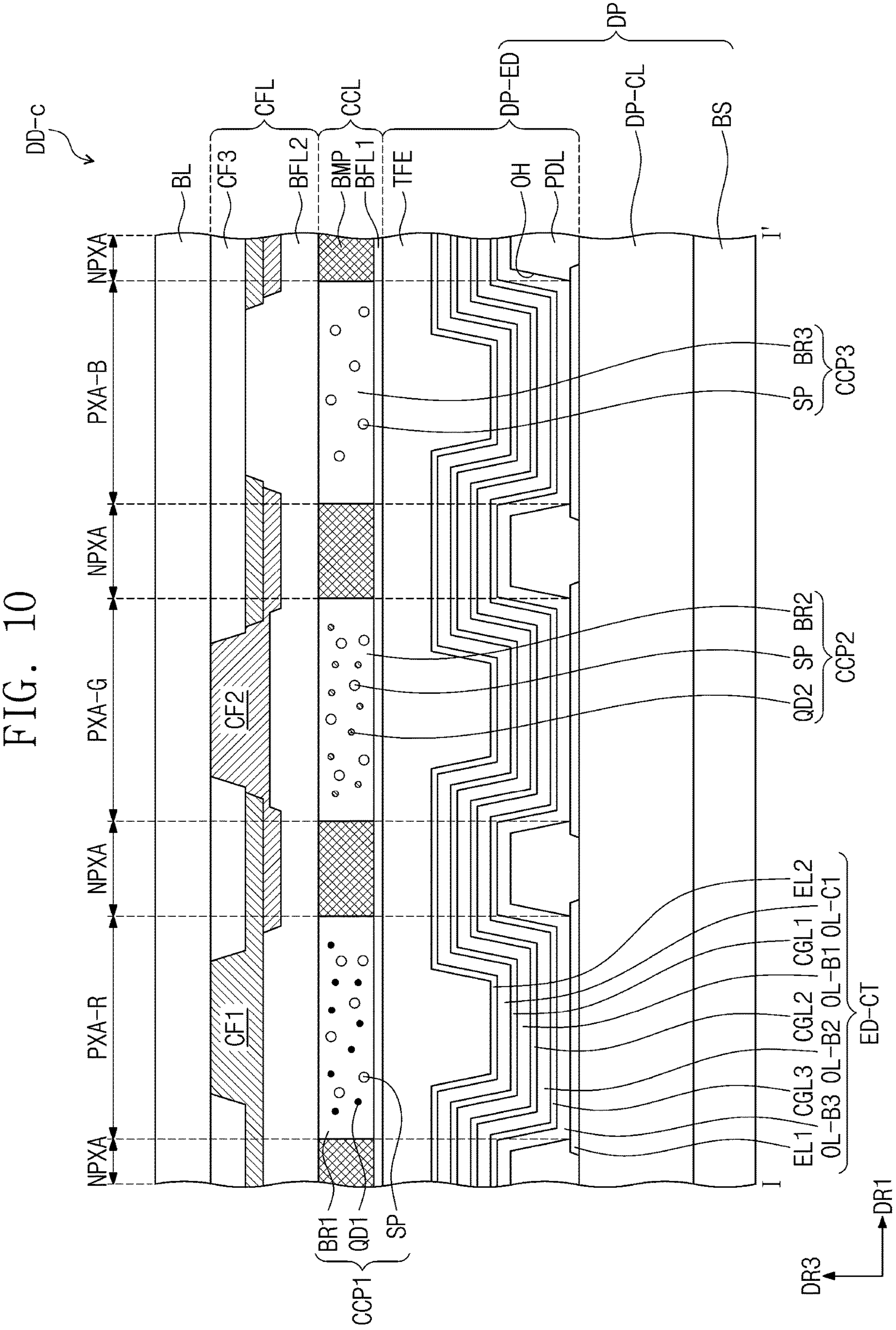
FIG. 10 is a cross-sectional view illustrating a display device according to an embodiment of the present disclosure.

Unlike FIGS. 8 and 9, FIG. 10 illustrates that a display device DD-c includes four light emitting structures OL-B1, OL-B2, OL-B3, and OL-C1. A light emitting element ED-CT may include a first electrode EL1 and a second electrode EL2 which face each other, and first to fourth light emitting structures OL-B1, OL-B2, OL-B3, and OL-C1 that are sequentially stacked in the thickness direction between the first electrode EL1 and the second electrode EL2.

Charge generation layers CGL1, CGL2, and CGL3 may be between the first to fourth light emitting structures OL-B1, OL-B2, OL-B3, and OL-C1. The charge generation layers CGL1, CGL2 and CGL3 may include a p-type charge generation layer and/or an n-type charge generation layer. Among the four light emitting structures, the first to third light emitting structures OL-B1, OL-B2, and OL-B3 may emit blue light, and the fourth light emitting structure OL-C1 may emit green light. However, embodiments of the present disclosure are not limited thereto, and the first to fourth light emitting structures OL-B1, OL-B2, OL-B3, and OL-C1 may emit light beams in different wavelength regions.

Hereinafter, with reference to Examples and Comparative Examples, an amine compound according to embodiments of the present disclosure and a light emitting element of embodiments of the present disclosure will be described in more detail. In addition, the Examples described below are only illustrations to assist the understanding of the present disclosure, and the scope of the present disclosure is not limited thereto.

EXAMPLES

1. Synthesis of Amine Compound of Examples

First, a synthetic method of an amine compound according to the present embodiment will be described in more detail by illustrating the synthetic methods of Compounds 15, 18, 29, 30, 43, 48, 53, 60, 71, 74, 85, 89, 213, 217, 227, and 231. In addition, in the following descriptions, the synthetic method of the amine compound is provided as an example, but the synthetic method of the compound according to an embodiments of the present disclosure is not limited to the Examples below.

In the synthetic method of the amine compound described below, room temperature is from about 20° C. to about 29° C. In the synthetic method of the amine compound described below, a yield is a ratio of the mole number of products to the mole number of reactants when the weight of the reactants is converted to the mole number and the weight of the products is converted to the mole number. In the synthetic method of the amine compound described below, "RT" means room temperature.

(1) Synthesis of Compound 15

Amine Compound 15 according to an example may be synthesized by, for example, the steps shown in Reaction Scheme 1 below:

Reaction Scheme 1

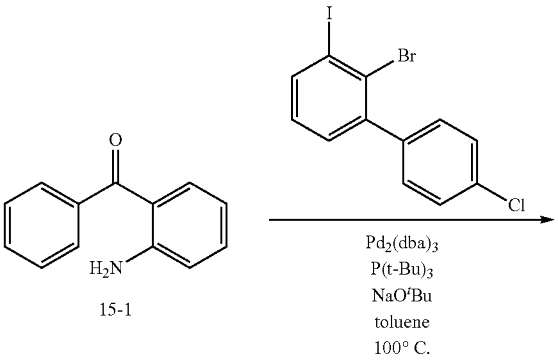

15-1

-continued

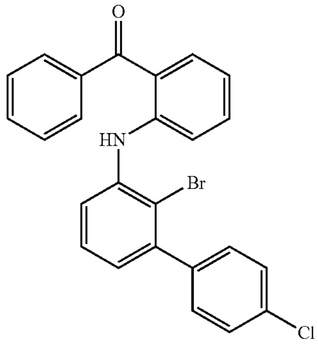

15-2

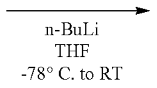

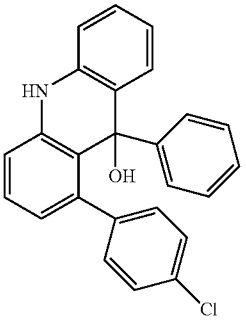

15-3

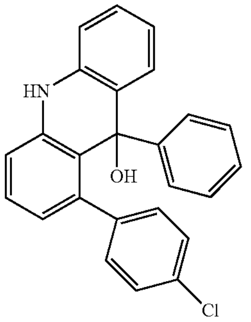

15-3

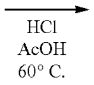

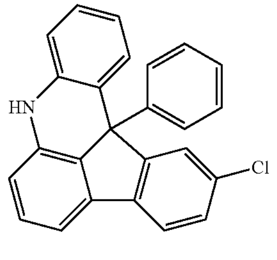

15-4

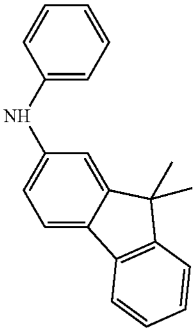

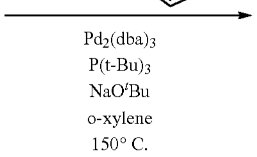

-continued

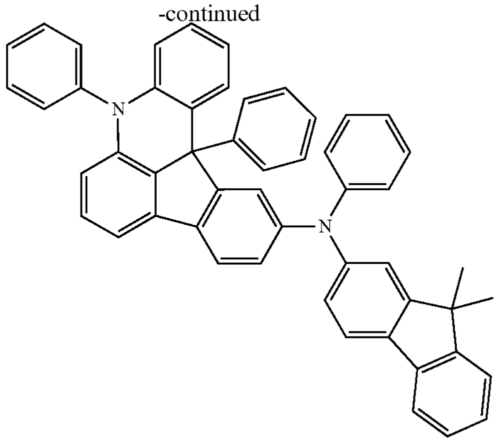

15

Synthesis of Intermediate 15-2

Intermediate 15-1 (1.97 g), 2-bromo-4'-chloro-3-iodo-1,1'-biphenyl (3.93 g), $Pd_2(dba)_3$ (0.46 g), $P(t\text{-}Bu)_3$ (0.21 g) and $NaO^tBu$ (2.44 g) were dissolved in toluene (50 mL) and then the resulting mixture was stirred at about 100° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 15-2 (3.47 g, yield: 75%).

Synthesis of Intermediate 15-3

A solution, in which Intermediate 15-2 (4.62 g) was dissolved in tetrahydrofuran (THF, 50 mL), was stirred at about −78° C. n-BuLi (2.5 M in hexane, 8 mL) was slowly added dropwise to this solution at about −78° C. This solution was stirred at room temperature for about 12 hours. This reaction solution was quenched with water and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 15-3 (2.15 g, yield: 56%).

Synthesis of Intermediate 15-4

Intermediate 15-3 (3.83 g) was dissolved in HCl (6 mL) and acetic acid (AcOH, 30 mL), and then the resulting mixture was stirred at about 60° C. for about 6 hours. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 15-4 (2.92 g, yield: 80%).

Synthesis of Compound 15

Intermediate 15-4 (3.65 g), 9,9-dimethyl-N-phenyl-9H-fluoren-2-amine (2.85 g), $Pd_2(dba)_3$ (0.46 g), $P(t\text{-}Bu)_3$ (0.21 g), and NaO$^t$Bu (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 15 (5.31 g, yield: 77%).

(2) Synthesis of Compound 18

Amine Compound 18 according to an example may be synthesized by, for example, the steps shown in Reaction Scheme 2 below:

Reaction Scheme 2

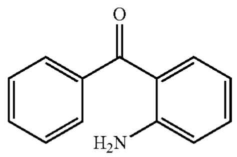

15-1

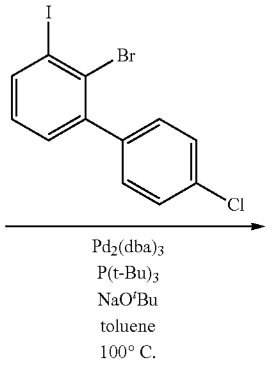

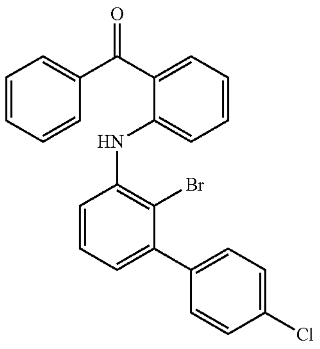

15-2

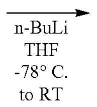

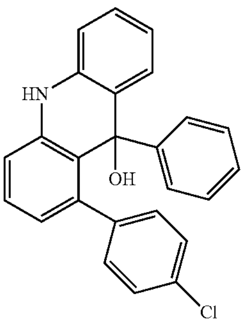

15-3

-continued

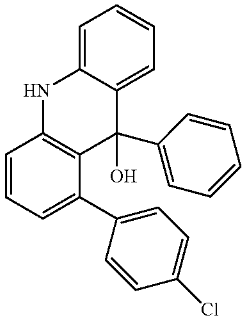

15-3

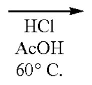

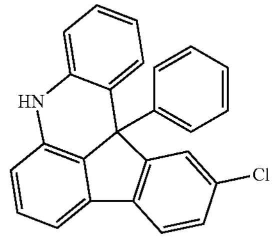

15-4

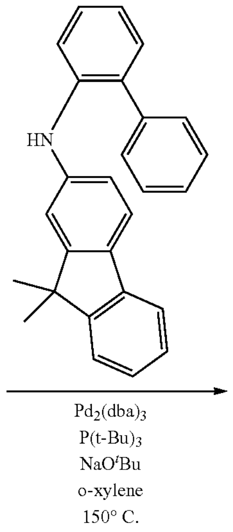

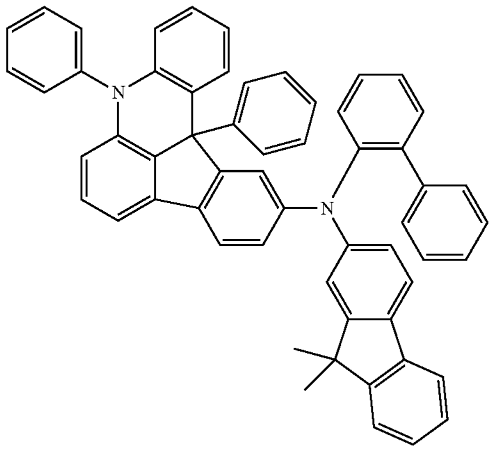

18

Synthesis of Compound 18

Intermediate 15-4 (3.65 g), N-([1,1'-biphenyl]-2-yl)-9,9-dimethyl-9H-fluoren-2-amine (3.61 g), $Pd_2(dba)_3$ (0.46 g), $P(t\text{-}Bu)_3$ (0.21 g), and NaO$^t$Bu (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 18 (6.35 g, yield: 83%).

(3) Synthesis of Compound 29

Amine Compound 29 according to an example may be synthesized by, for example, the steps shown in Reaction Scheme 3 below:

Reaction Scheme 3

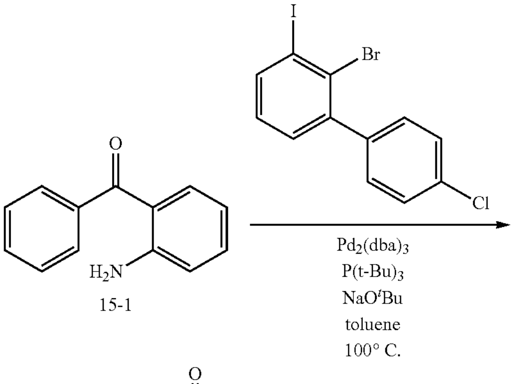

15-1

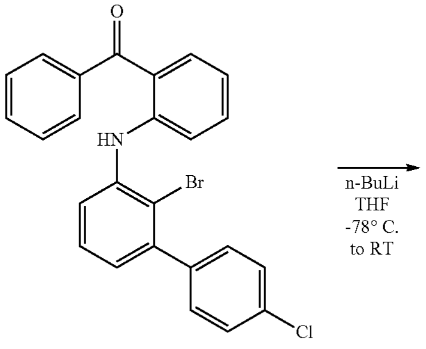

15-2

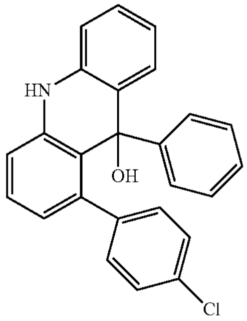

15-3

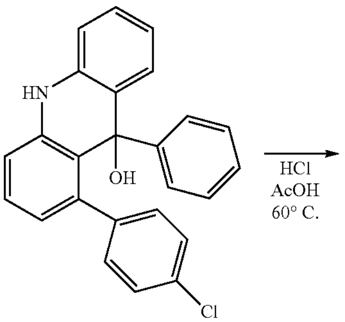

15-3

-continued

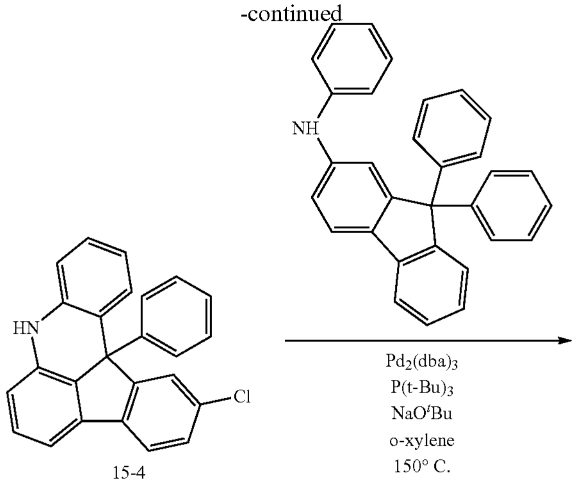

15-4

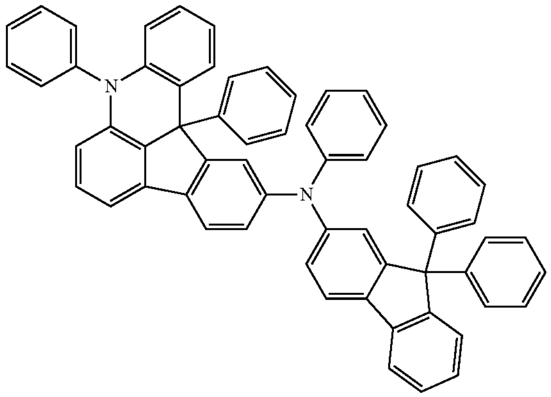

29

Synthesis of Compound 29

Intermediate 15-4 (3.65 g), N,9,9-triphenyl-9H-fluoren-2-amine (4.09 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 29 (5.57 g, yield: 78%).

(4) Synthesis of Compound 30

Amine Compound 30 according to an example may be synthesized by, for example, the steps shown in Reaction Scheme 4 below:

Reaction Scheme 4

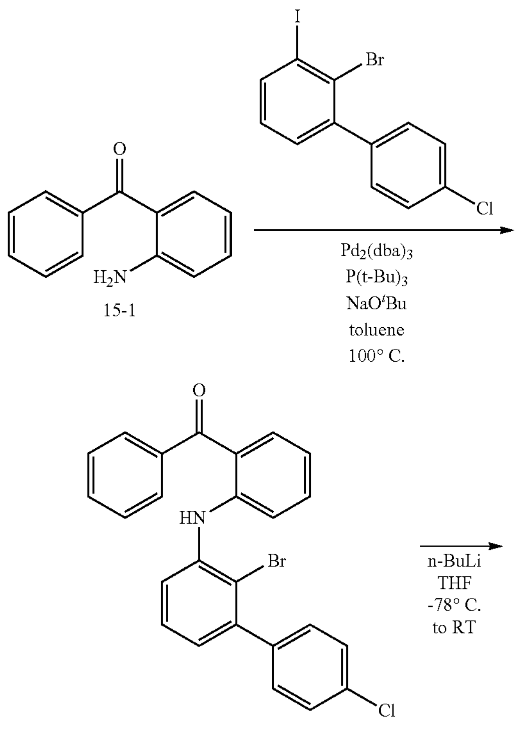

15-1

15-2

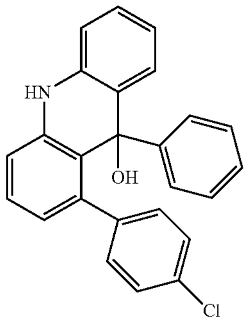

15-3

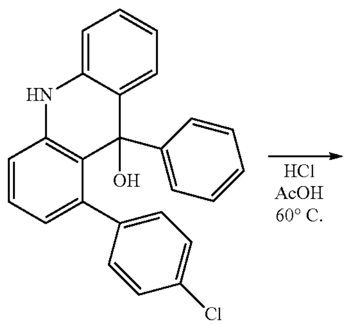

15-3

-continued

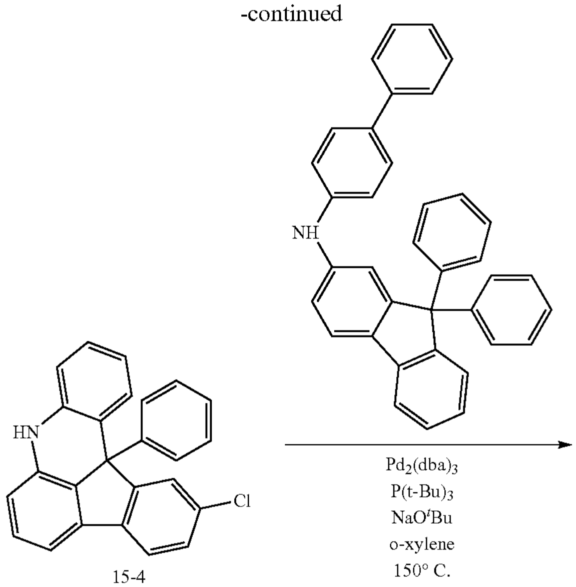

15-4

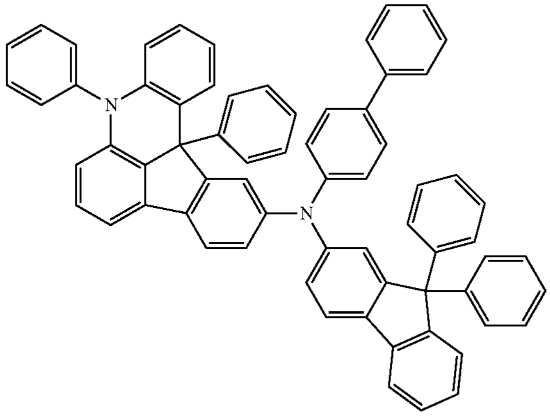

30

Synthesis of Compound 30

Intermediate 15-4 (3.65 g), N-([1,1'-biphenyl]-4-yl)-9,9-diphenyl-9H-fluoren-2-amine (4.85 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 30 (6.77 g, yield: 76%).

(5) Synthesis of Compound 43

Amine Compound 43 according to an example may be synthesized by, for example, the steps shown in Reaction Scheme 5 below:

Reaction Scheme 5

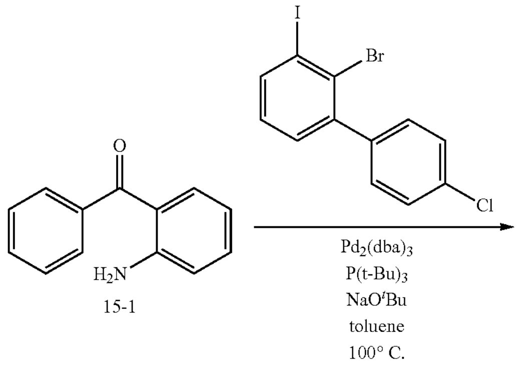

15-1

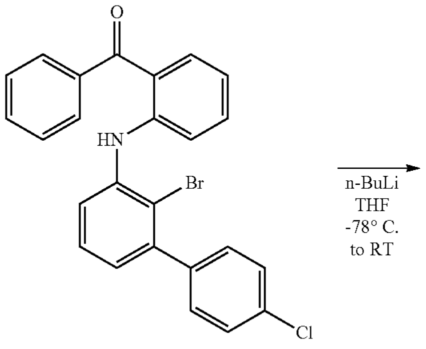

15-2

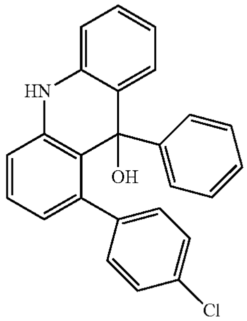

15-3

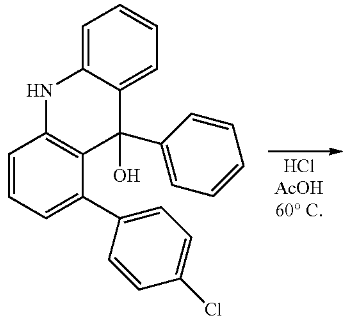

15-3

-continued

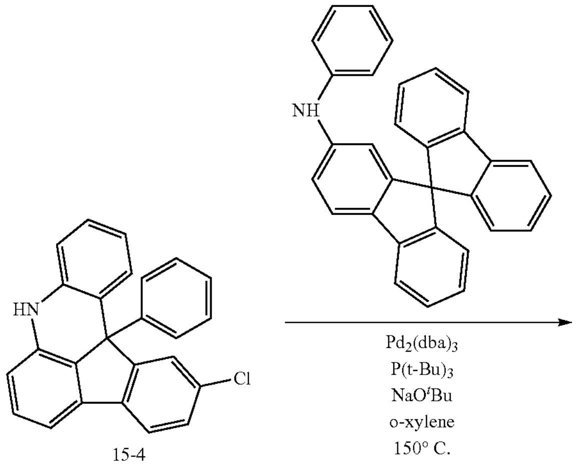

15-4

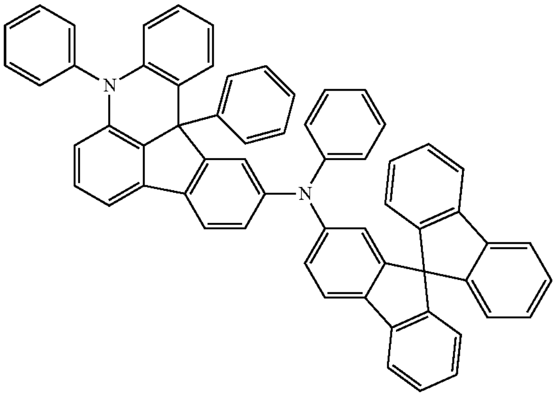

43

Synthesis of Compound 43

Intermediate 15-4 (3.65 g), N-phenyl-9,9'-spirobi[fluoren]-2-amine (4.07 g), $Pd_2(dba)_3$ (0.46 g), $P(t-Bu)_3$ (0.21 g), and NaO$^t$Bu (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 43 (6.99 g, yield: 86%).

(6) Synthesis of Compound 48

Amine Compound 48 according to an example may be synthesized by, for example, the steps shown in Reaction Scheme 6 below:

Reaction Scheme 6

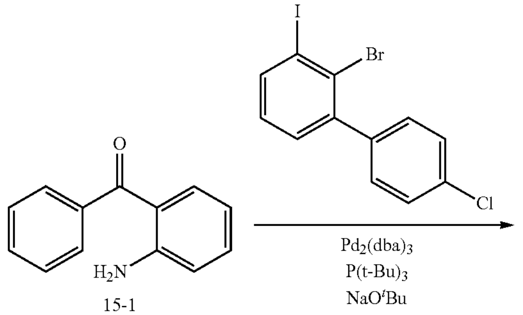

15-1

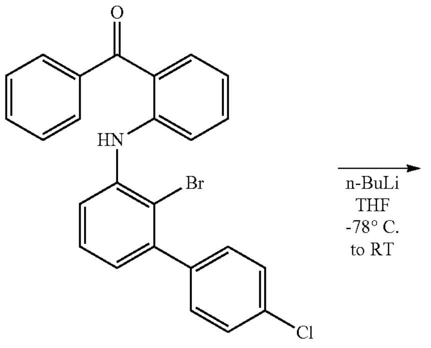

15-2

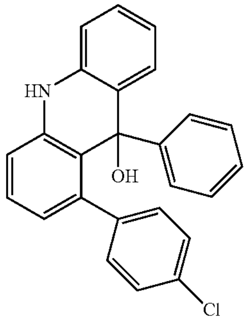

15-3

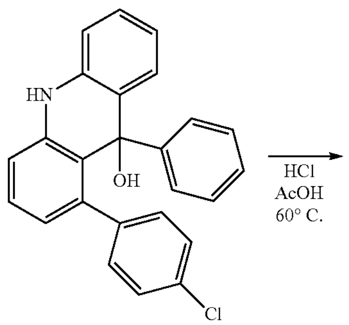

15-3

-continued

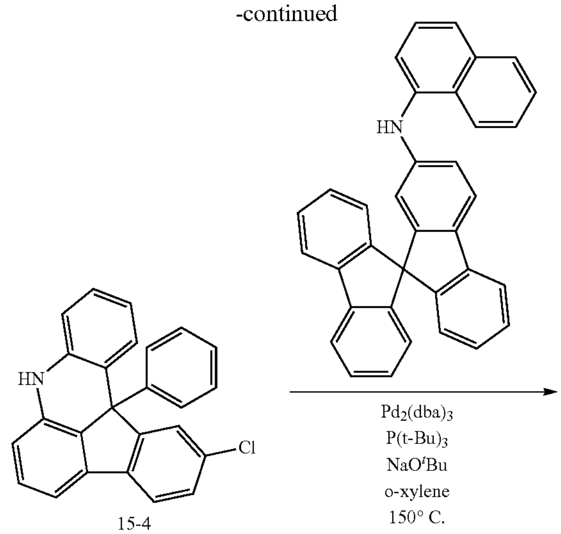

15-4

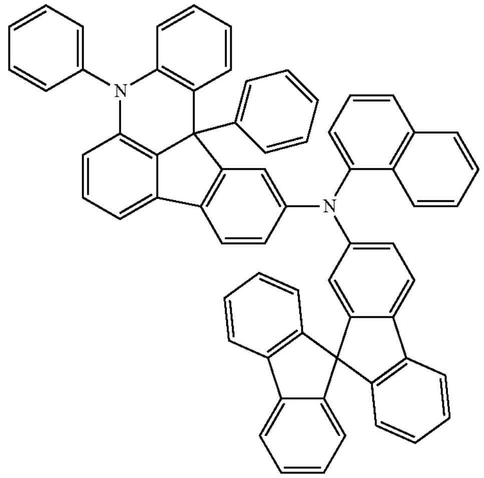

48

Synthesis of Compound 48

Intermediate 15-4 (3.65 g), N-(naphthalen-1-yl)-9,9'-spirobi[fluoren]-2-amine (4.57 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 48 (7.76 g, yield: 90%).

(7) Synthesis of Compound 53

Amine Compound 53 according to an example may be synthesized by, for example, the steps shown in Reaction Scheme 7 below:

Reaction Scheme 7

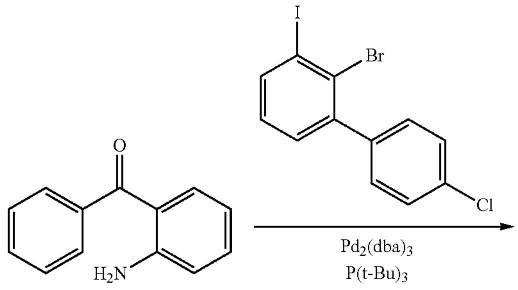

15-1

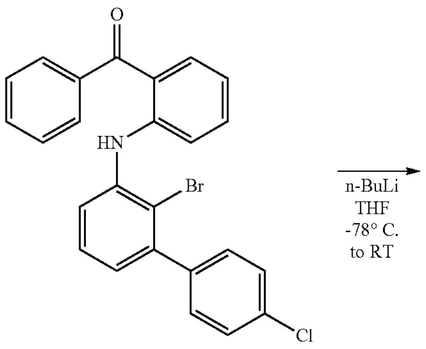

15-2

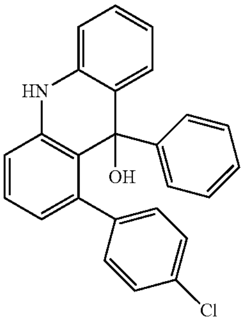

15-3

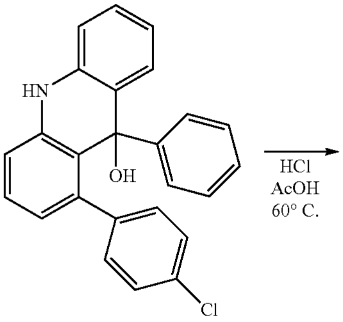

15-3

-continued

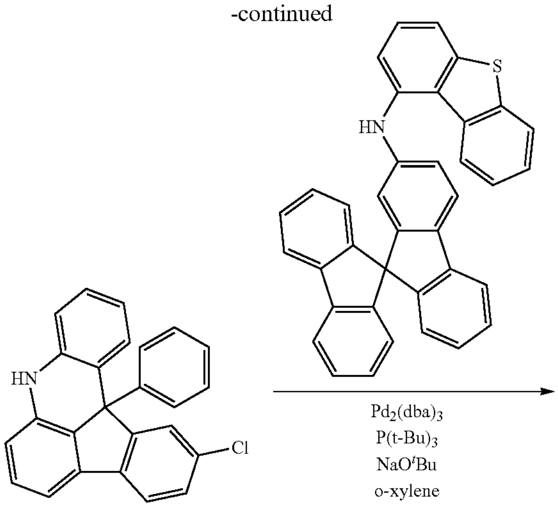

15-4

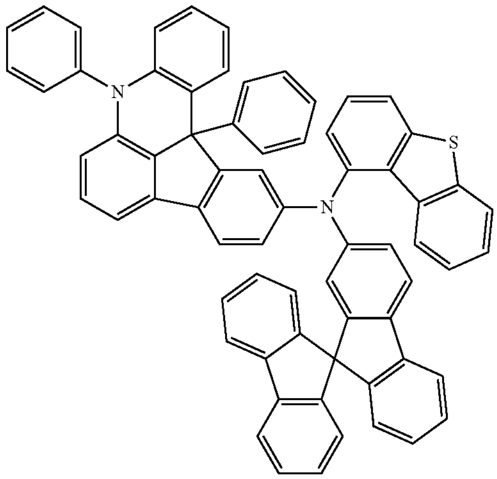

53

Synthesis of Compound 53

Intermediate 15-4 (3.65 g), N-(9,9'-spirobi[fluoren]-2-yl) dibenzo[b,d]thiophen-1-amine (5.13 g), $Pd_2(dba)_3$ (0.46 g), $P(t-Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 53 (7.44 g, yield: 81%).

(8) Synthesis of Compound 60

Amine Compound 60 according to an example may be synthesized by, for example, the steps shown in Reaction Scheme 8 below:

Reaction Scheme 8

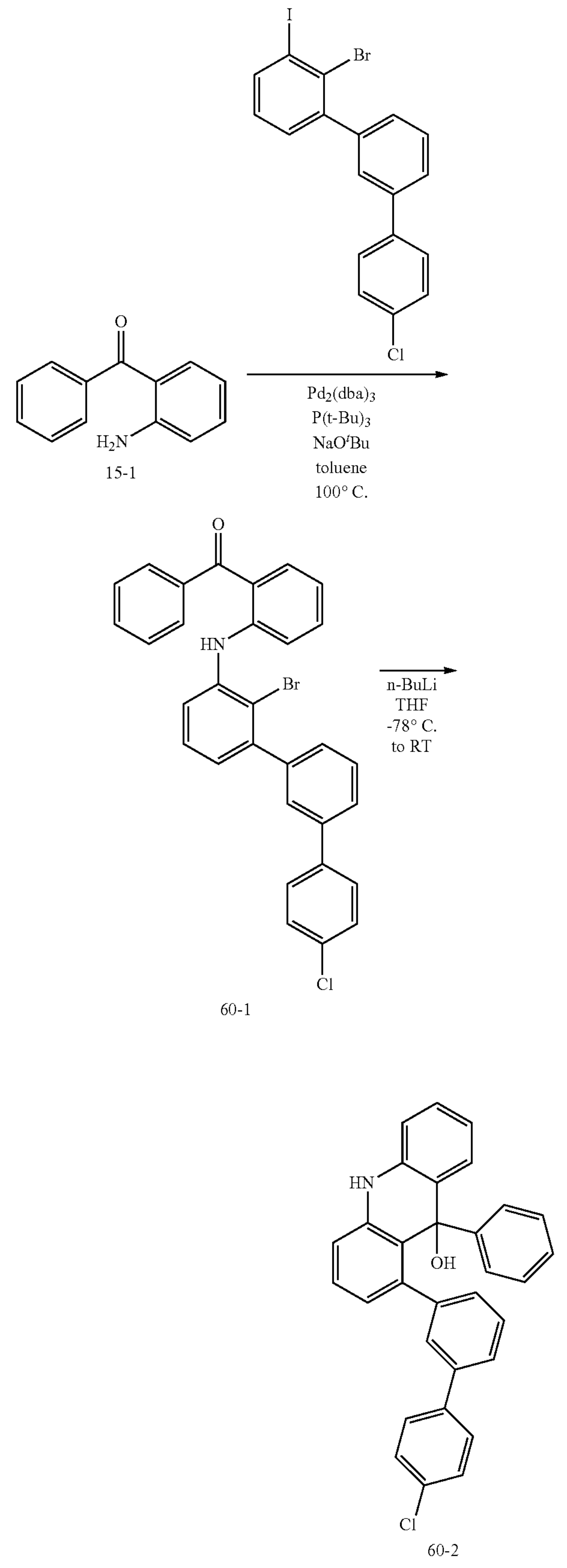

-continued

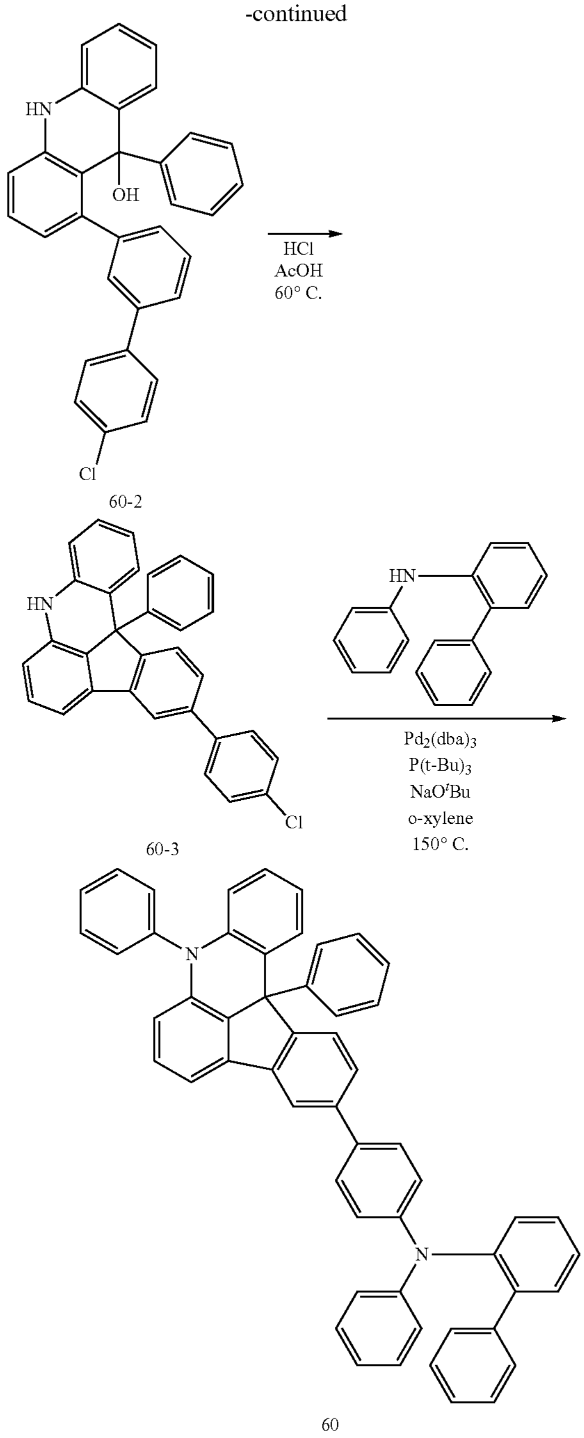

Synthesis of Intermediate 60-1

Intermediate 15-1 (1.97 g), 2-bromo-4"-chloro-3-iodo-1,1':3',1"-terphenyl (4.69 g), $Pd_2(dba)_3$ (0.46 g), $P(t\text{-}Bu)_3$ (0.21 g), and $NaO^tBu$ (2.44 g) were dissolved in toluene (50 mL) and then the resulting mixture was stirred at about 100° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 60-1 (3.87 g, yield: 72%).

Synthesis of Intermediate 60-2

A solution, in which Intermediate 60-1 (5.38 g) was dissolved in THF (50 mL), was stirred at about −78° C. n-BuLi (2.5 M in hexane, 8 mL) was slowly added dropwise to this solution at about −78° C. This solution was stirred at room temperature for about 12 hours. This reaction solution was quenched with water and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 60-2 (2.75 g, yield: 60%).

Synthesis of Intermediate 60-3

Intermediate 60-2 (4.59 g) was dissolved in HCl (6 mL) and AcOH (30 mL), and then the resulting mixture was stirred at about 60° C. for about 6 hours. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 60-3 (3.17 g, yield: 72%).

Synthesis of Compound 60

Intermediate 60-3 (4.41 g), N-phenyl-[1,1'-biphenyl]-2-amine (2.45 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 60 (5.00 g, yield: 69%).

(9) Synthesis of Compound 71

Amine Compound 71 according to an example may be synthesized by, for example, the steps shown in Reaction Scheme 9 below:

Reaction Scheme 9

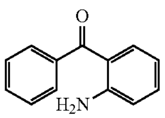

15-1

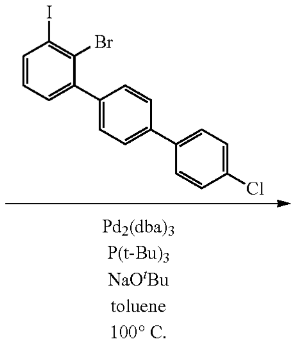

-continued

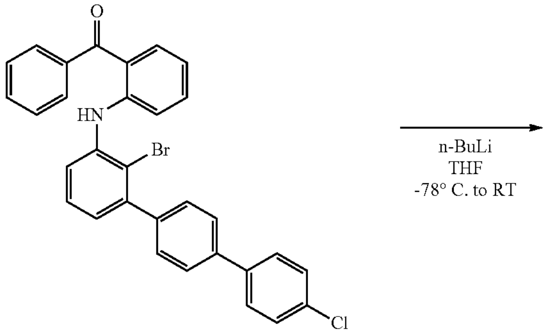

71-1

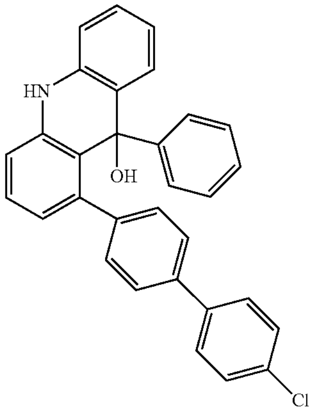

71-2

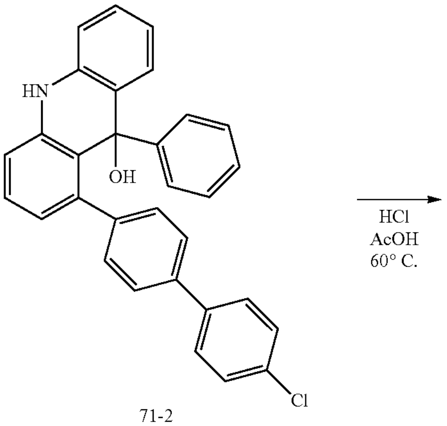

71-2

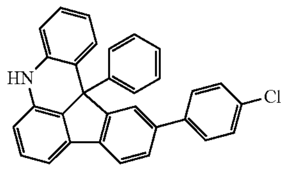

71-3

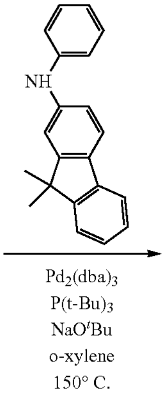

-continued

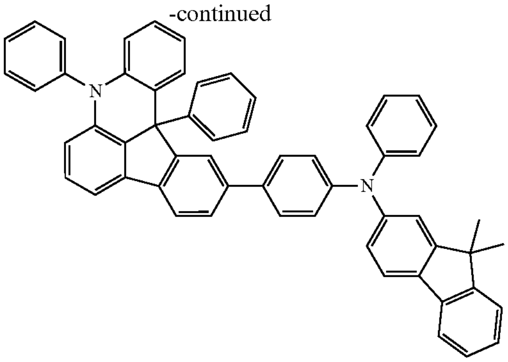

71

Synthesis of Intermediate 71-1

Intermediate 15-1 (1.97 g), 2-bromo-4"-chloro-3-iodo-1,1':4',1"-terphenyl (4.69 g), $Pd_2(dba)_3$ (0.46 g), $P(t\text{-}Bu)_3$ (0.21 g), and $NaO^tBu$ (2.44 g) were dissolved in toluene (50 mL) and then the resulting mixture was stirred at about 100° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 71-1 (4.03 g, yield: 75%).

Synthesis of Intermediate 71-2

A solution, in which Intermediate 71-1 (5.38 g) was dissolved in THF (50 mL), was stirred at about −78° C. n-BuLi (2.5 M in hexane, 8 mL) was slowly added dropwise to this solution at about −78° C. This solution was stirred at room temperature for about 12 hours. This reaction solution was quenched with water and extracted three times with ethyl ether to separate an organic layer. The separated organic layer was dried over anhydrous magnesium sulfate and distilled under reduced pressure to obtain residues. The obtained residues were separated and purified by column chromatography to obtain Intermediate 71-2 (2.75 g, yield: 60%).

Synthesis of Intermediate 71-3

Intermediate 71-2 (4.59 g) was dissolved in HCl (6 mL) and AcOH (30 mL), and then the resulting mixture was stirred at about 60° C. for about 6 hours. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 71-3 (3.17 g, yield: 72%).

Synthesis of Compound 71

Intermediate 71-3 (4.41 g), 9,9-dimethyl-N-phenyl-9H-fluoren-2-amine (2.85 g), $Pd_2(dba)_3$ (0.46 g), $P(t\text{-}Bu)_3$ (0.21 g), and $NaO^tBu$ (2.44 g) were dissolved in o-xylene (50 mL), and then stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 71 (6.28 g, yield: 82%).

(10) Synthesis of Compound 74

Amine Compound 74 according to an example may be synthesized by, for example, the steps shown in Reaction Scheme 10 below:

Reaction Scheme 10

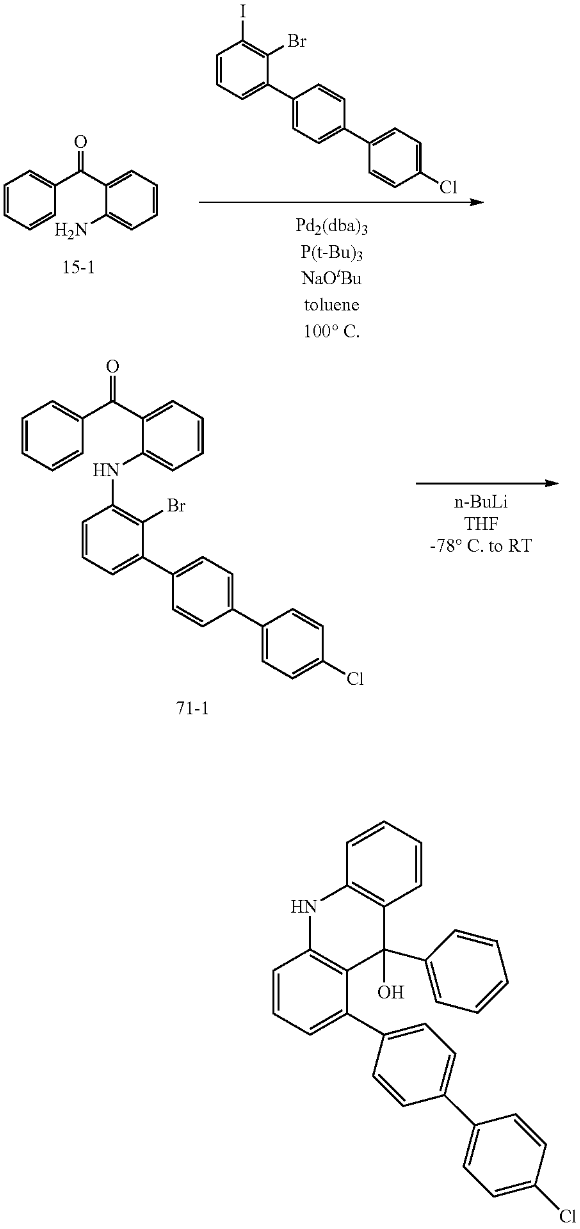

71-2

-continued

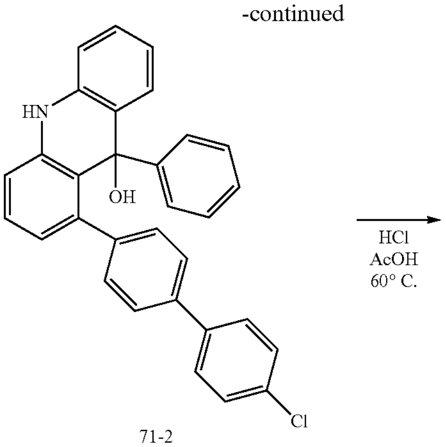

71-2

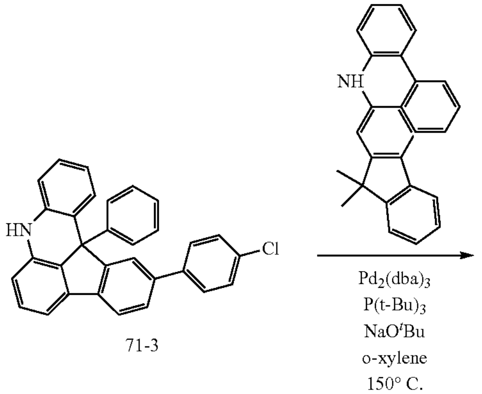

71-3

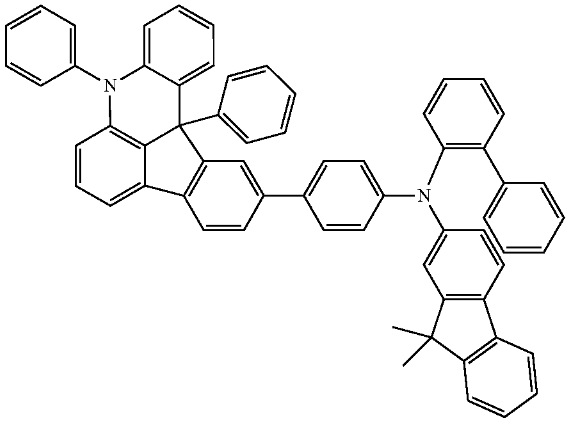

74

Synthesis of Compound 74

Intermediate 71-3 (4.41 g), N-([1,1'-biphenyl]-2-yl)-9,9-dimethyl-9H-fluoren-2-amine (3.61 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 74 (6.92 g, yield: 82%).

(11) Synthesis of Compound 85

Amine Compound 85 according to an example may be synthesized by, for example, the steps shown in Reaction Scheme 11 below:

Reaction Scheme 11

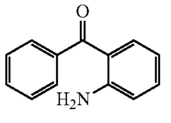

15-1

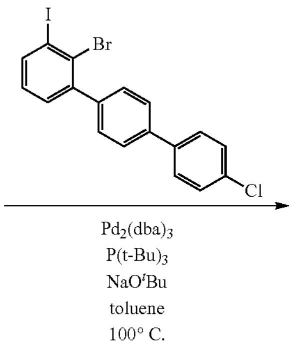

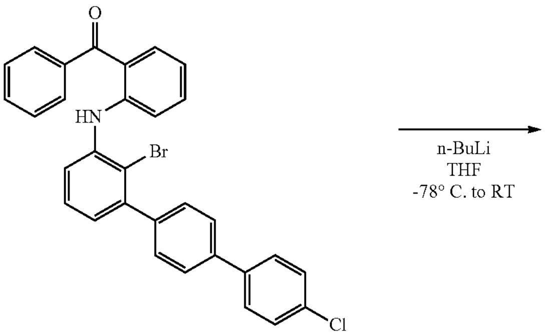

71-1

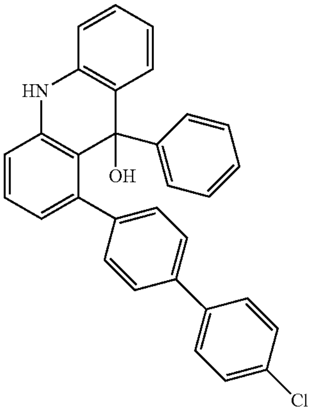

71-2

-continued

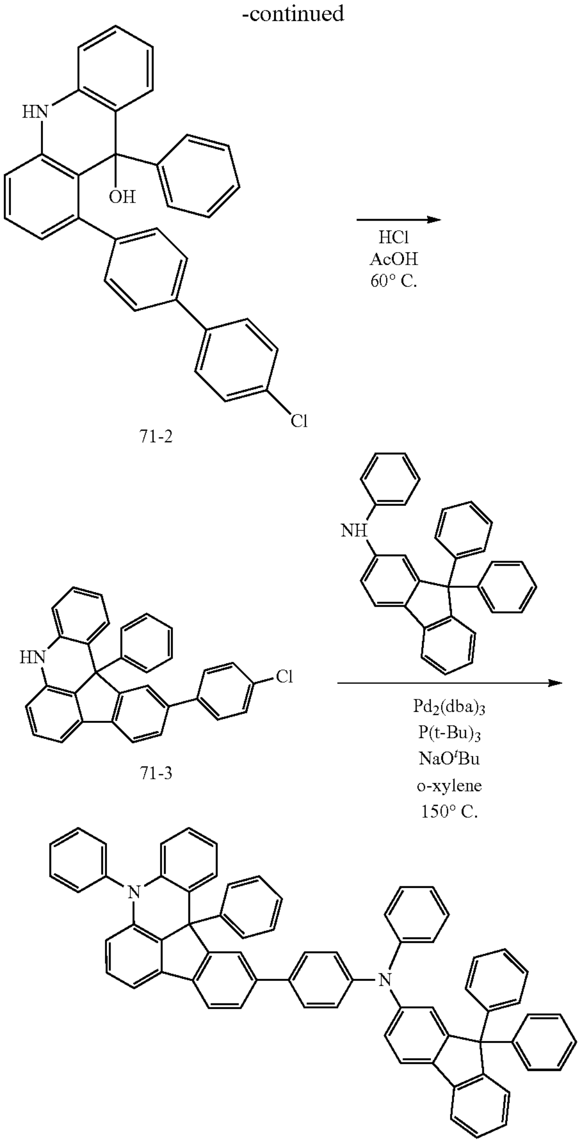

71-2

71-3

85

Synthesis of Compound 85

Intermediate 71-3 (4.41 g), N,9,9-triphenyl-9H-fluoren-2-amine (4.09 g), $Pd_2(dba)_3$ (0.46 g), $P(t-Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 85 (6.86 g, yield: 77%).

(12) Synthesis of Compound 89

Amine Compound 89 according to an example may be synthesized by, for example, the steps shown in Reaction Scheme 12 below:

Reaction Scheme 12

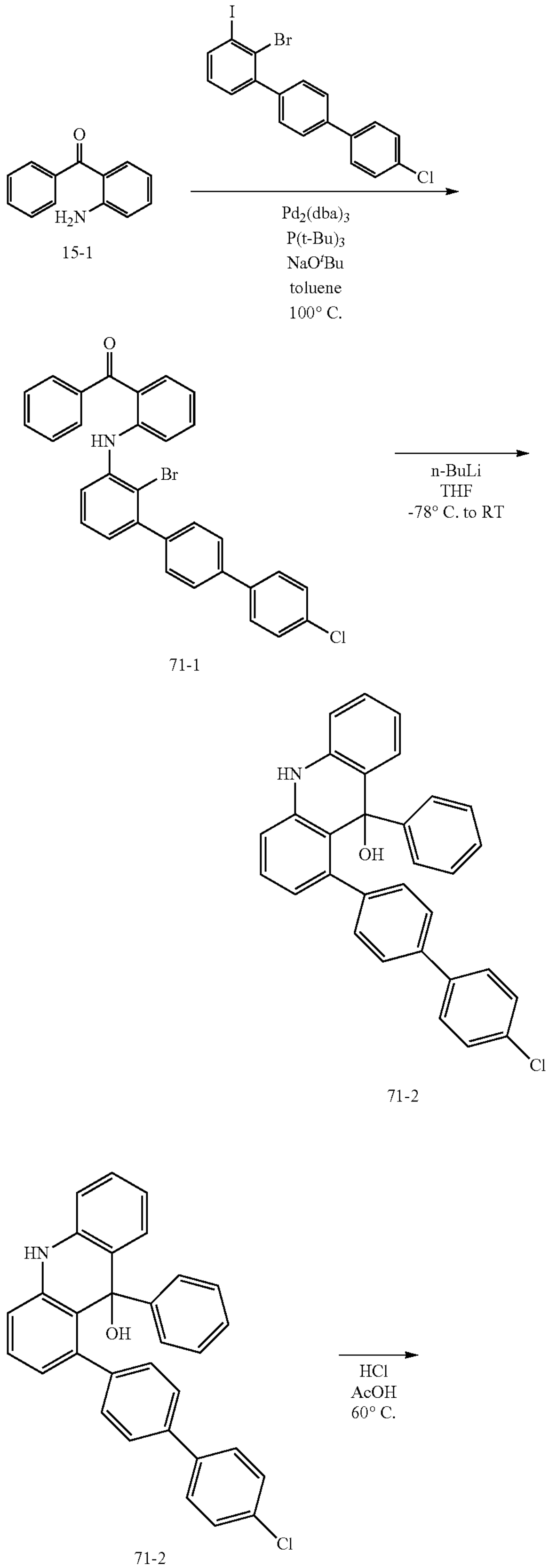

15-1

71-1

71-2

71-2

-continued

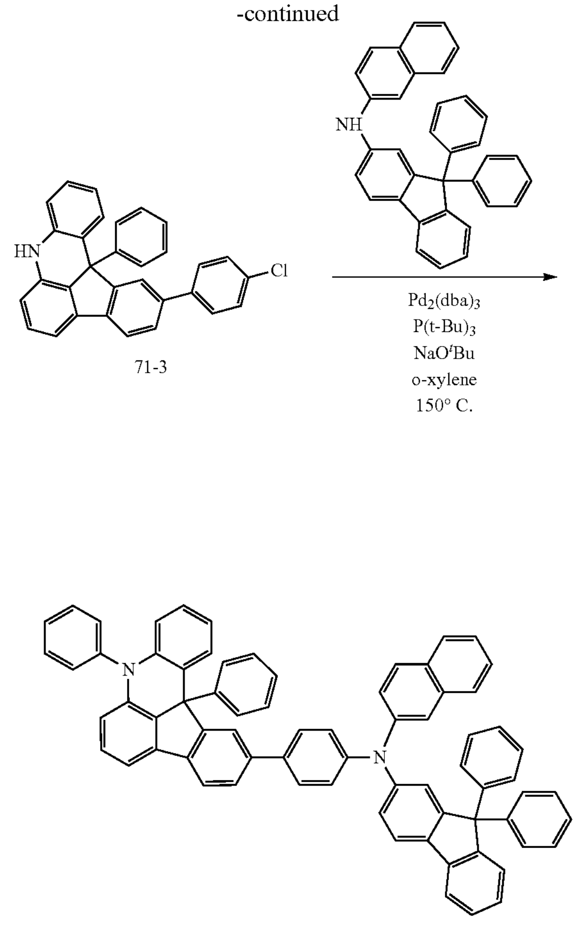

71-3

89

Synthesis of Compound 89

Intermediate 71-3 (4.41 g), N-(naphthalen-2-yl)-9,9-diphenyl-9H-fluoren-2-amine (4.59 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 89 (8.09 g, yield: 86%).

(13) Synthesis of Compound 213

Amine Compound 213 according to an example may be synthesized by, for example, the steps shown in Reaction Scheme 13 below:

Reaction Scheme 13

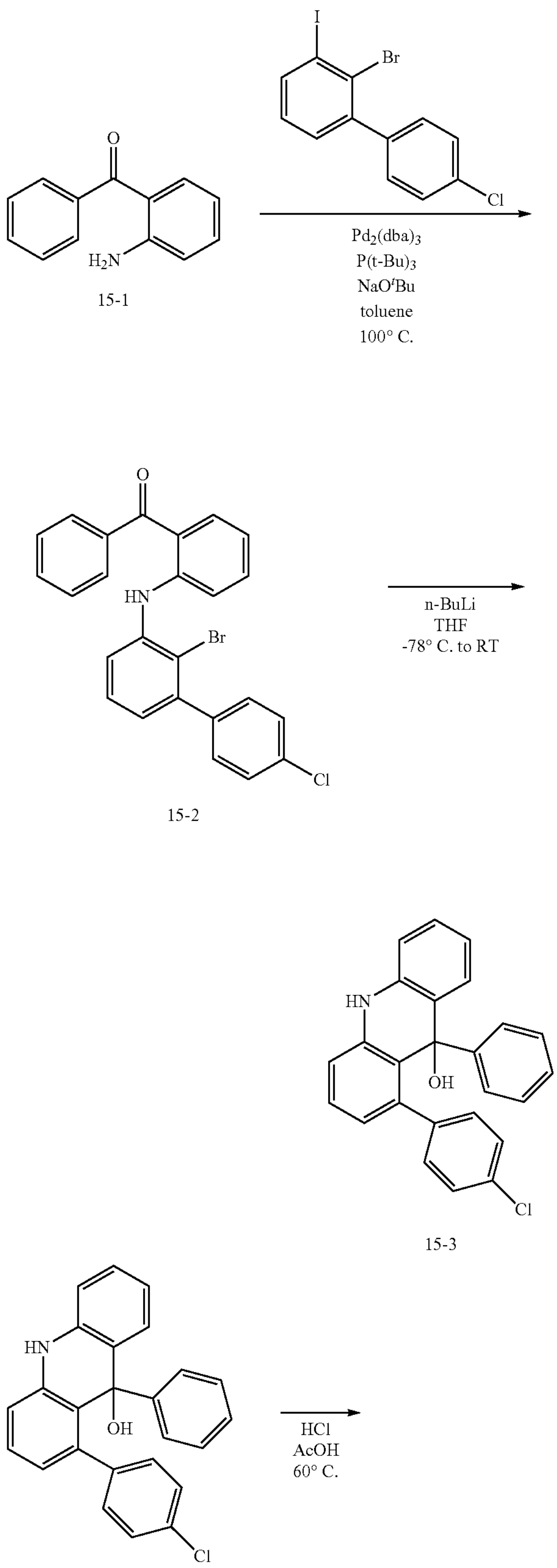

15-1

15-2

15-3

15-3

-continued

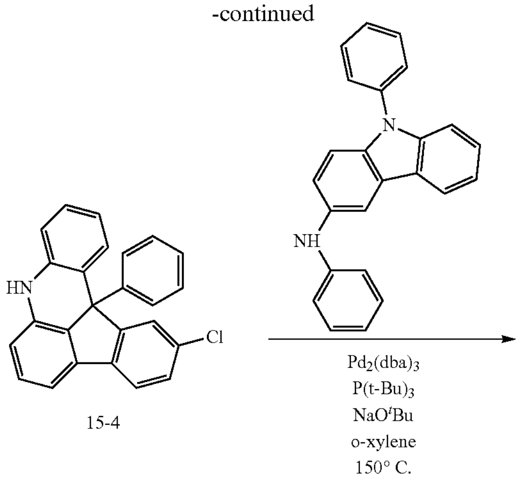

15-4

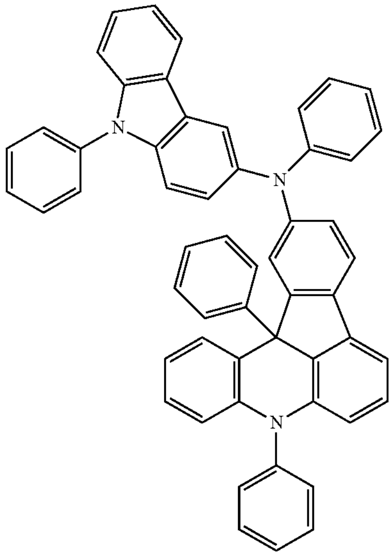

213

Synthesis of Compound 213

Intermediate 15-4 (3.65 g), N,9-diphenyl-9H-carbazol-3-amine (3.34 g), $Pd_2(dba)_3$ (0.46 g), $P(t\text{-}Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 213 (5.54 g, yield: 75%).

(14) Synthesis of Compound 217

Amine Compound 217 according to an example may be synthesized by, for example, the steps shown in Reaction Scheme 14 below:

Reaction Scheme 14

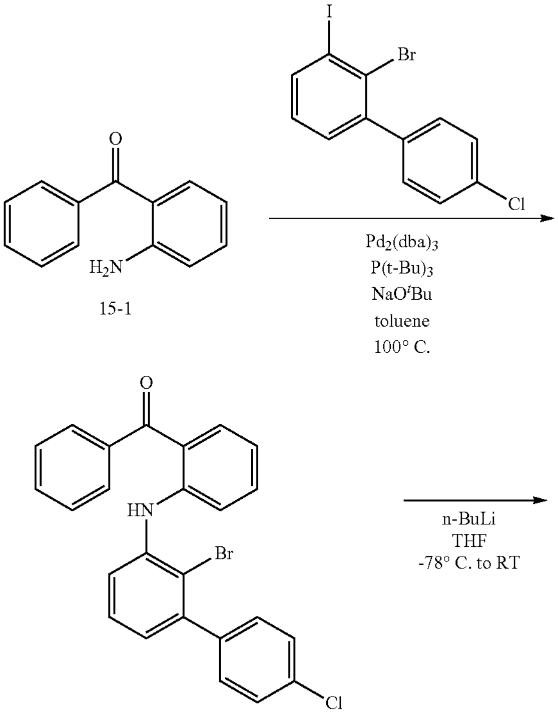

15-1

15-2

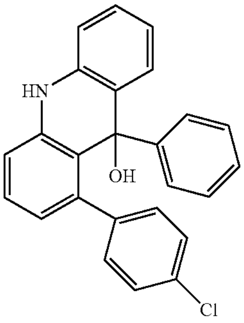

15-3

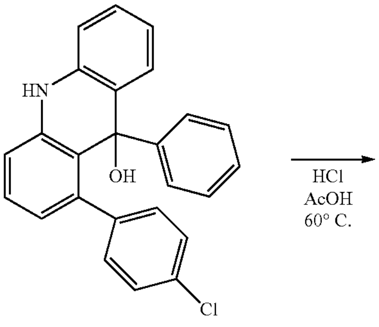

15-3

-continued

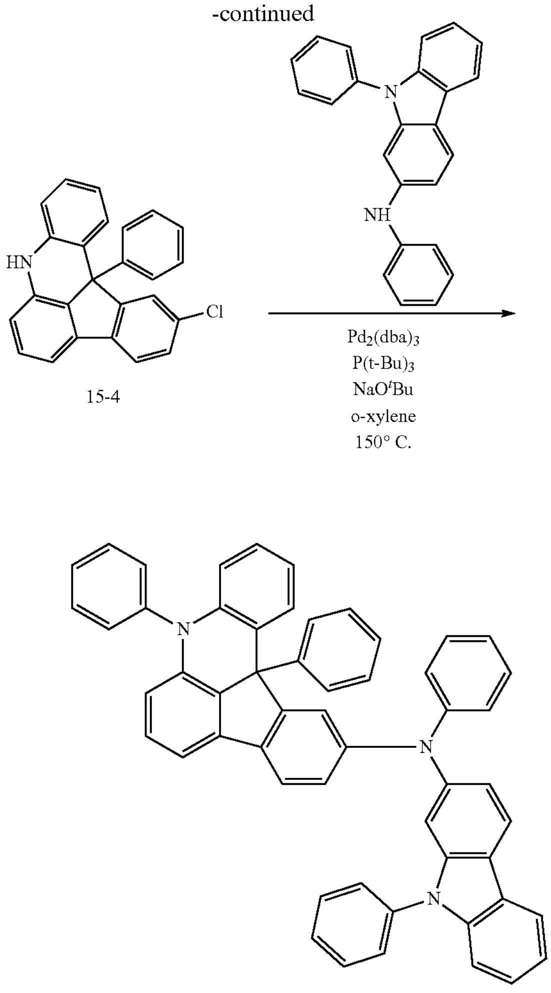

15-4

217

Synthesis of Compound 217

Intermediate 15-4 (3.65 g), N,9-diphenyl-9H-carbazol-2-amine (3.34 g), $Pd_2(dba)_3$ (0.46 g), $P(t-Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 217 (5.61 g, yield: 64%).

(15) Synthesis of Compound 227

Amine Compound 227 according to an example may be synthesized by, for example, the steps shown in Reaction Scheme 15 below:

Reaction Scheme 15

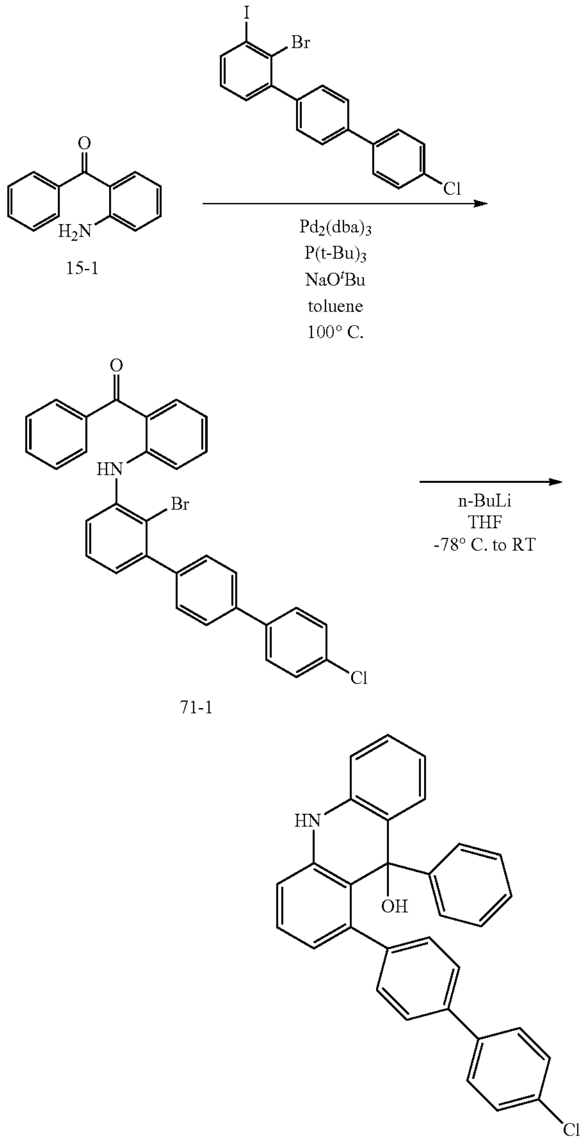

15-1

71-1

71-2

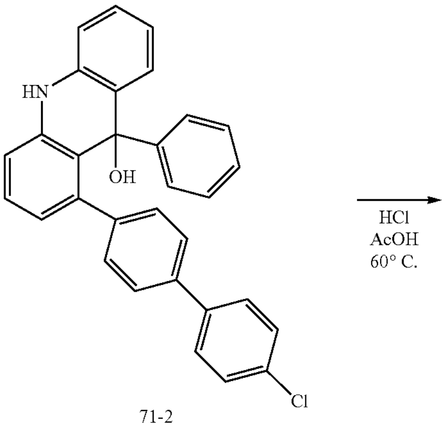

71-2

-continued

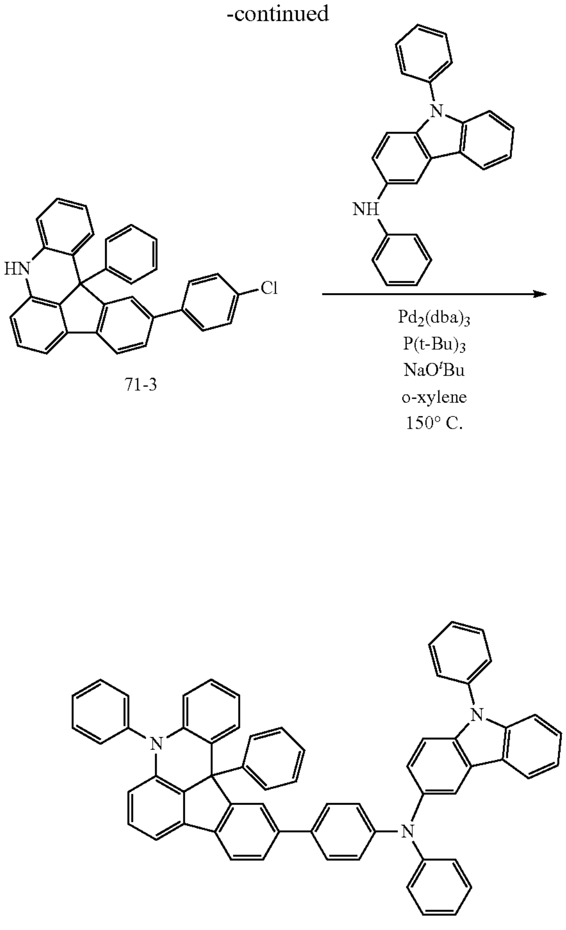

71-3

227

Synthesis of Compound 227

Intermediate 71-3 (4.41 g), N,9-diphenyl-9H-carbazol-3-amine (3.34 g), $Pd_2(dba)_3$ (0.46 g), $P(t\text{-}Bu)_3$ (0.21 g), and NaO$^t$Bu (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 227 (7.18 g, yield: 88%).

(16) Synthesis of Compound 231

Amine Compound 231 according to an example may be synthesized by, for example, the steps shown in Reaction Scheme 16 below:

Reaction Scheme 16

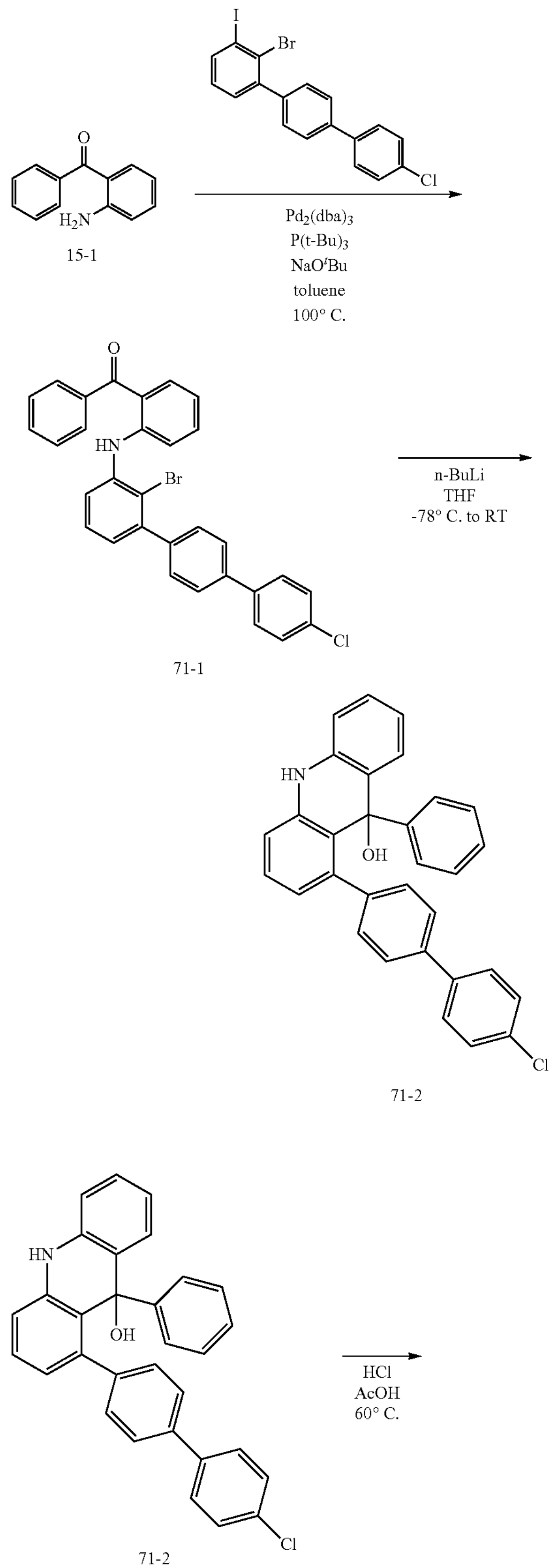

15-1

71-1

71-2

71-2

-continued

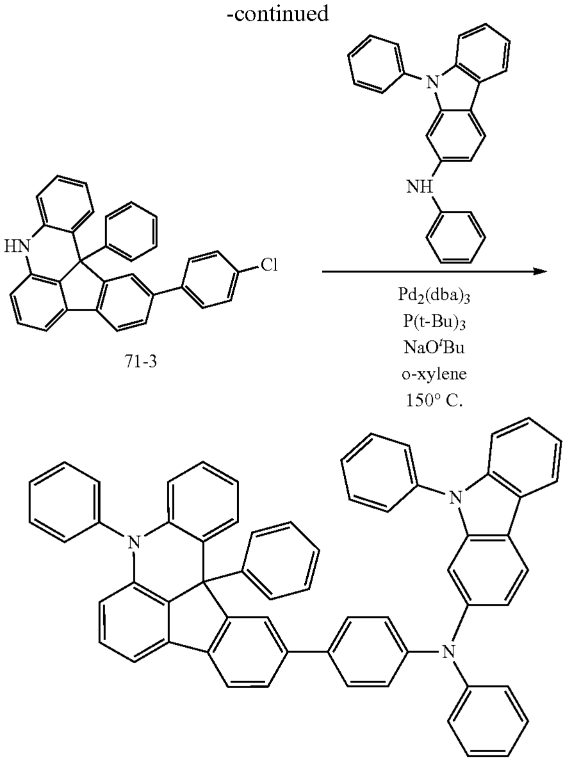

71-3

231

Synthesis of Compound 231

Intermediate 71-3 (4.41 g), N,9-diphenyl-9H-carbazol-2-amine (3.34 g), $Pd_2(dba)_3$ (0.46 g), $P(t-Bu)_3$ (0.21 g), and $NaO^tBu$ (2.44 g) were dissolved in o-xylene (50 mL), and then the resulting mixture was stirred at about 150° C. for about 1 hour. This reaction solution was cooled to room temperature and then quenched with water, and extracted three times with ethyl ether to separate an organic layer. The separated organic layer was dried over anhydrous magnesium sulfate and distilled under reduced pressure to obtain residues. The obtained residues were separated and purified by column chromatography to obtain Compound 231 (7.13 g, yield: 87%).

2. Manufacture and Evaluation of Light Emitting Elements (1) Manufacture of Light Emitting Elements Light emitting elements including an amine compound of an example or a Comparative Example Compound in a hole transport layer were manufactured as follows. Compounds 15, 18, 29, 30, 43, 48, 53, 60, 71, 74, 85, 89, 213, 217, 227, and 231, which are amine compounds of the examples, were used as a hole transport layer material to manufacture the light emitting elements of Examples 1 to 16, respectively. Comparative Example Compounds C1 to C3 were used as a hole transport layer material to manufacture the light emitting elements of Comparative Examples 1 to 3, respectively. N,N'-di(naphthalene-l-yl)-N,N'-diphenyl-benzidine (NPB) was used as Comparative Example Compound C1.

For a first electrode, an ITO glass substrate of about 15 $\Omega/cm^2$ (a thickness of about 1,200 Å) made by Corning Co. was cut to a size of 50 mm×50 mm×0.7 mm, cleansed by ultrasonic waves using isopropyl alcohol and pure water for about 5 minutes, and then irradiated with ultraviolet rays for about 30 minutes and exposed to ozone and cleansed. The glass substrate was installed on a vacuum deposition apparatus.

On the upper portion of the first electrode, 2-TNATA was deposited in vacuum to form a 600 Å-thick hole injection layer, and then a Comparative Example Compound or an Example Compound as a hole transporting compound was deposited in vacuum to form a 300 Å-thick hole transport layer.

On the upper portion of the hole transport layer, 9,10-di (naphthalen-2-yl)anthracene (ADN) as a blue fluorescent host and 4,4'-bis[2-(4-(N,N-diphenylamino)phenyl)vinyl] biphenyl (DPAVBi) as a blue fluorescent dopant were co-deposited at a weight ratio of 98:2 to form a 300 Å-thick emission layer.

On the upper portion of the emission layer, $Alq_3$ was deposited to form a 300 Å-thick electron transport layer, and then on the upper portion of the electron transport layer, LiF, which is a alkali metal halide, was deposited to form 10 Å-thick electron injection layer. Then, Al was deposited in vacuum to form a 3000 Å-thick second electrode of LiF/Al.

Materials Used to Manufacture Light Emitting Elements

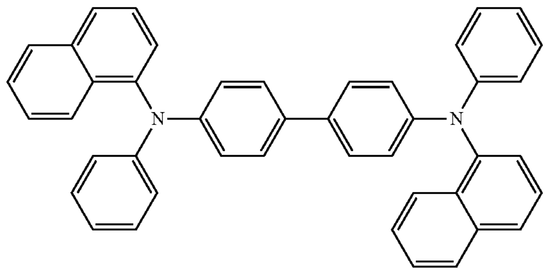 [SMILES: c1ccc(N(c2ccc(-c3ccc(N(c4ccccc4)c4cccc5ccccc45)cc3)cc2)c2cccc3ccccc23)cc1]

NPB

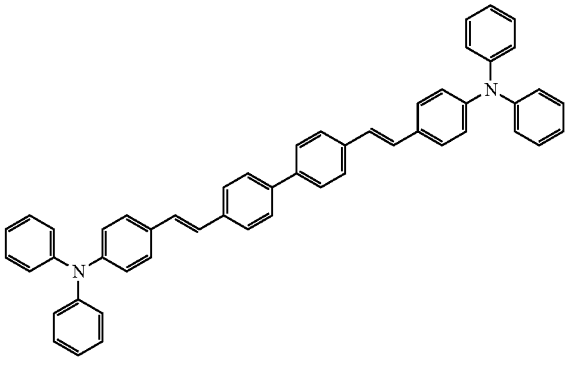

DPAVBi

-continued
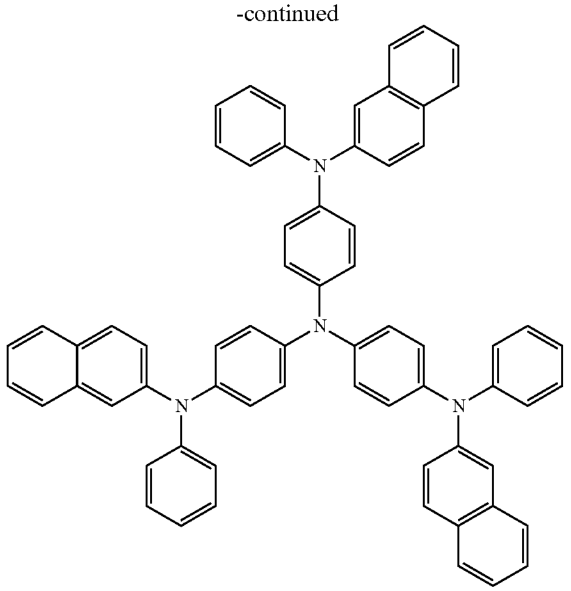
2-TNATA
-continued
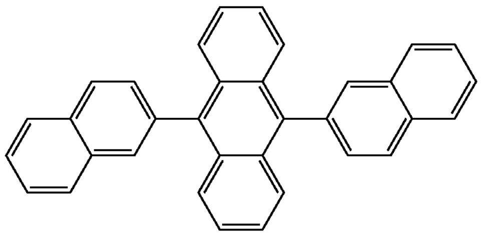
ADN
The Example Compounds and Comparative Example Compounds used in Examples 1 to 16 and Comparative Examples 1 to 3 are listed in Table 1.
TABLE 1
| | |
|---|---|
| 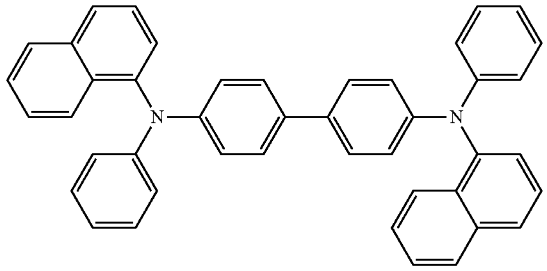<br>C1(NPB) | Comparative Example Compound C1 |
| 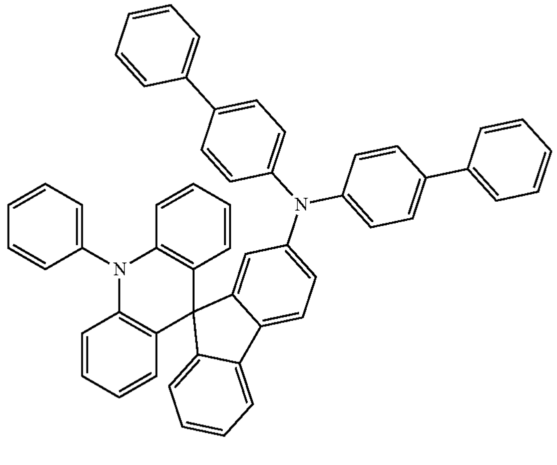 [SMILES: c1ccc(-c2ccc(N(c3ccc(-c4ccccc4)cc3)c3ccc4c(c3)C3(c5ccccc5-4)c4ccccc4N(c4ccccc4)c4ccccc43)cc2)cc1]<br>C2 | Comparative Example Compound C2 |

TABLE 1-continued
Comparative Example Compound C3
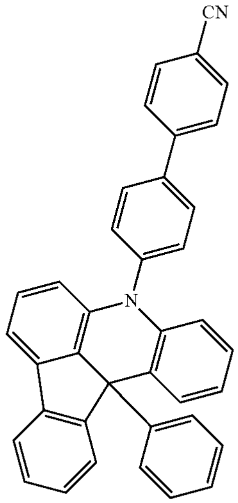 [SMILES: N#Cc1ccc(-c2ccc(N3c4ccccc4C4(c5ccccc5)c5ccccc5-c5cccc3c54)cc2)cc1]
C3
—
Compound 15
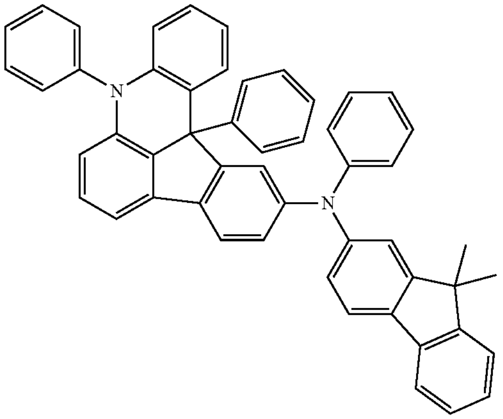 [SMILES: CC1(C)c2ccccc2-c2ccc(N(c3ccccc3)c3ccc4c(c3)C3(c5ccccc5)c5ccccc5N(c5ccccc5)c5cccc-4c53)cc21]
15
Compound 18
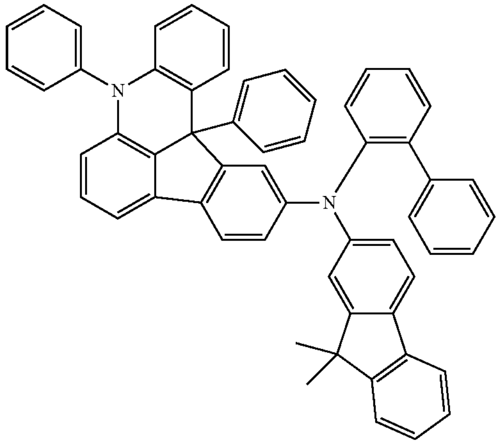 [SMILES: CC1(C)c2ccccc2-c2ccc(N(c3ccc4c(c3)C3(c5ccccc5)c5ccccc5N(c5ccccc5)c5cccc-4c53)c3ccccc3-c3ccccc3)cc21]
18

TABLE 1-continued
Compound 29
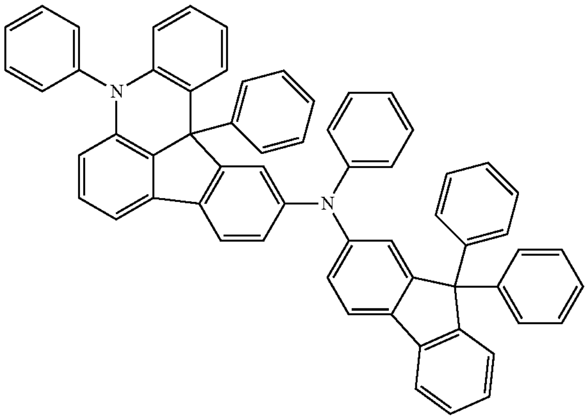 [SMILES: c1ccc(N(c2ccc3c(c2)C(c2ccccc2)(c2ccccc2)c2ccccc2-3)c2ccc3c(c2)C2(c4ccccc4)c4ccccc4N(c4ccccc4)c4cccc-3c42)cc1]
29
Compound 30
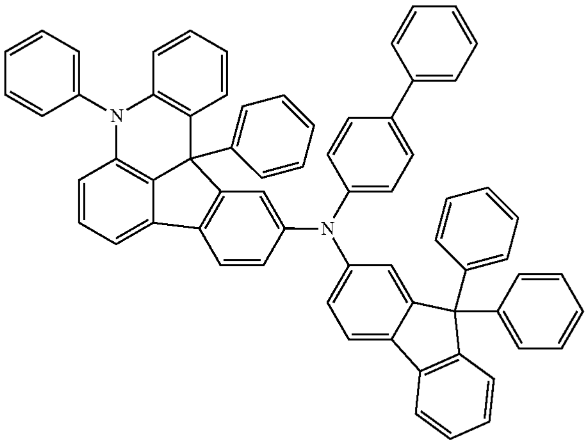 [SMILES: c1ccc(-c2ccc(N(c3ccc4c(c3)C(c3ccccc3)(c3ccccc3)c3ccccc3-4)c3ccc4c(c3)C3(c5ccccc5)c5ccccc5N(c5ccccc5)c5cccc-4c53)cc2)cc1]
30
Compound 43
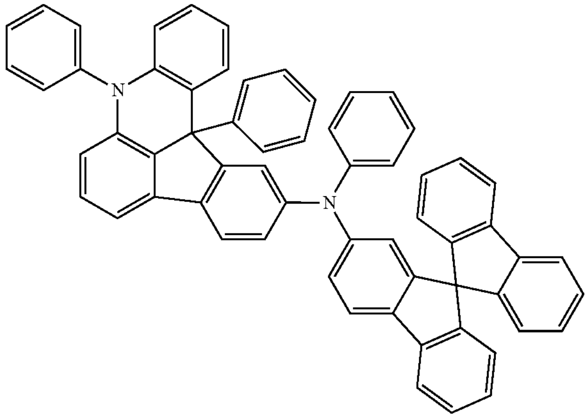 [SMILES: c1ccc(N(c2ccc3c(c2)C2(c4ccccc4-c4ccccc42)c2ccccc2-3)c2ccc3c(c2)C2(c4ccccc4)c4ccccc4N(c4ccccc4)c4cccc-3c42)cc1]
43

TABLE 1-continued
Compound 48
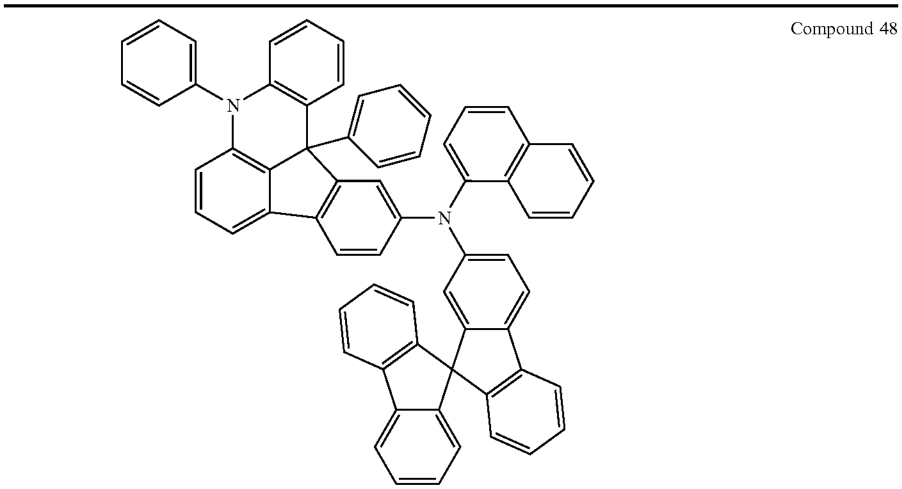
48
Compound 53
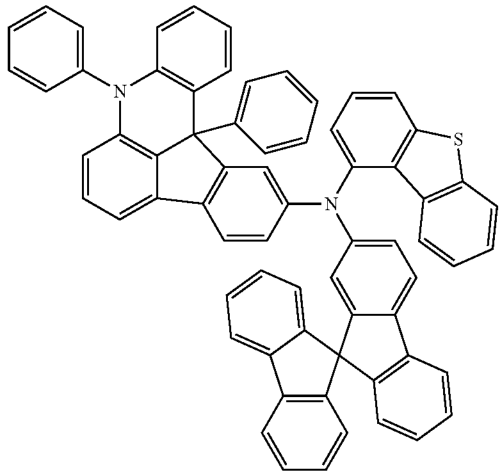 [SMILES: c1ccc(N2c3ccccc3C3(c4ccccc4)c4cc(N(c5ccc6c(c5)C5(c7ccccc7-c7ccccc75)c5ccccc5-6)c5cccc6sc7ccccc7c56)ccc4-c4cccc2c43)cc1]
53
Compound 60
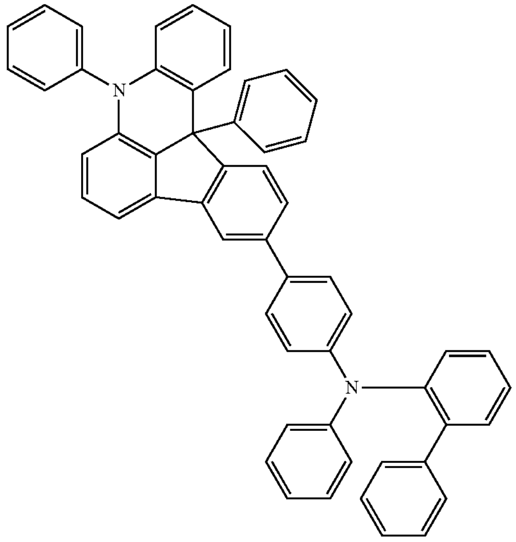 [SMILES: c1ccc(-c2ccccc2N(c2ccccc2)c2ccc(-c3ccc4c(c3)-c3cccc5c3C4(c3ccccc3)c3ccccc3N5c3ccccc3)cc2)cc1]
60

TABLE 1-continued
Compound 71
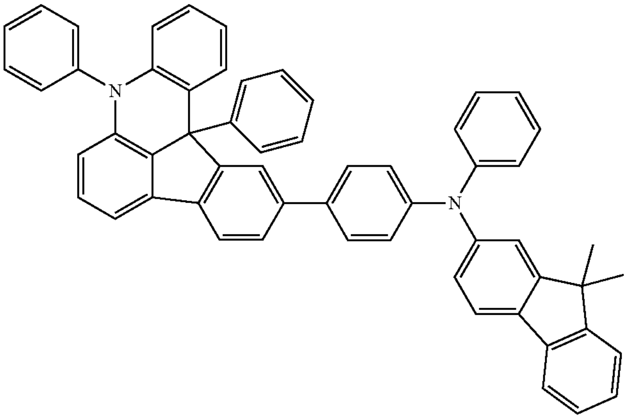 [SMILES: CC1(C)c2ccccc2-c2ccc(N(c3ccccc3)c3ccc(-c4ccc5c(c4)C4(c6ccccc6)c6ccccc6N(c6ccccc6)c6cccc-5c64)cc3)cc21]
71
Compound 74
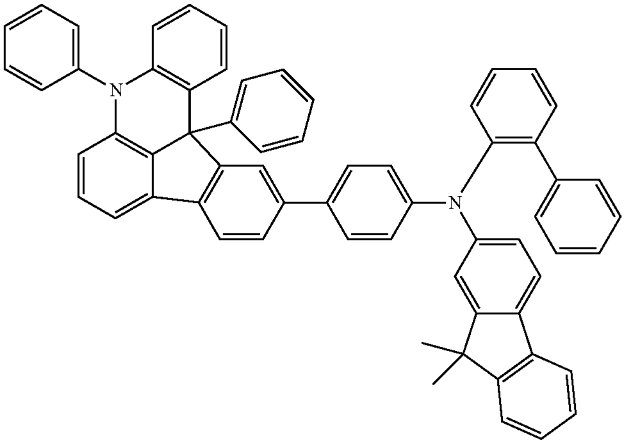 [SMILES: CC1(C)c2ccccc2-c2ccc(N(c3ccc(-c4ccc5c(c4)C4(c6ccccc6)c6ccccc6N(c6ccccc6)c6cccc-5c64)cc3)c3ccccc3-c3ccccc3)cc21]
74
Compound 85
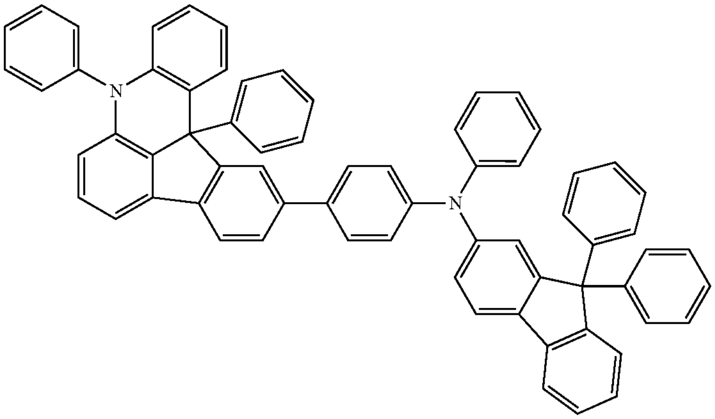 [SMILES: c1ccc(N(c2ccc(-c3ccc4c(c3)C3(c5ccccc5)c5ccccc5N(c5ccccc5)c5cccc-4c53)cc2)c2ccc3c(c2)C(c2ccccc2)(c2ccccc2)c2ccccc2-3)cc1]
85

TABLE 1-continued
Compound 89
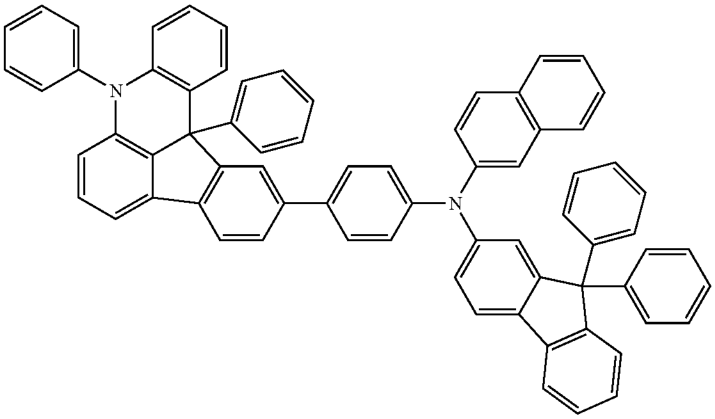 [SMILES: c1ccc(N2c3ccccc3C3(c4ccccc4)c4cc(-c5ccc(N(c6ccc7c(c6)C(c6ccccc6)(c6ccccc6)c6ccccc6-7)c6ccc7ccccc7c6)cc5)ccc4-c4cccc2c43)cc1]
89
Compound 213
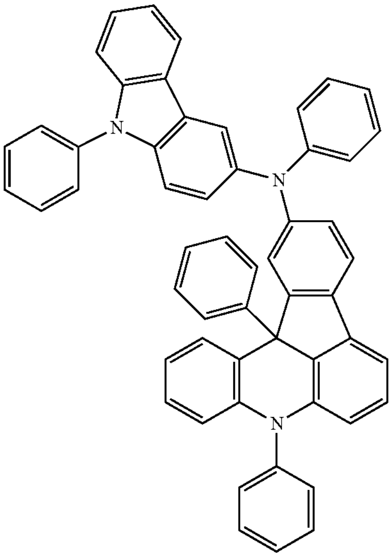 [SMILES: c1ccc(N(c2ccc3c(c2)C2(c4ccccc4)c4ccccc4N(c4ccccc4)c4cccc-3c42)c2ccc3c(c2)c2ccccc2n3-c2ccccc2)cc1]
213
Compound 217
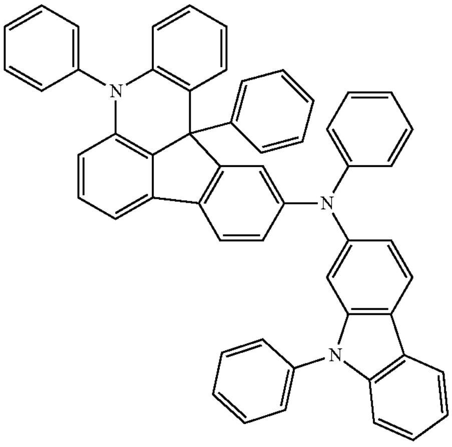 [SMILES: c1ccc(N(c2ccc3c(c2)C2(c4ccccc4)c4ccccc4N(c4ccccc4)c4cccc-3c42)c2ccc3c4ccccc4n(-c4ccccc4)c3c2)cc1]
217

TABLE 1-continued

Compound 227

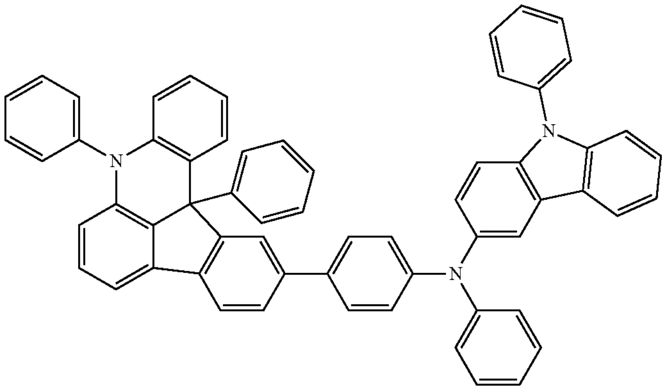 [SMILES: c1ccc(N(c2ccc(-c3ccc4c(c3)C3(c5ccccc5)c5ccccc5N(c5ccccc5)c5cccc-4c53)cc2)c2ccc3c(c2)c2ccccc2n3-c2ccccc2)cc1]

227

Compound 231

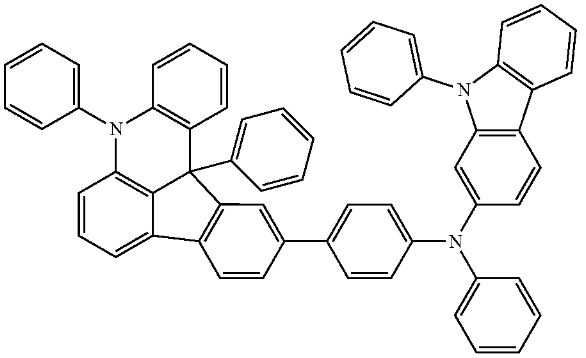 [SMILES: c1ccc(N(c2ccc(-c3ccc4c(c3)C3(c5ccccc5)c5ccccc5N(c5ccccc5)c5cccc-4c53)cc2)c2ccc3c4ccccc4n(-c4ccccc4)c3c2)cc1]

231

(2) Evaluation of Light Emitting Element Property

Properties of the light emitting elements of the Examples and Comparative Examples were evaluated and the results are listed in Table 2. The properties of the light emitting elements of the Examples and Comparative Examples were measured by using a V7000 OLED IVL Test System, (Polaronix) (Mcscience Inc.). Driving voltages, brightness, and efficiencies of the light emitting elements of the Examples and Comparative Examples were measured with respect to a current density of 50 mA/cm$^2$. Half service lives of the light emitting elements of Examples and Comparative Examples were measured with respect to a current density of 100 mA/cm$^2$. The half service lives were determined by measuring a time taken to reduce the brightness to half of an initial brightness.

TABLE 2

| Examples of manufactured elements | Hole transport layer | Driving voltage (V) | Brightness (cd/m$^2$) | Efficiency (cd/A) | Luminous color | Half service life (hr) |
|---|---|---|---|---|---|---|
| Comparative Example 1 | Comparative Example Compound C1 (NPB) | 7.01 | 2645 | 5.29 | Blue | 258 |
| Comparative Example 2 | Comparative Example Compound C2 | 4.73 | 3170 | 6.34 | Blue | 283 |
| Comparative Example 3 | Comparative Example Compound C3 | 6.94 | 2980 | 5.96 | Blue | 213 |
| Example 1 | Compound 15 | 4.52 | 3700 | 7.40 | Blue | 353 |
| Example 2 | Compound 18 | 4.44 | 3600 | 7.00 | Blue | 345 |
| Example 3 | Compound 29 | 4.33 | 3475 | 6.95 | Blue | 399 |
| Example 4 | Compound 30 | 4.27 | 3675 | 7.35 | Blue | 359 |
| Example 5 | Compound 43 | 4.23 | 3725 | 7.45 | Blue | 355 |
| Example 6 | Compound 48 | 4.46 | 3620 | 7.24 | Blue | 350 |
| Example 7 | Compound 53 | 4.40 | 3615 | 7.23 | Blue | 348 |
| Example 8 | Compound 60 | 4.30 | 3735 | 7.47 | Blue | 376 |
| Example 9 | Compound 71 | 4.41 | 3780 | 7.56 | Blue | 375 |

TABLE 2-continued

| Examples of manufactured elements | Hole transport layer | Driving voltage (V) | Brightness ($cd/m^2$) | Efficiency (cd/A) | Luminous color | Half service life (hr) |
|---|---|---|---|---|---|---|
| Example 10 | Compound 74 | 4.40 | 3890 | 7.78 | Blue | 360 |
| Example 11 | Compound 85 | 4.15 | 3725 | 7.45 | Blue | 340 |
| Example 12 | Compound 89 | 4.32 | 3550 | 7.10 | Blue | 372 |
| Example 13 | Compound 213 | 4.15 | 3625 | 7.25 | Blue | 365 |
| Example 14 | Compound 217 | 4.43 | 3800 | 7.60 | Blue | 355 |
| Example 15 | Compound 227 | 4.52 | 3725 | 7.45 | Blue | 350 |
| Example 16 | Compound 231 | 4.41 | 3775 | 7.55 | Blue | 350 |

Referring to Table 2, it can be seen that the light emitting elements of Examples 1 to 16 have a decrease in driving voltage, and have an improvement in brightness and efficiency compared to the light emitting elements of Comparative Examples 1 to 3. In addition, it can be seen that the light emitting elements of Examples 1 to 16 have significantly longer service lives compared to the light emitting elements of Comparative Examples 1 to 3. The light emitting elements of Examples 1 to 16 include, in the hole transport layer, Compounds 15, 18, 29, 30, 43, 48, 53, 60, 71, 74, 85, 89, 213, 217, 227, and 231, respectively, which are the amine compounds of the examples. The amine compound of an example includes a pentacyclic fused ring containing an acridine moiety and an amine group directly or indirectly bonded to the pentacyclic fused ring. Accordingly, the light emitting element including the amine compound of an example may exhibit characteristics in which the driving voltage is reduced, and the brightness, efficiency, and service life are improved.

The light emitting element of Comparative Example 1 includes Comparative Example Compound C1, which corresponds to NPB. The light emitting element of Comparative Example 2 includes Comparative Example Compound C2, which includes an acridine moiety, but two phenyl groups bonded to the acridine moiety are not fused. The light emitting element of Comparative Example 3 includes Comparative Example Compound C3, which includes a pentacyclic fused ring in which two rings are further fused to the acridine moiety, but does not include an amine group. Therefore, it is believed that the light emitting elements of Comparative Examples 1 to 3 have no decrease in driving voltage and no improvement in brightness, efficiency, and service life.

Provided is a light emitting element including a first electrode, a second electrode on the first electrode, and at least one functional layer between the first electrode and the second electrode. The at least one functional layer may include the amine compound of an embodiment.

The amine compound of an example may include a pentacyclic fused ring containing an acridine moiety and an amine group directly or indirectly bonded to the pentacyclic fused ring. Accordingly, the amine compound of an example may contribute to improving a hole transport property and improving the driving voltage, brightness, efficiency, and service life of the light emitting element. The light emitting element including the amine compound of an example may exhibit characteristics in which the driving voltage is reduced, and the brightness, efficiency, and service life are excellent.

A light emitting element of an embodiment includes an amine compound of an embodiment, and thus, may exhibit characteristics such that the driving voltage is reduced, the brightness and efficiency are improved, and a service life is excellent.

An amine compound of an embodiment may contribute to reducing the driving voltage of the light emitting element, improving the brightness and efficiency, and improving a service life.

Although the subject matter of the present disclosure has been described with reference to example embodiments of the present disclosure, it will be understood that the present disclosure should not be limited to these example embodiments but various changes and modifications can be made by those skilled in the art without departing from the spirit and scope of the present disclosure.

Accordingly, the technical scope of the present disclosure is not intended to be limited to the contents set forth in the detailed description of the specification, but is intended to be defined by the appended claims, and equivalents thereof.

What is claimed is:

1. A light emitting element comprising:

a first electrode;

a second electrode on the first electrode; and at least one functional layer between the first electrode and the second electrode and comprising an amine compound represented by Formula 1-A1:

Formula 1-A1

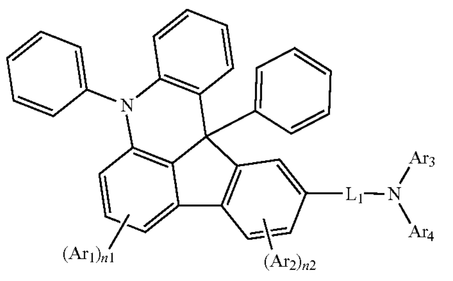

wherein, in Formula 1-A1, $L_1$ is a direct linkage, a substituted or unsubstituted arylene group having 6 to 30 carbon atoms for forming a ring, or a substituted or unsubstituted heteroarylene group having 2 to 30 carbon atoms for forming a ring, n1 and n2 are each independently an integer of 0 to 3, $Ar_1$ and $Ar_2$ are each independently a hydrogen atom, a deuterium atom, a substituted or unsubstituted aryl group having 6 to 30 ring-forming carbon atoms, or a substituted or unsubstituted heteroaryl group having 2 to 30 ring-forming carbon atoms, and $Ar_3$ and $Ar_4$ are each independently a substituted or unsubstituted aryl group having 6 to 30 ring-forming carbon atoms, or a substituted or unsubstituted heteroaryl group having 2 to 30 ring-forming carbon atoms.

2. The light emitting element of claim 1, wherein, in Formula 1-A1, $Ar_3$ and $Ar_4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

3. The light emitting element of claim 1, wherein, in Formula 1-A1, $Ar_3$ and $Ar_4$ are each independently represented by any one selected from among A-1 to A-7:

A-1

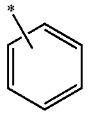

A-2

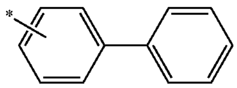

A-3

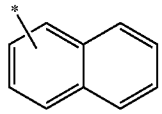

A-4

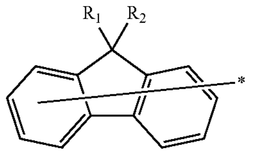

A-5

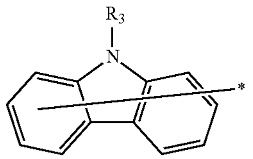

A-6

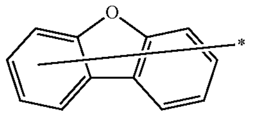

A-7

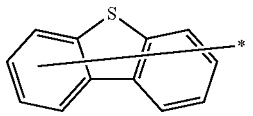

wherein, in A-4, $R_1$ and $R_2$ are each independently a substituted or unsubstituted alkyl group having 1 to 10 carbon atoms, or a substituted or unsubstituted aryl group having 6 to 30 ring-forming carbon atoms, or are bonded to an adjacent group to form a ring, and wherein, in A-5, $R_3$ is a substituted or unsubstituted aryl group having 6 to 30 ring-forming carbon atoms.

4. The light emitting element of claim 1, wherein, in Formula 1-A1, $L_1$ is a direct linkage or a phenylene group.

5. The light emitting element of claim 1, wherein the at least one functional layer comprises an emission layer, a hole transport region between the first electrode and the emission layer, and an electron transport region between the emission layer and the second electrode, and the hole transport region comprises the amine compound.

6. The light emitting element of claim 5, wherein the hole transport region comprises a hole injection layer on the first electrode, a hole transport layer on the hole injection layer, and an electron blocking layer on the hole transport layer, and at least one of the hole injection layer, the hole transport layer, or the electron blocking layer comprises the amine compound.

7. The light emitting element of claim 5, wherein the emission layer comprises a compound represented by Formula E-1:

Formula E-1

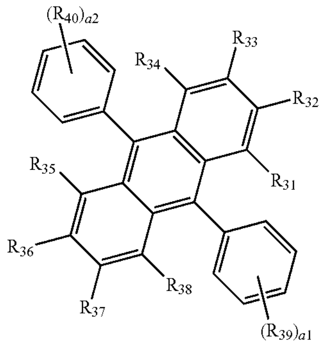

wherein, in Formula E-1, a1 and a2 are each independently an integer of 0 to 5, and $R_{31}$ to $R_{40}$ are each independently a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 10 carbon atoms, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

8. The light emitting element of claim 1, wherein the amine compound is represented by any one selected from among compounds of Compound Group 1:

Compound Group 1

1

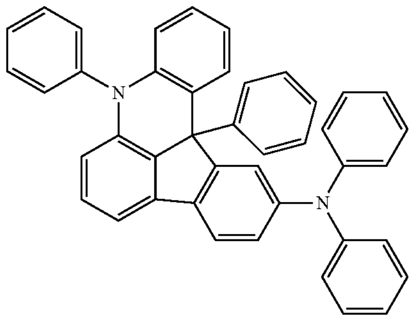

-continued
2
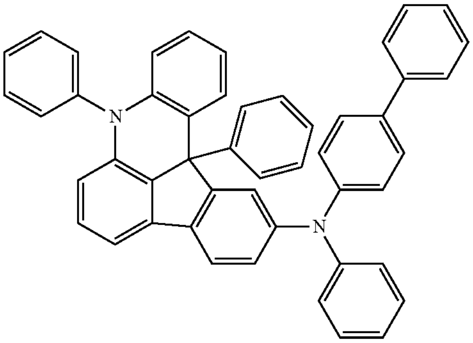
3
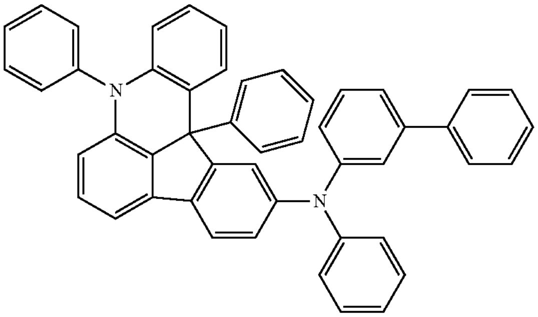
4
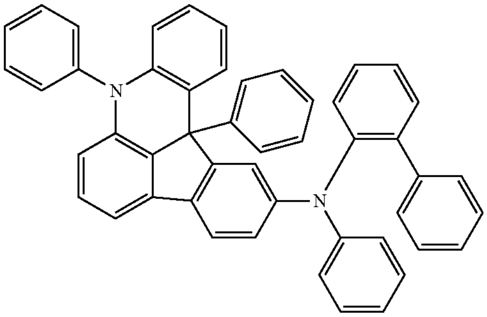
5
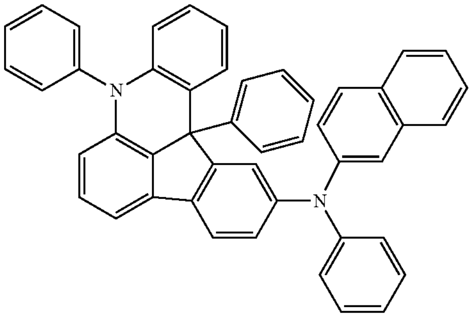
6
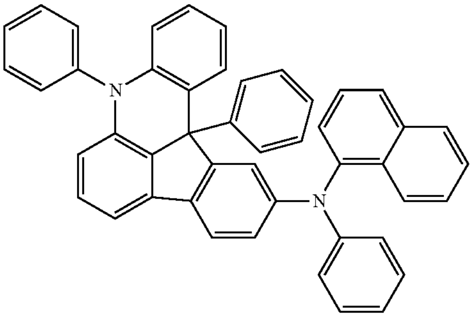
-continued
7
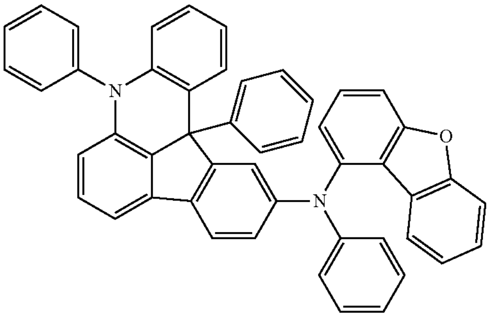
8
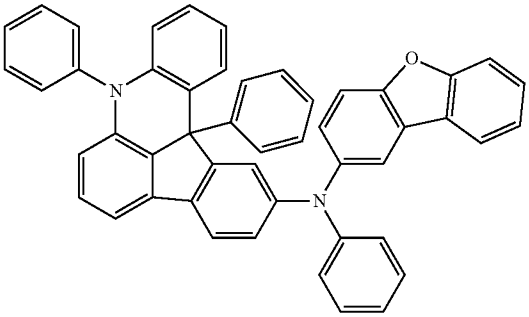
9
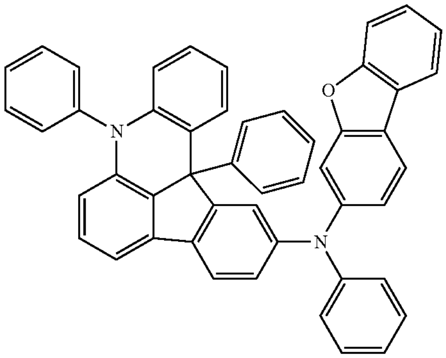
10
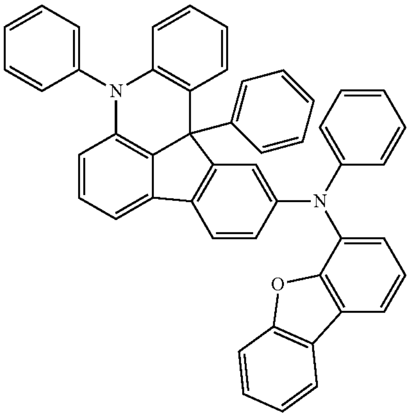

-continued
11
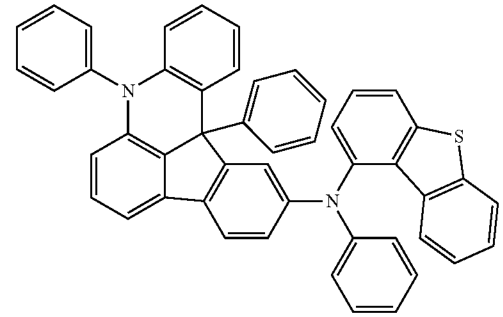
12
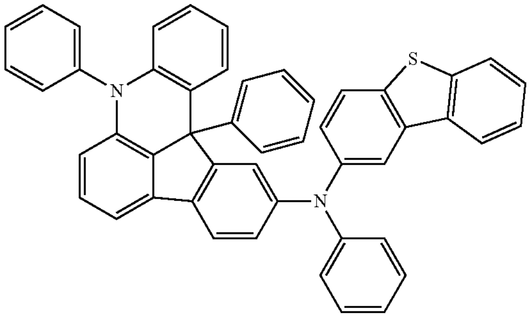
13
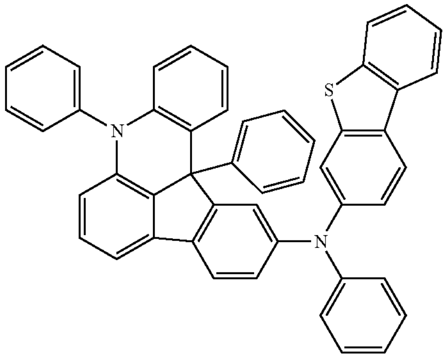
14
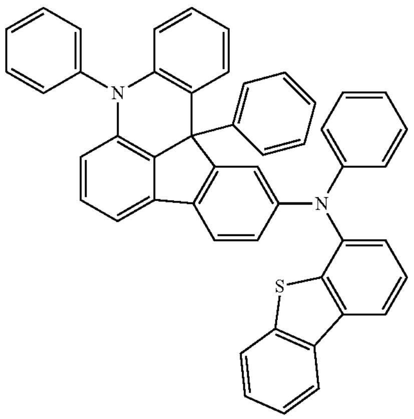
-continued
15
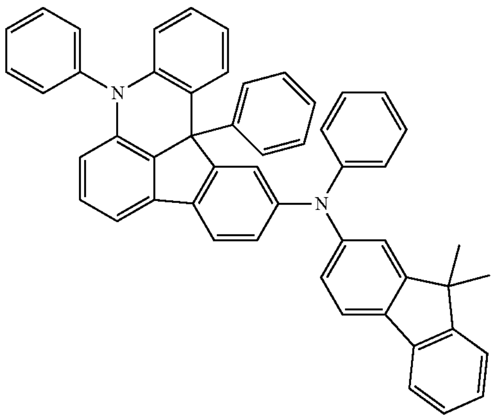
16
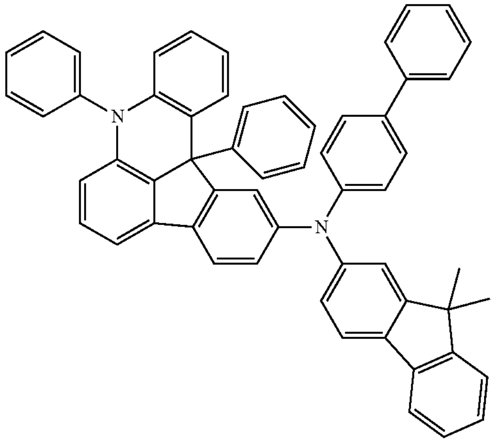
17
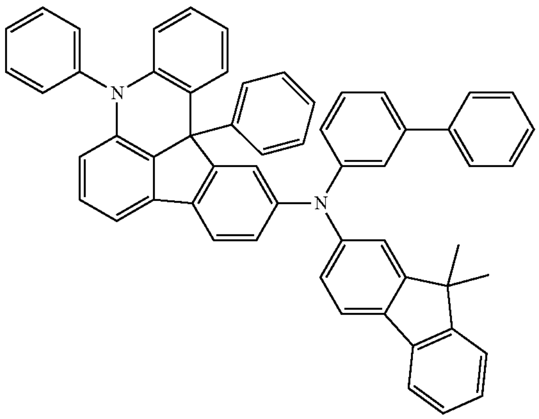

-continued
18
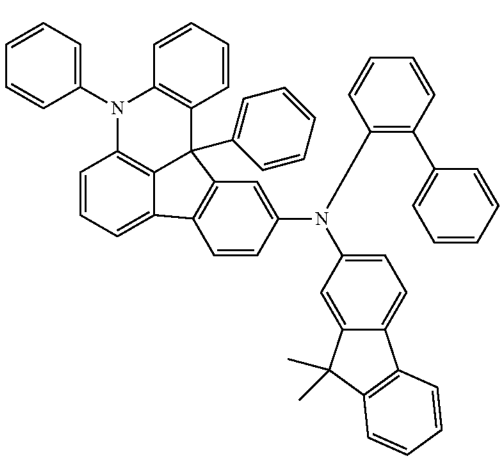
19
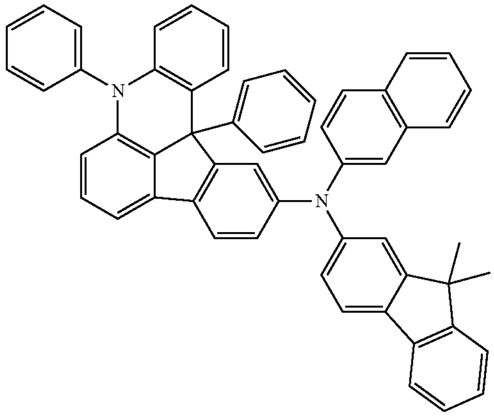
20
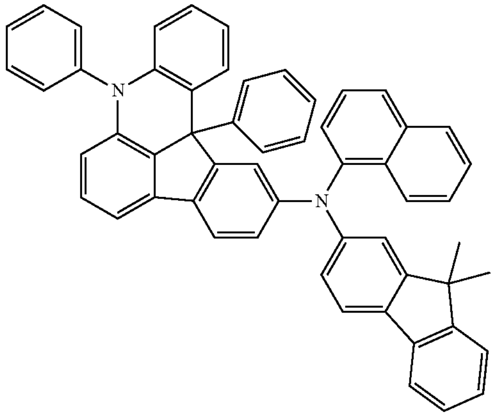
-continued
21
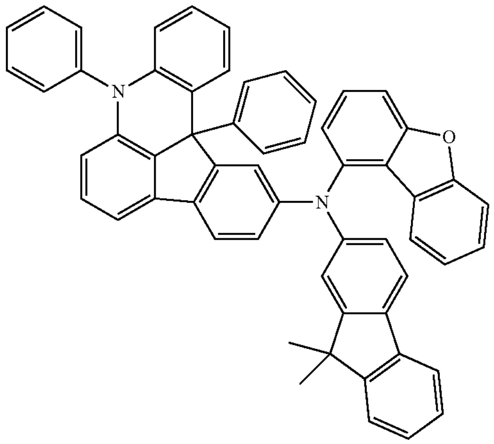
22
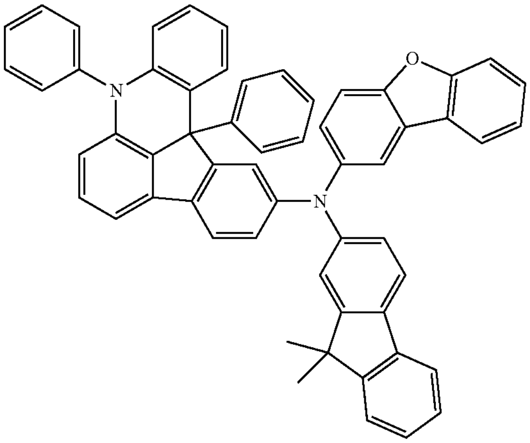
23
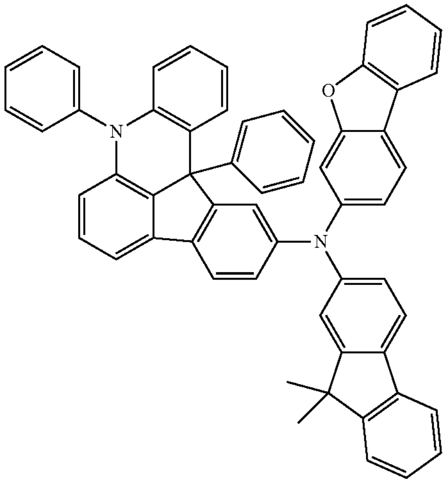

-continued
24
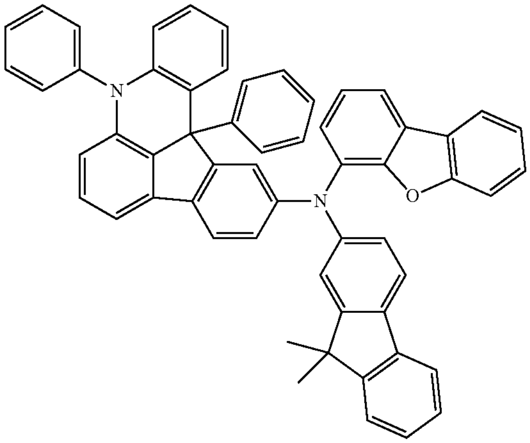
25
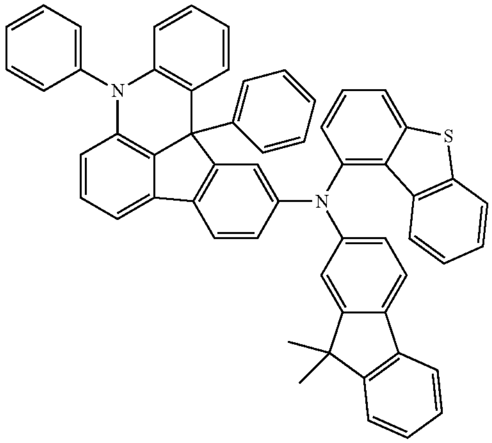
26
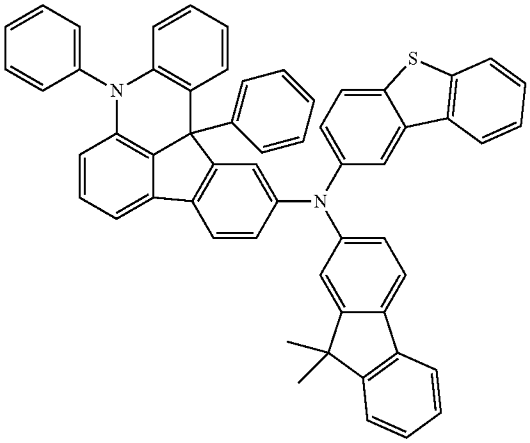
-continued
27
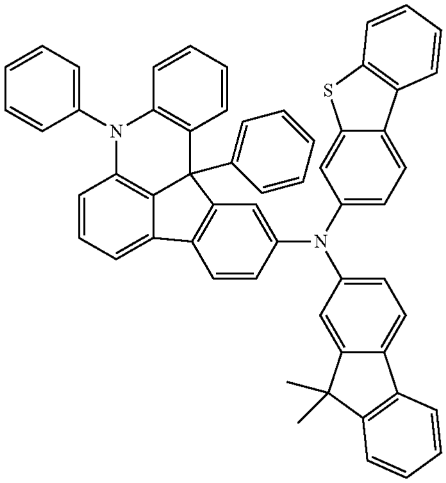
28
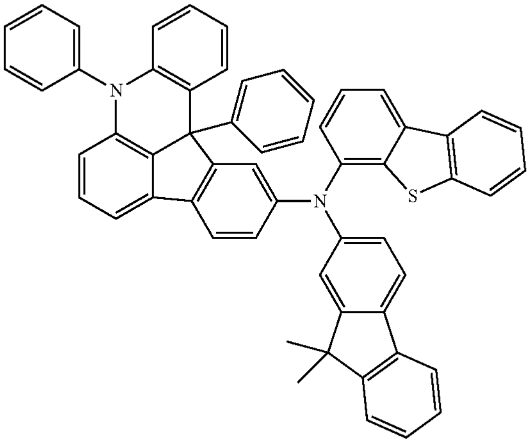
29
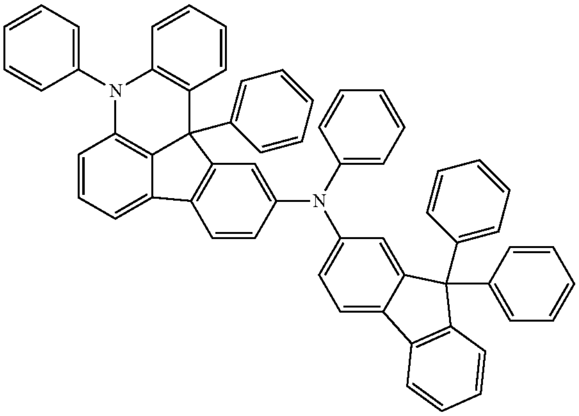

-continued
30
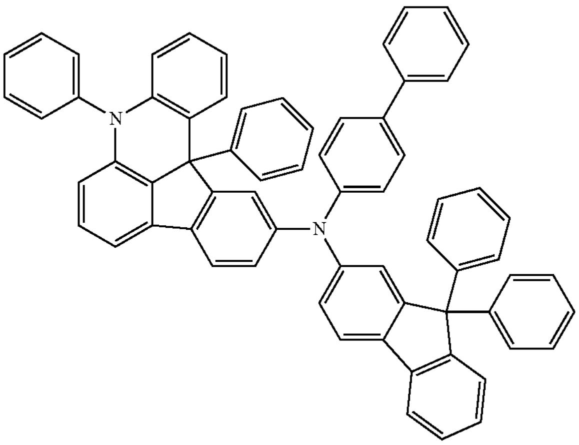
31
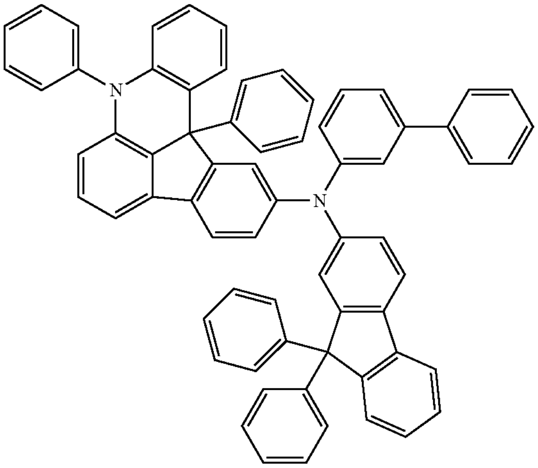
32
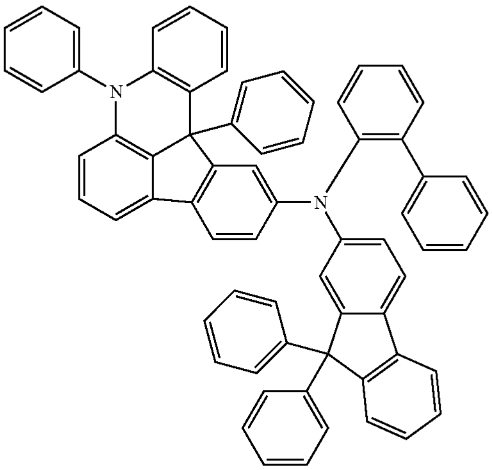
-continued
33
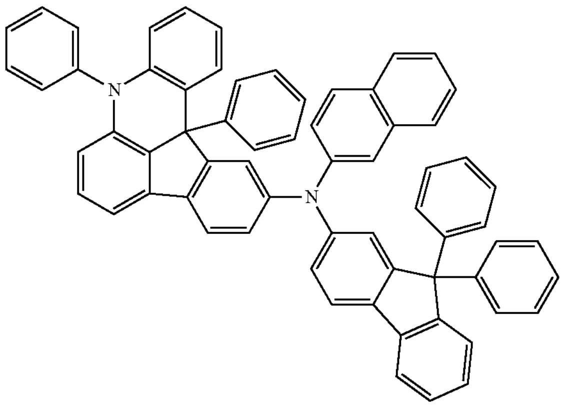
34
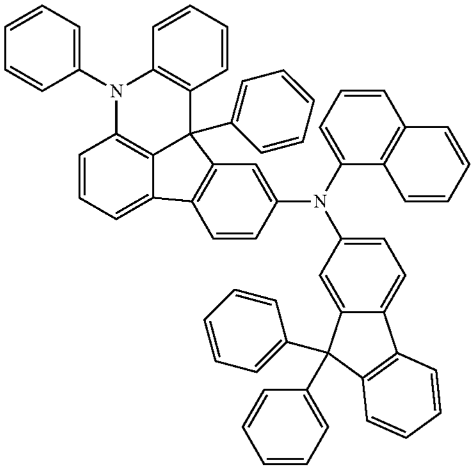
35
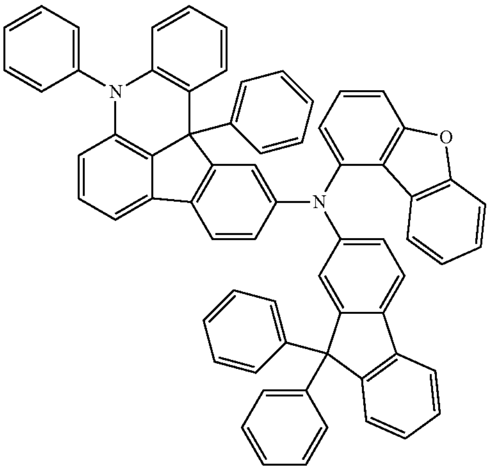

-continued
36
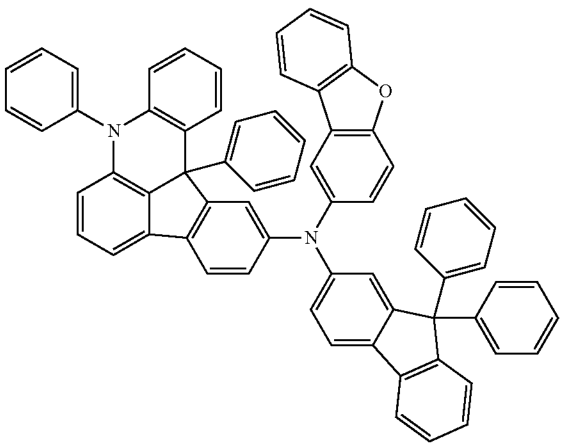
37
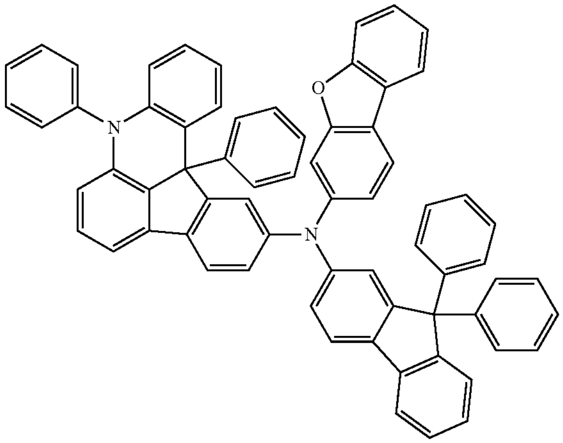
38
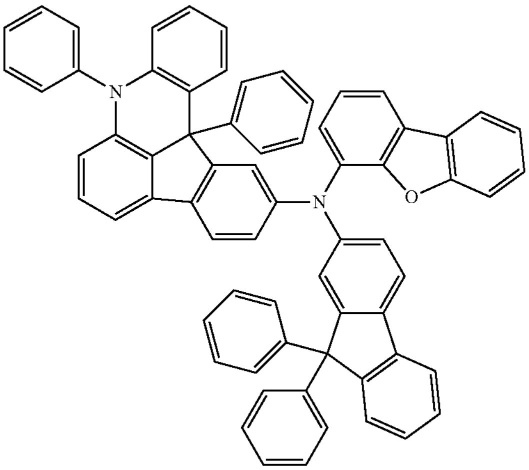
-continued
39
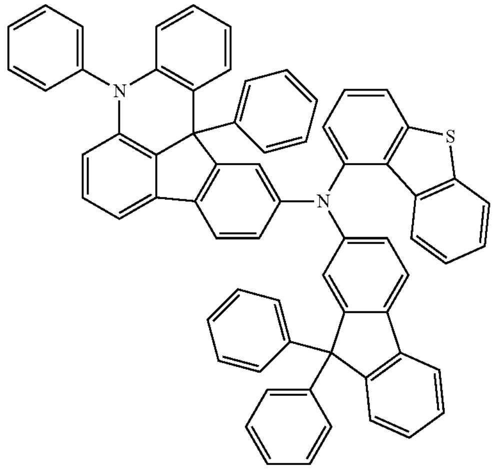
40
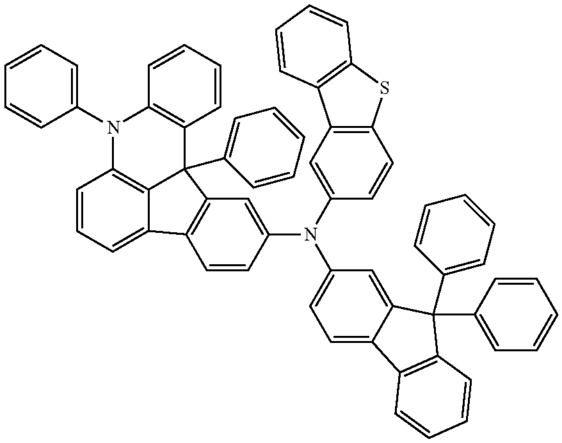
41
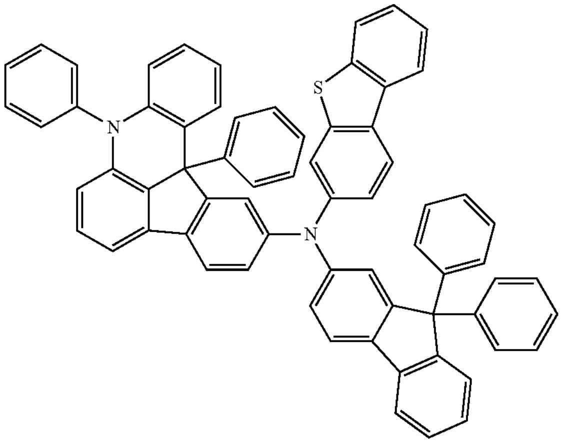

-continued
42
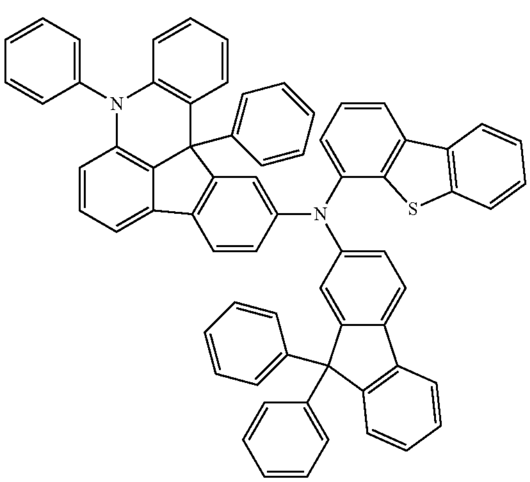
43
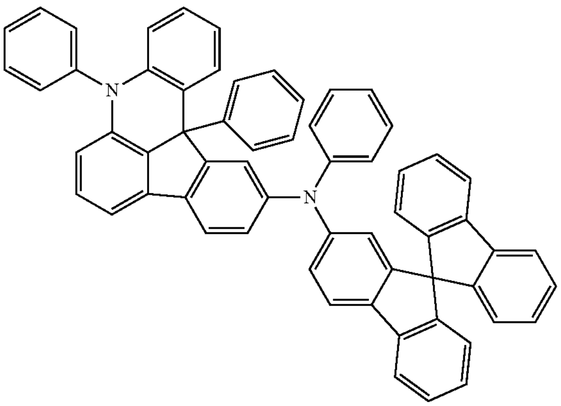
44
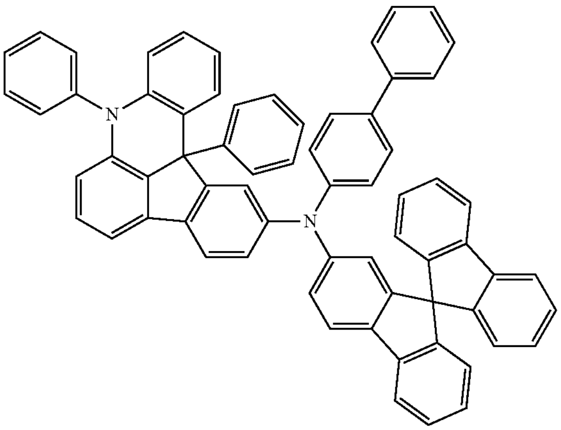
-continued
45
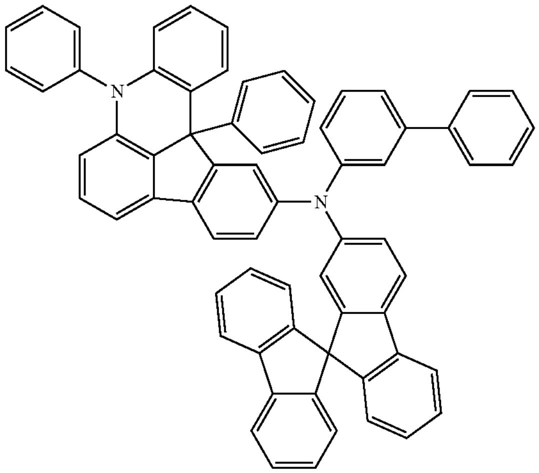
46
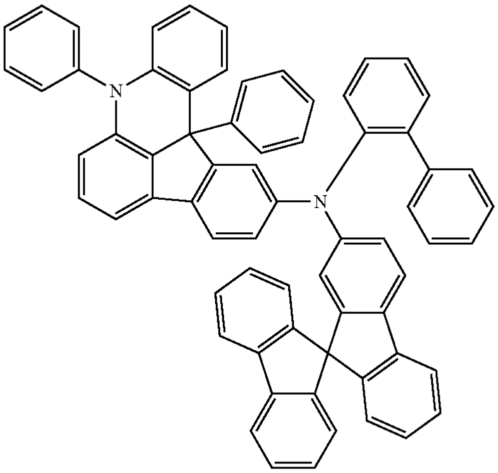
47
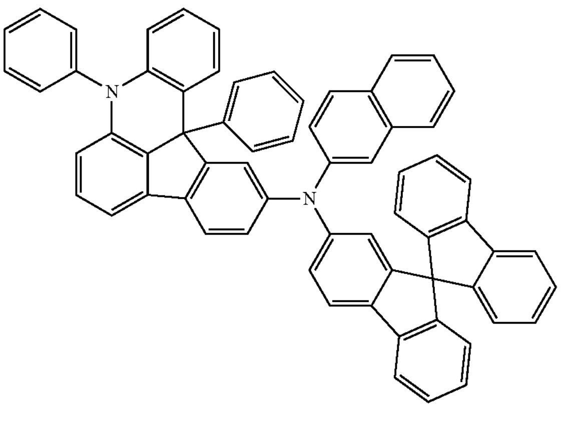

-continued
48
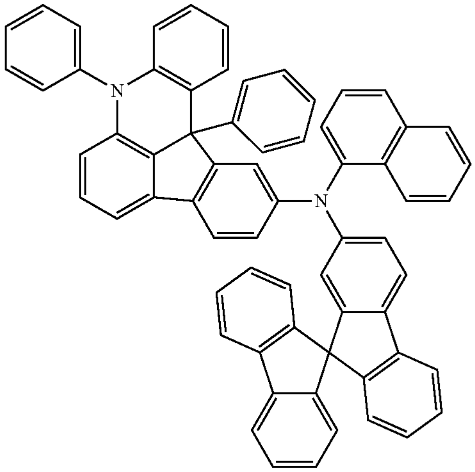
49
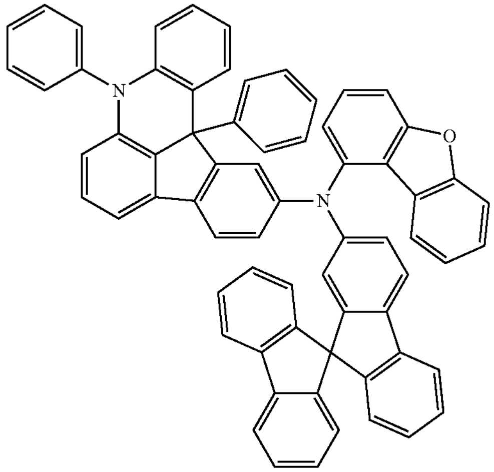
50
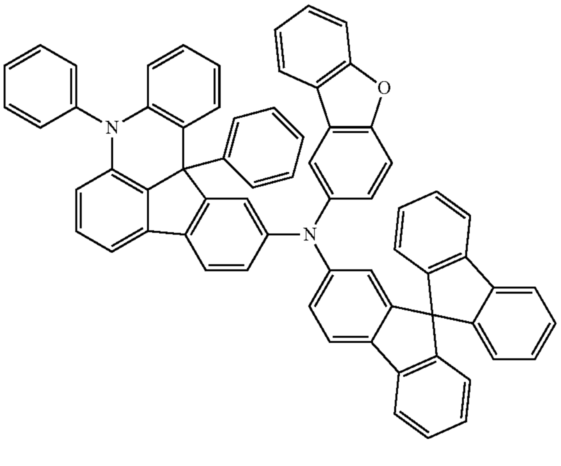
-continued
51
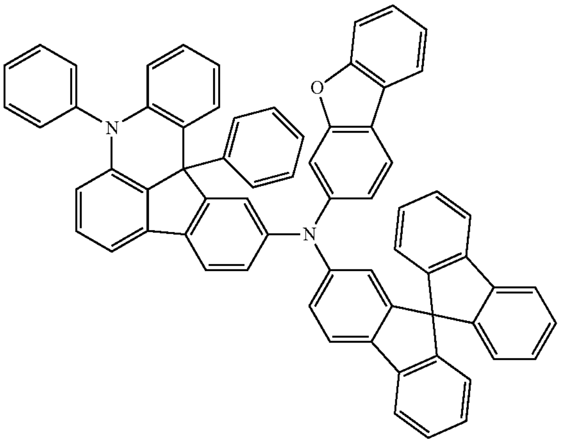
52
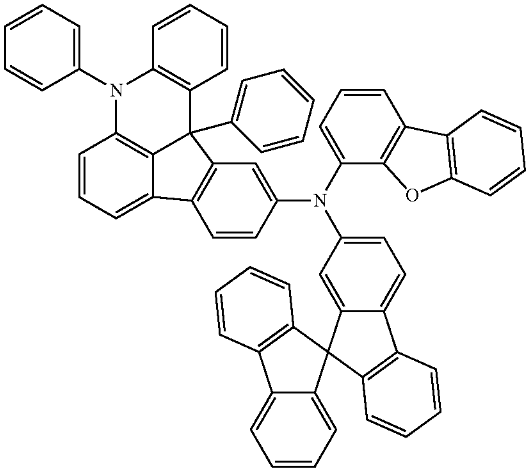
53
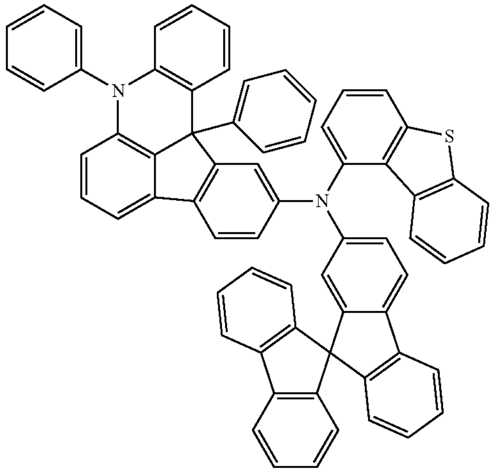

-continued
54
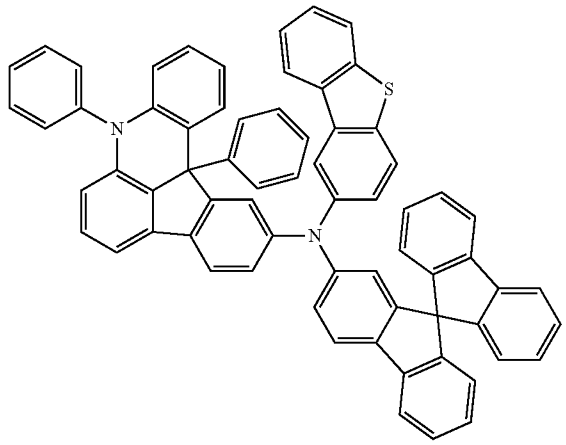
55
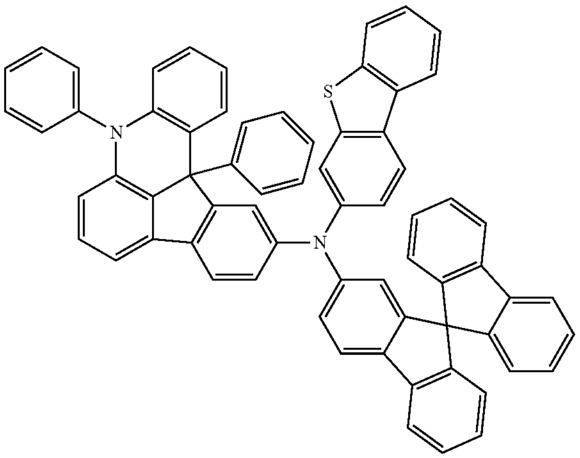
56
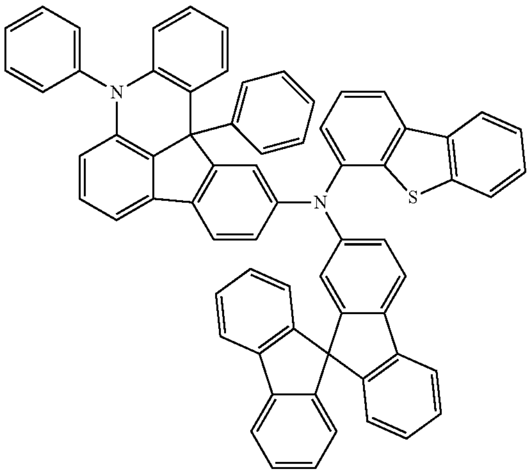
-continued
57
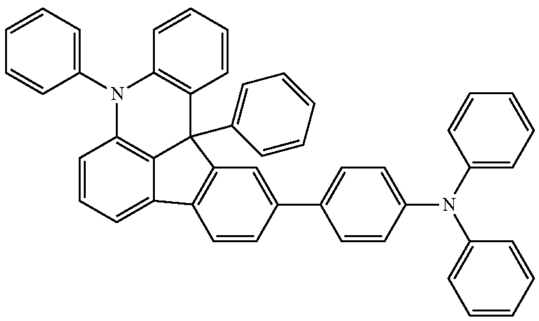
58
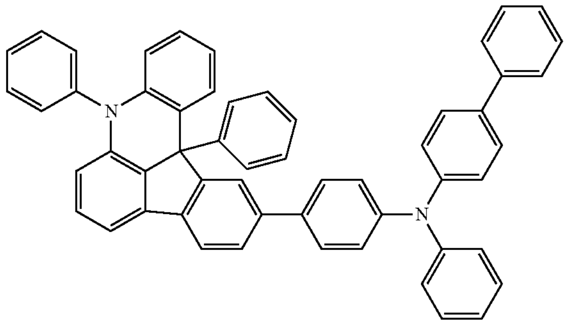
59
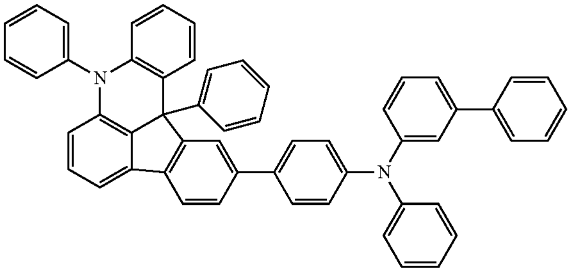
61
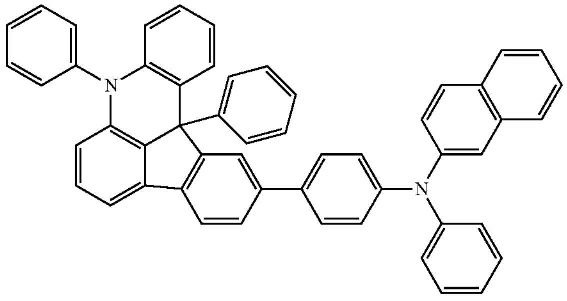
62
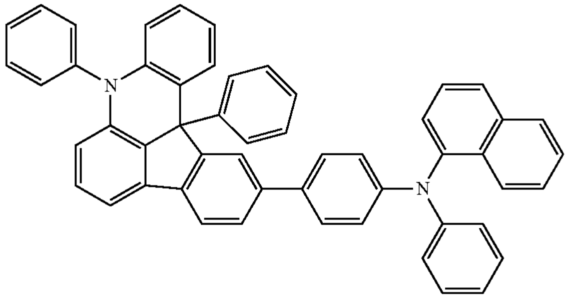

-continued
63
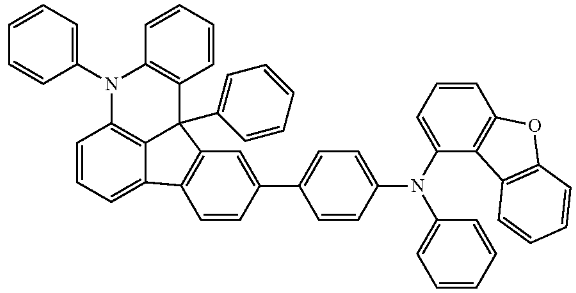
64
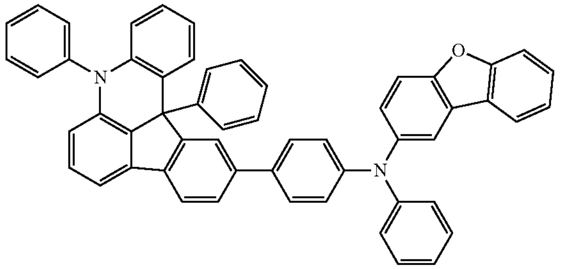
65
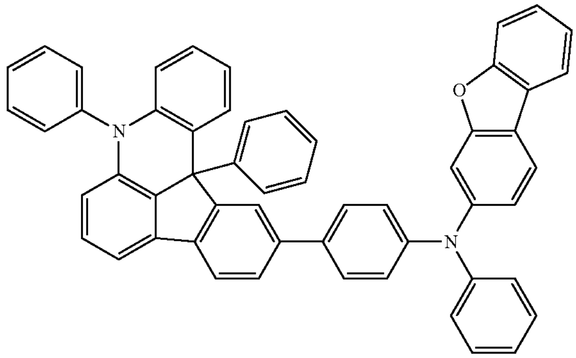
66
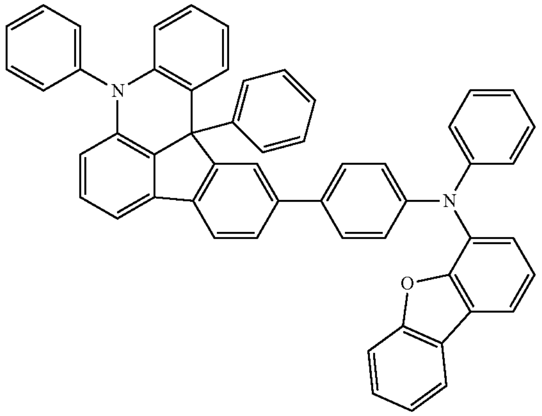
-continued
67
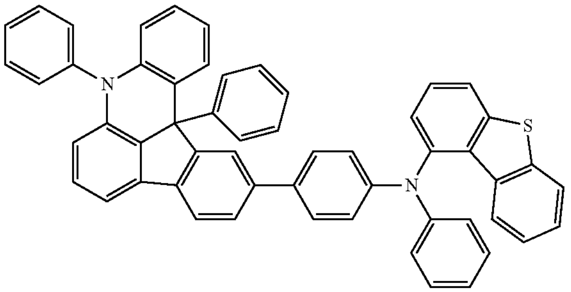
68
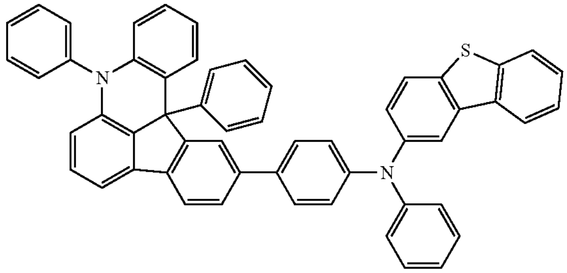
69
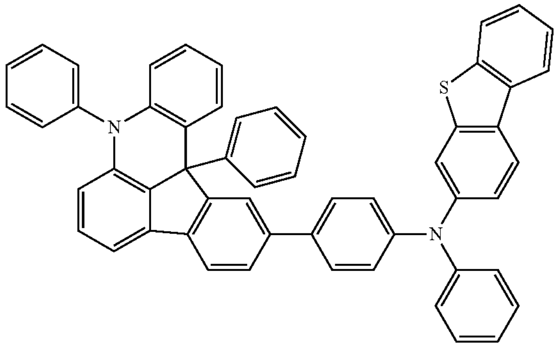
70
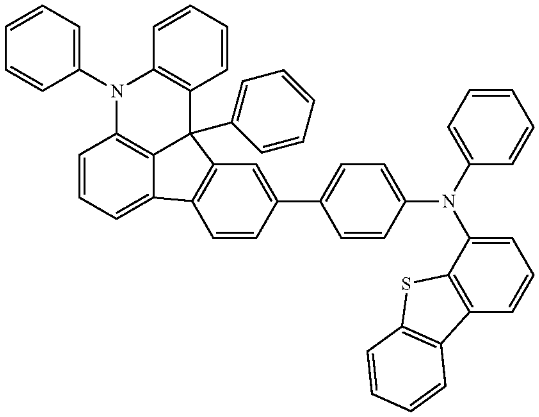

71
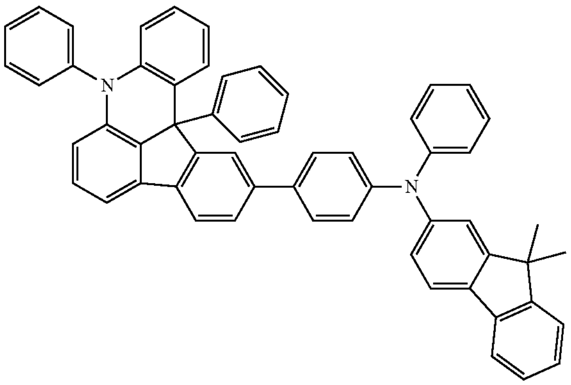
72
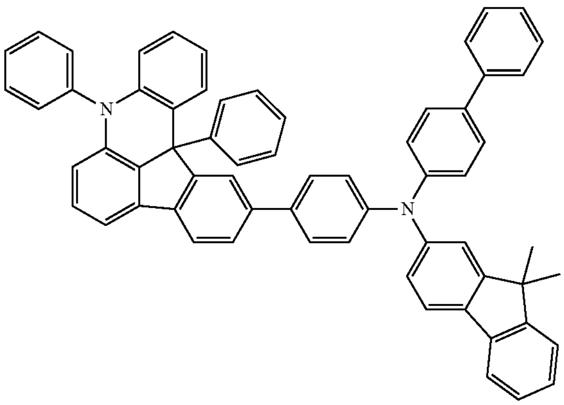
73
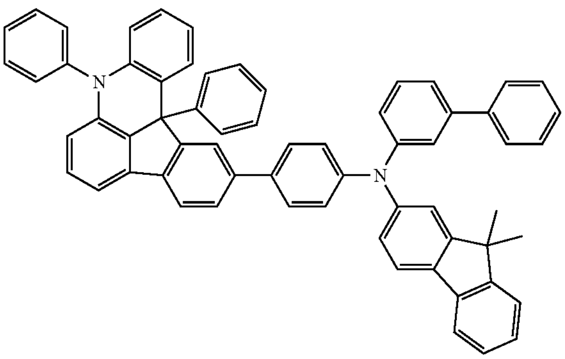
74
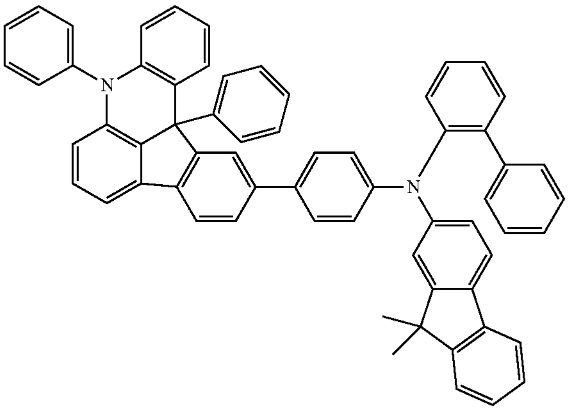
75
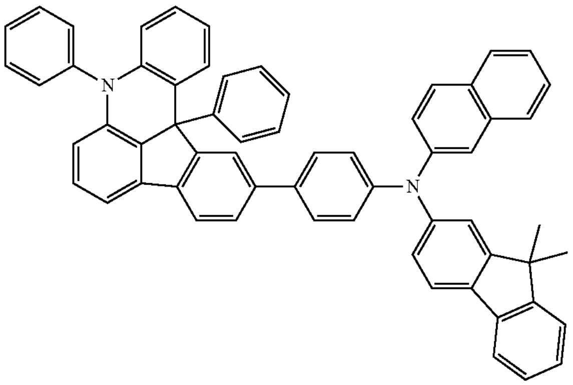
76
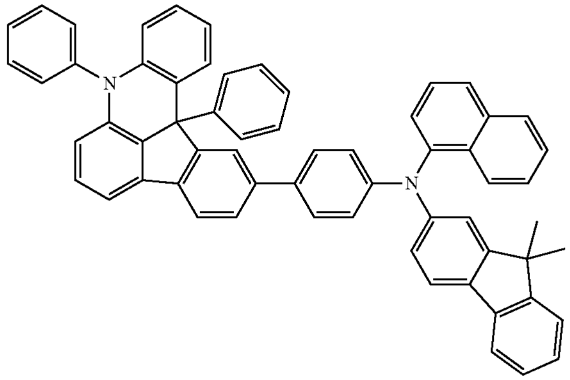
77
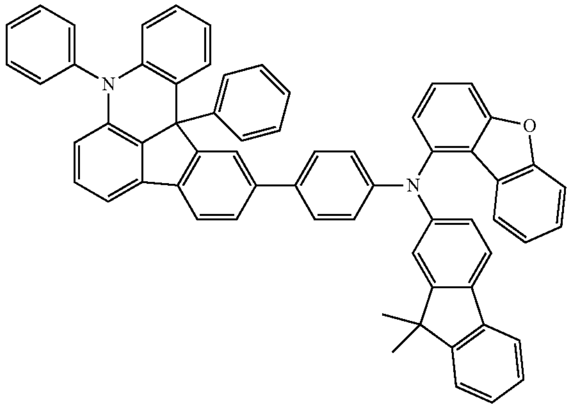
78
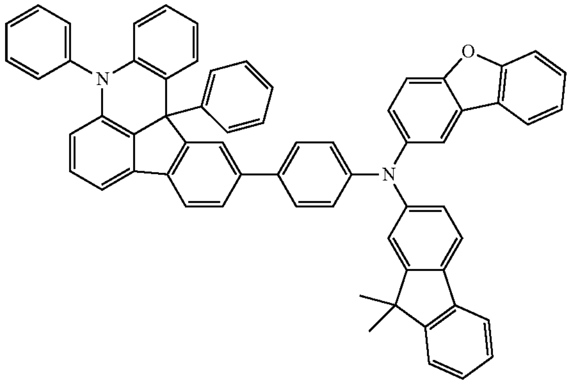

-continued
79
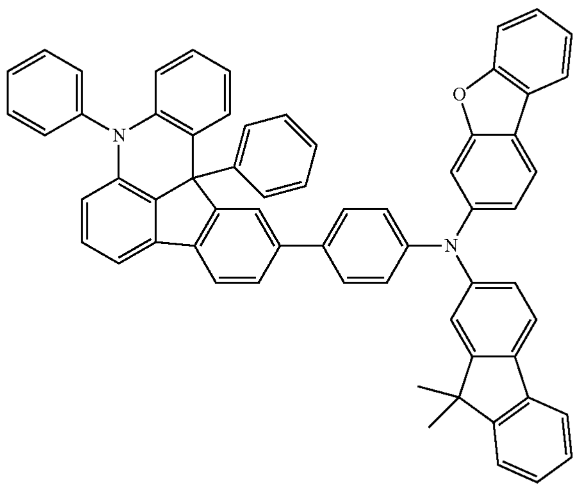
81
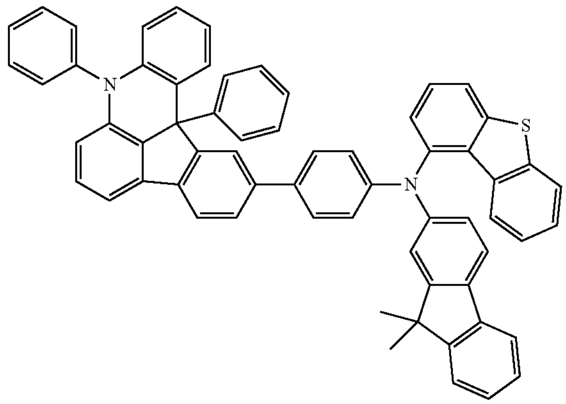
82
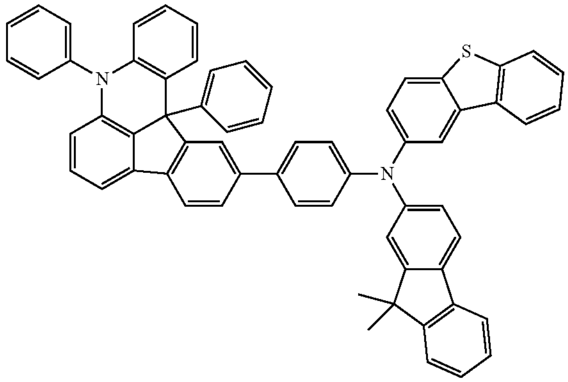
-continued
83
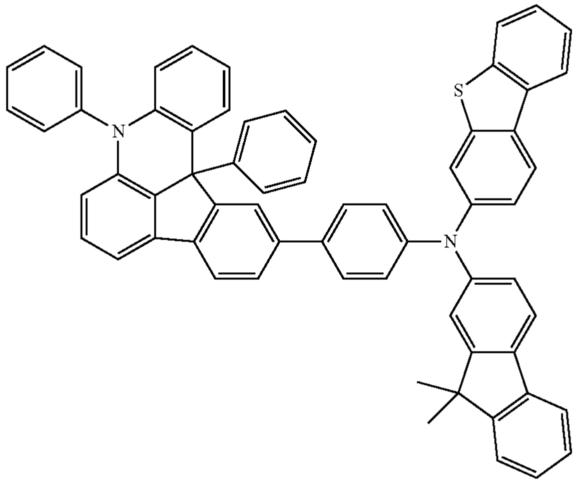
85
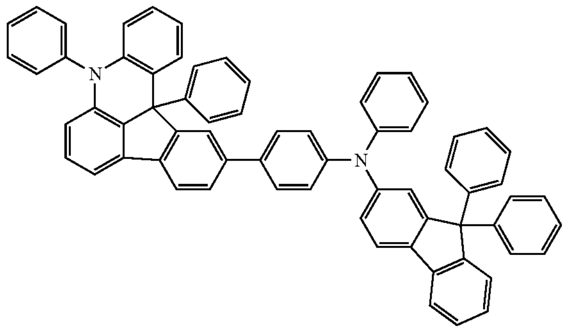
86
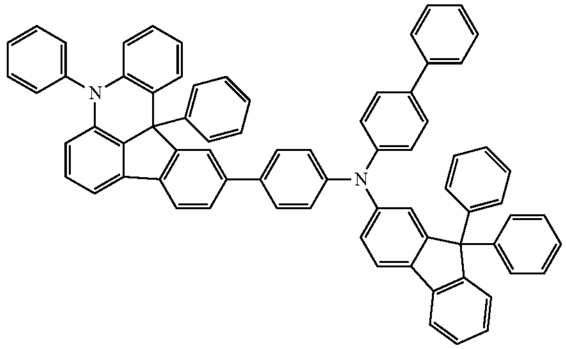

-continued
87
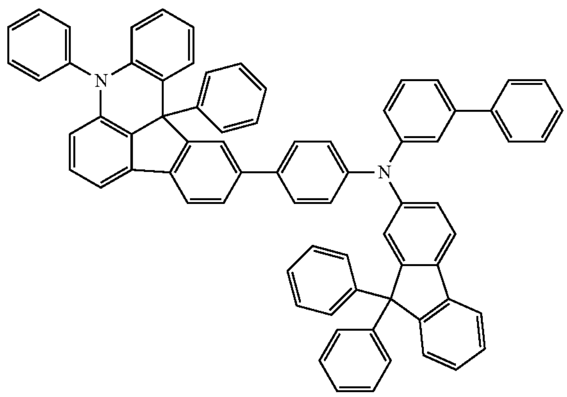
88
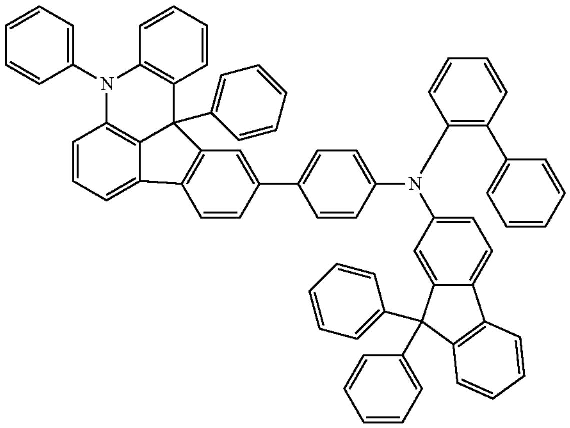
89
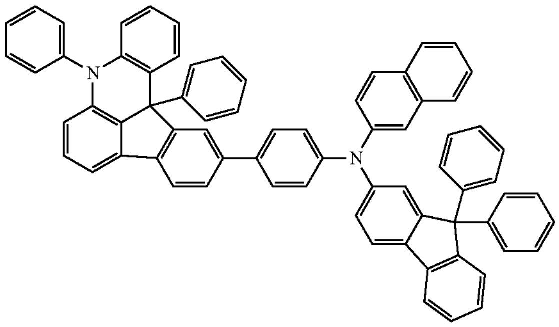
90
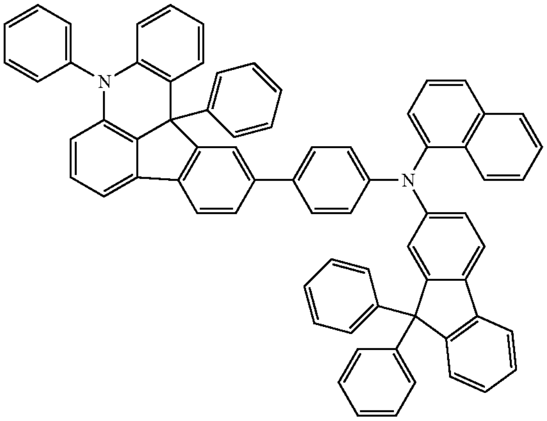
-continued
91
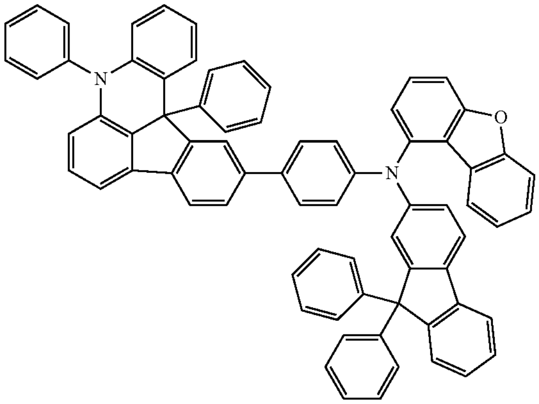
92
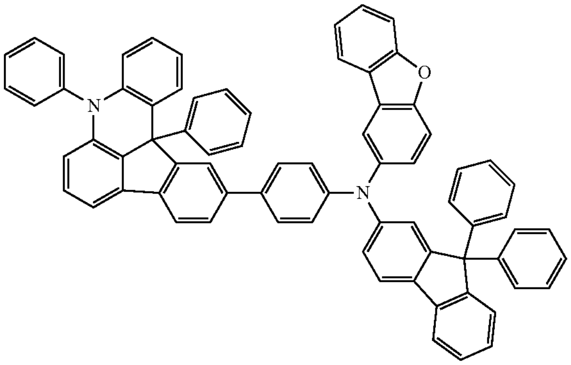
93
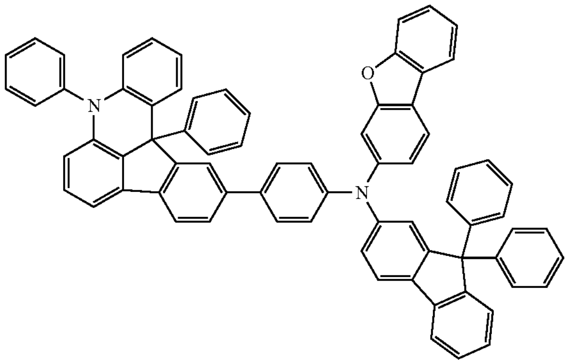
94
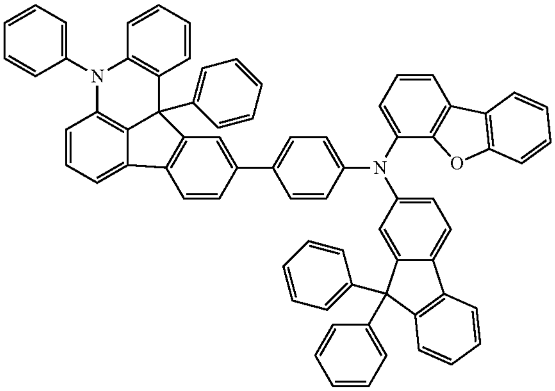

-continued
95
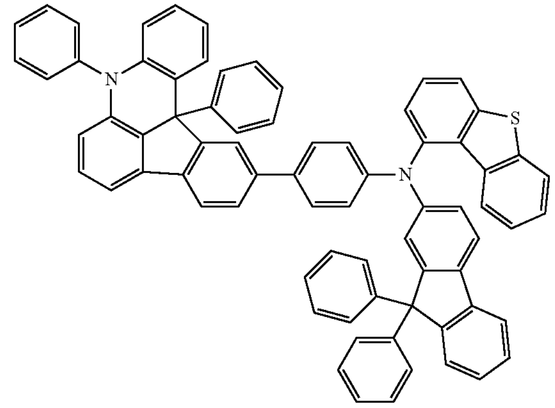
96
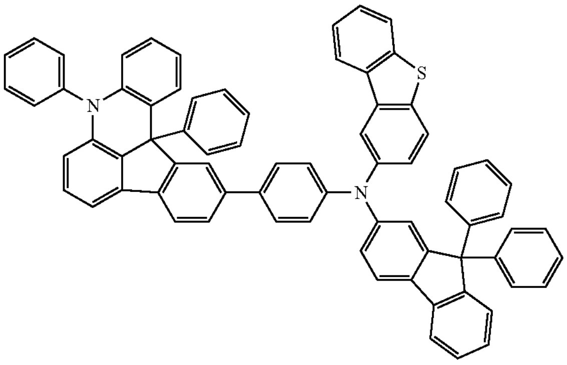
97
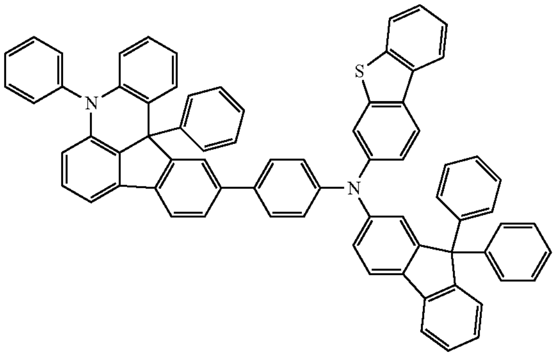
98
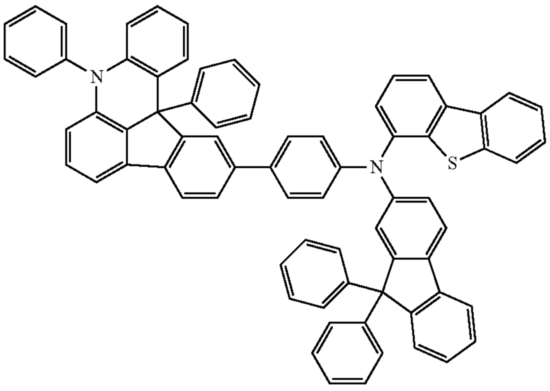
-continued
99
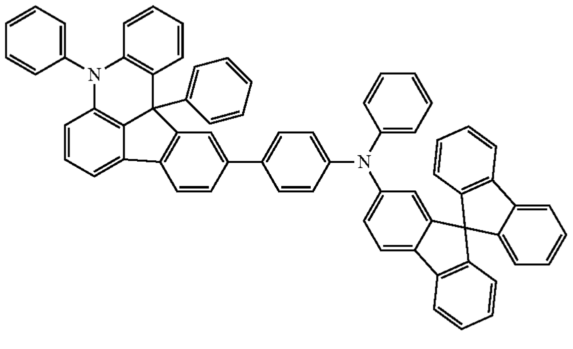
100
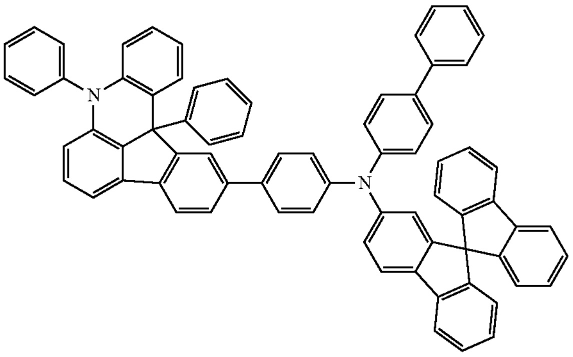
101
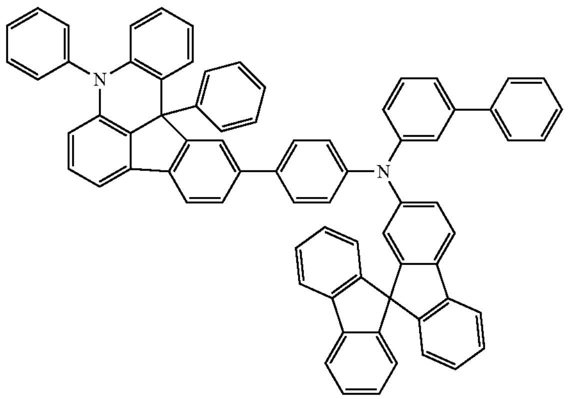
102
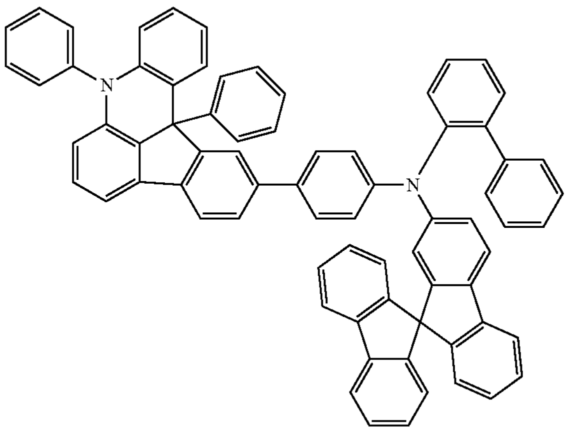

-continued
103
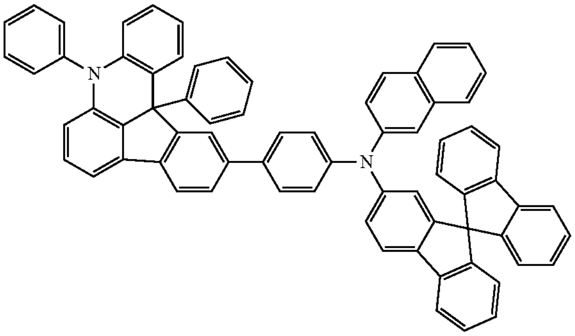
104
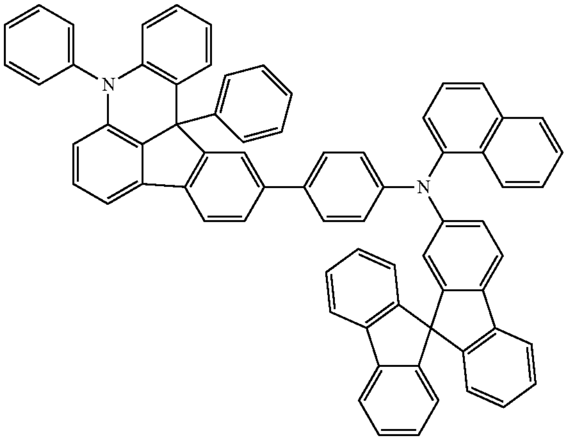
105
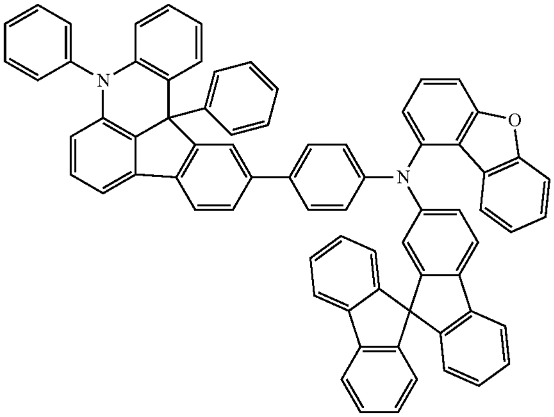
106
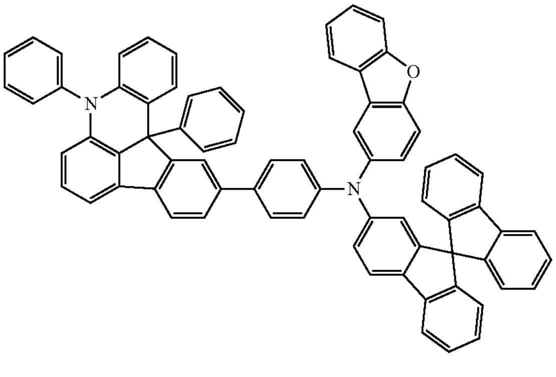
-continued
107
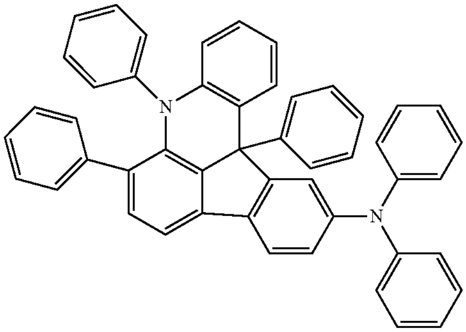
108
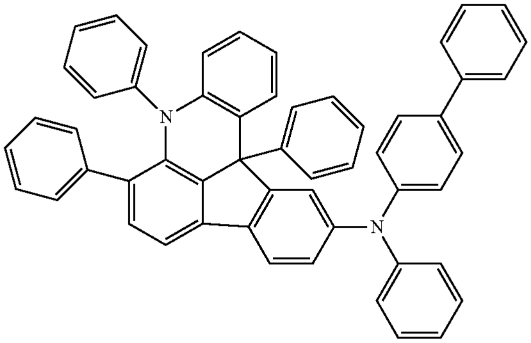
109
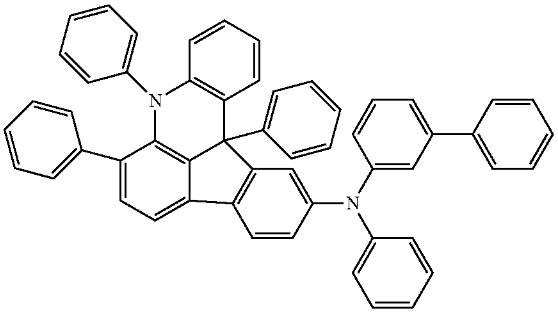
110
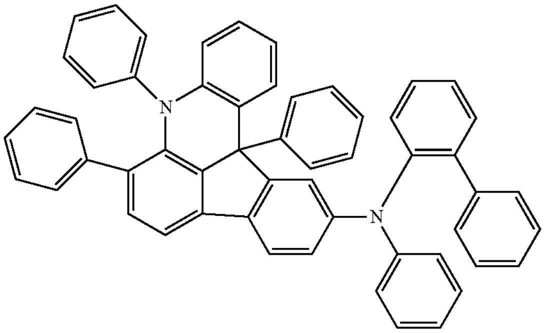

-continued
111
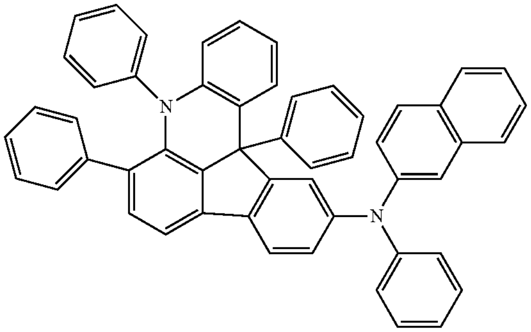
112
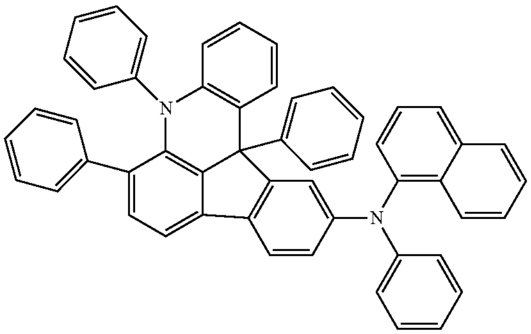
113
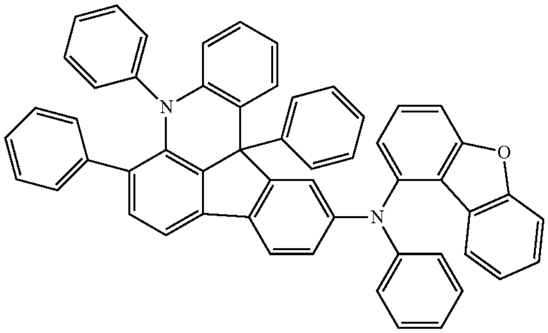
114
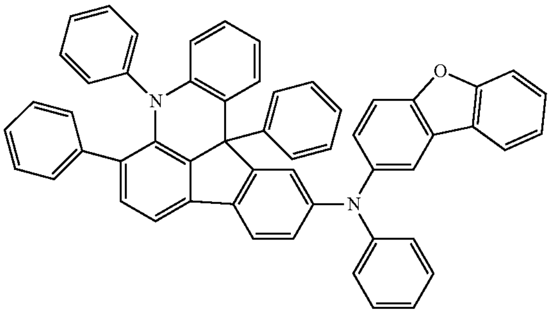
-continued
115
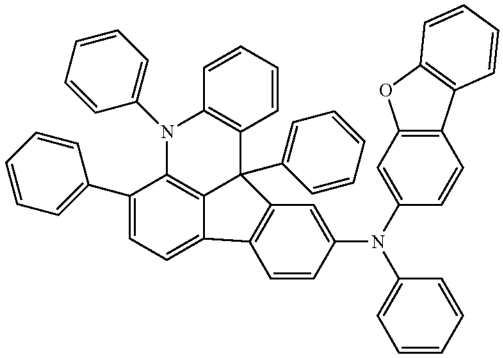
116
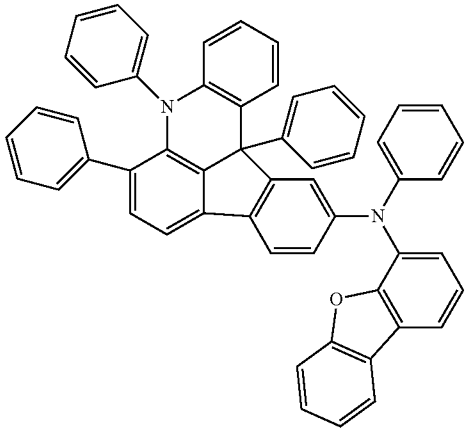
117
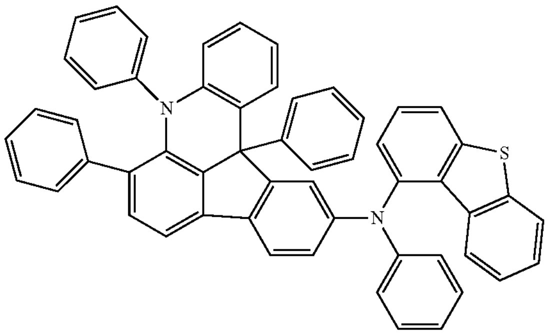
118
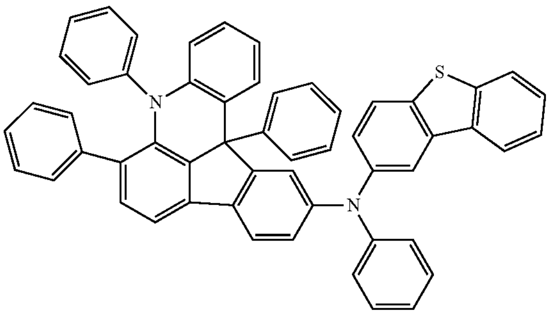

-continued
119
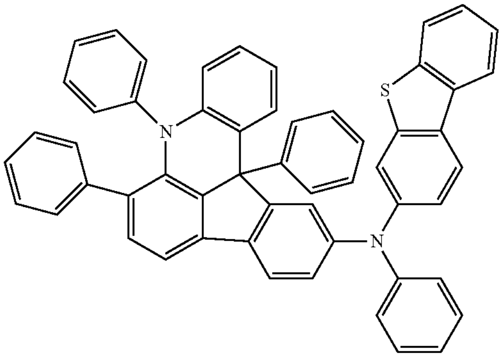
120
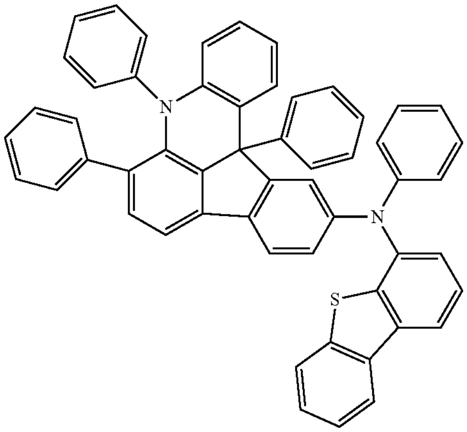
121
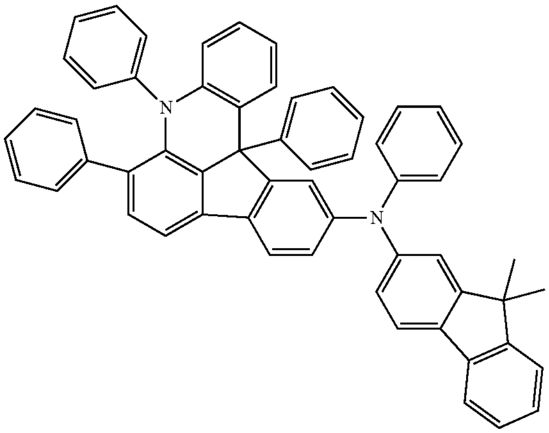
-continued
122
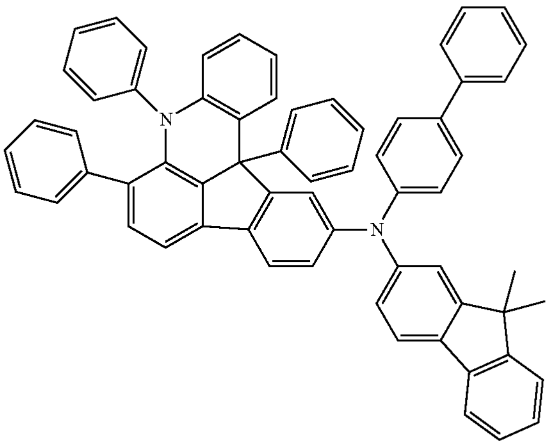
123
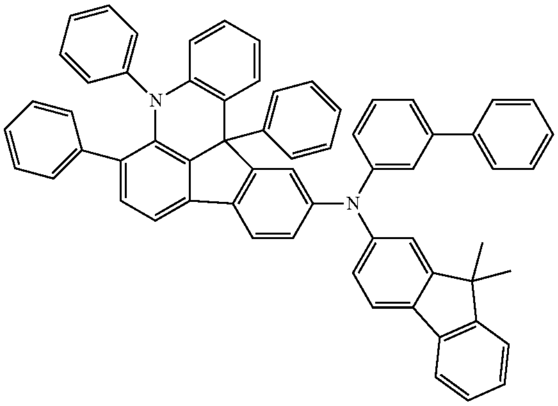
124
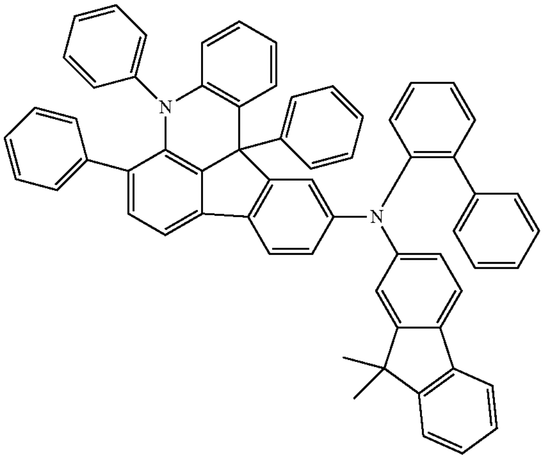

125
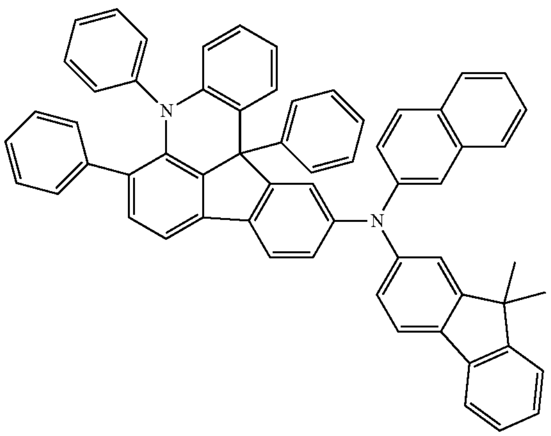
126
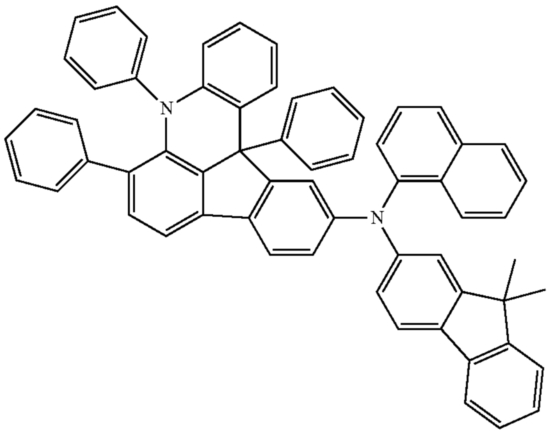
127
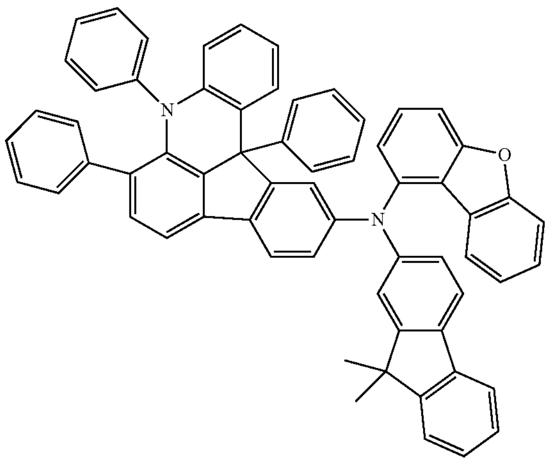
128
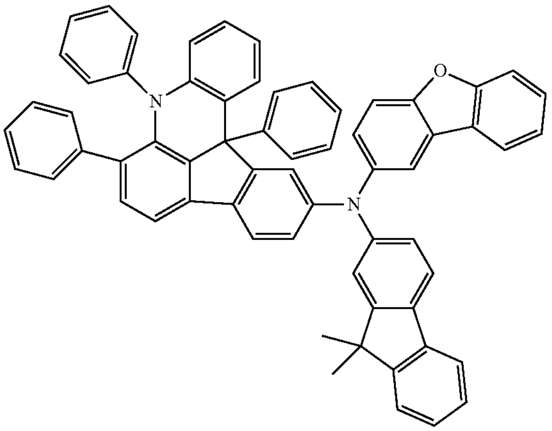
129
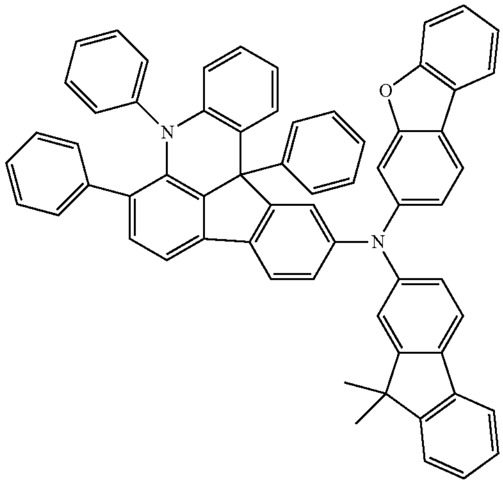
130
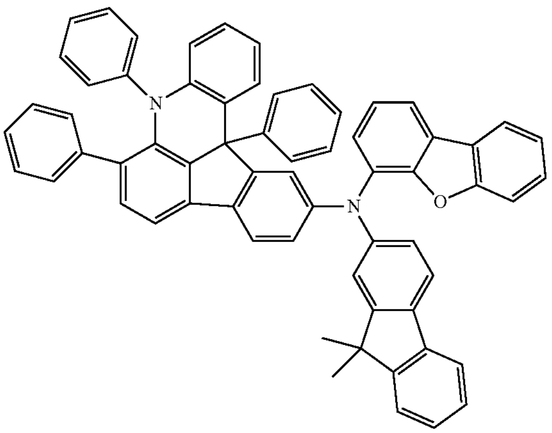

-continued
131
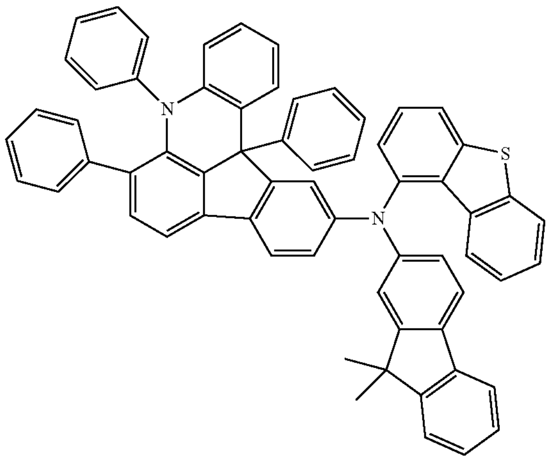
132
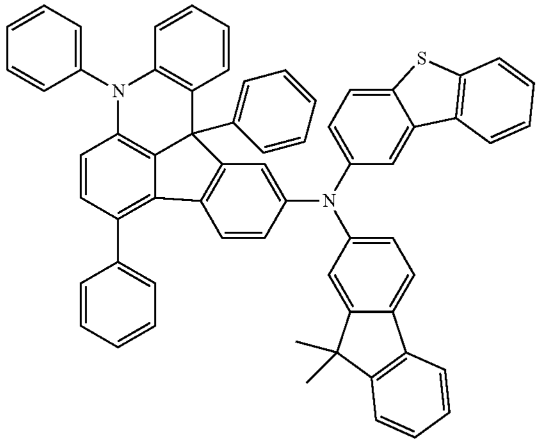
133
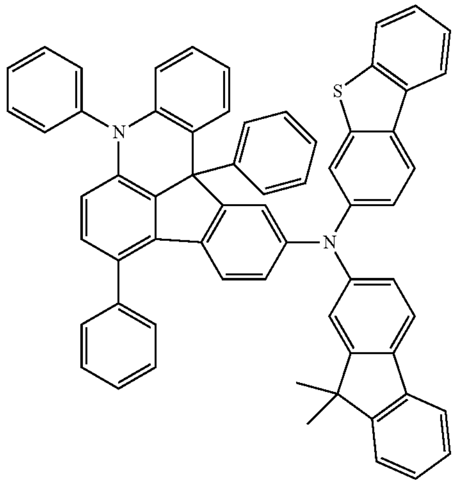
-continued
134
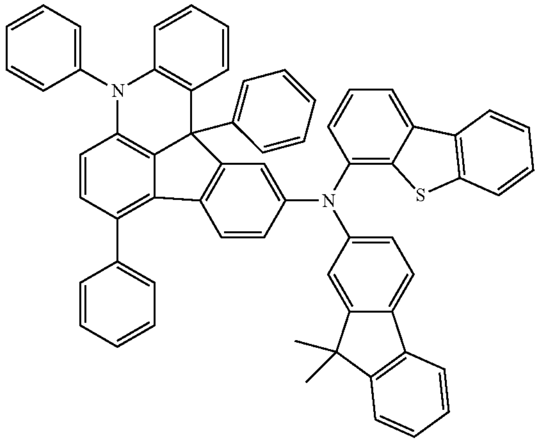
135
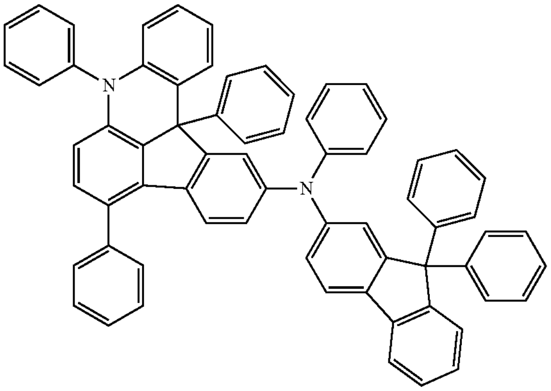
136
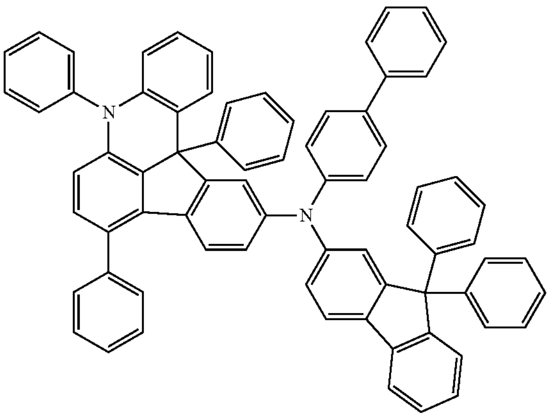

-continued
137
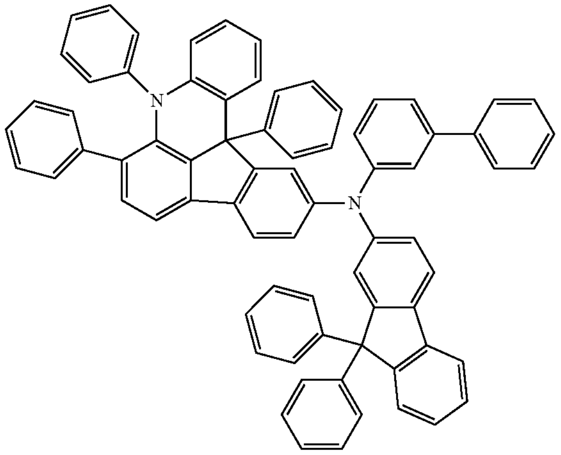
138
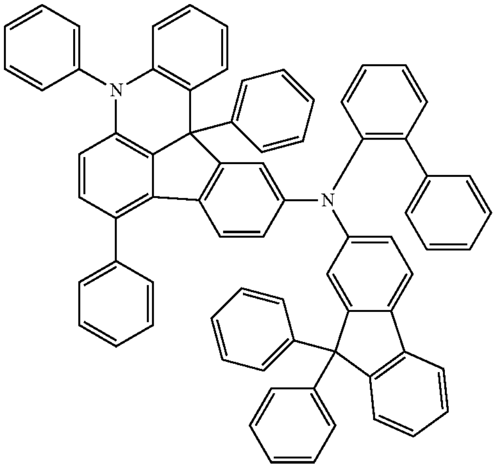
139
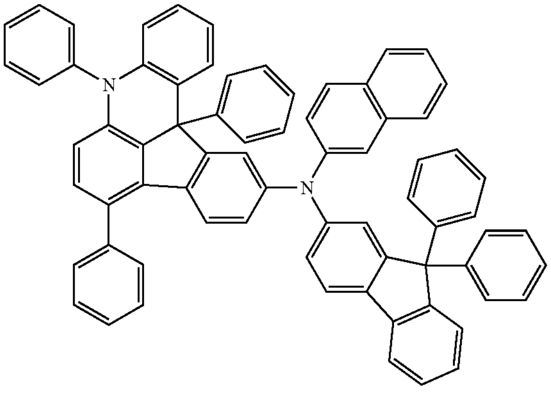
-continued
140
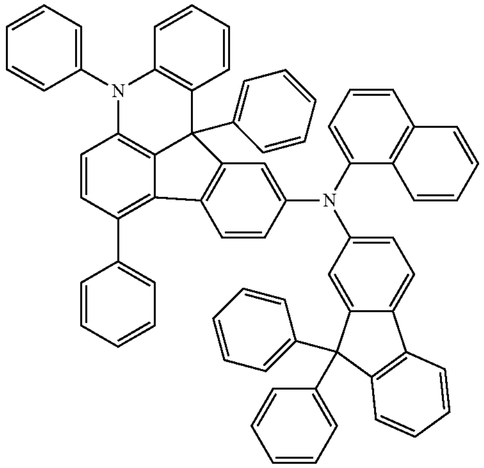
141
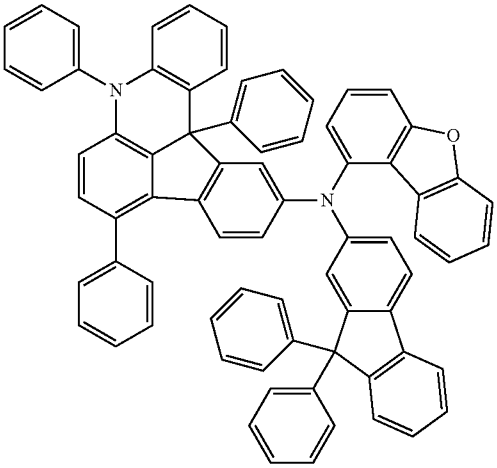
142
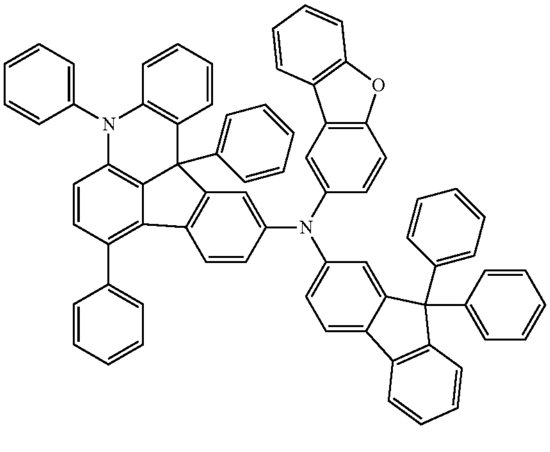

-continued
143
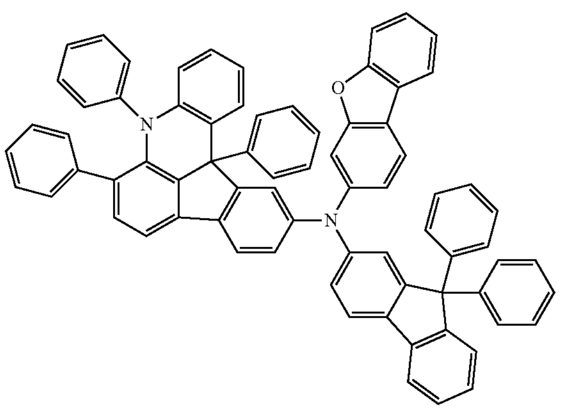
144
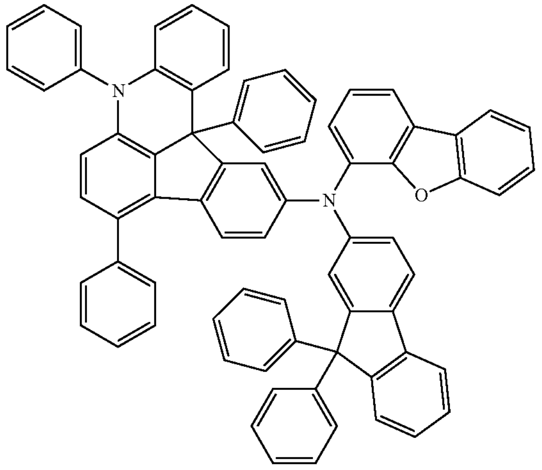
145
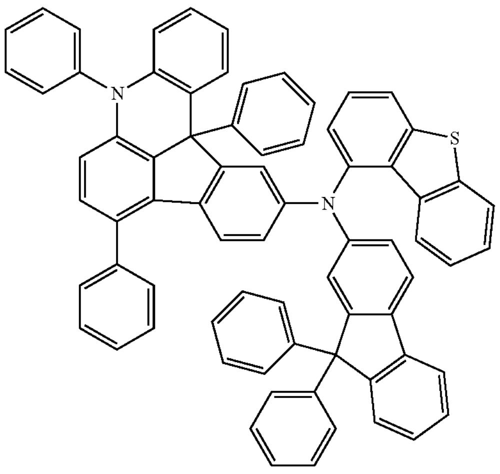
-continued
146
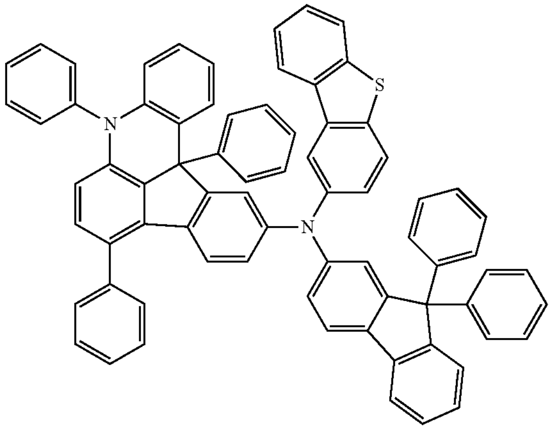
147
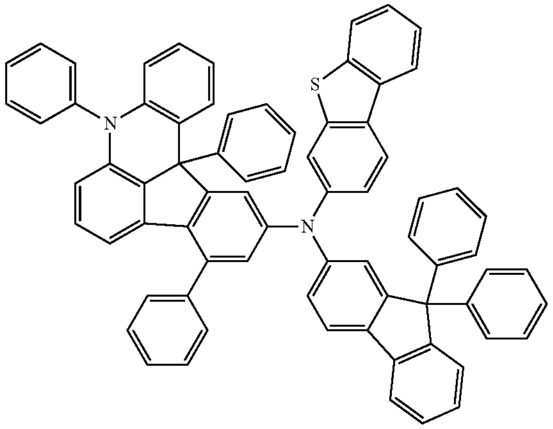
148
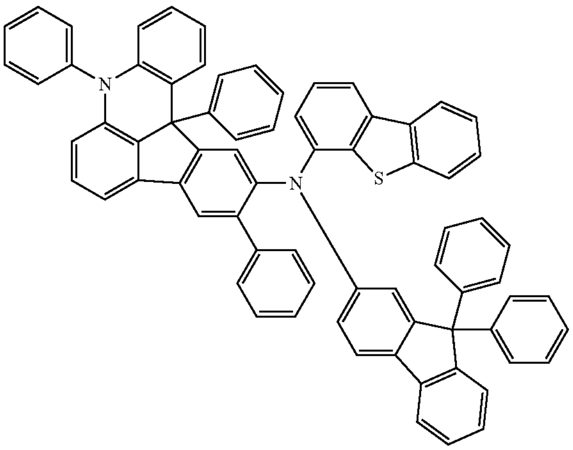

-continued
149
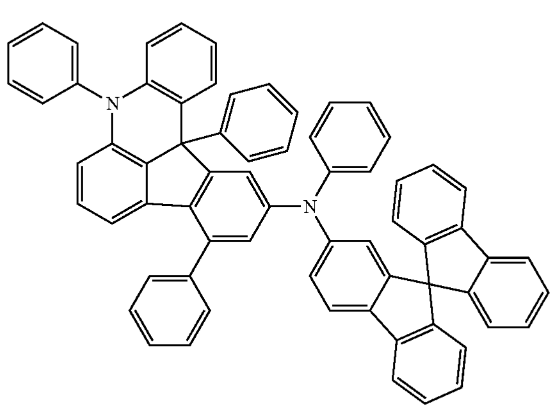
150
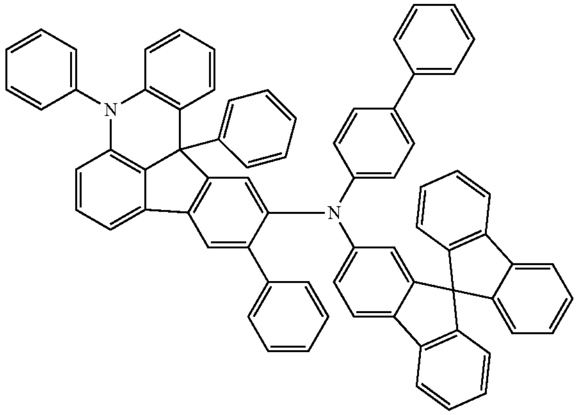
151
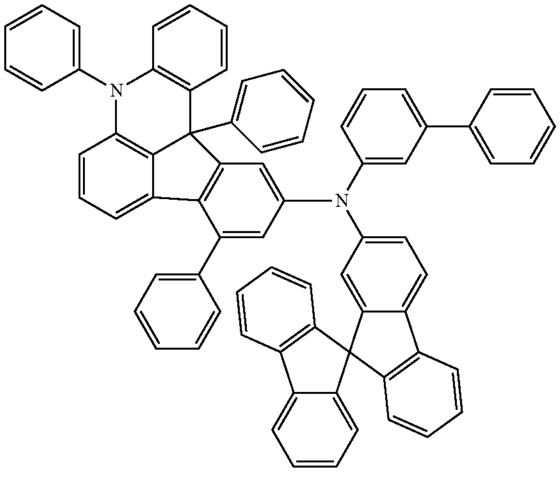
-continued
152
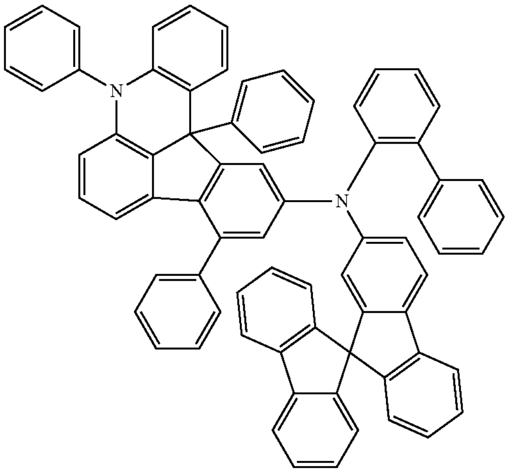
153
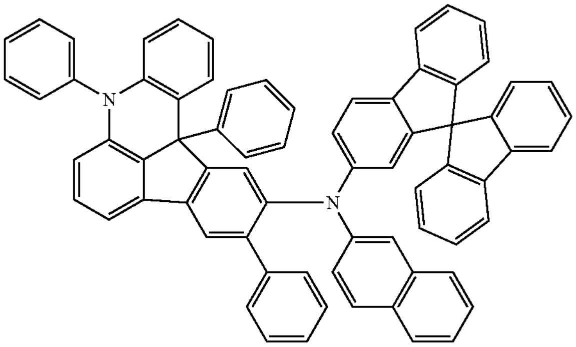
154
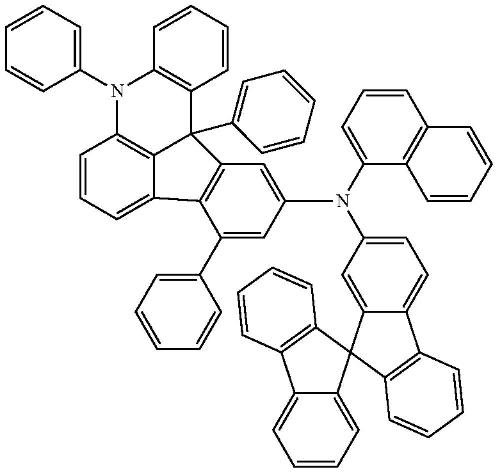

-continued
155
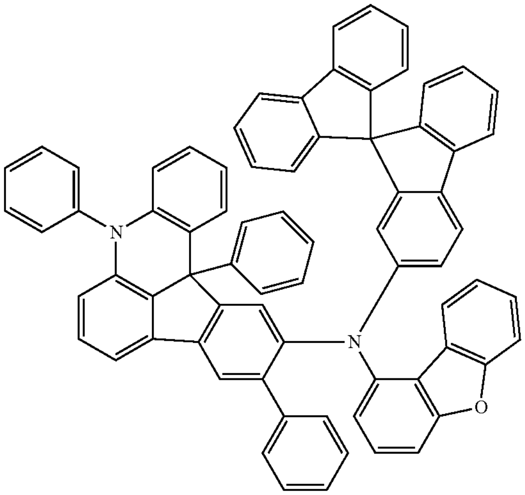
156
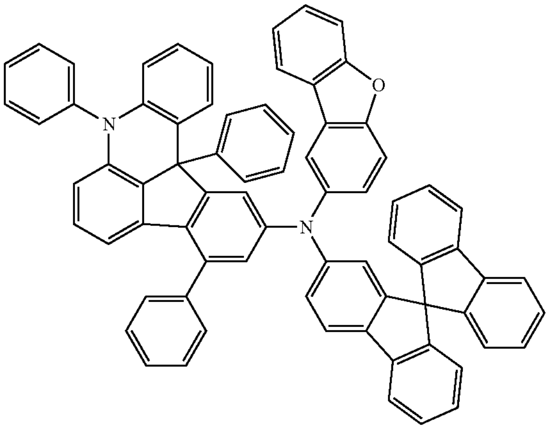
157
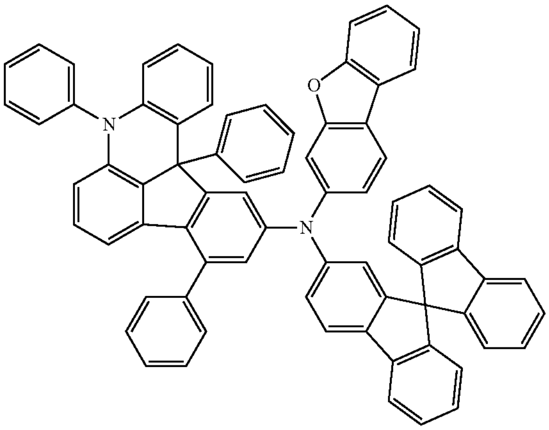
-continued
158
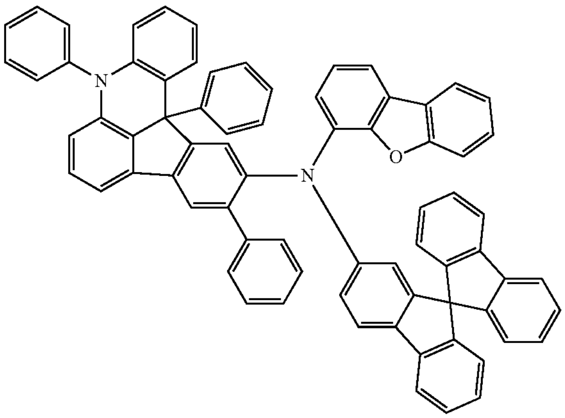
159
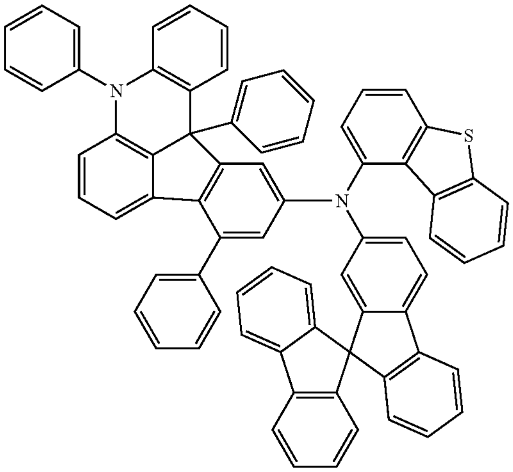
160
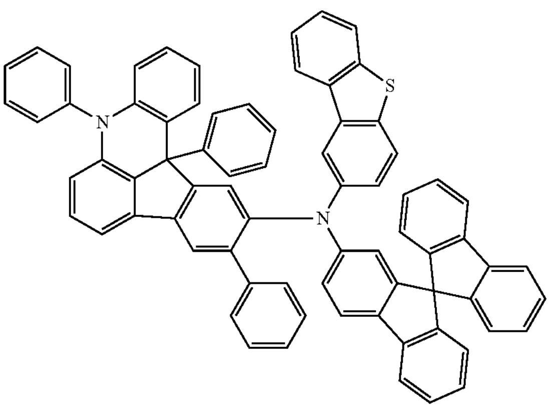

-continued
161
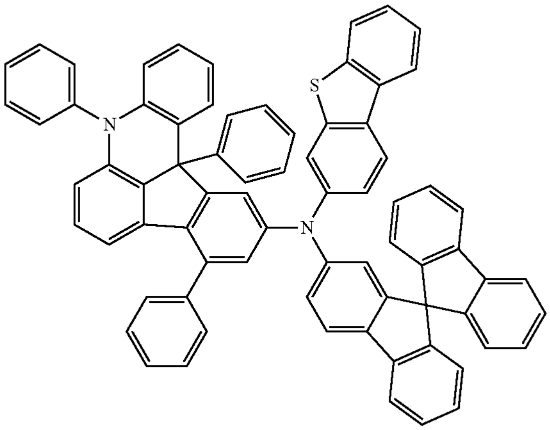
162
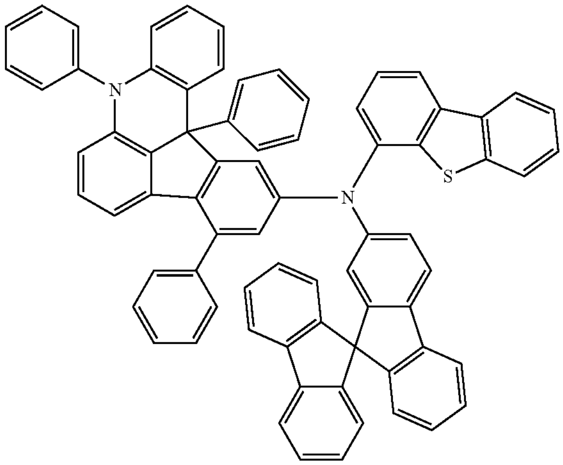
163
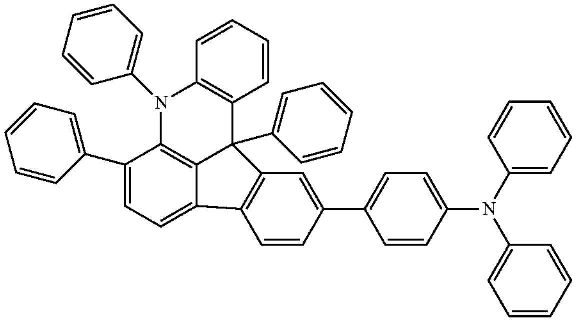
-continued
164
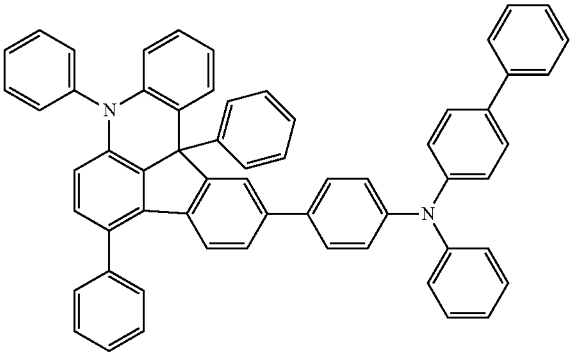
165
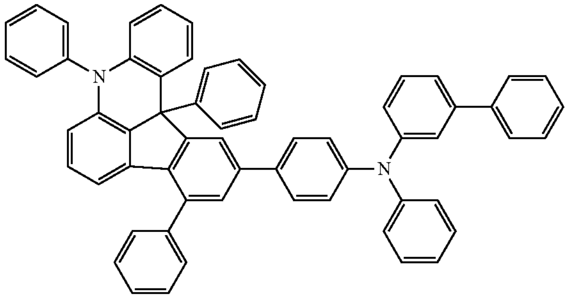
166
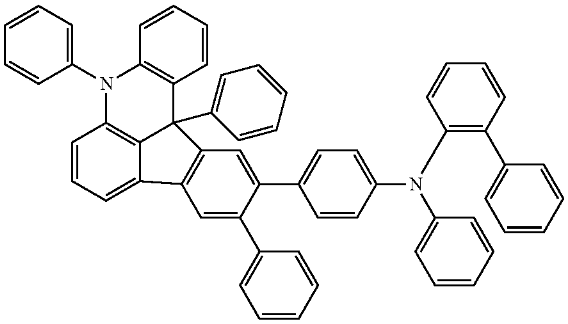
167
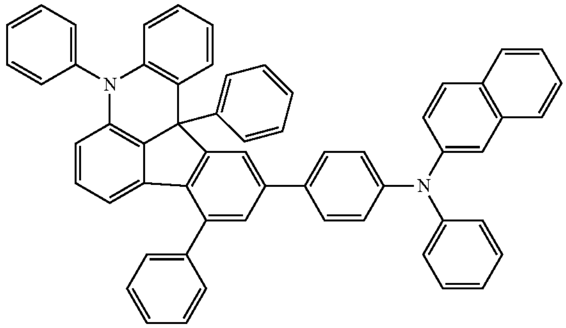

168
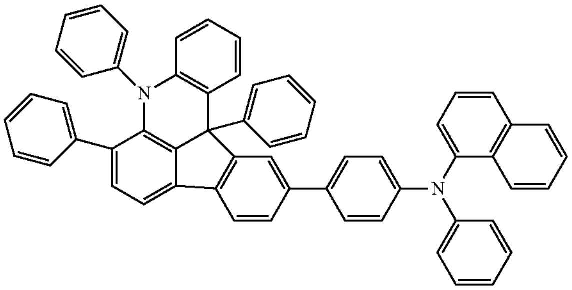
169
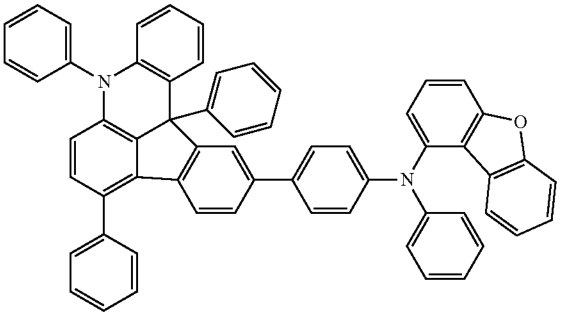
170
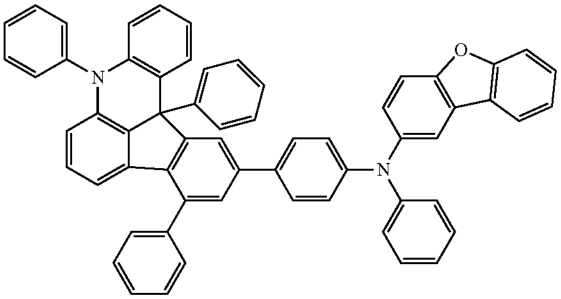
171
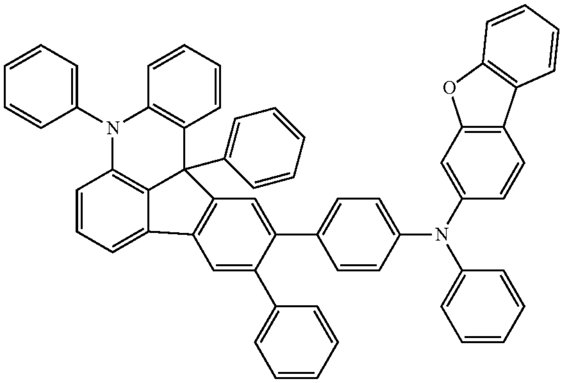
172
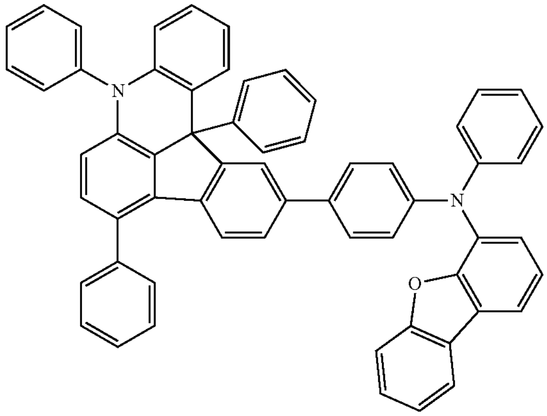
173
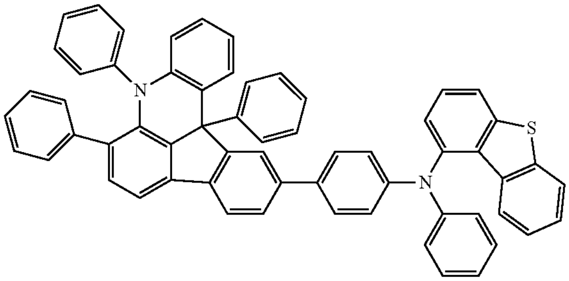
174
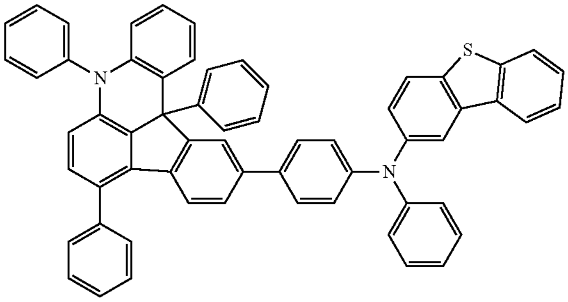
175
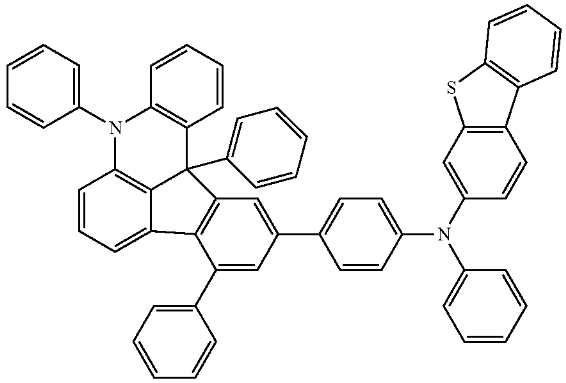

-continued
176
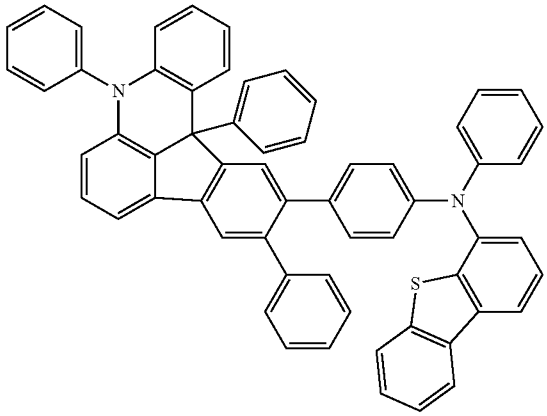
177
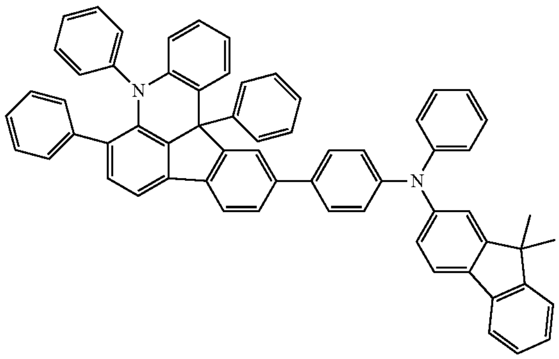
178
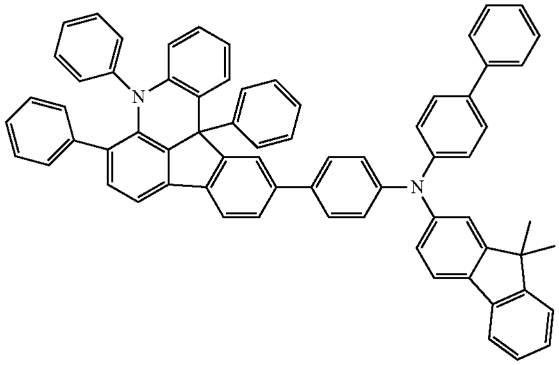
179
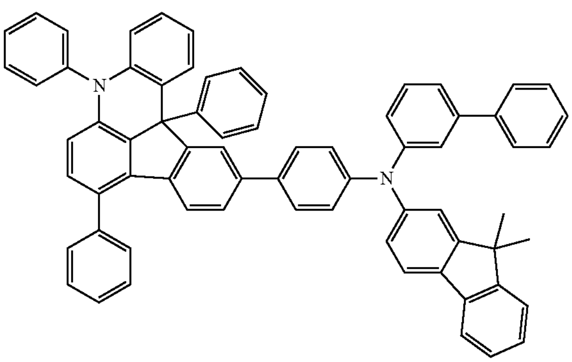
-continued
180
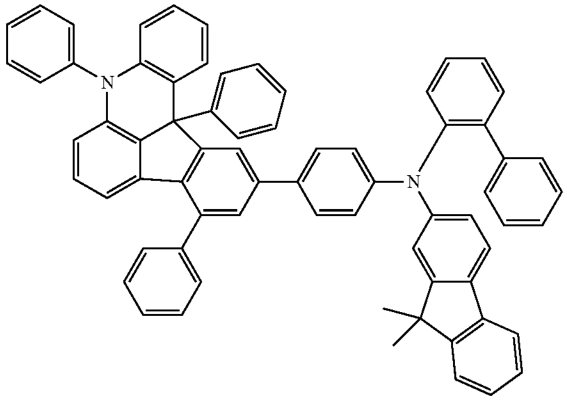
181
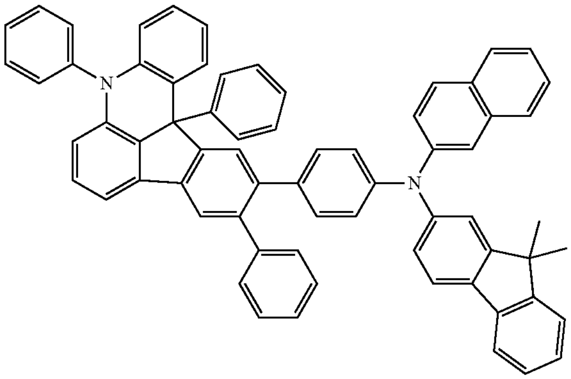
182
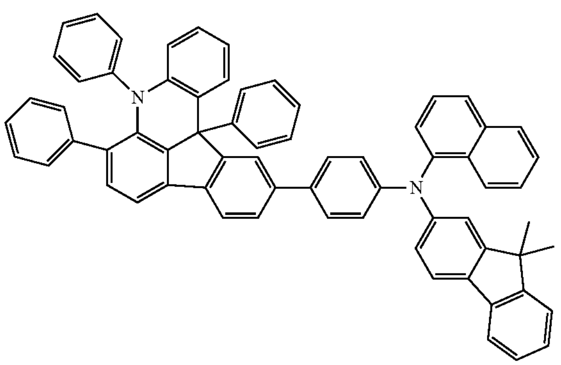
183
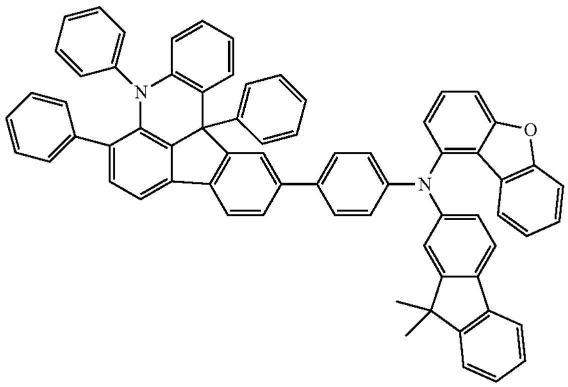

-continued
184
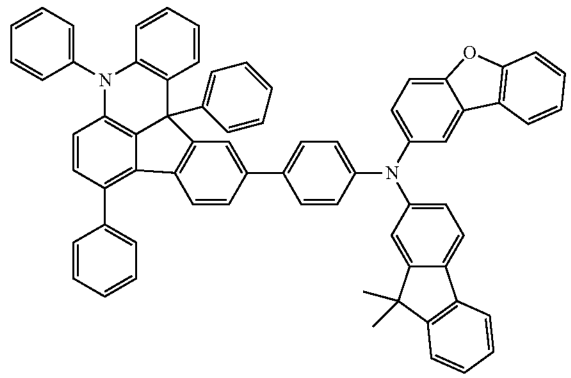
185
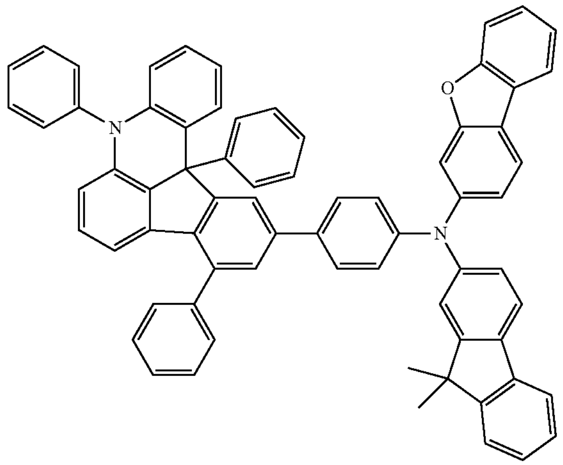
186
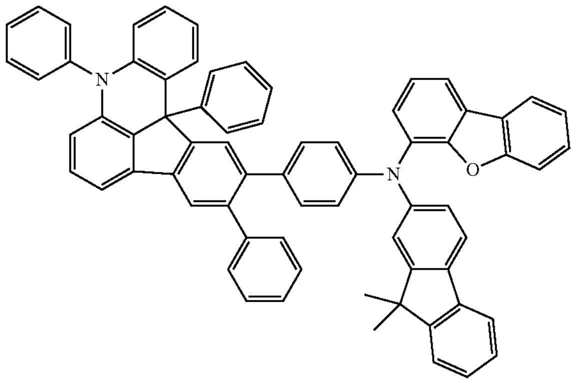
-continued
187
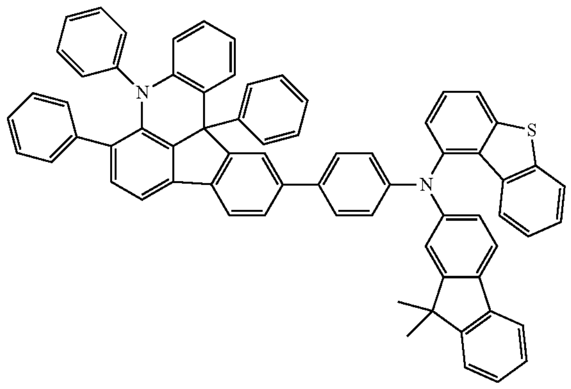
188
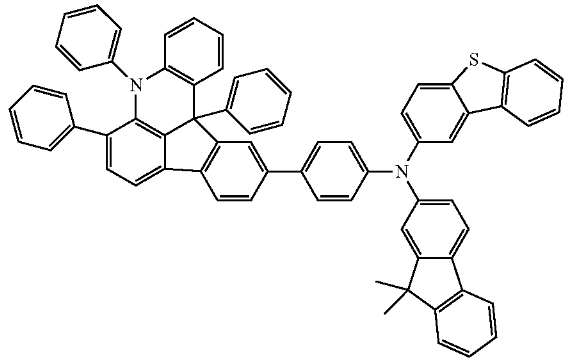
189
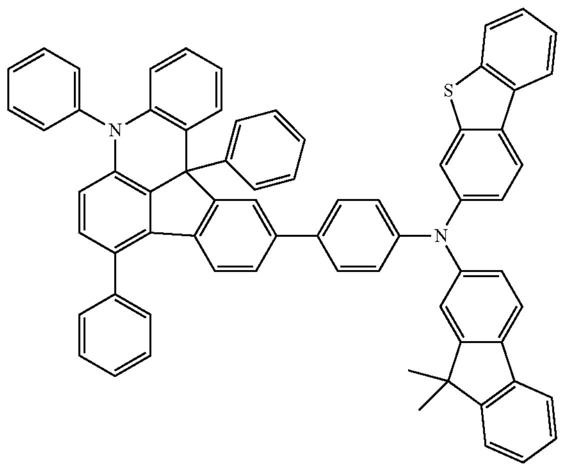

-continued
190
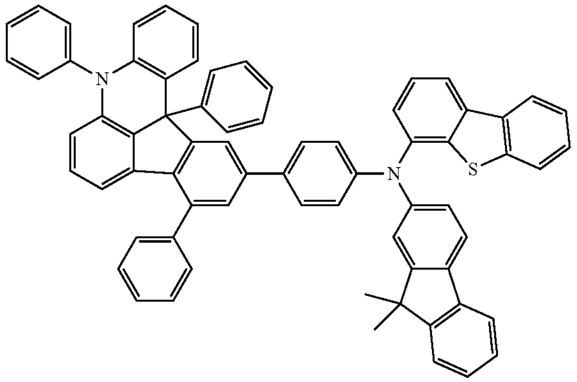
191
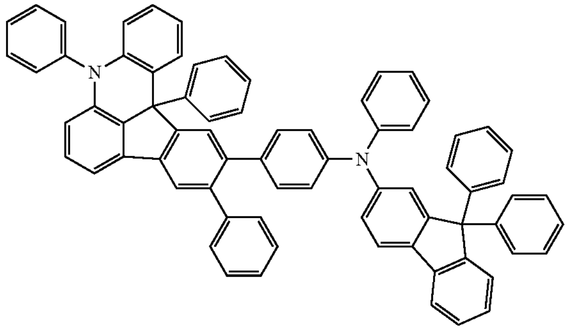
192
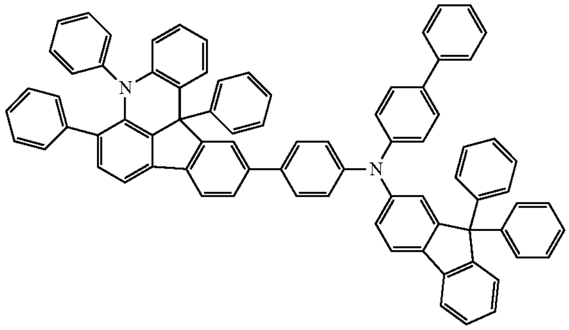
193
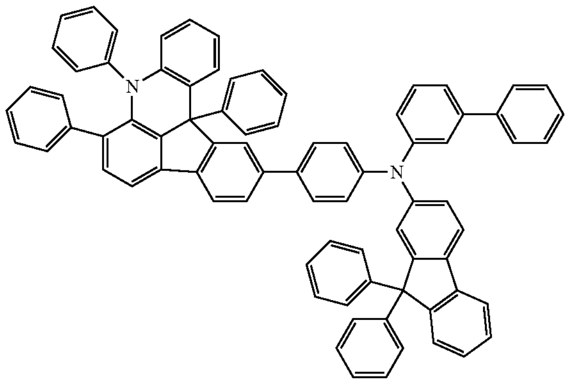
-continued
194
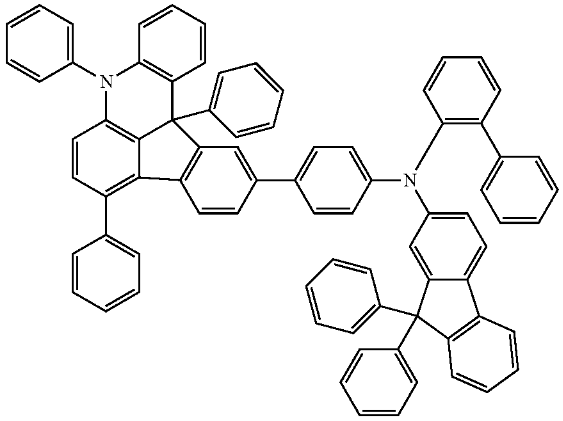
195
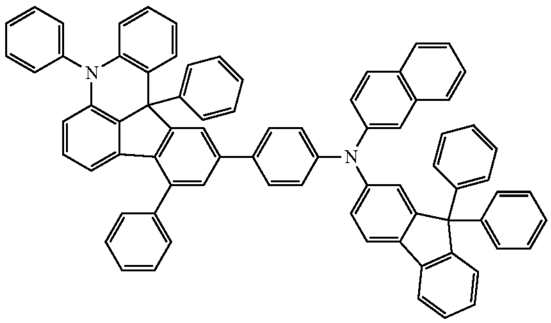
196
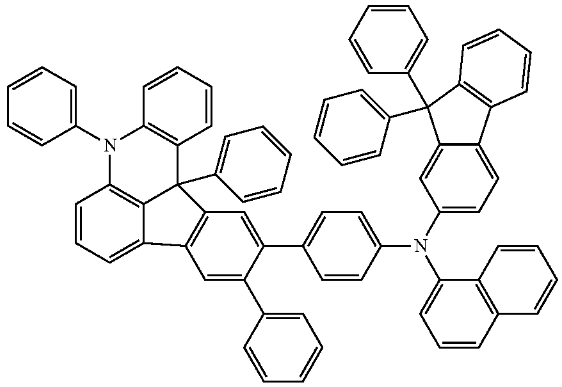
197
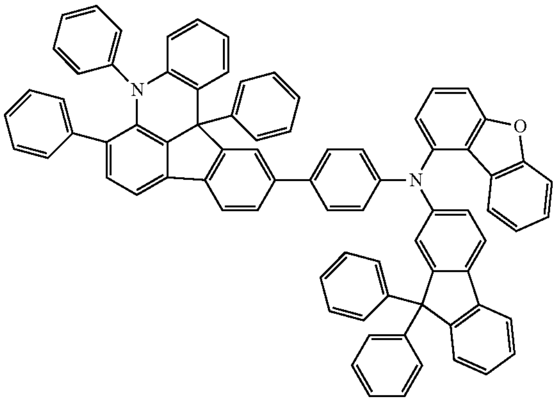

-continued
198
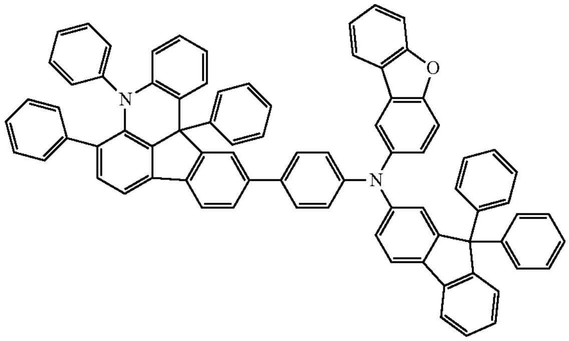
199
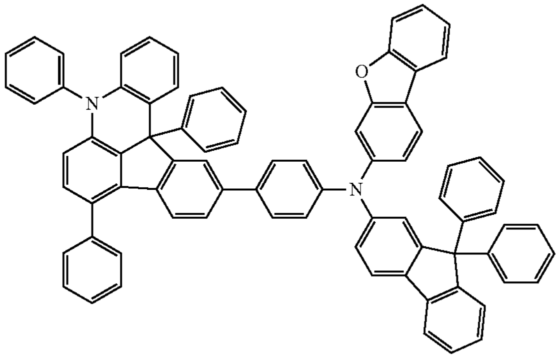
200
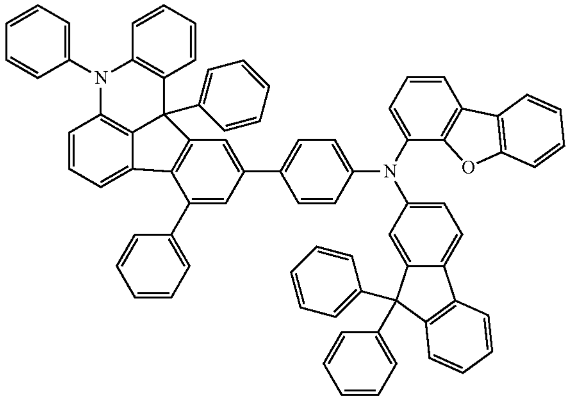
201
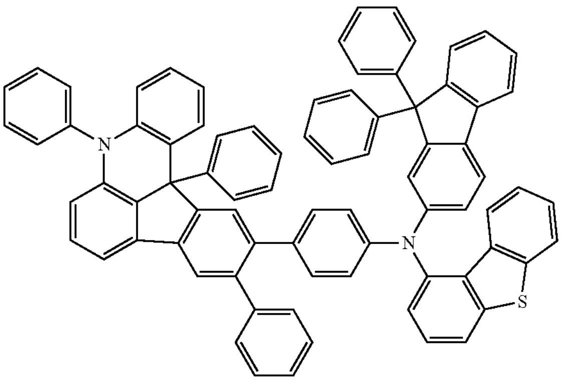
-continued
202
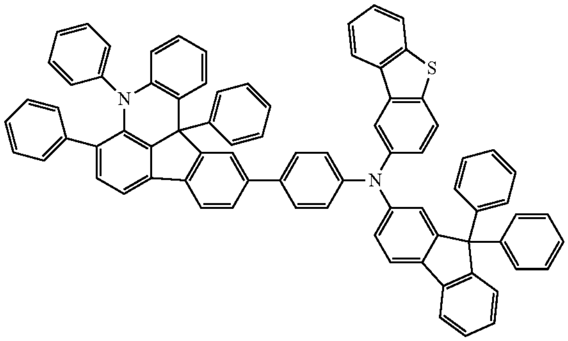
203
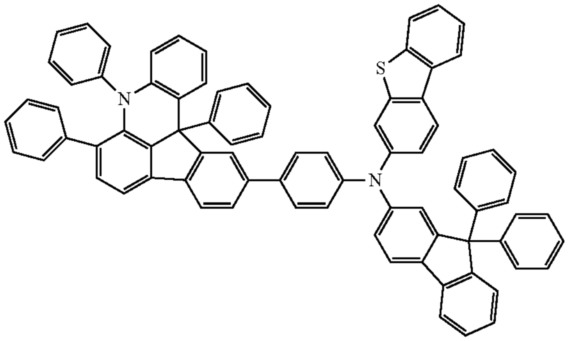
204
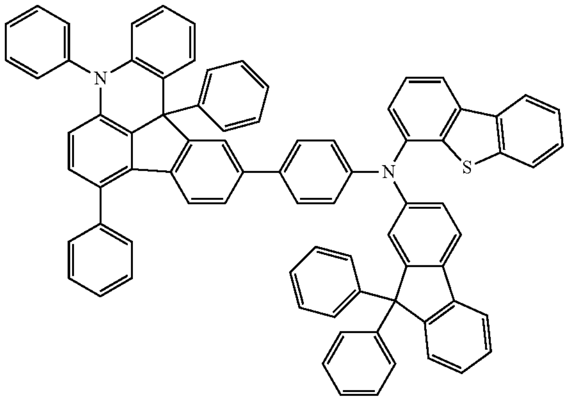
205
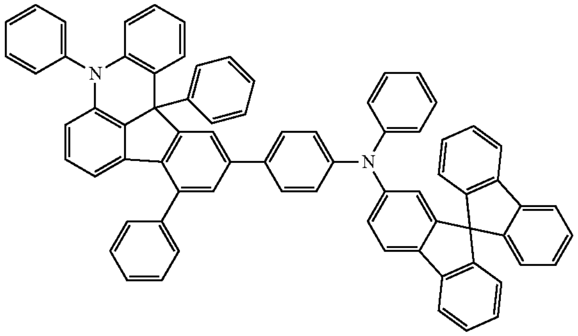

-continued
206
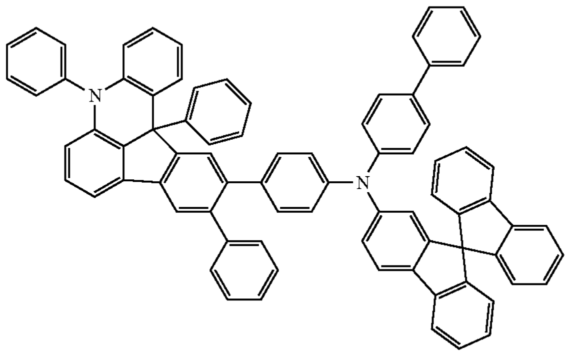
207
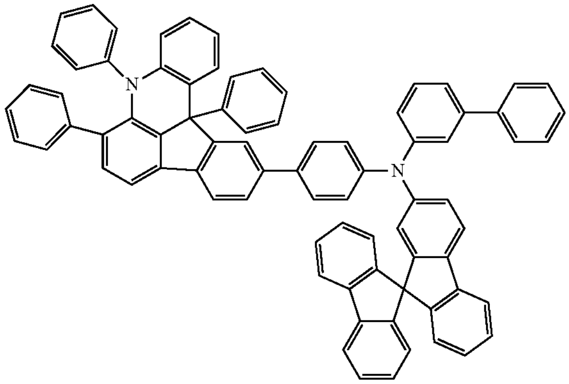
208
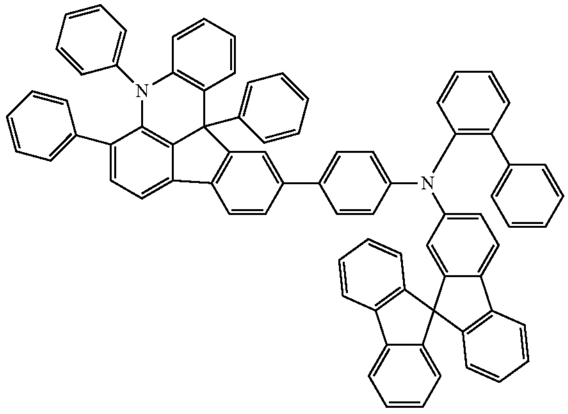
209
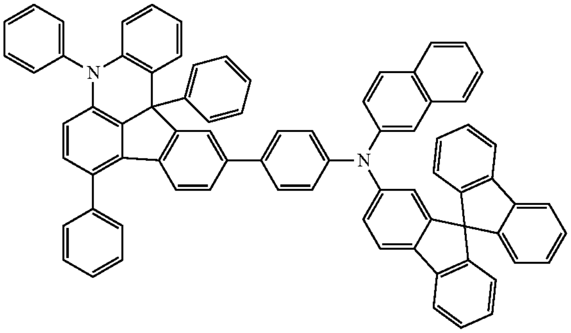
-continued
210
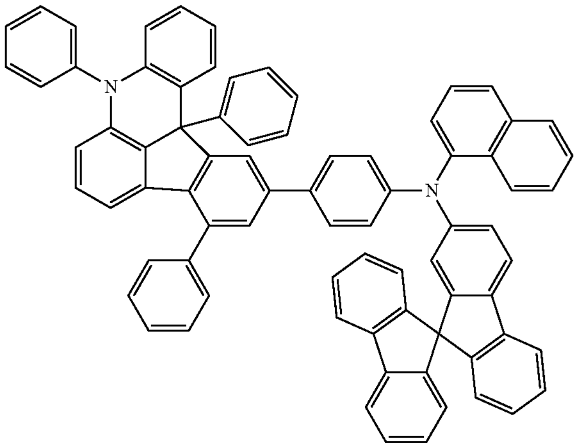
211
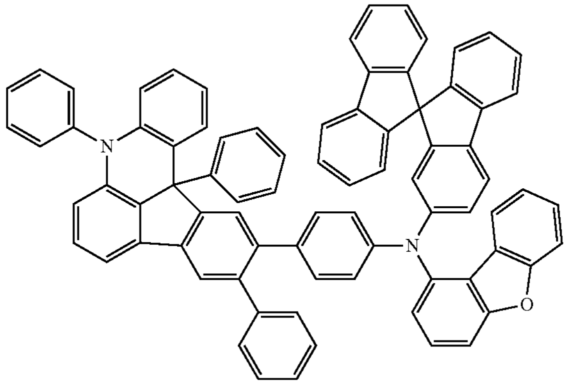
212
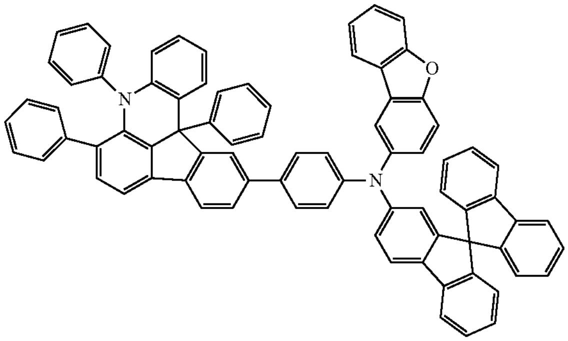

-continued
213
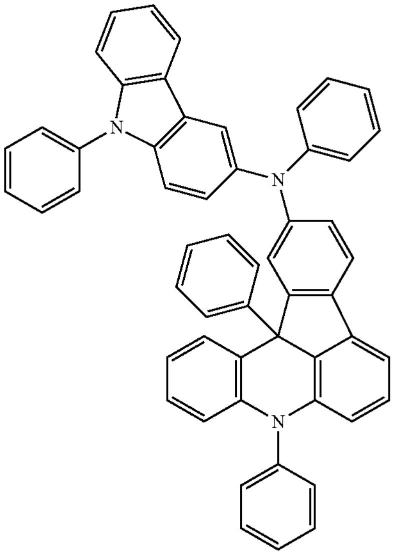
214
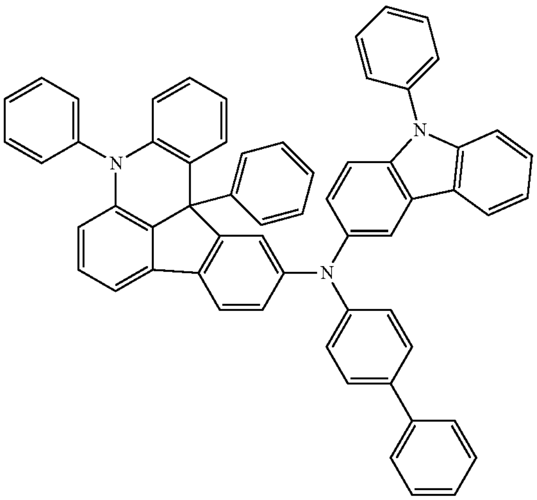
215
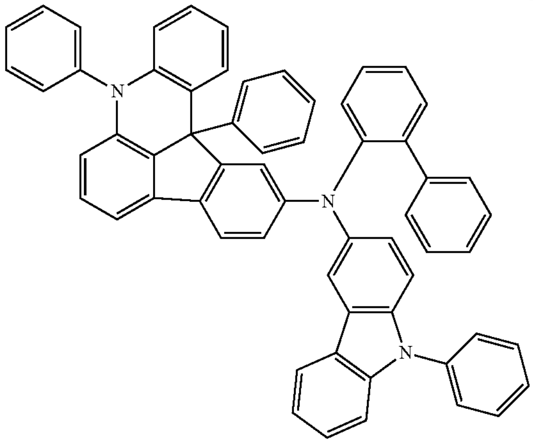
-continued
216
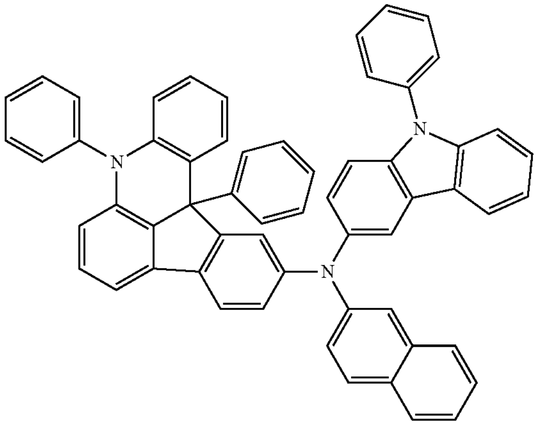
217
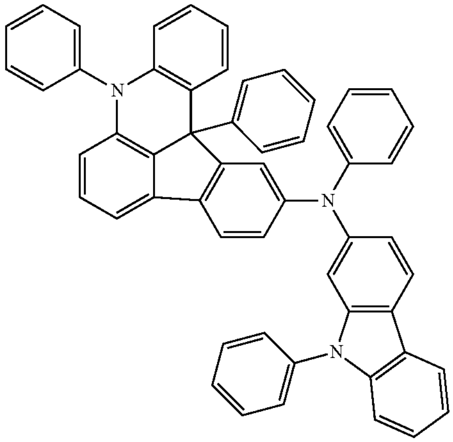
218
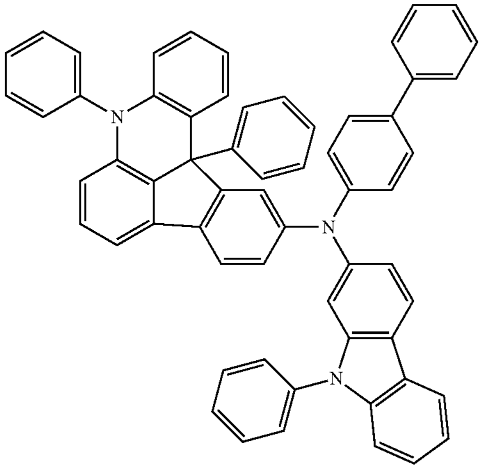

-continued
219
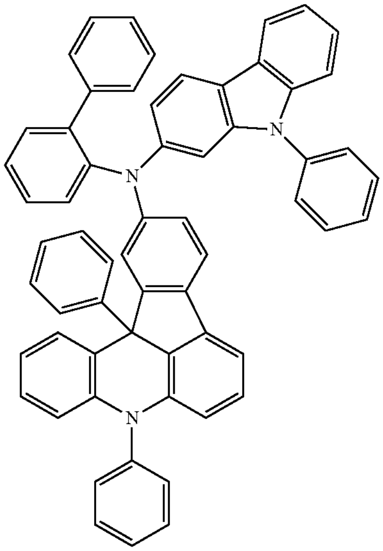
220
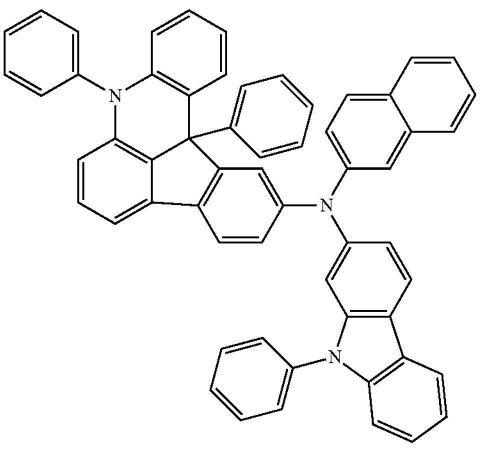
-continued
221
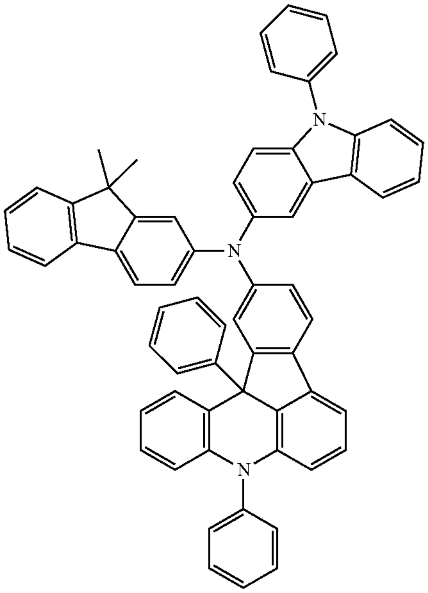
222
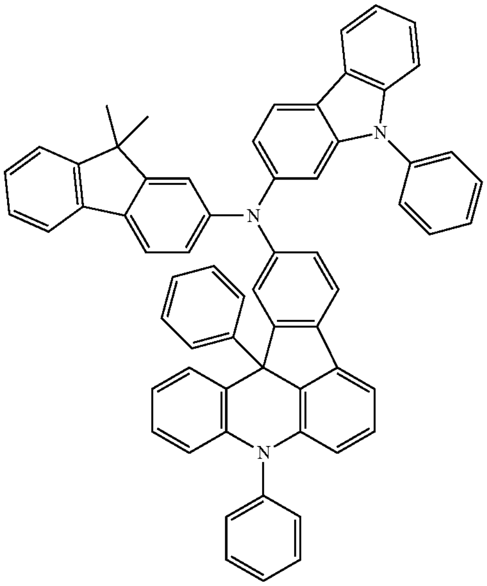

223
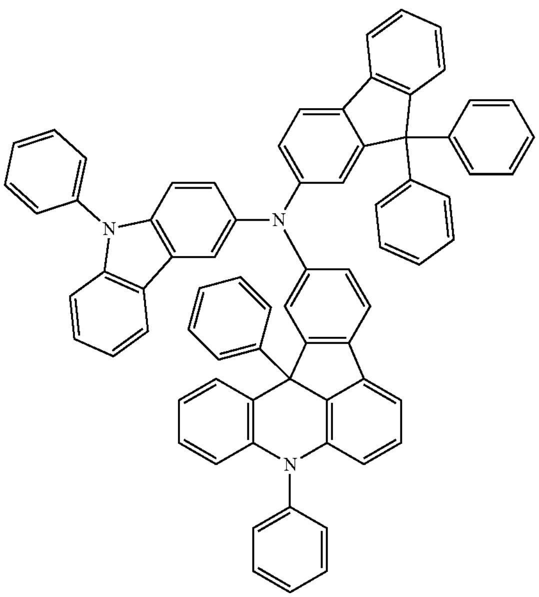
224
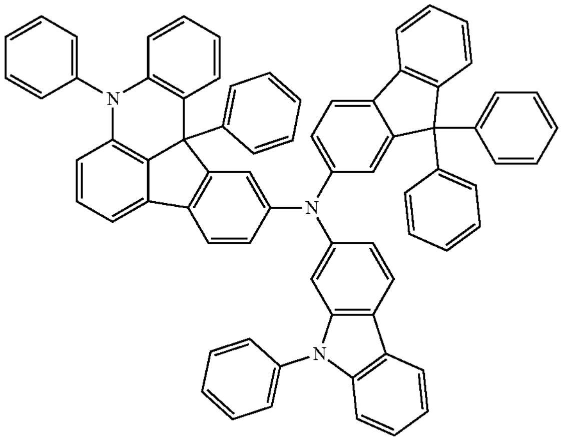
225
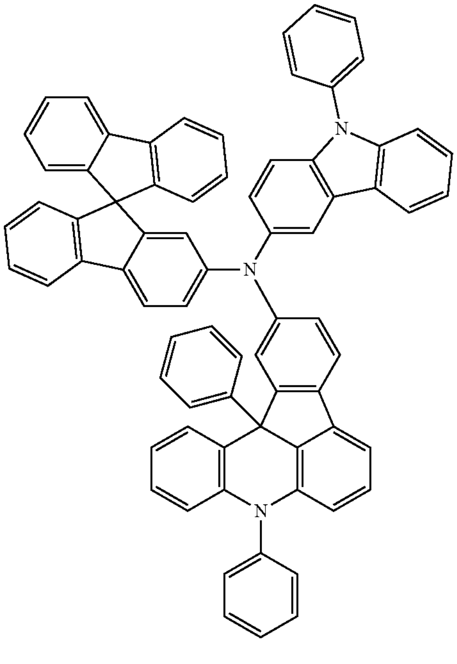
226
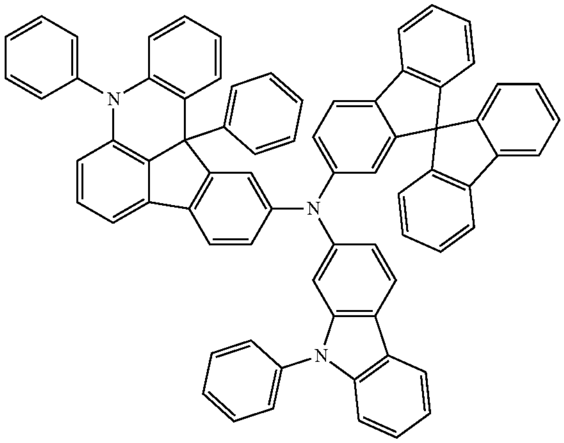

-continued
227
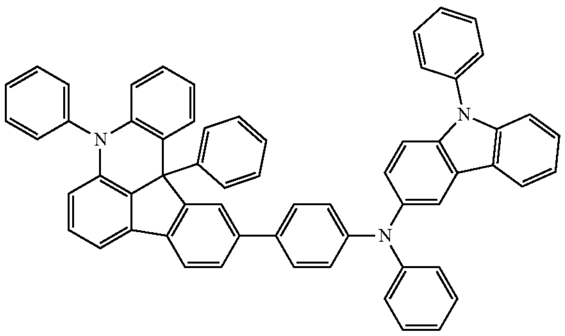
228
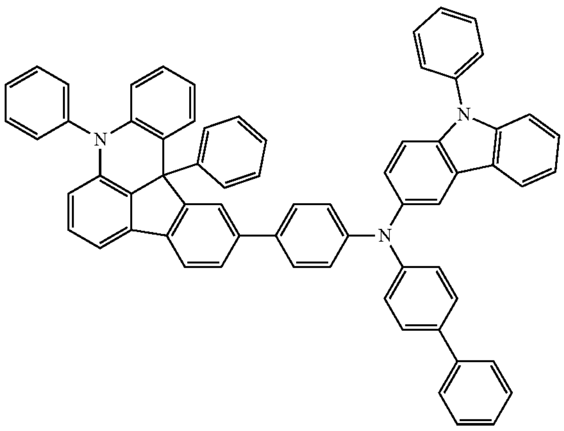
229
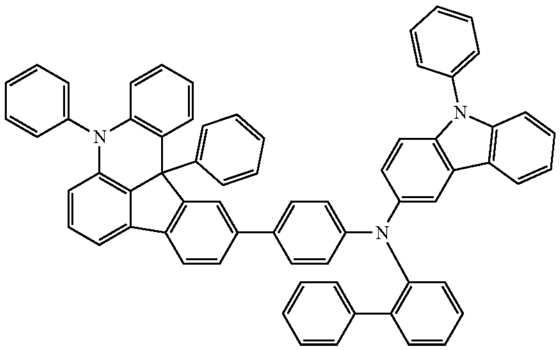
230
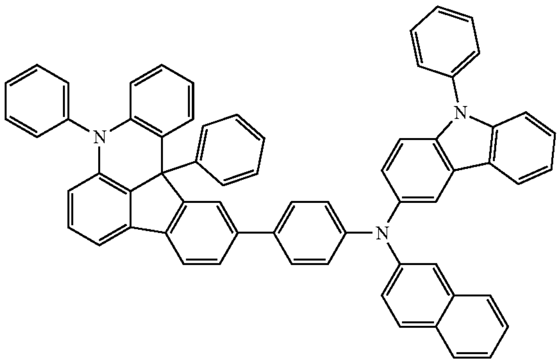
231
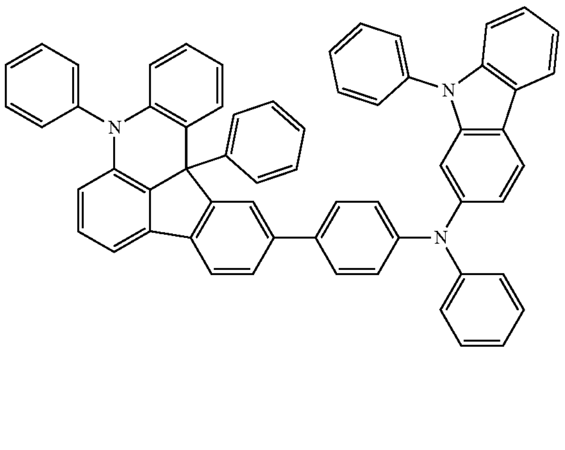
232
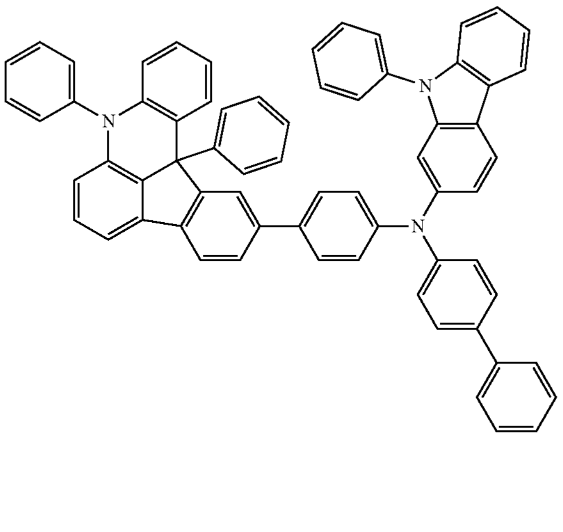

-continued
233
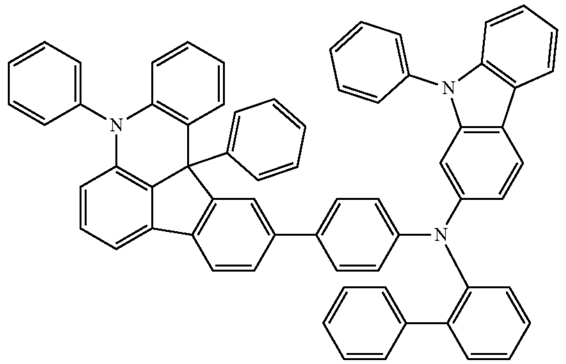
234
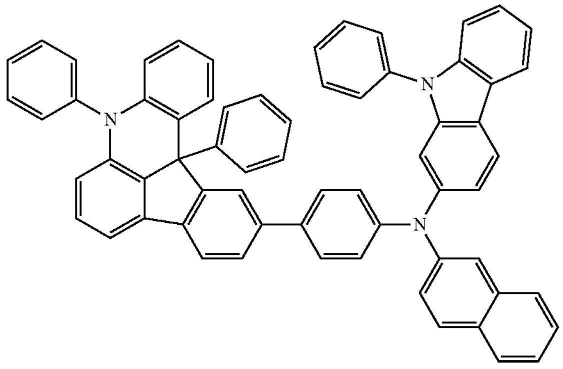
235
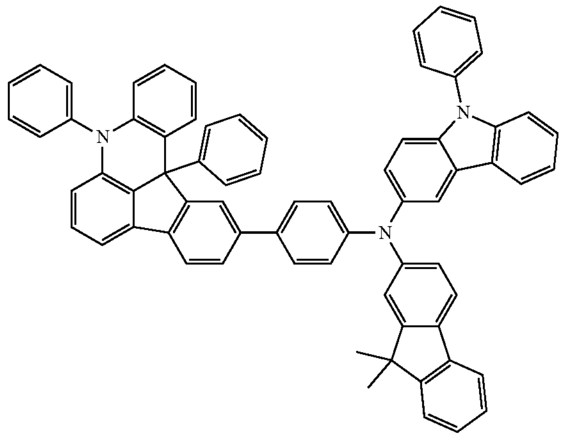
236
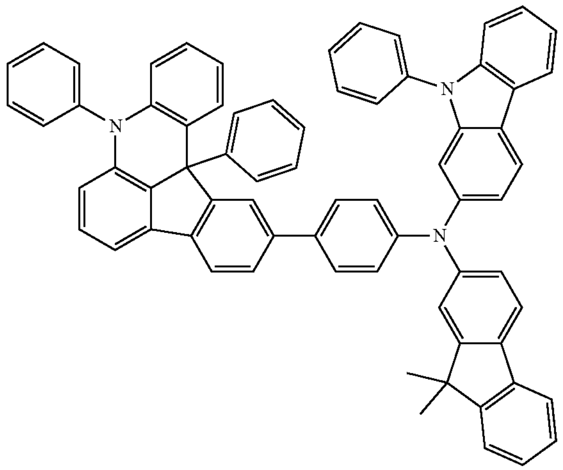
237
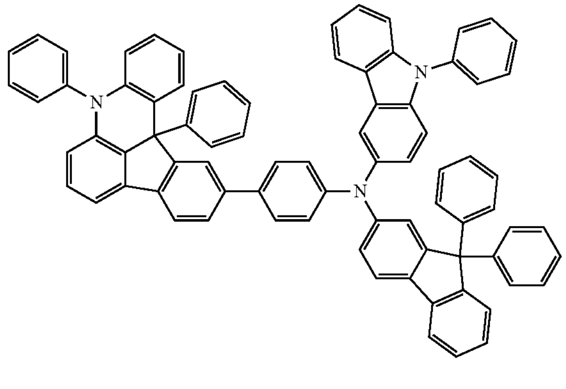
238
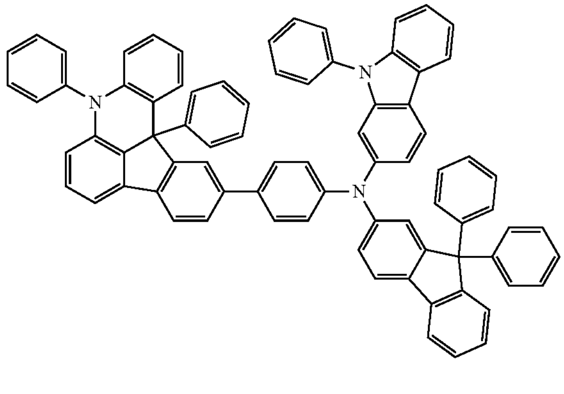

-continued
239
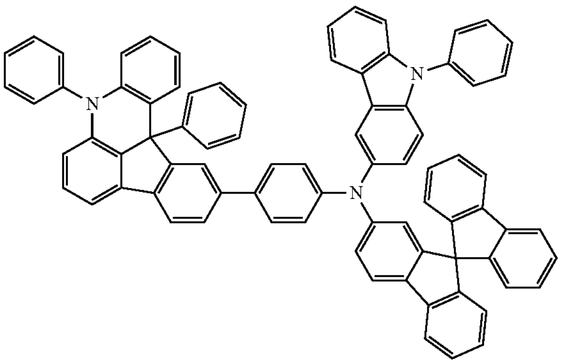
240
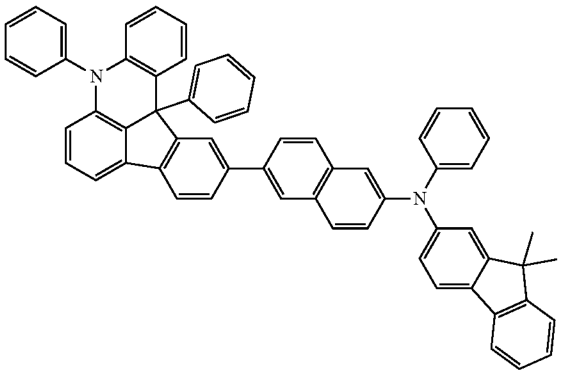
241
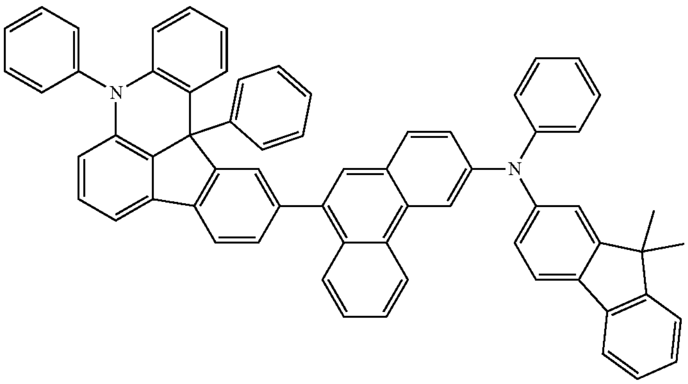
242
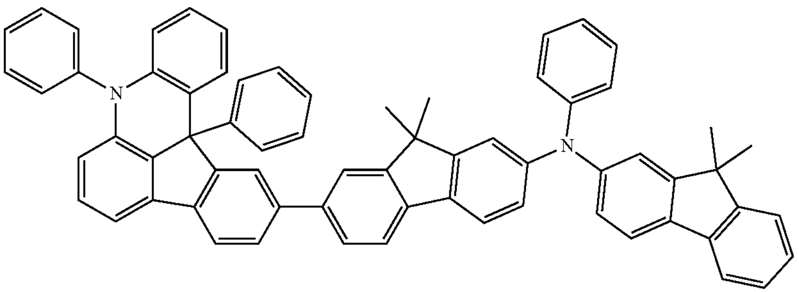
243
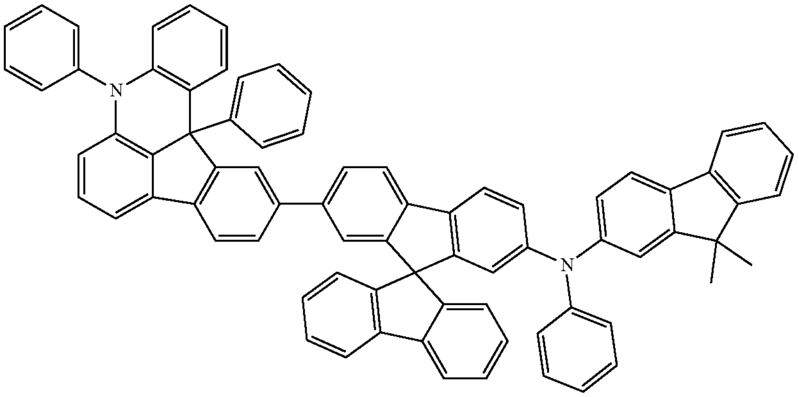

-continued

244

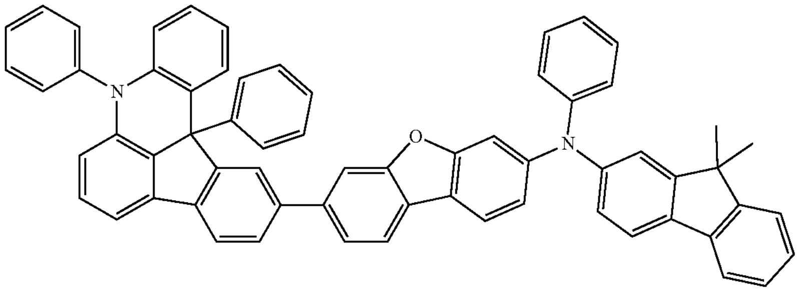

245

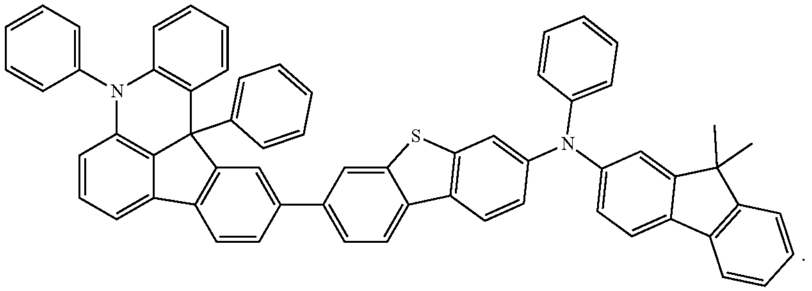

9. An amine compound represented by Formula 1-A1

Formula 1-A1

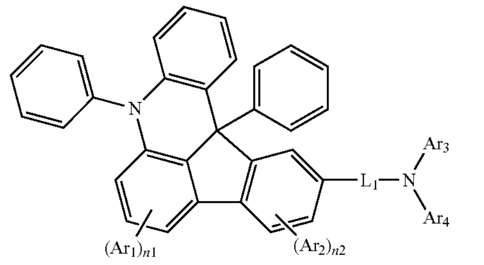

wherein, in Formula 1-A1, $L_1$ is a direct linkage, a substituted or unsubstituted arylene group having 6 to 30 carbon atoms for forming a ring, or a substituted or unsubstituted heteroarylene group having 2 to 30 carbon atoms for forming a ring, n1 and n2 are each independently an integer of 0 to 3, $Ar_1$ and $Ar_2$ are each independently a hydrogen atom, a deuterium atom, a substituted or unsubstituted aryl group having 6 to 30 ring-forming carbon atoms, or a substituted or unsubstituted heteroaryl group having 2 to 30 ring-forming carbon atoms, and $Ar_3$ and $Ar_4$ are each independently a substituted or unsubstituted aryl group having 6 to 30 ring-forming carbon atoms, or a substituted or unsubstituted heteroaryl group having 2 to 30 ring-forming carbon atoms.

10. The amine compound of claim 9, wherein, in Formula 1-A1, $Ar_3$ and $Ar_4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted carbazole group, a substituted or unsubstituted dibenzofuran group, or a substituted or unsubstituted dibenzothiophene group.

11. The amine compound of claim 9, wherein, in Formula 1-A1, $Ar_3$ and $Ar_4$ are each independently represented by any one selected from among A-1 to A-7:

A-1

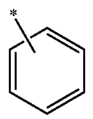

A-2

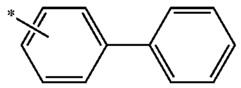

A-3

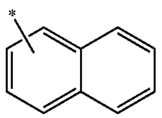

A-4

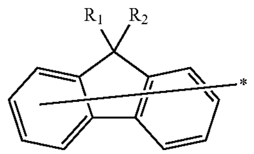

A-5

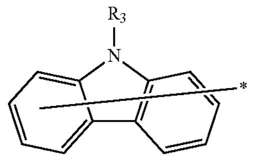

A-6

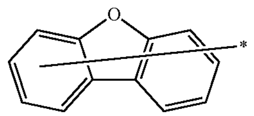

-continued

A-7

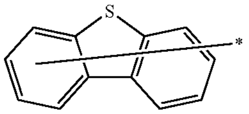

wherein, in A-4, $R_1$ and $R_2$ are each independently a substituted or unsubstituted alkyl group having 1 to 10 carbon atoms, or a substituted or unsubstituted aryl group having 6 to 30 ring-forming carbon atoms, or are bonded to an adjacent group to form a ring, and wherein, in A-5, $R_3$ is a substituted or unsubstituted aryl group having 6 to 30 ring-forming carbon atoms.

12. An amine compound, wherein the amine compound is represented by any one among Formula 1-B1, Formula 1-B2, Formula 1-C1, and Formula 1-C2:

Formula 1-B1

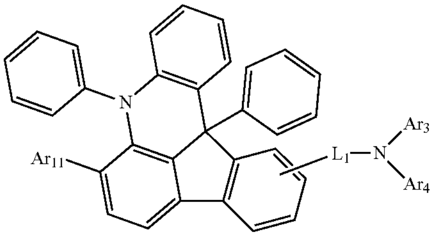

Formula 1-B2

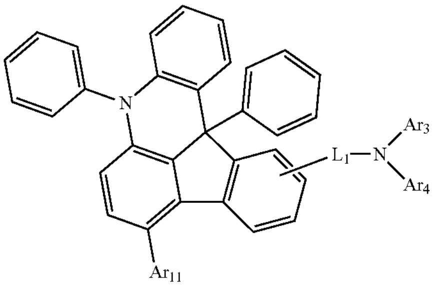

Formula 1-C1

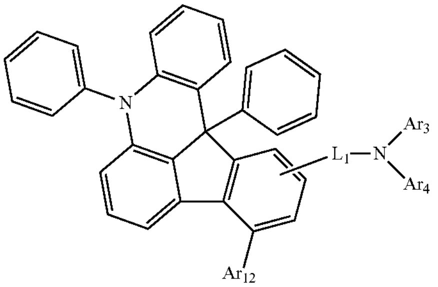

Formula 1-C2

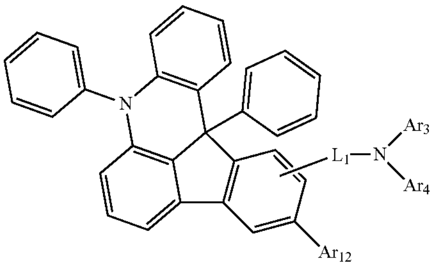

wherein, in Formulae 1-B1, 1-B2, 1-C1, and 1-C2

$Ar_{11}$ is a substituted or unsubstituted aryl group having 6 to 30 ring-forming carbon atoms, $Ar_{12}$ is a substituted or unsubstituted aryl group having 6 to 30 ring-forming carbon atoms, $L_1$ is a direct linkage, a substituted or unsubstituted arylene group having 6 to 30 carbon atoms for forming a ring, or a substituted or unsubstituted heteroarylene group having 2 to 30 carbon atoms for forming a ring, and $Ar_3$ and $Ar_4$ are each independently a substituted or unsubstituted aryl group having 6 to 30 ring-forming carbon atoms, or a substituted or unsubstituted heteroaryl group having 2 to 30 ring-forming carbon atoms.

13. The amine compound of claim 9, wherein Formula 1A1 is represented by any one selected from among compounds of Compound Group 1:

[Compound Group 1]

1

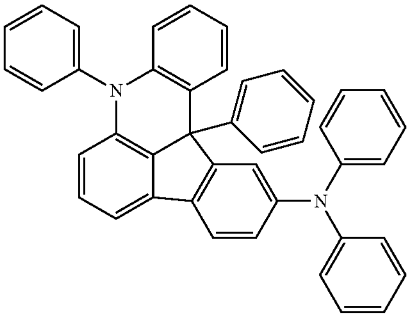

2

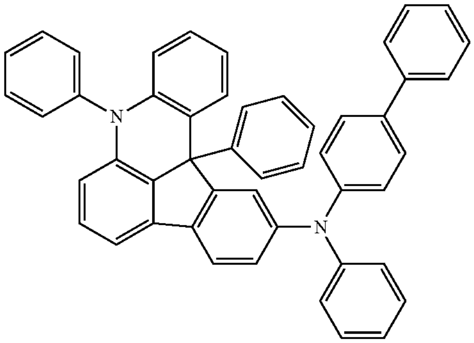

3

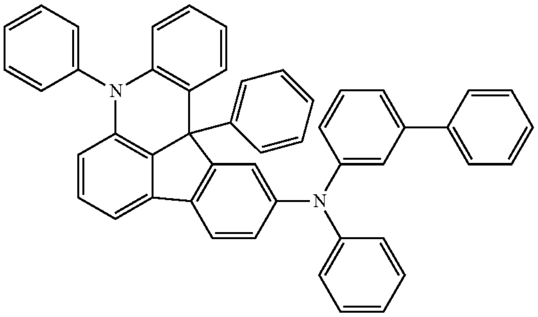

-continued
4
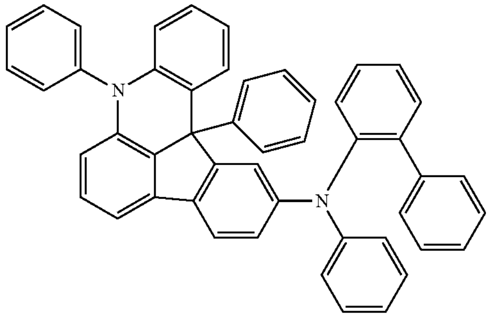
5
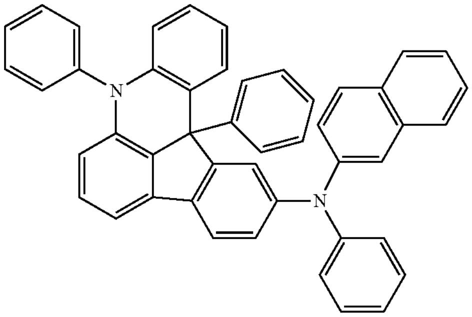
6
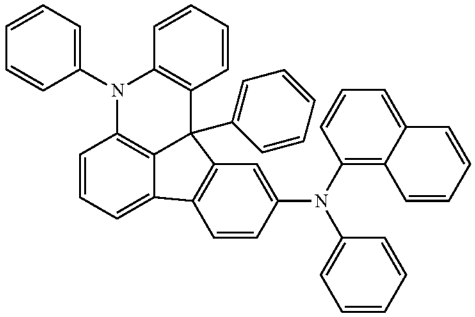
7
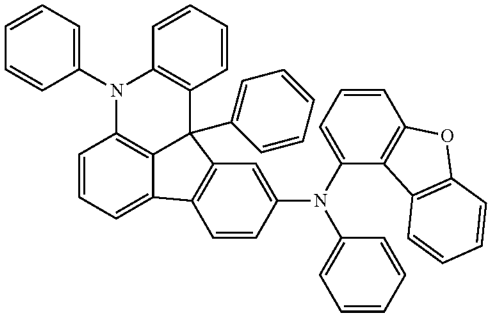
8
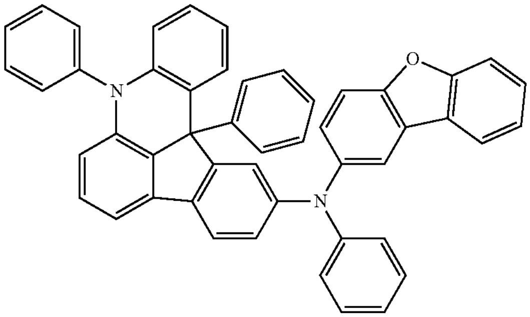
-continued
9
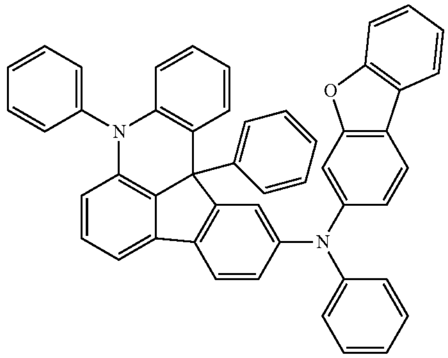
10
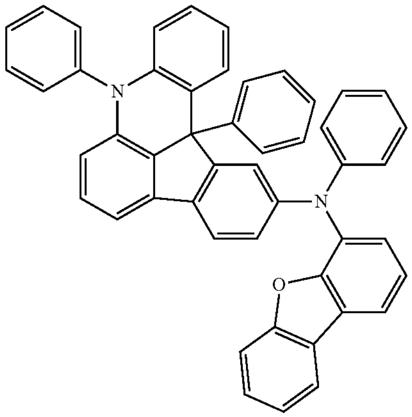
11
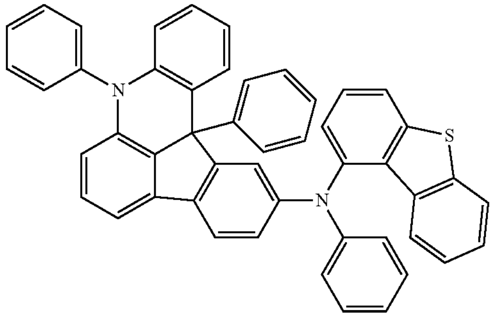
12
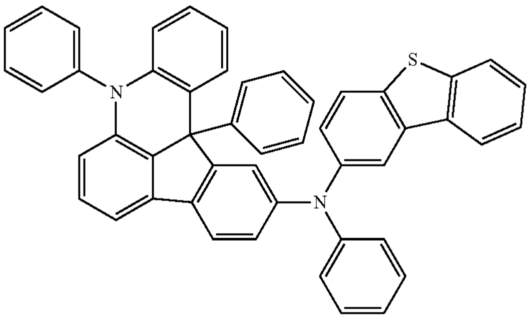

-continued
13
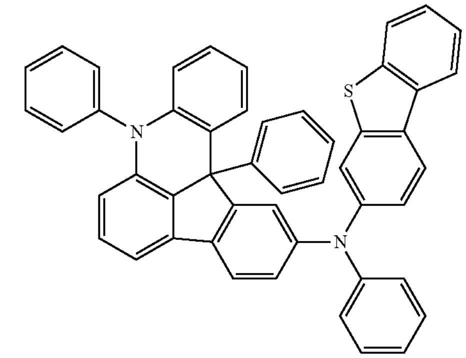
14
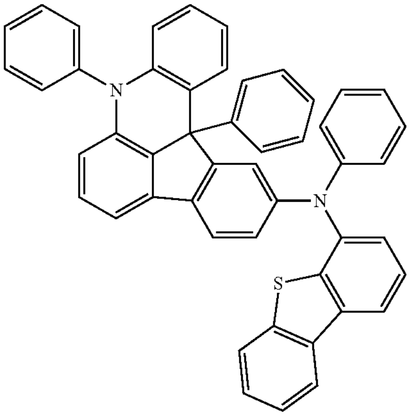
15
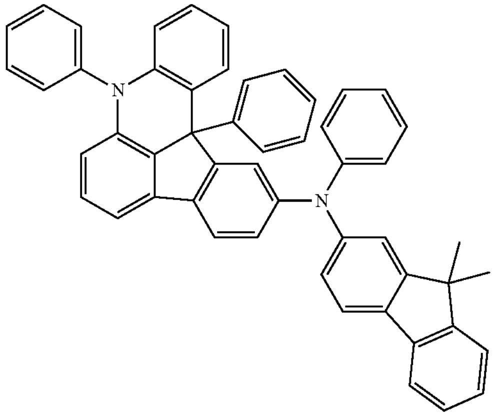
16
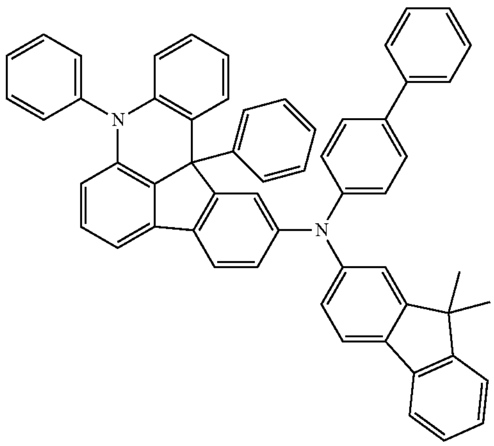
-continued
17
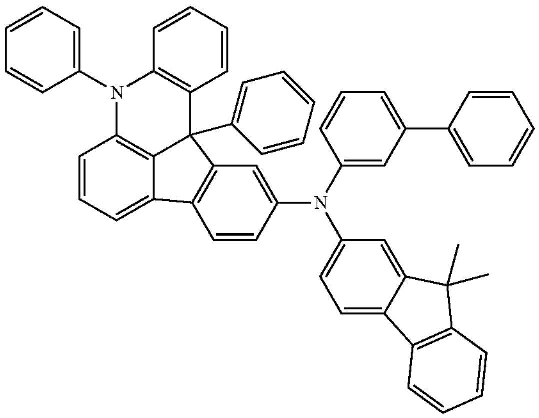
18
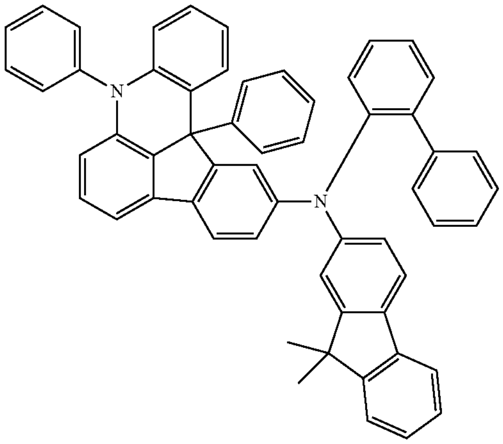
19
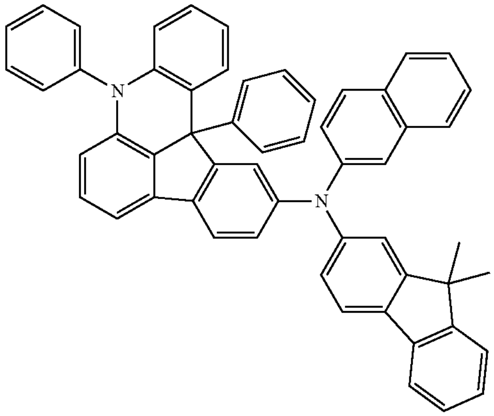

20
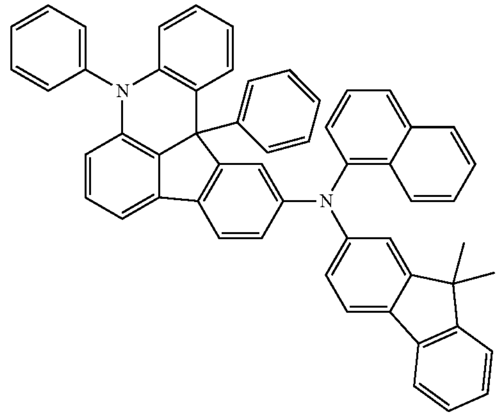
21
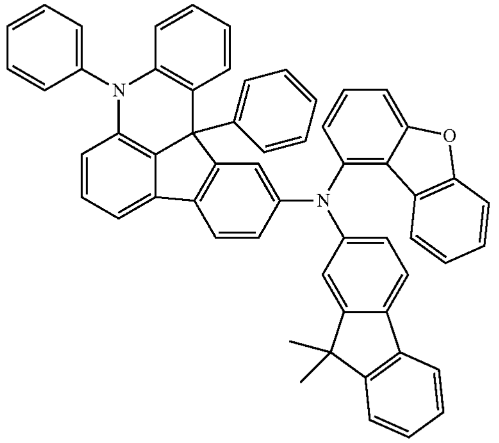
22
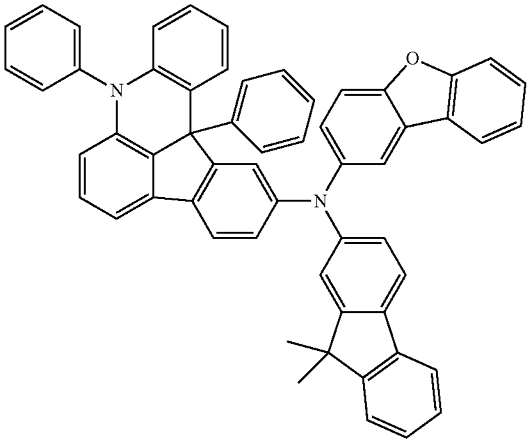
23
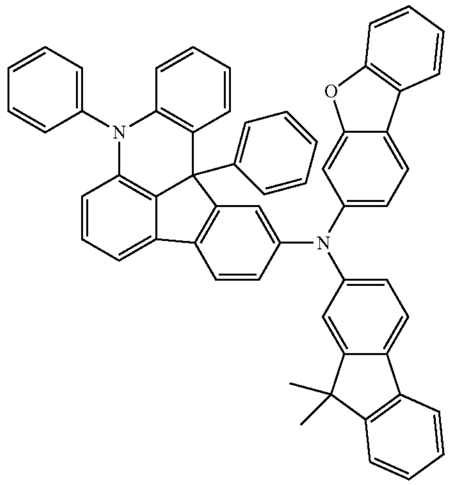
24
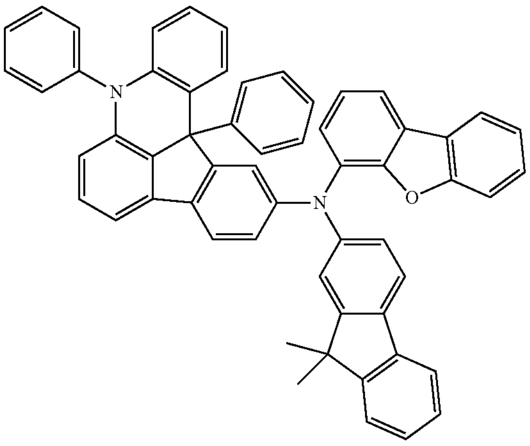
25
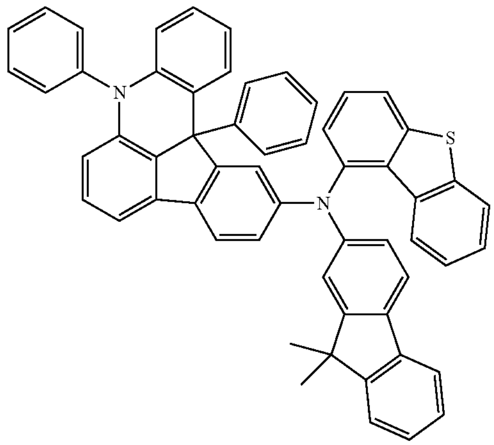

-continued
26
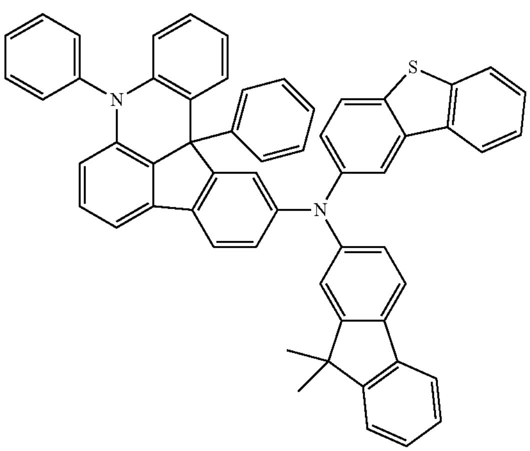
27
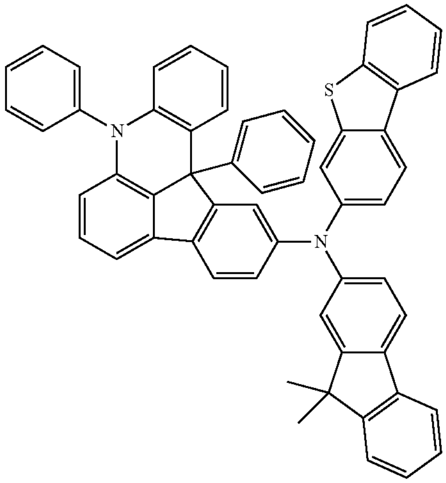
28
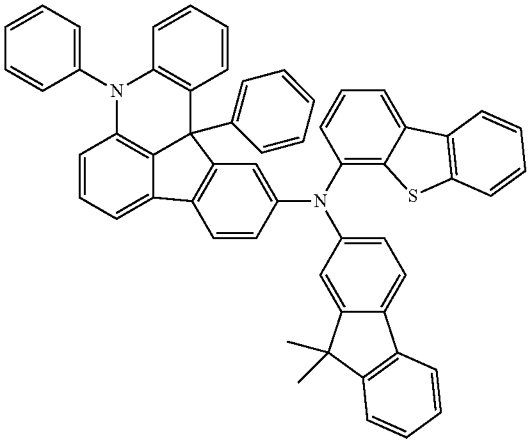
-continued
29
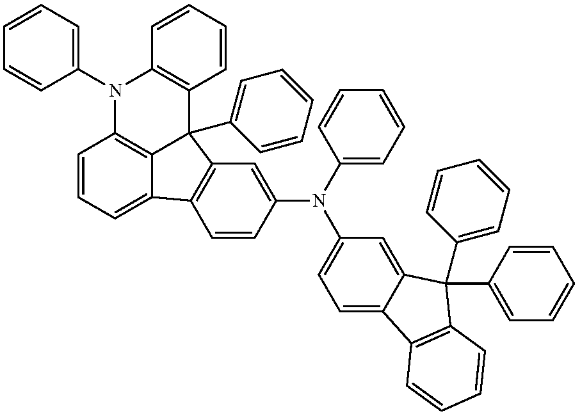
30
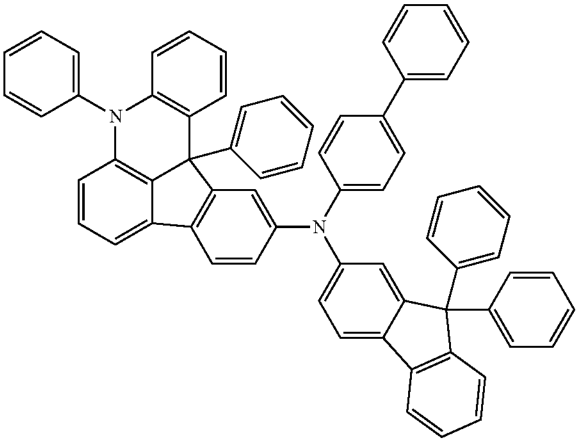
31
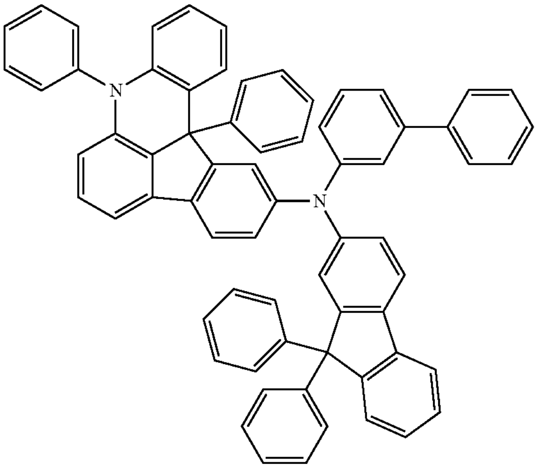

-continued
32
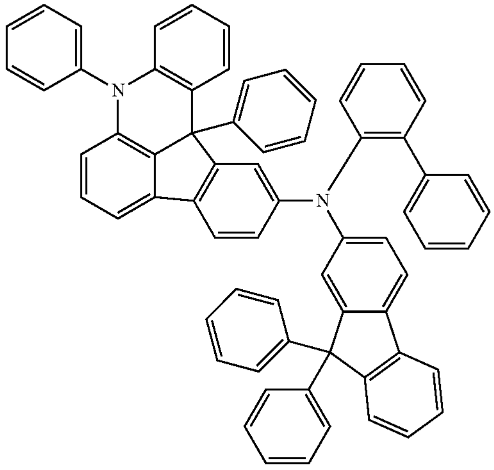
33
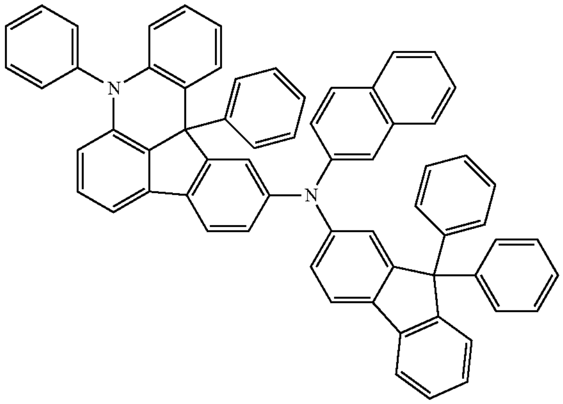
34
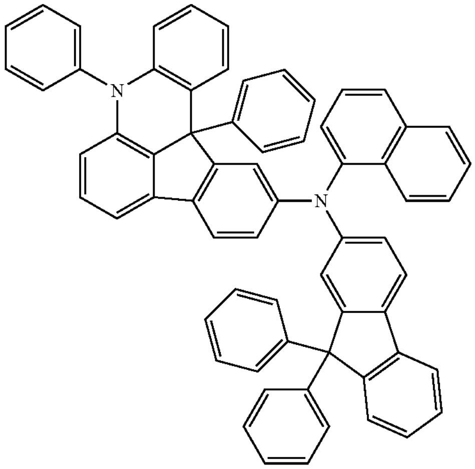
-continued
35
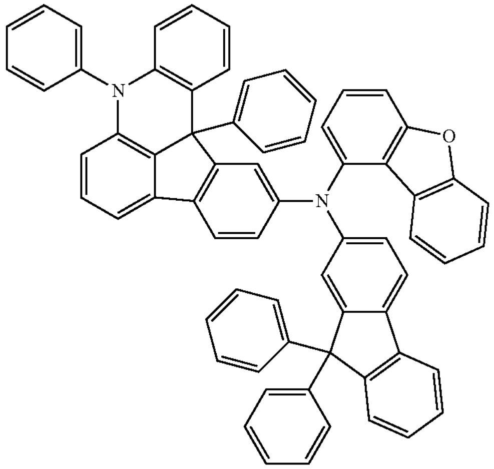
36
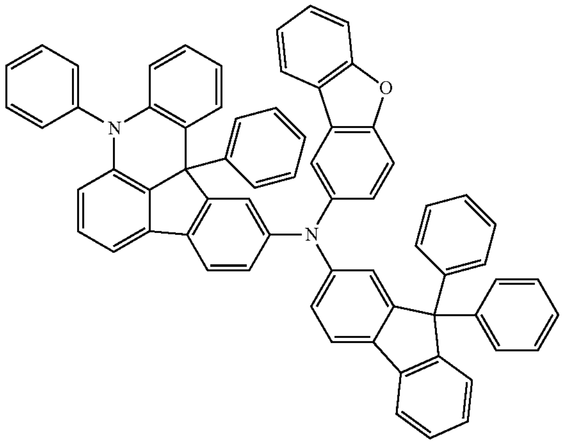
37
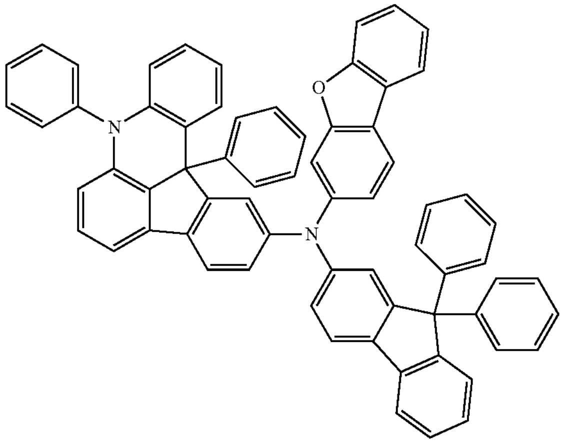

-continued
38
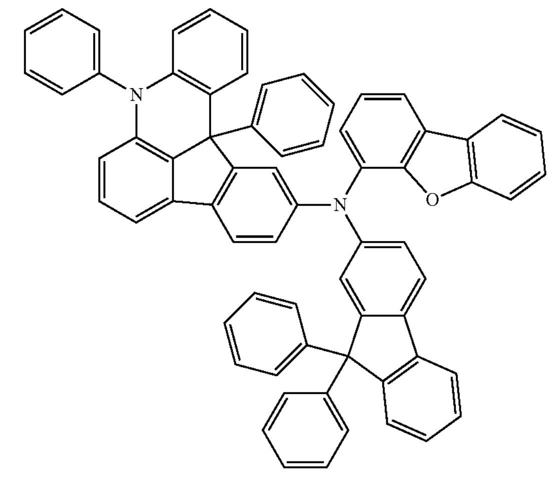
39
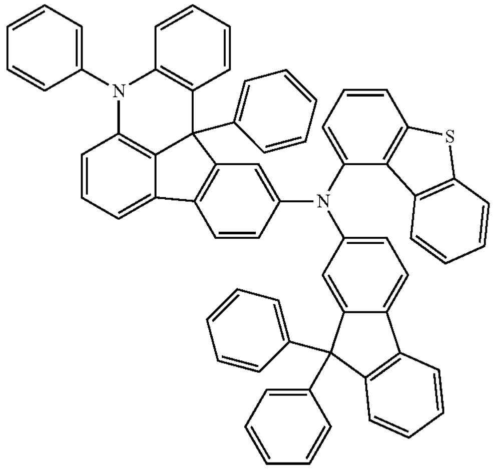
40
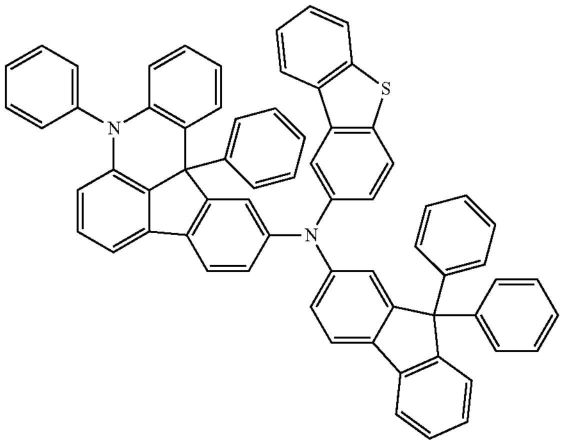
-continued
41
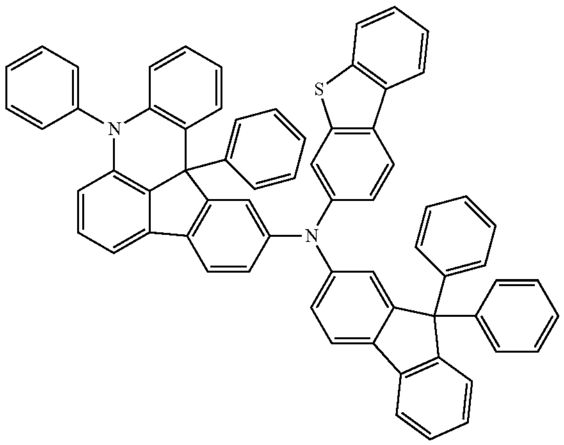
42
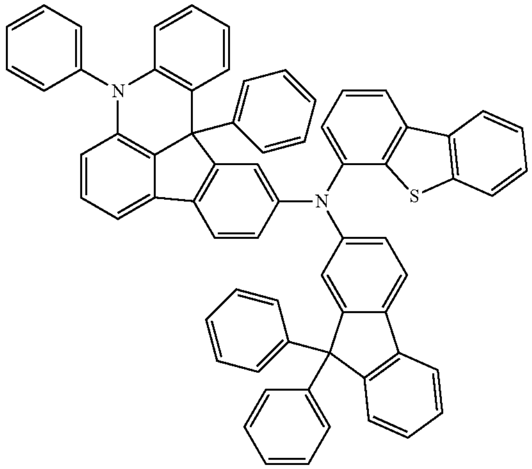
43
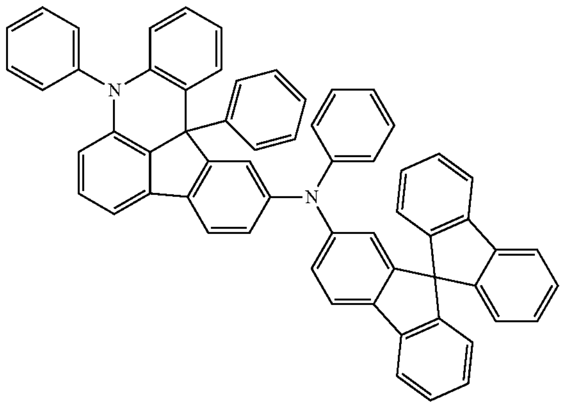

-continued
44
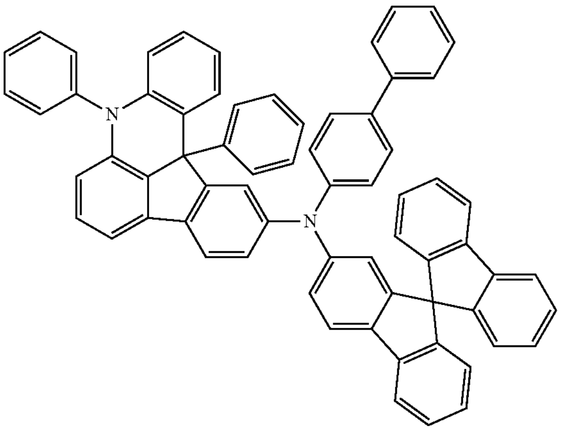
45
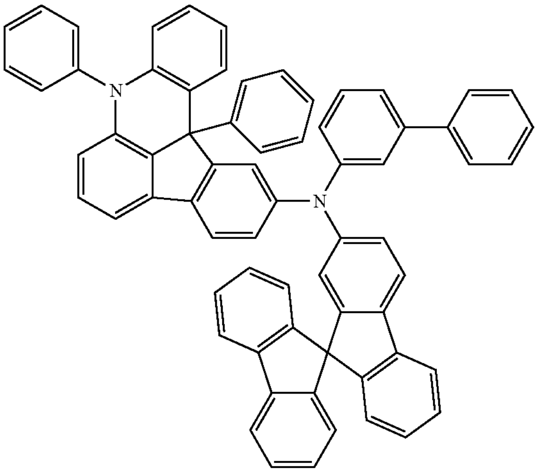
46
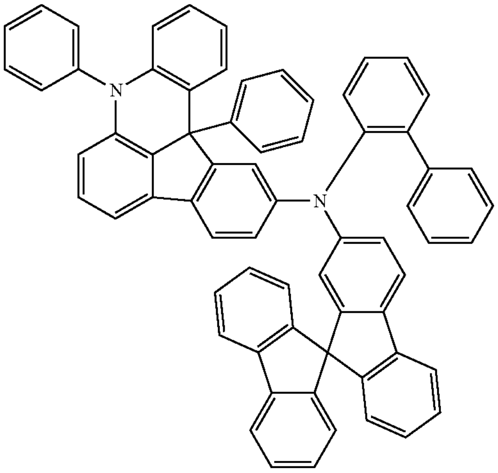
-continued
47
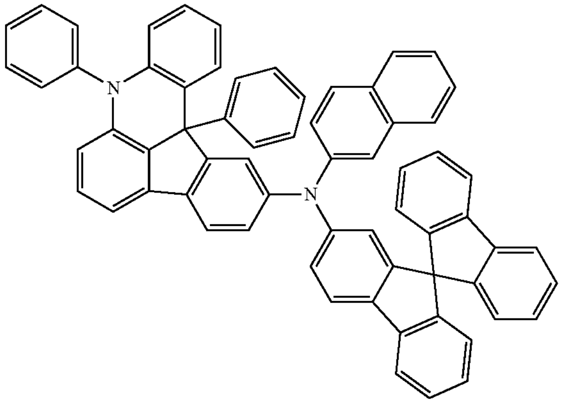
48
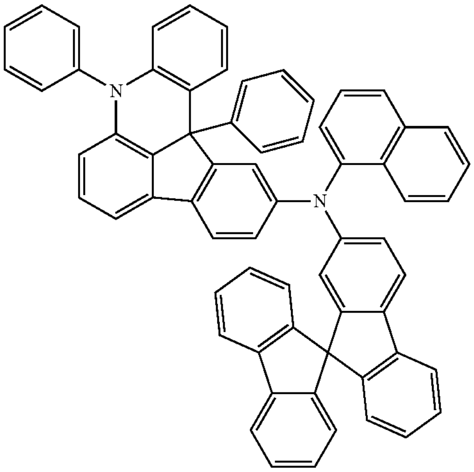
49
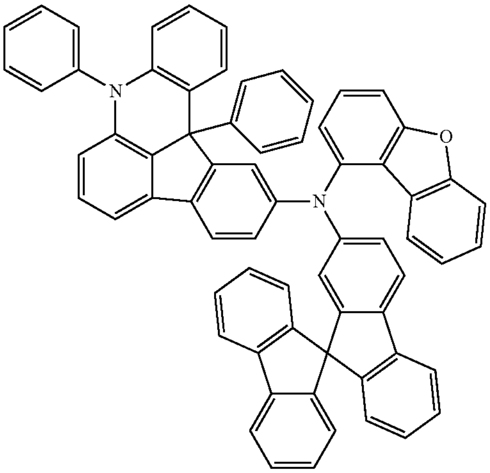

50
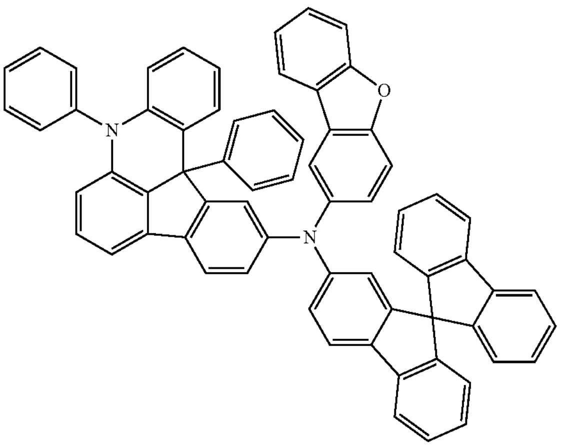
51
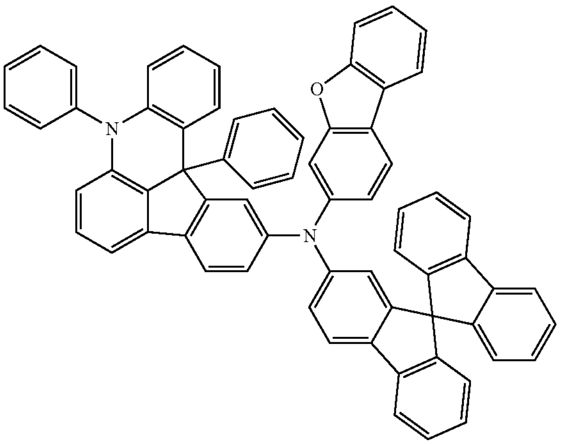
52
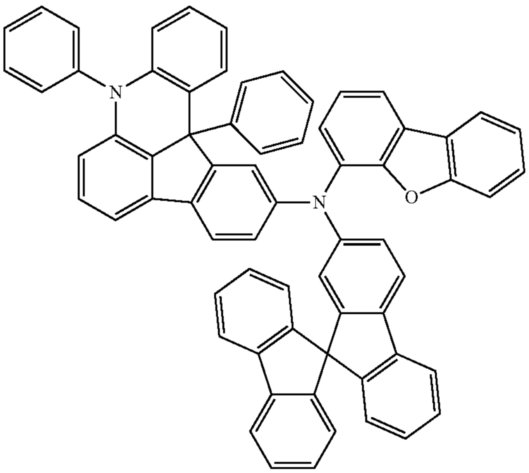
53
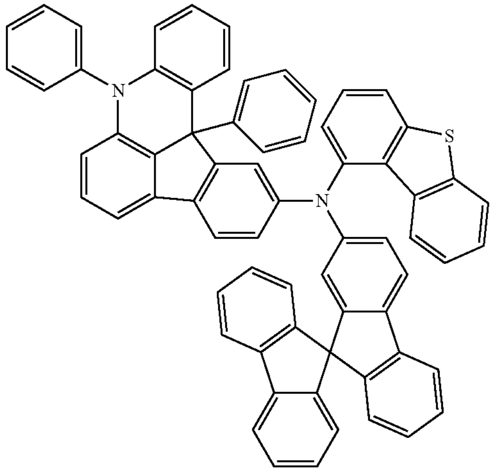
54
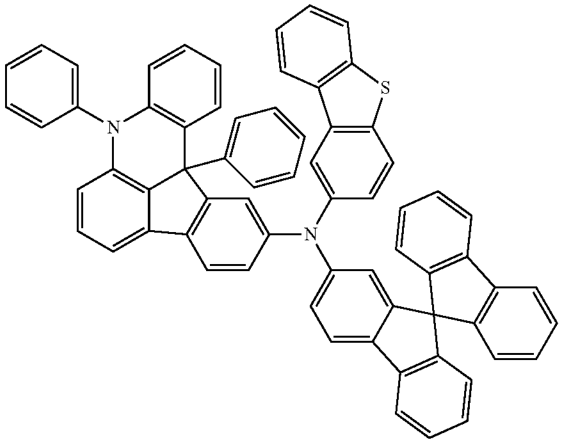
55
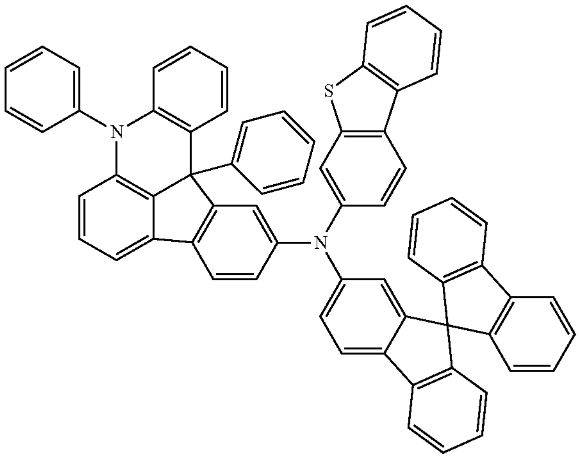

56
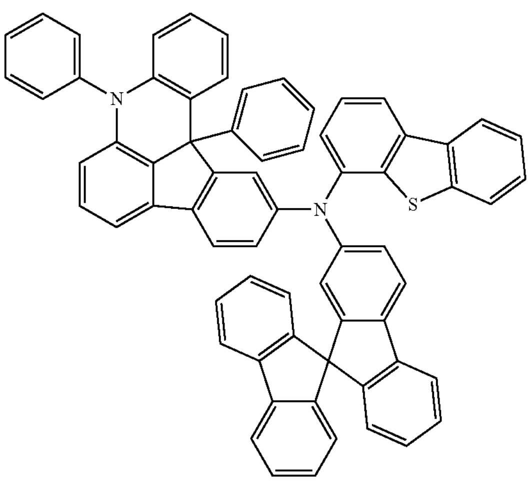
57
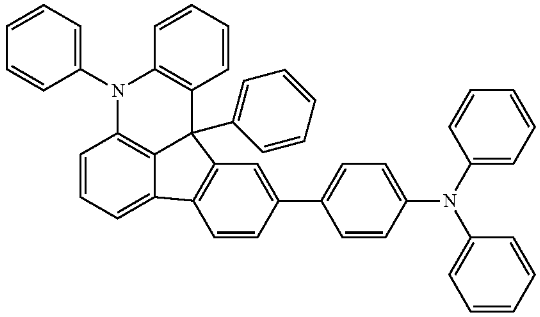
58
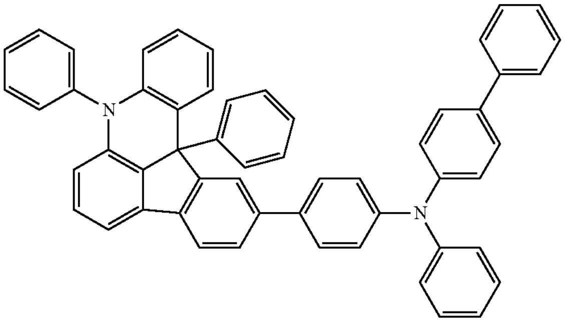
59
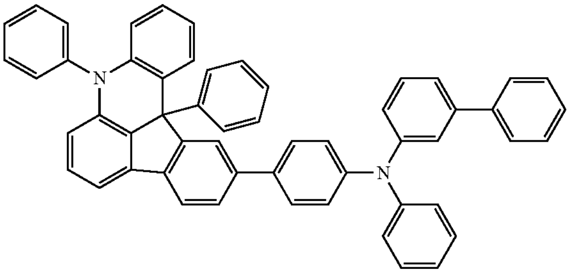
61
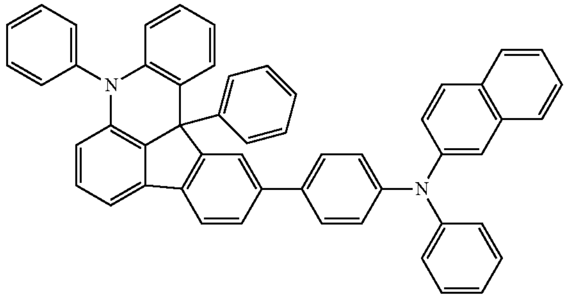
62
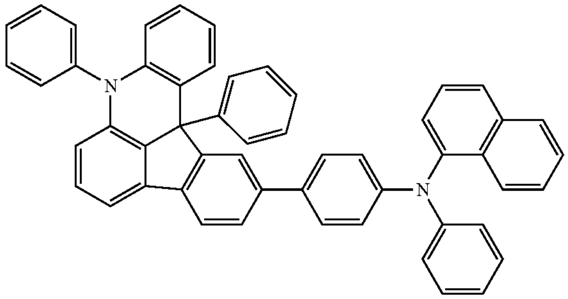
63
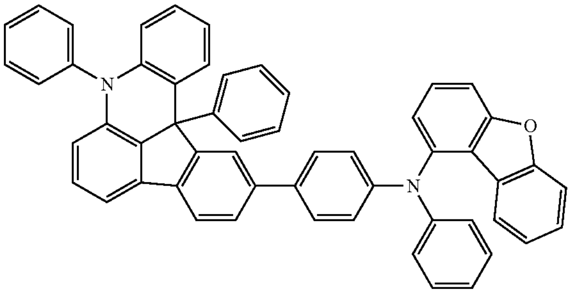
64
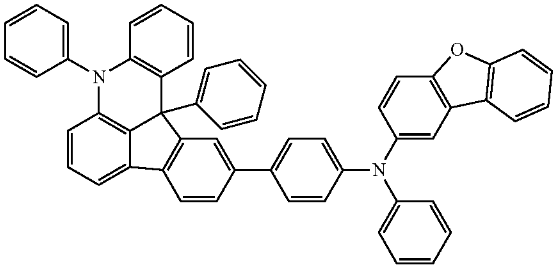
65
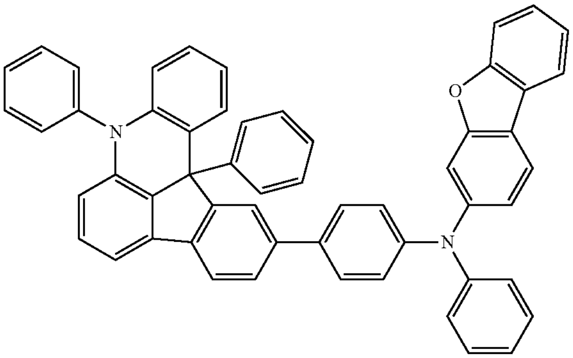

-continued
66
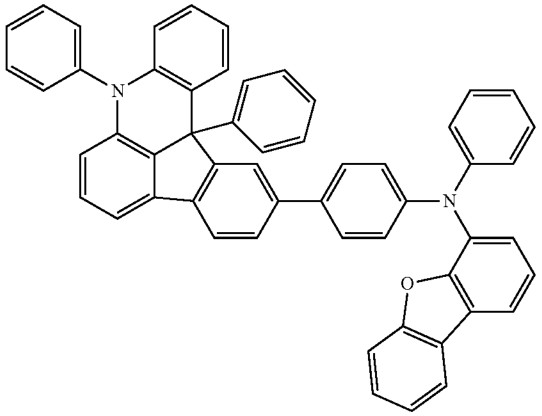
67
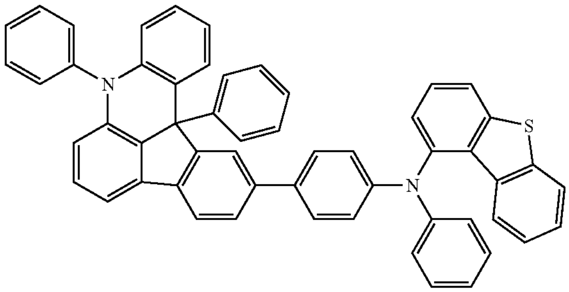
68
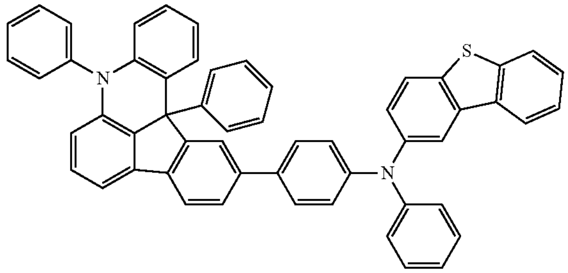
69
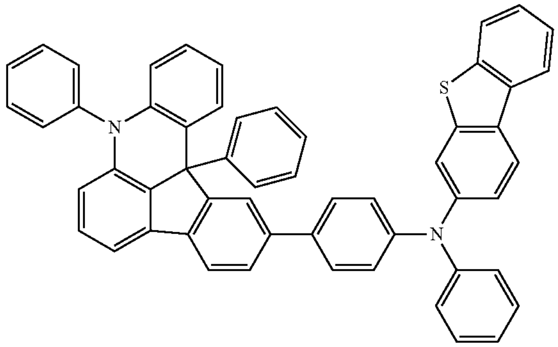
-continued
70
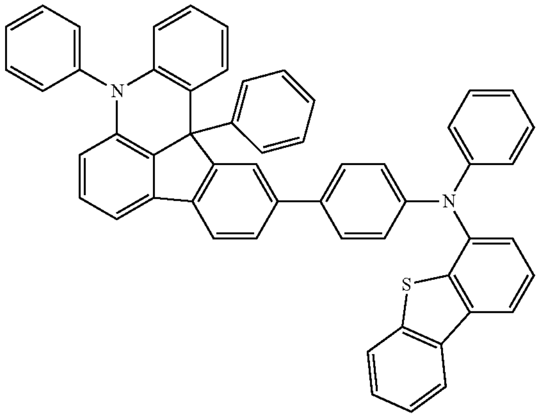
71
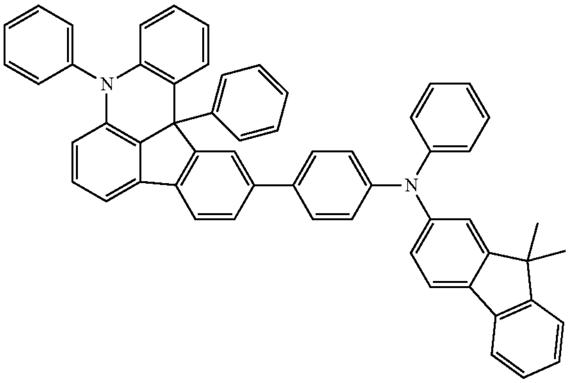
72
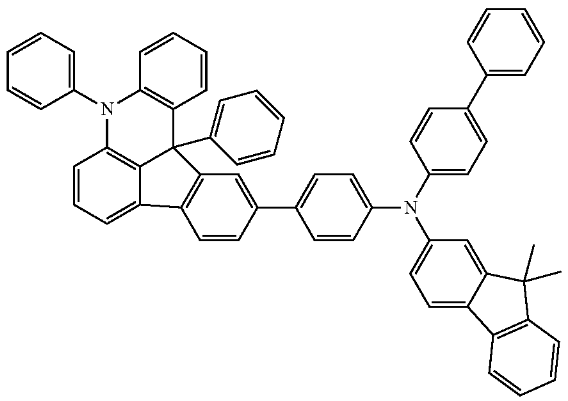

-continued
73
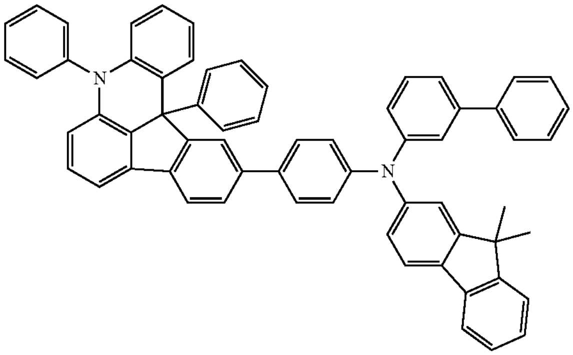
74
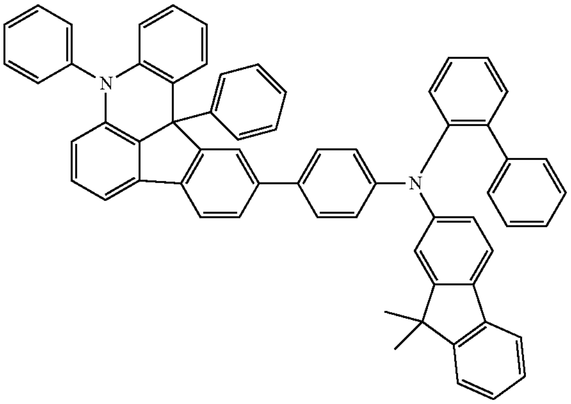
75
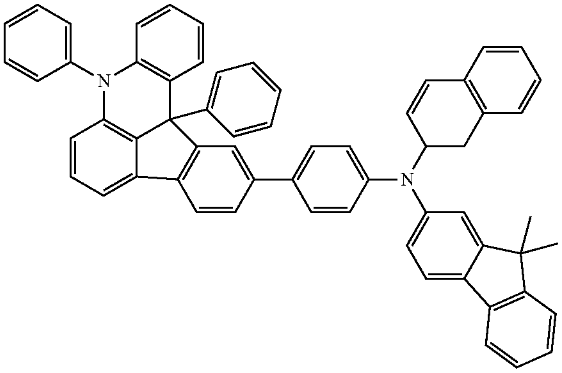
76
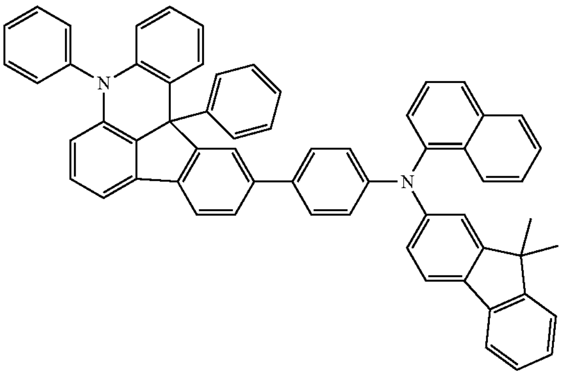
-continued
77
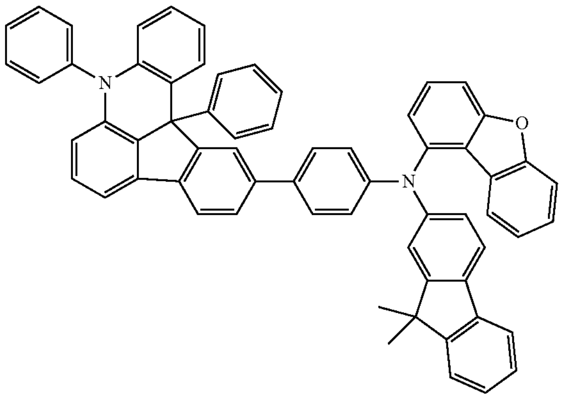
78
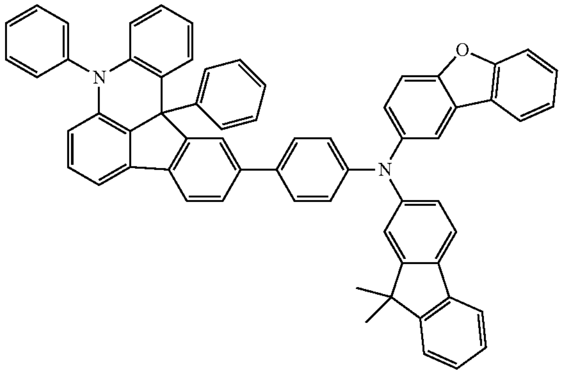
79
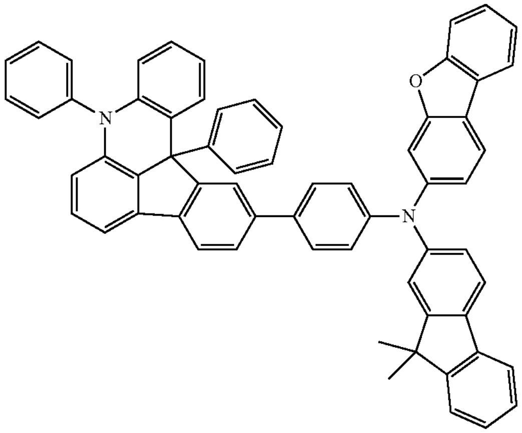

-continued
81
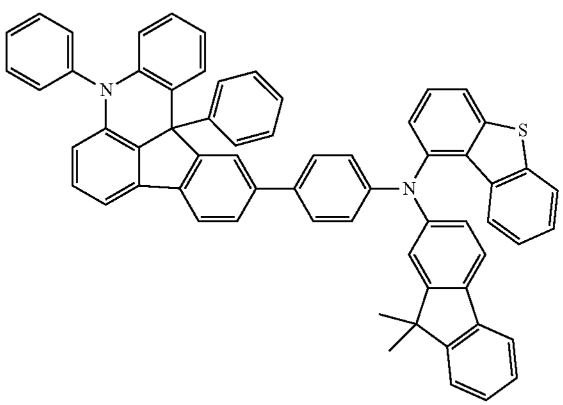
82
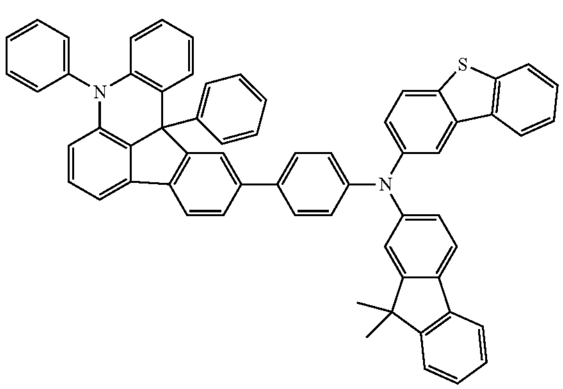
83
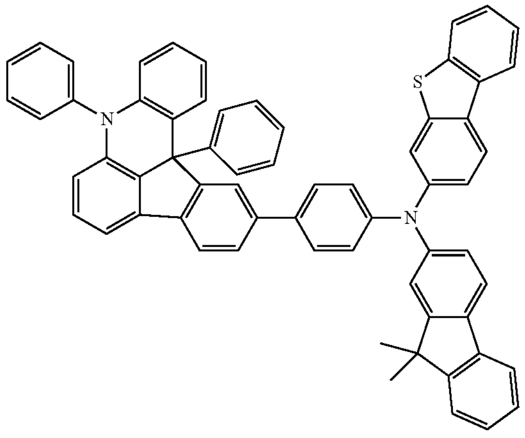
85
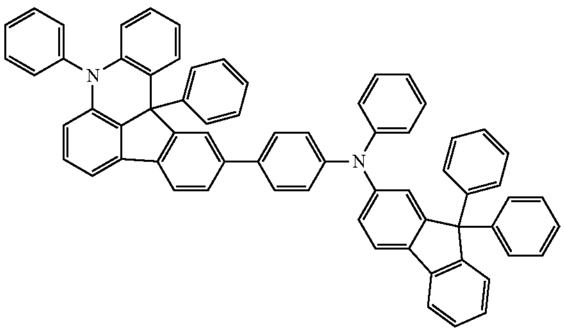
-continued
86
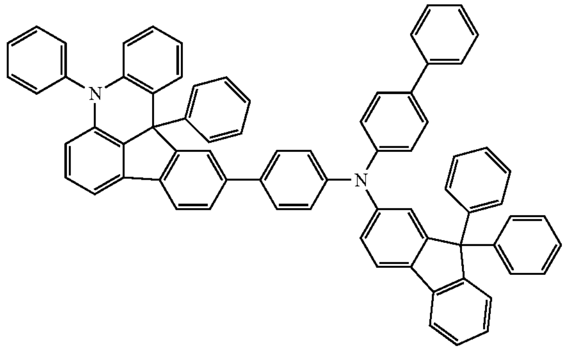
87
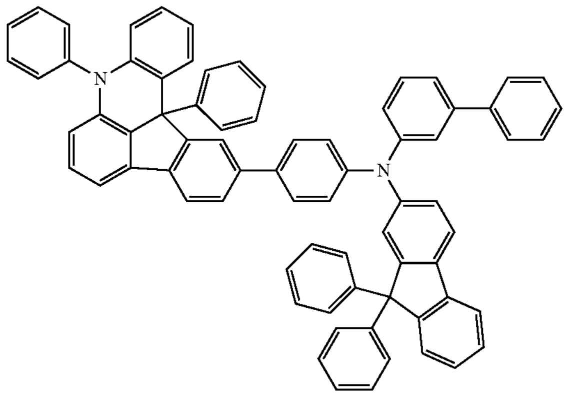
88
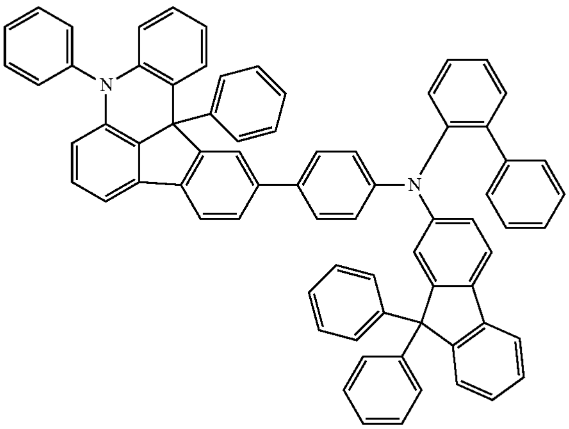
89
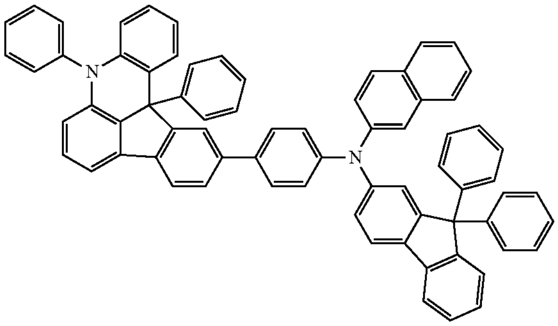

-continued
90
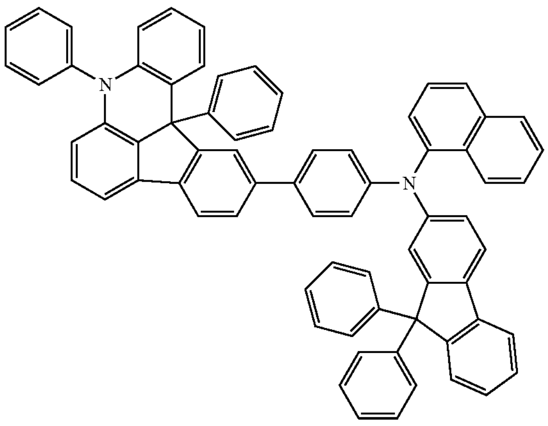
91
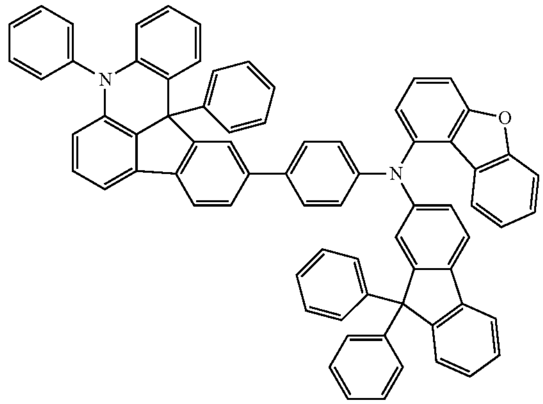
92
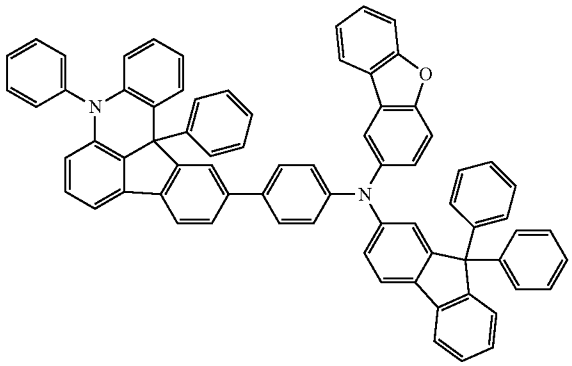
93
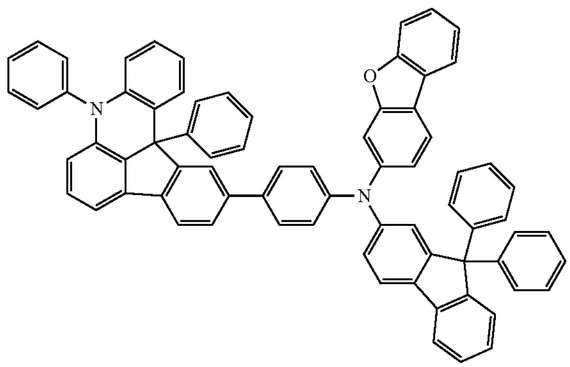
-continued
94
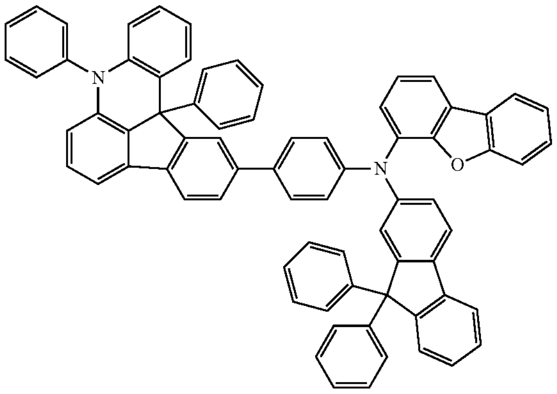
95
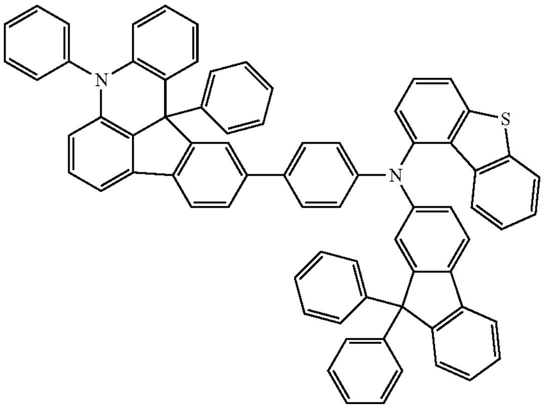
96
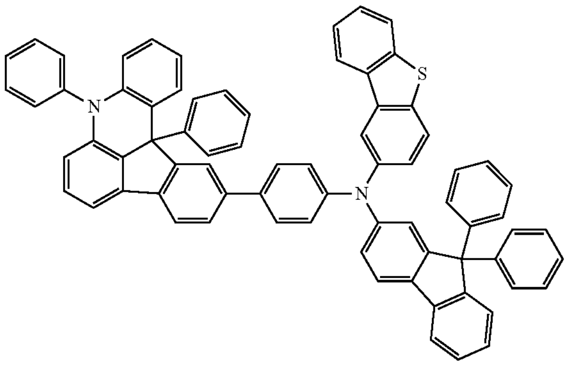
97
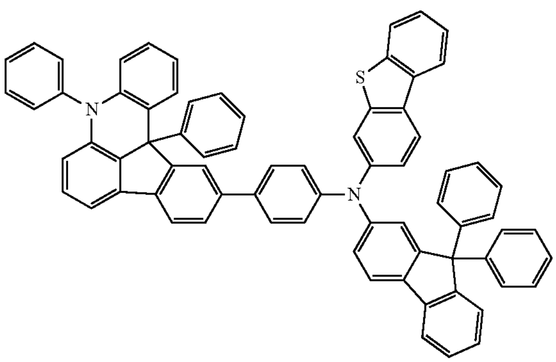

-continued
98
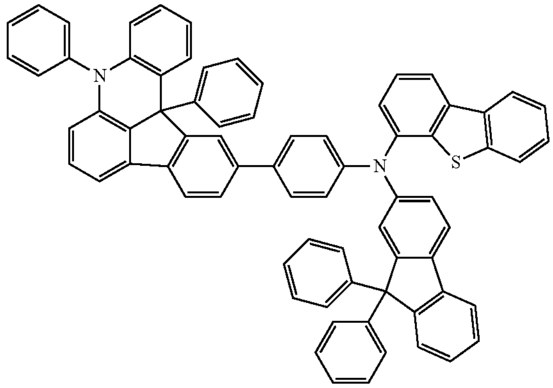
99
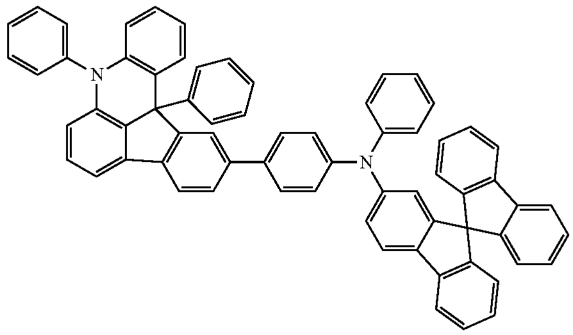
100
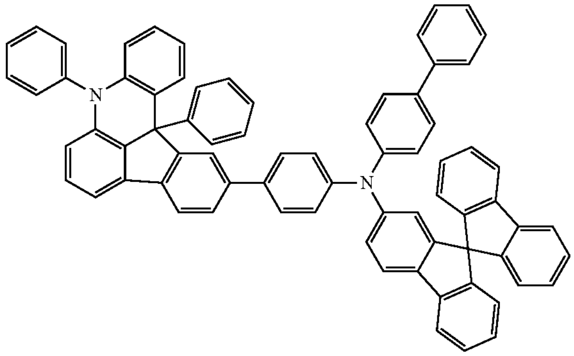
101
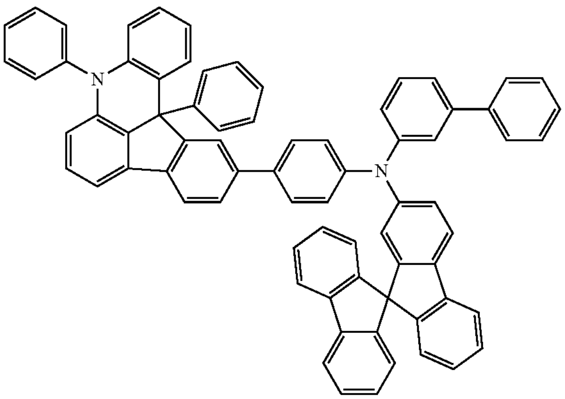
-continued
102
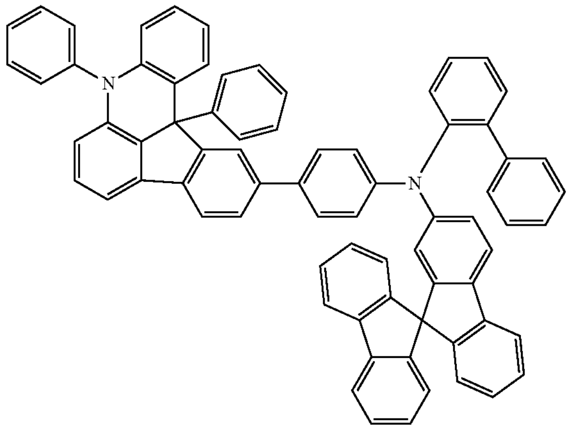
103
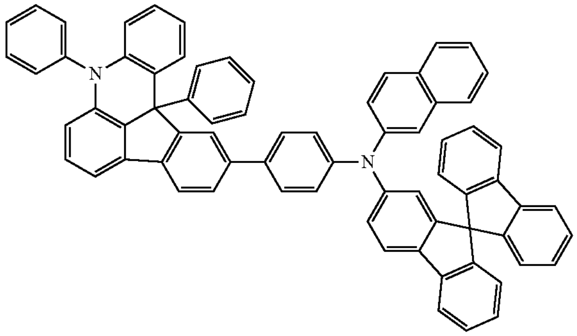
104
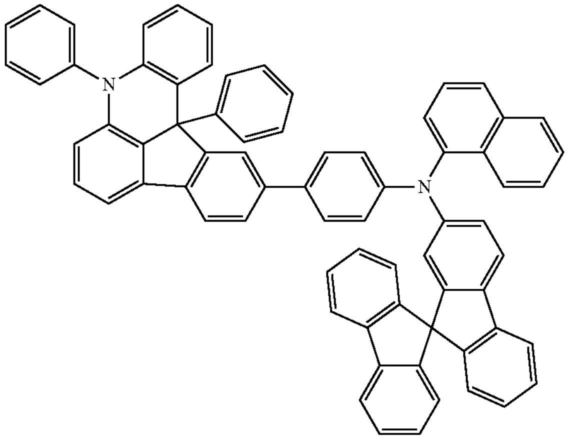

-continued
105
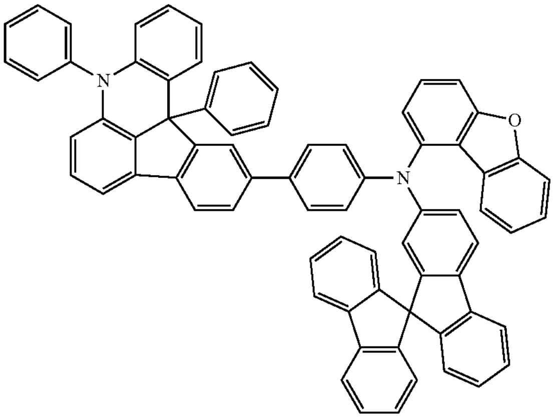
106
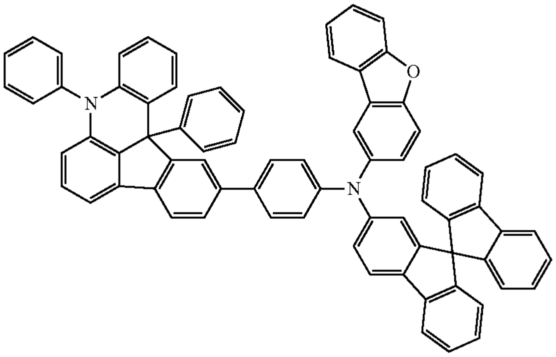
107
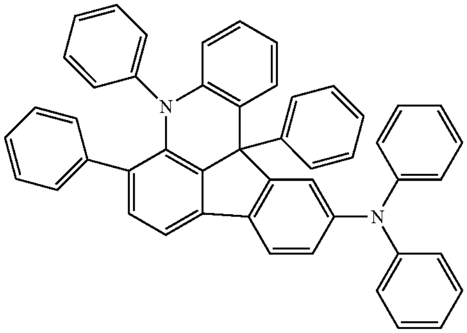
108
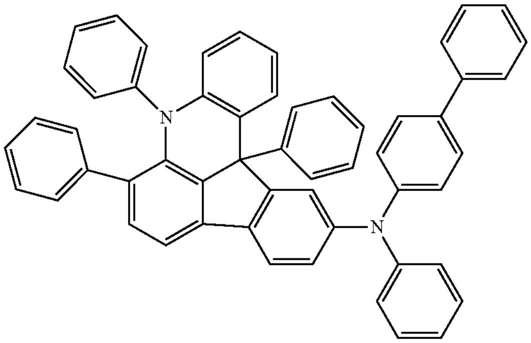
-continued
109
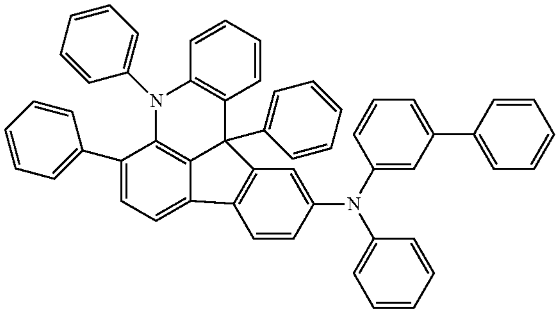
110
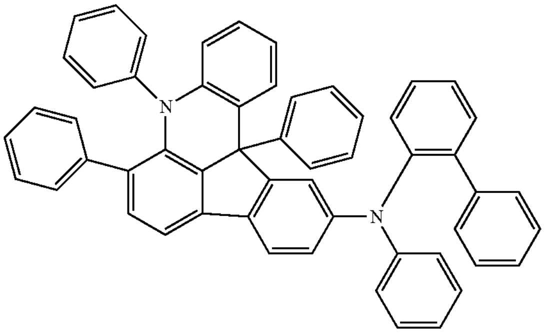
111
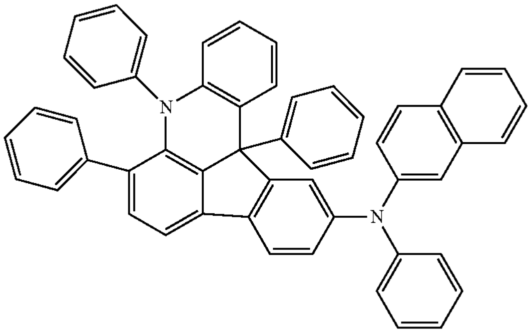
112
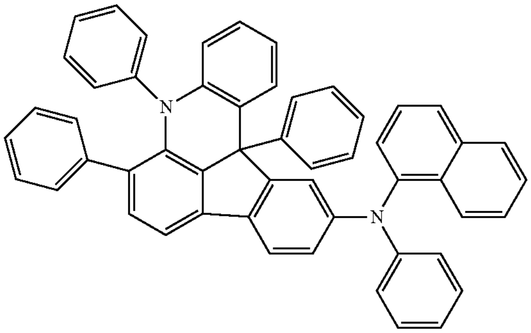

-continued
113
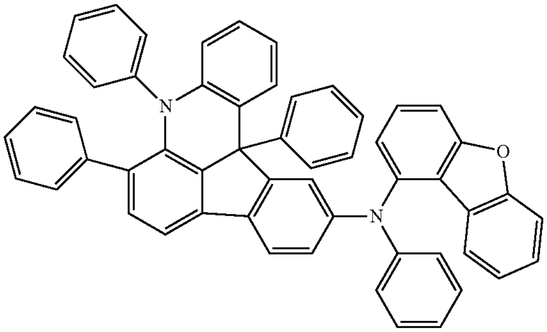
114
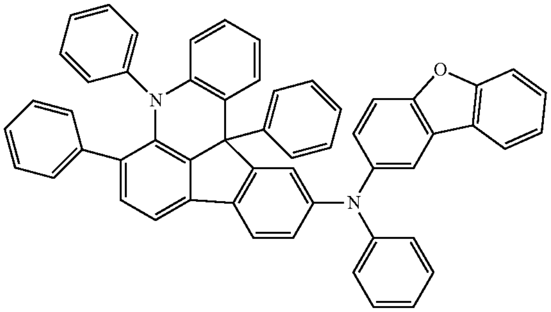
115
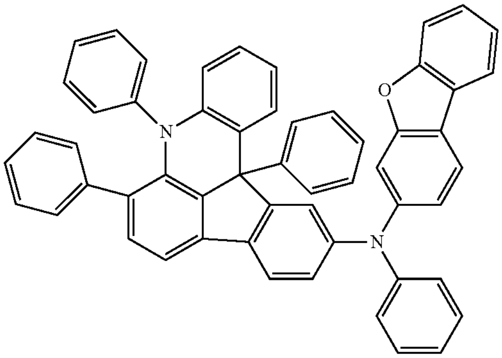
116
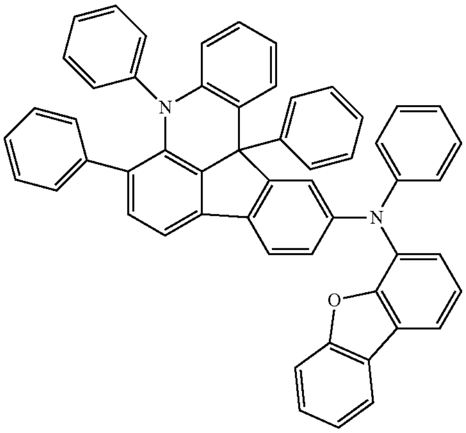
-continued
117
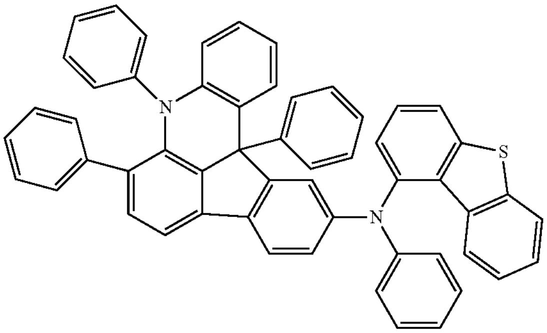
118
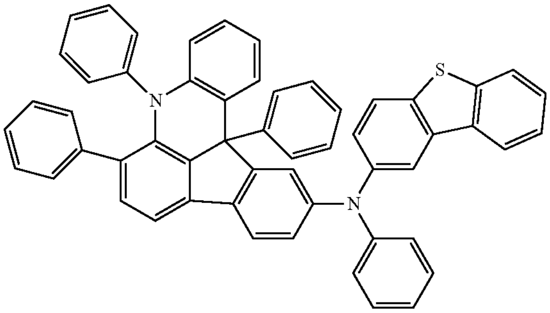
119
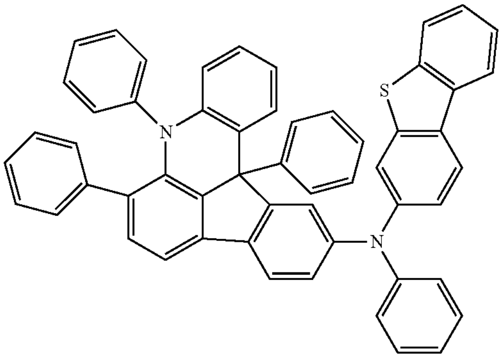
120
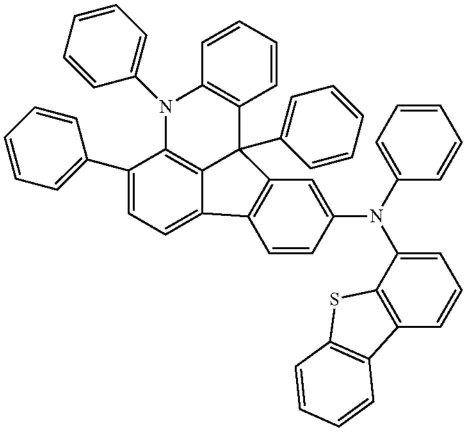

-continued
121
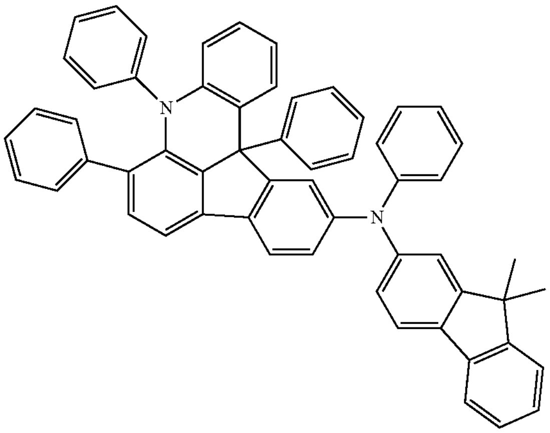
122
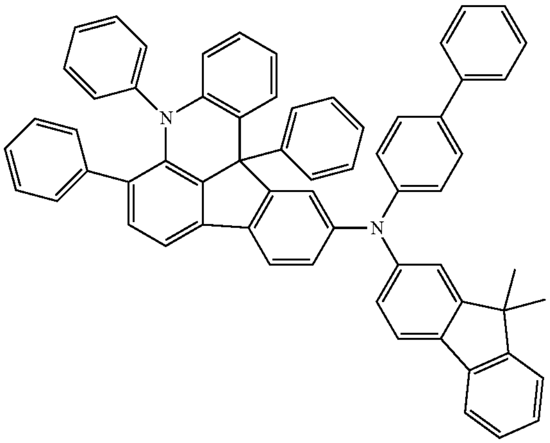
123
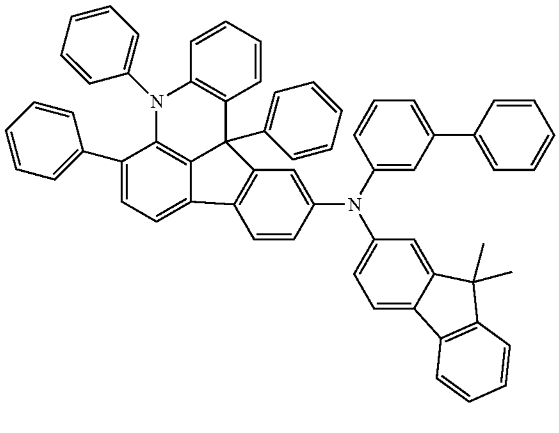
-continued
124
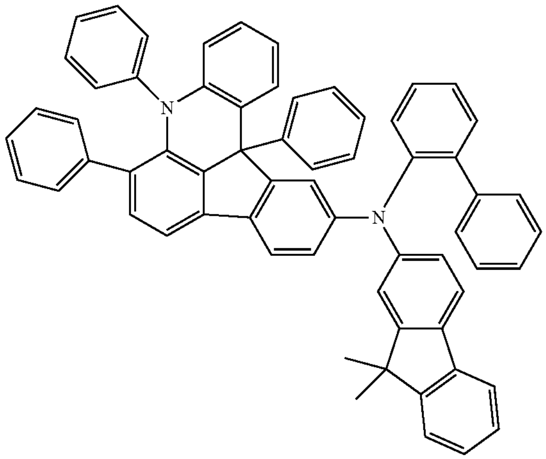
125
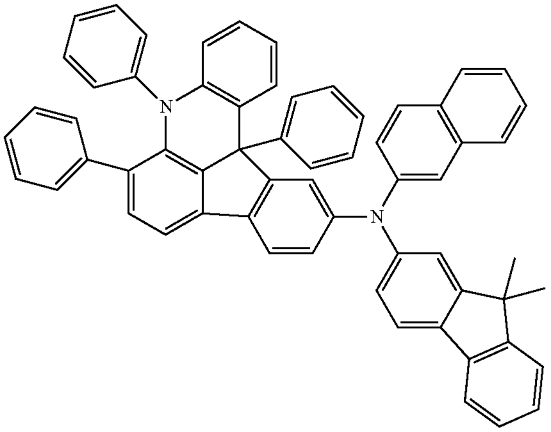
126
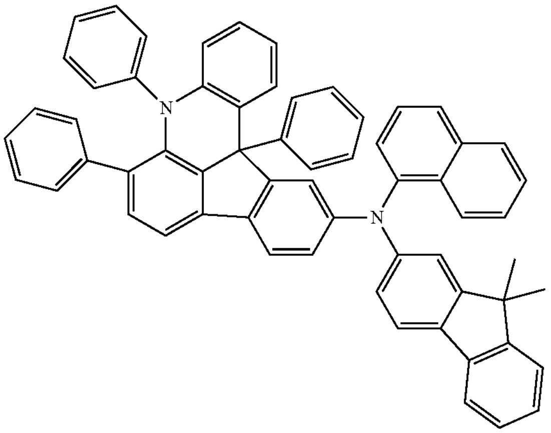

-continued
127
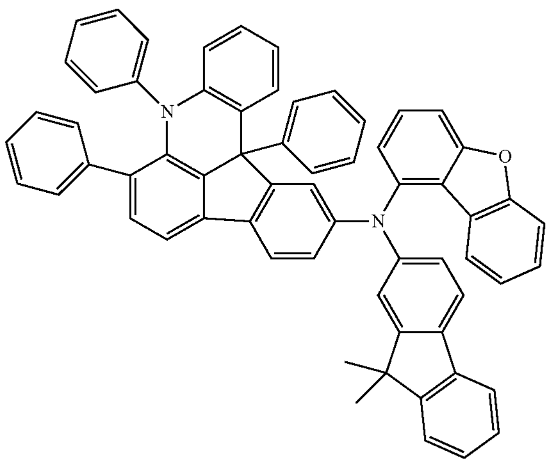
128
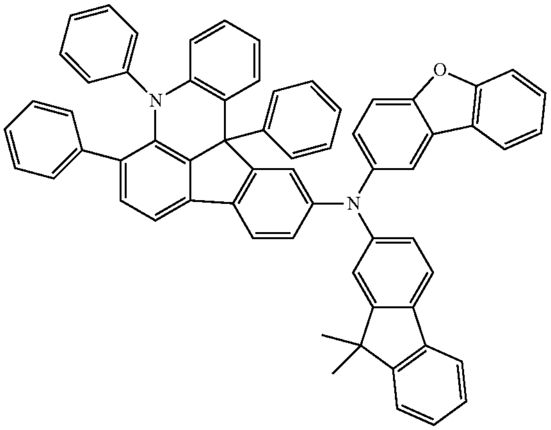
129
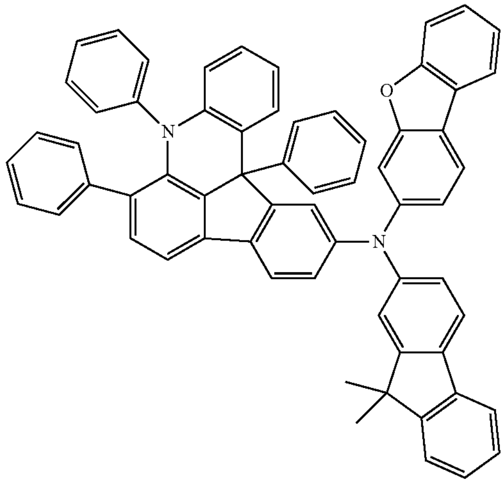
-continued
130
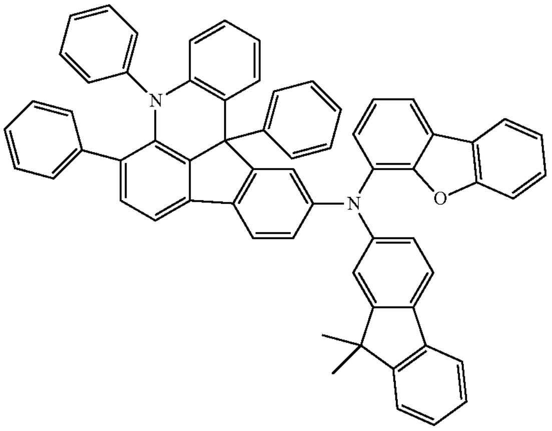
131
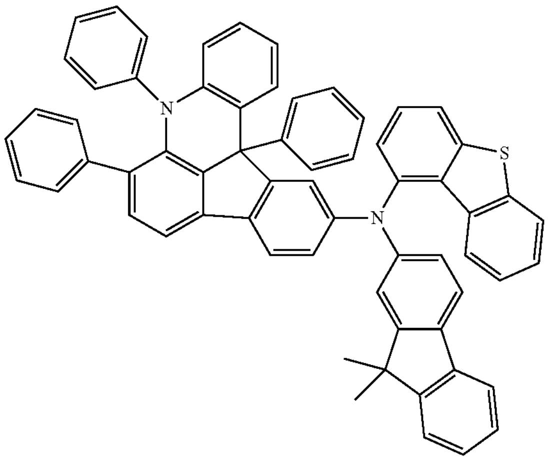
132
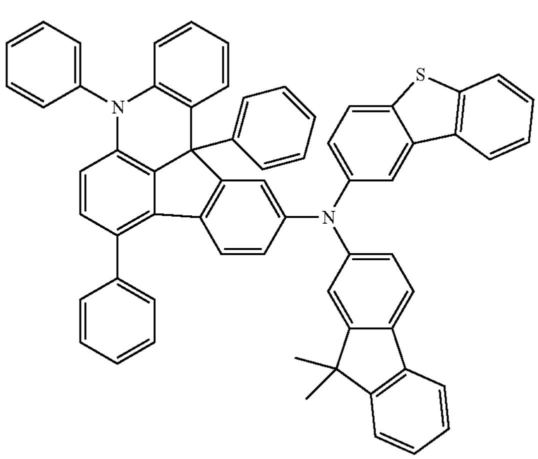

-continued
133
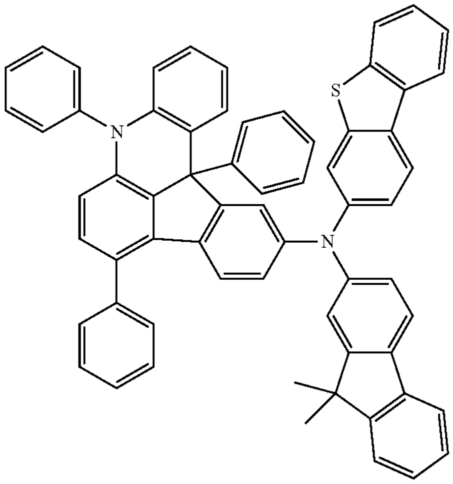
134
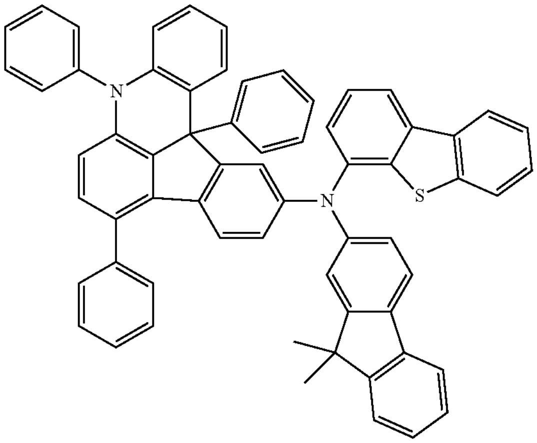
135
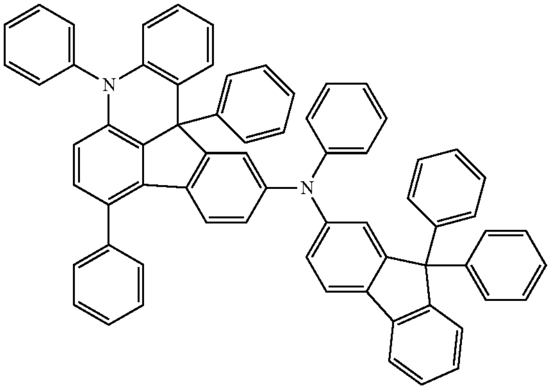
-continued
136
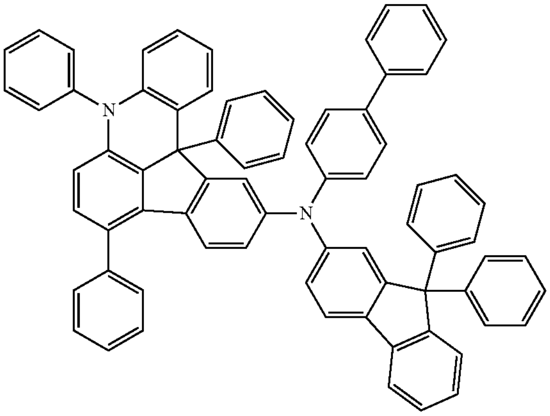
137
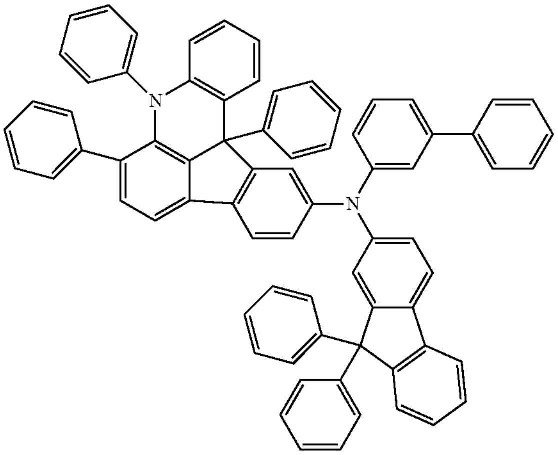
138
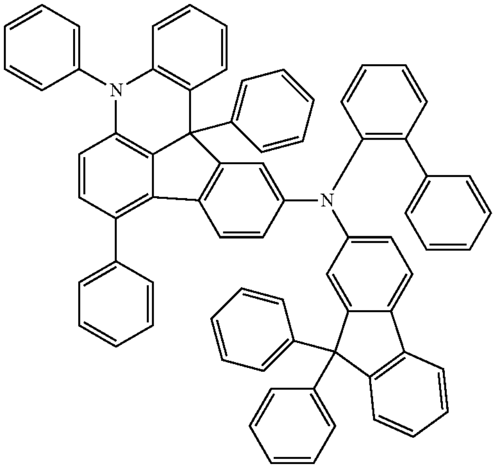

-continued
139
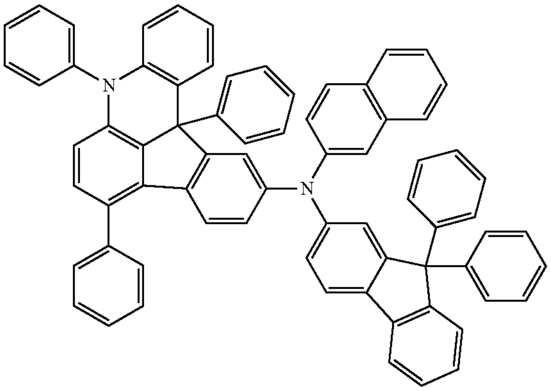
140
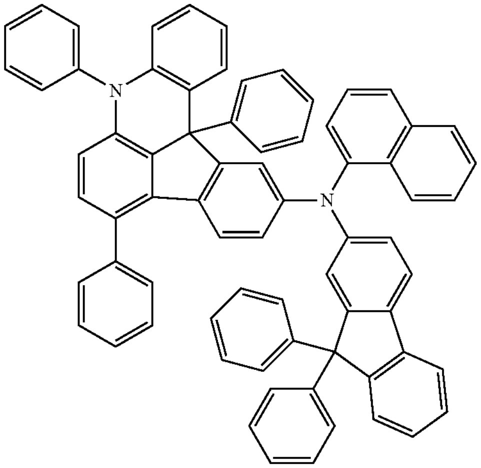
141
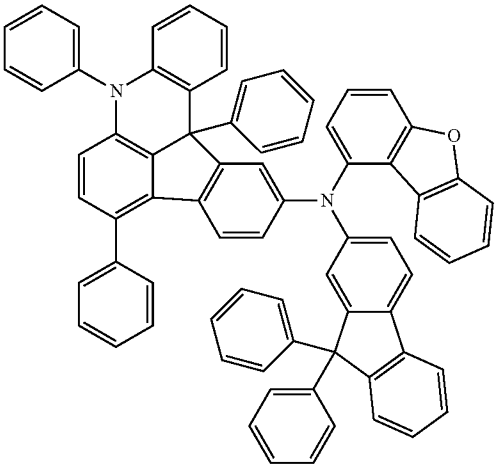
-continued
142
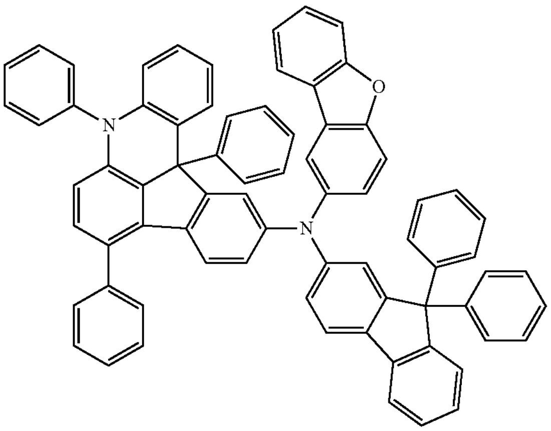
143
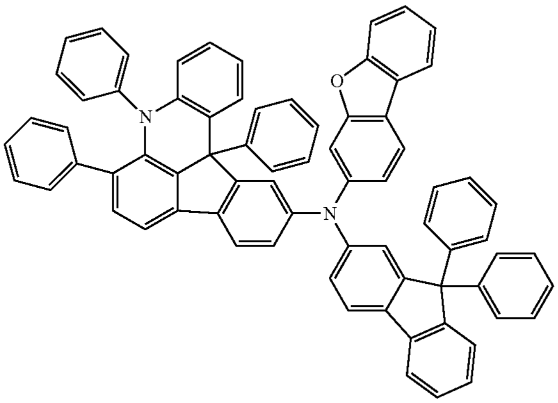
144
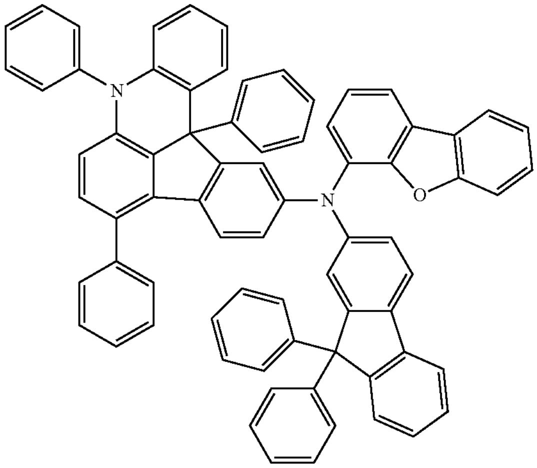

-continued
145
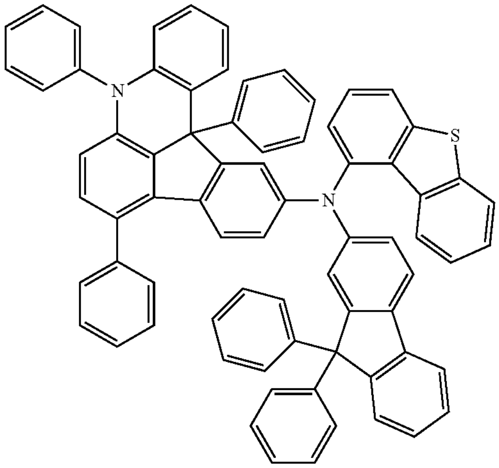
146
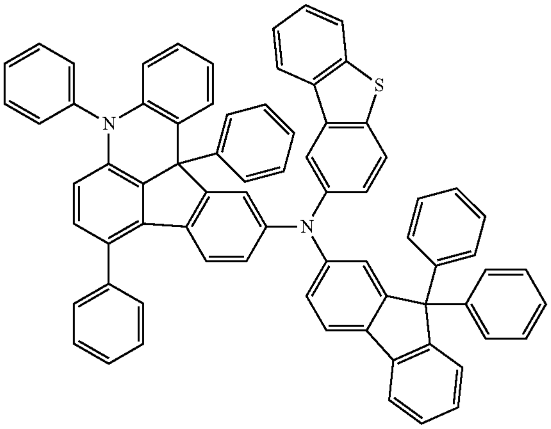
147
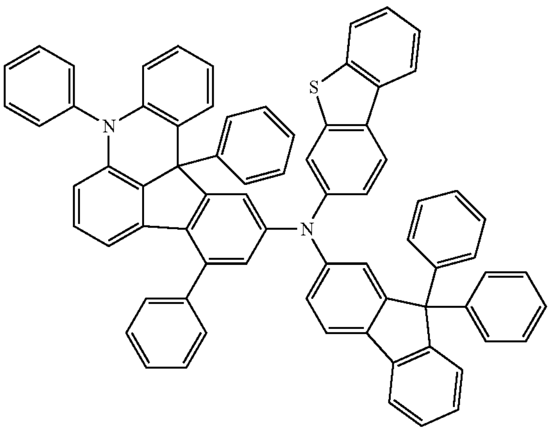
-continued
148
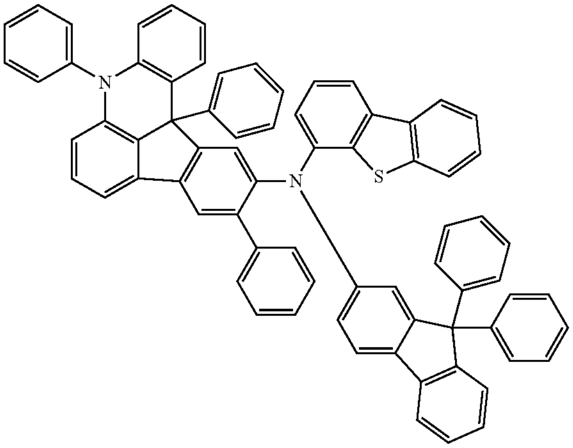
149
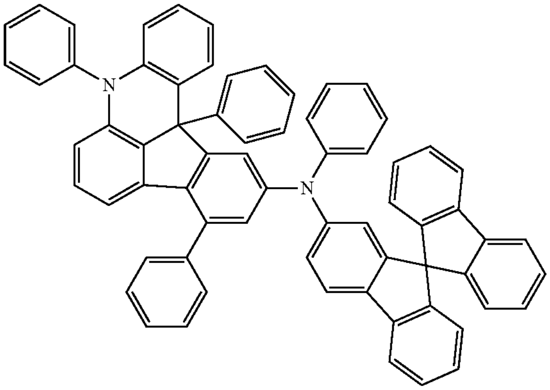
150
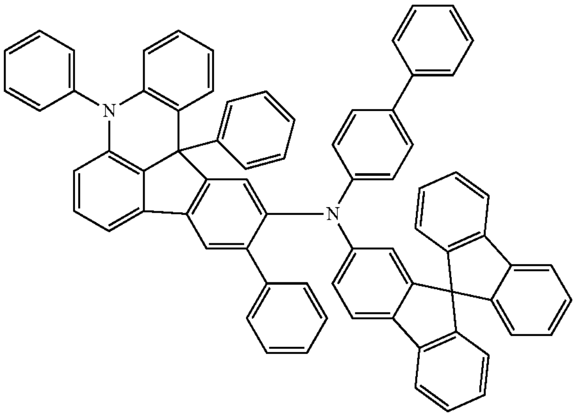

-continued
151
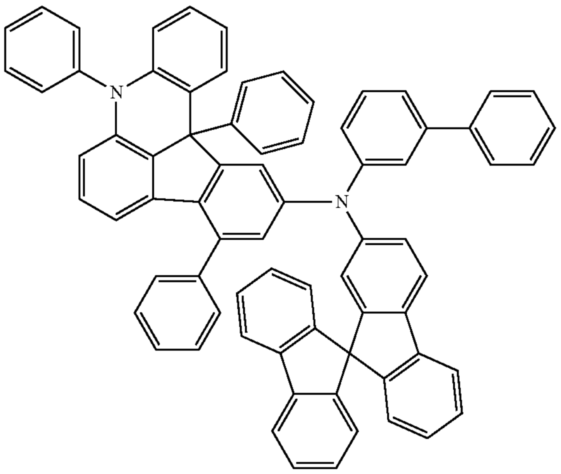
152
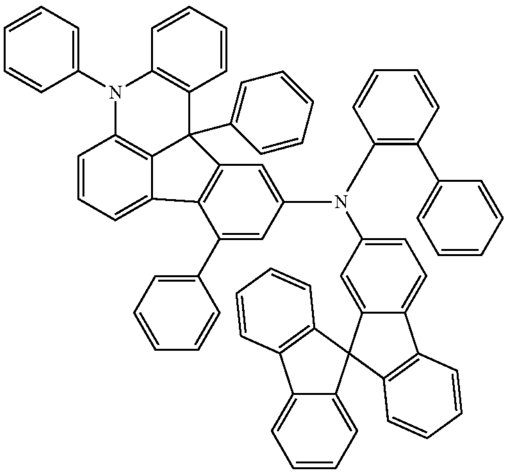
153
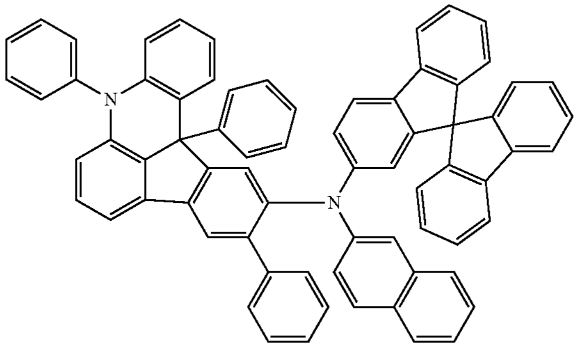
-continued
154
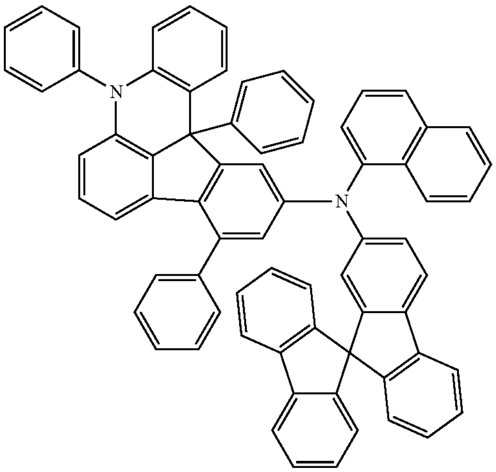
155
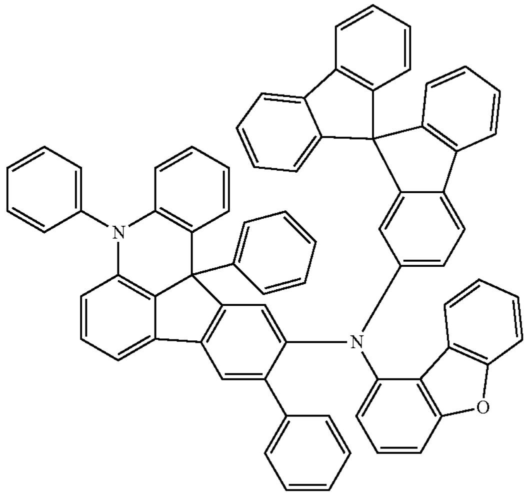
156
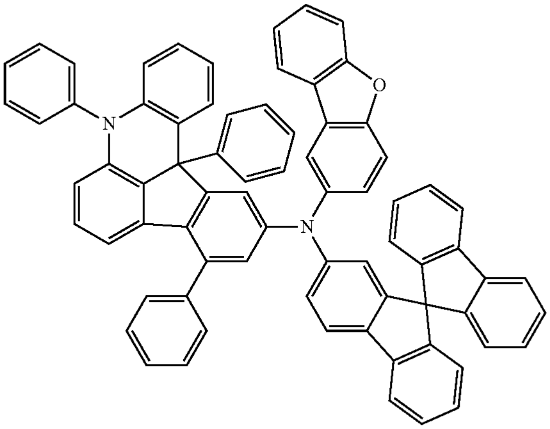

-continued
157
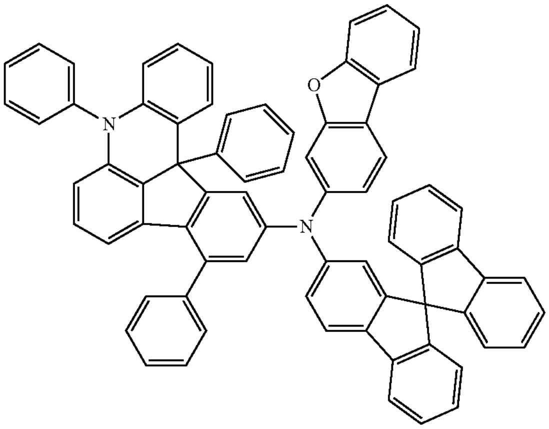
158
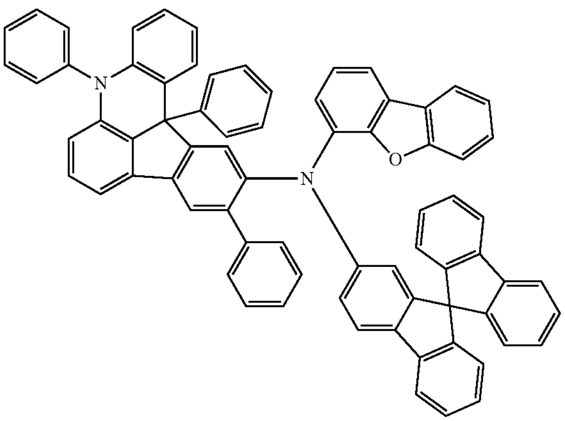
159
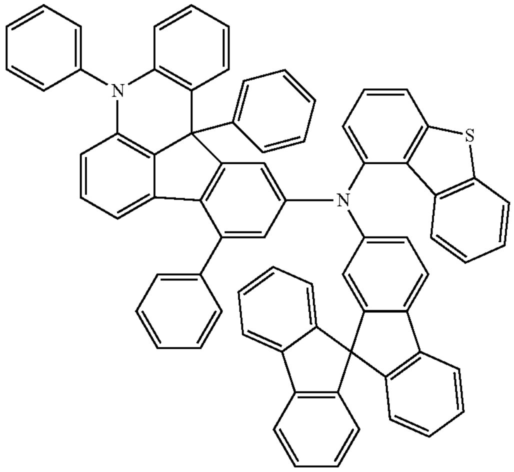
-continued
160
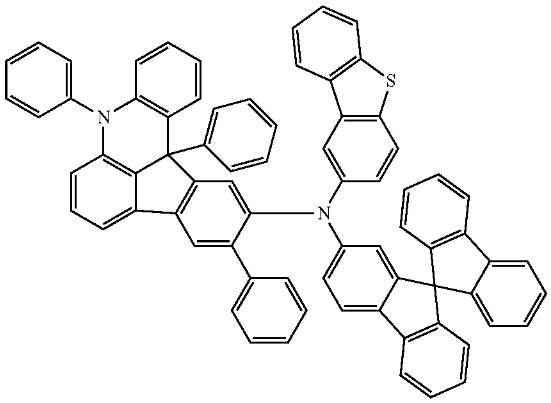
161
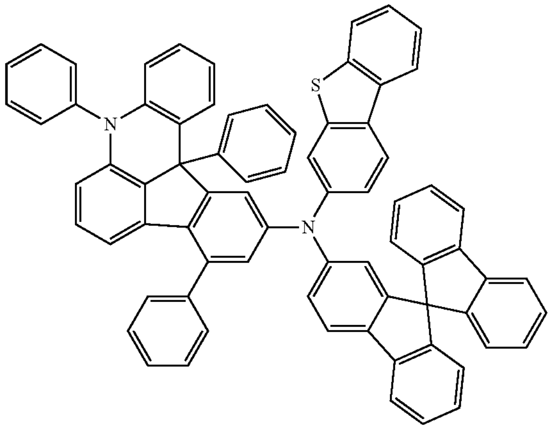
162
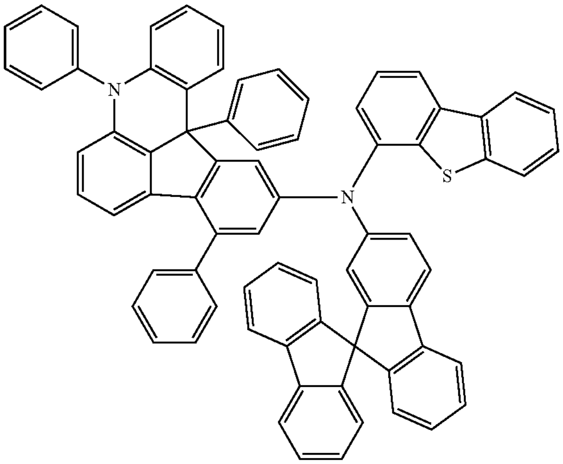

-continued
163
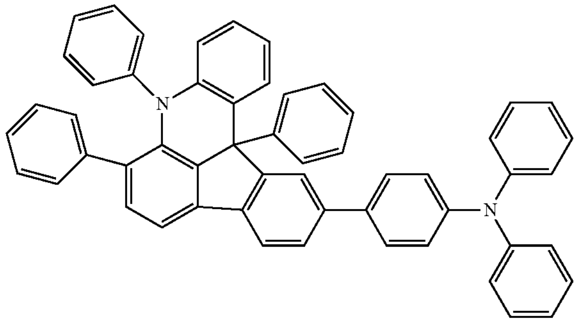
164
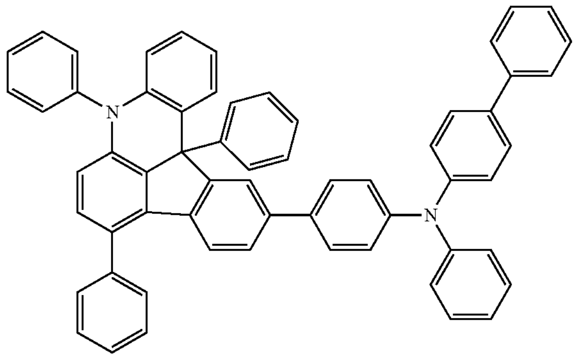
165
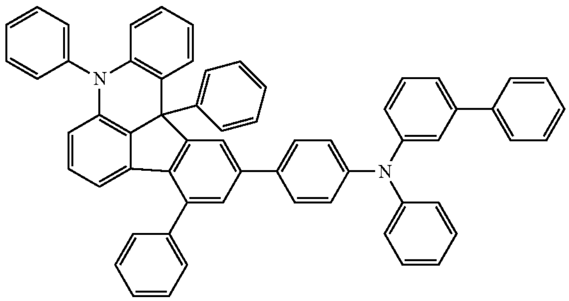
166
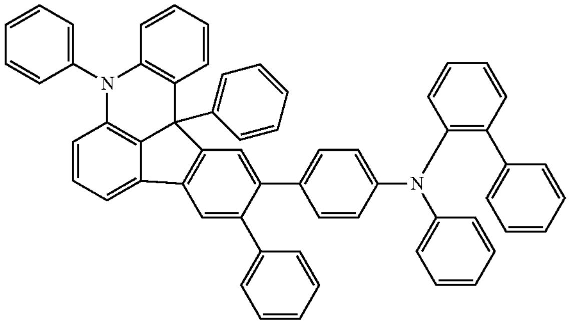
-continued
167
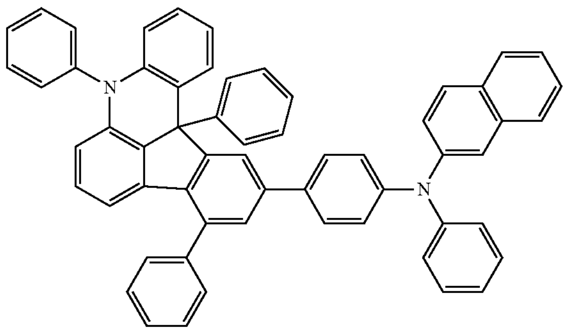
168
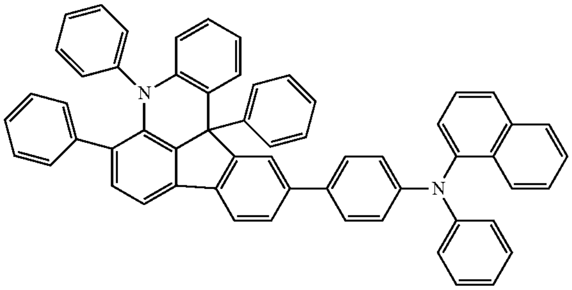
169
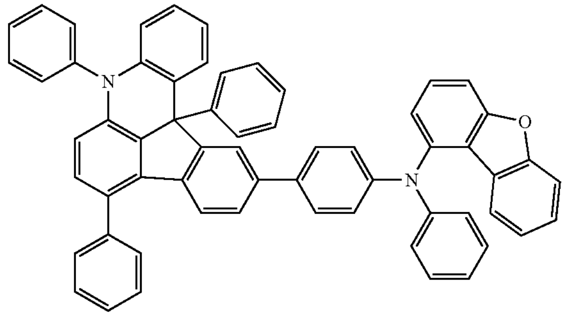
170
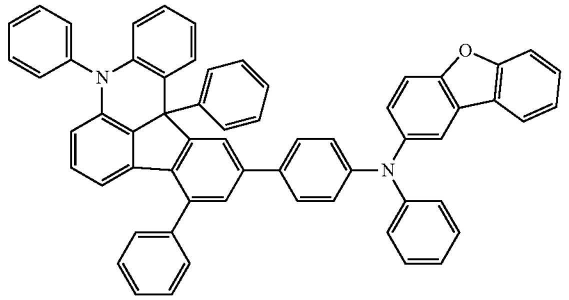

-continued
171
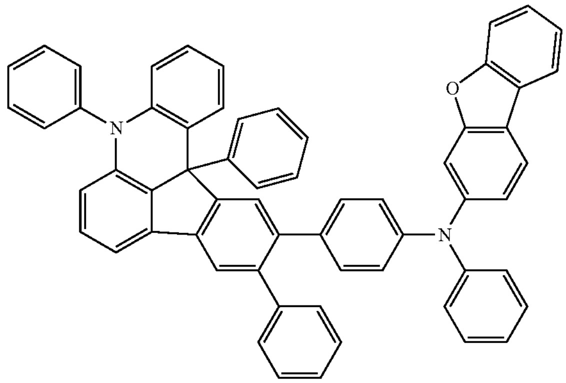
172
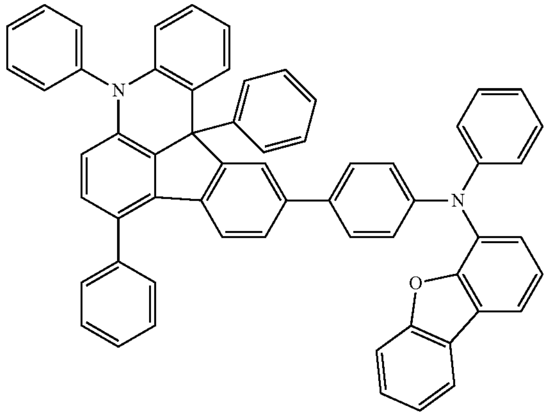
173
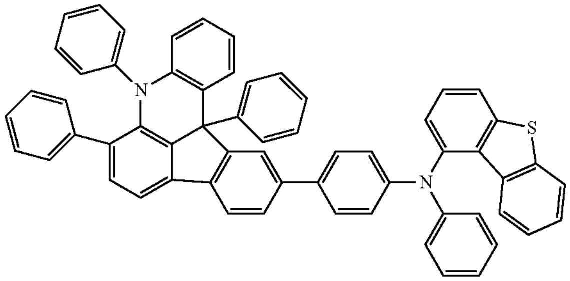
174
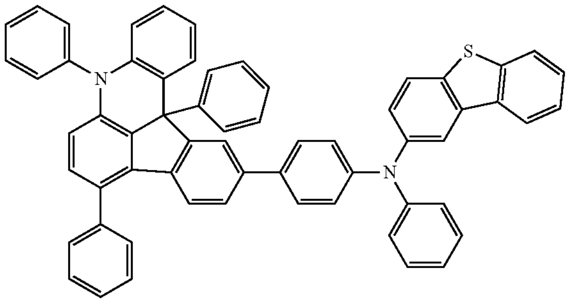
-continued
175
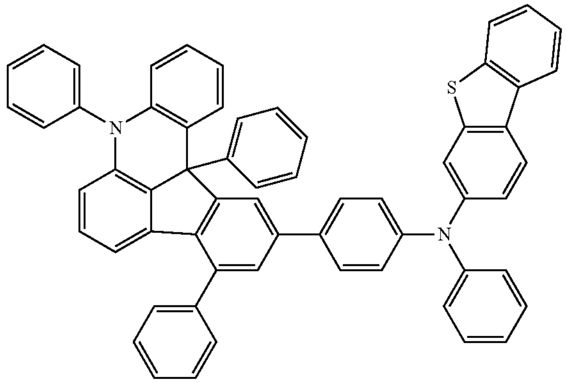
176
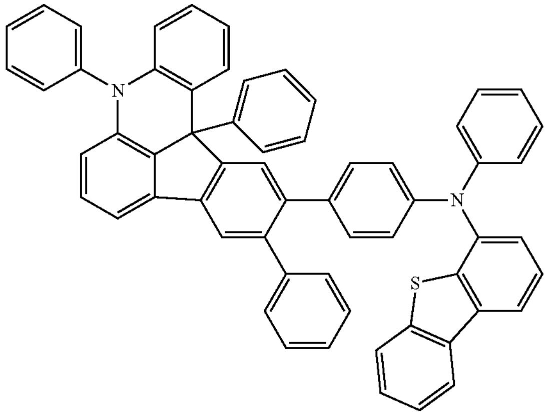
177
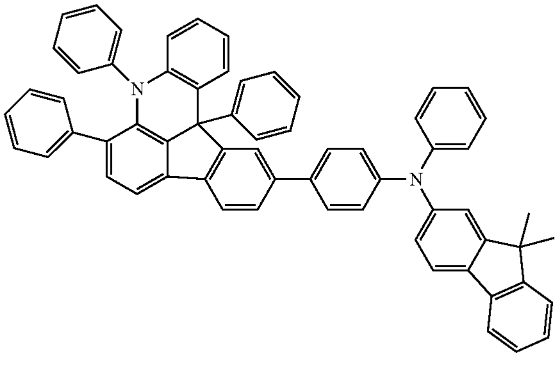
178
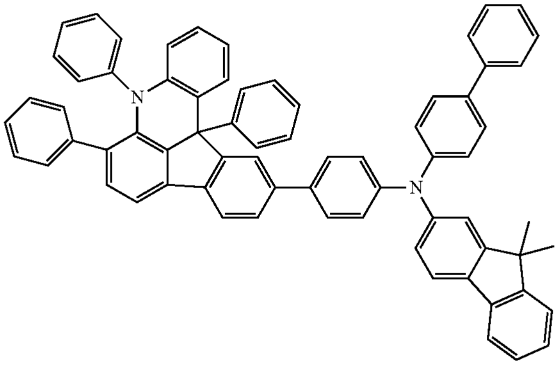

-continued
179
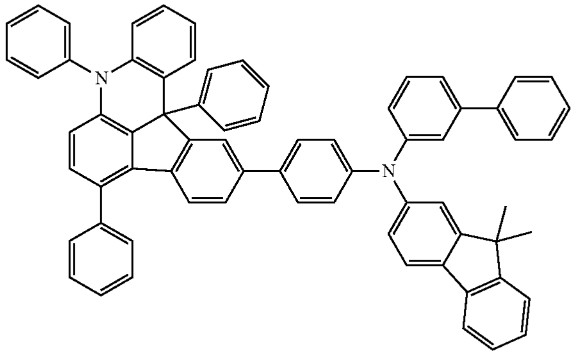
180
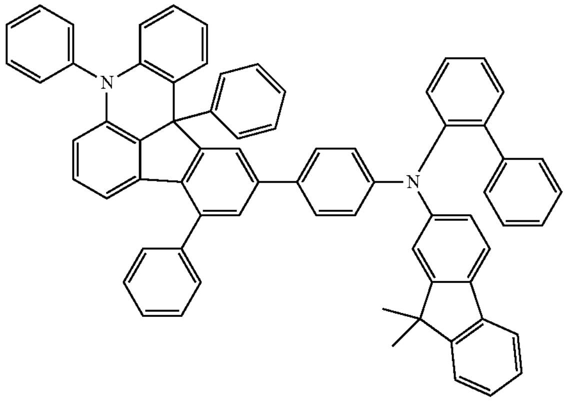
181
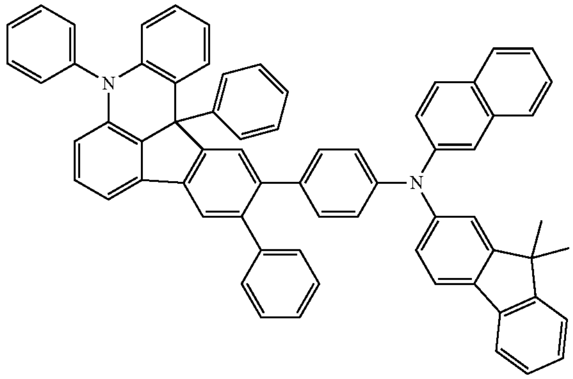
182
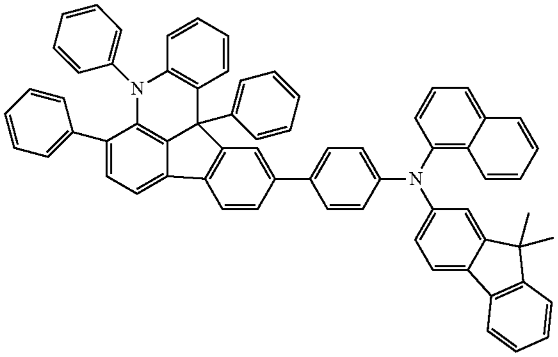
-continued
183
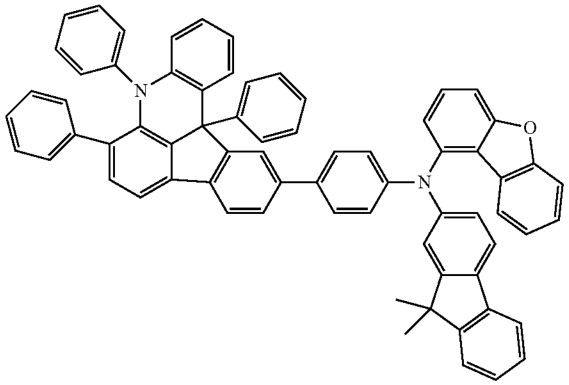
184
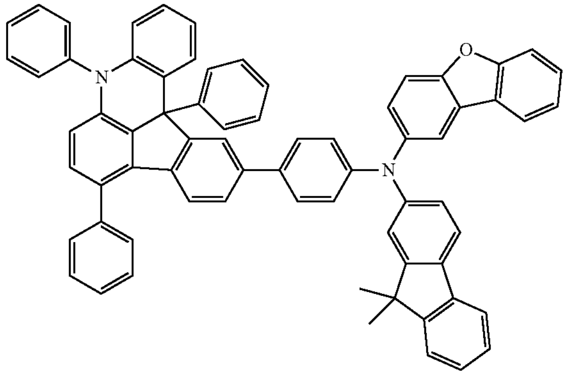
185
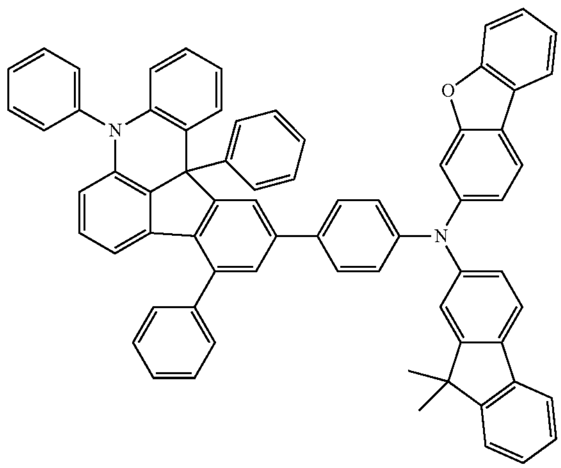

-continued
186
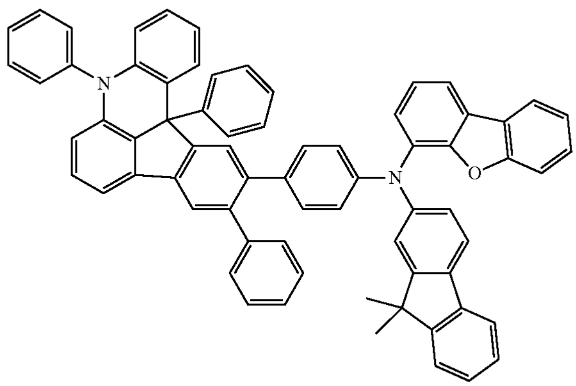
187
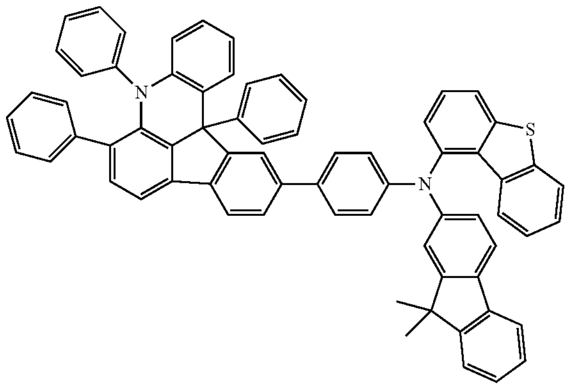
188
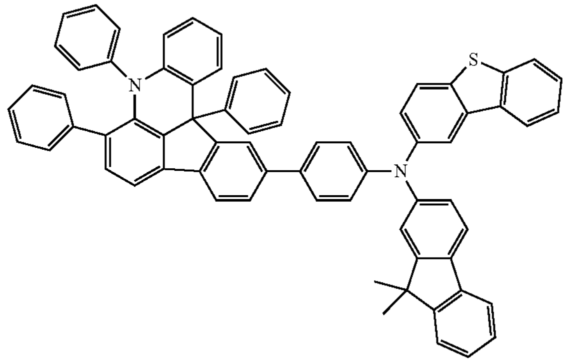
-continued
189
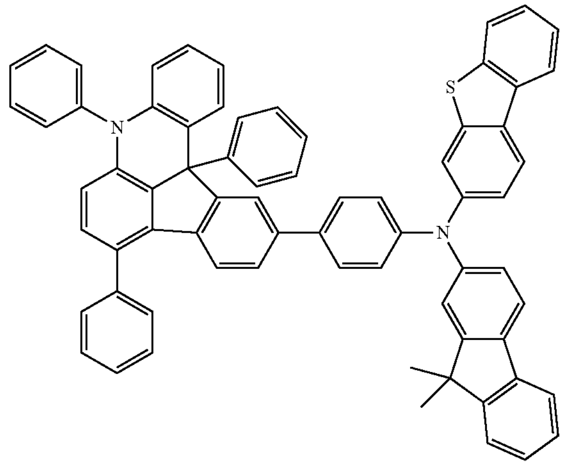
190
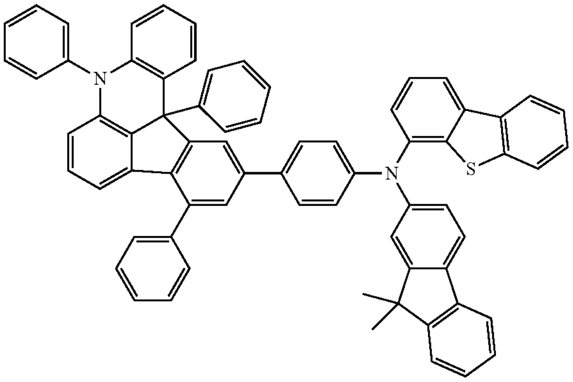
191
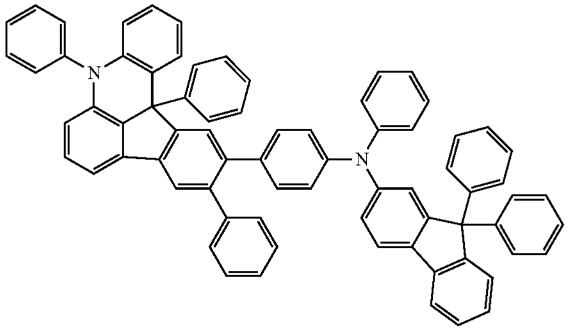
192
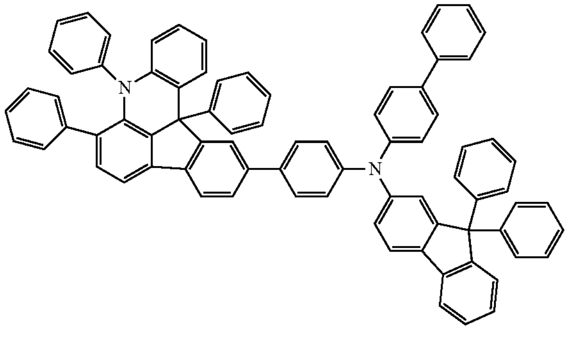

-continued
193
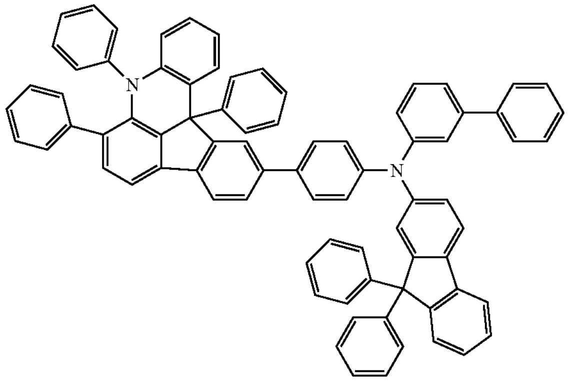
194
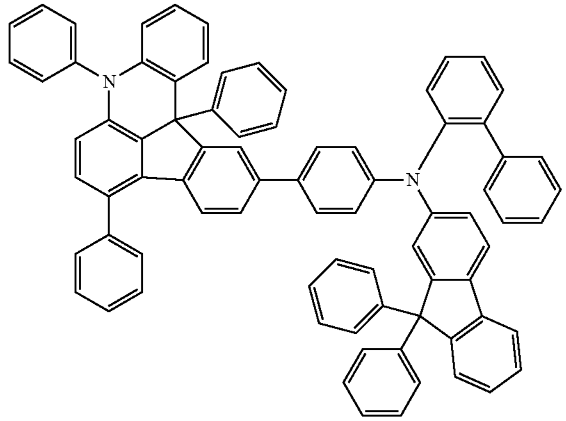
195
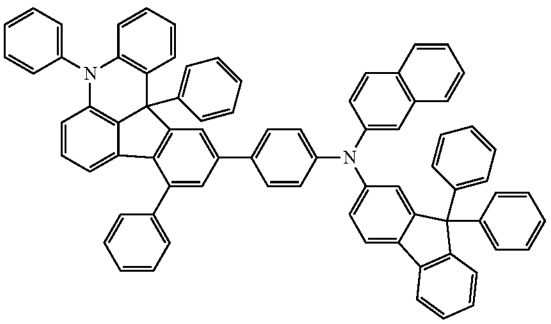
196
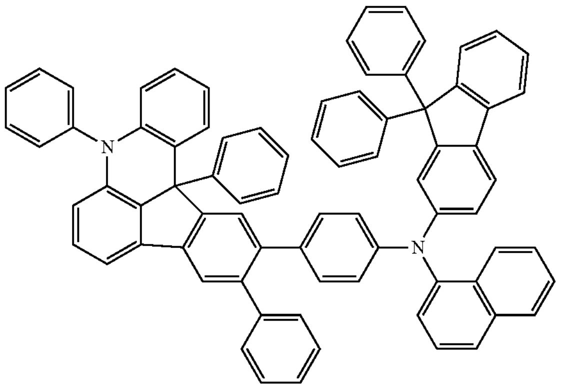
-continued
197
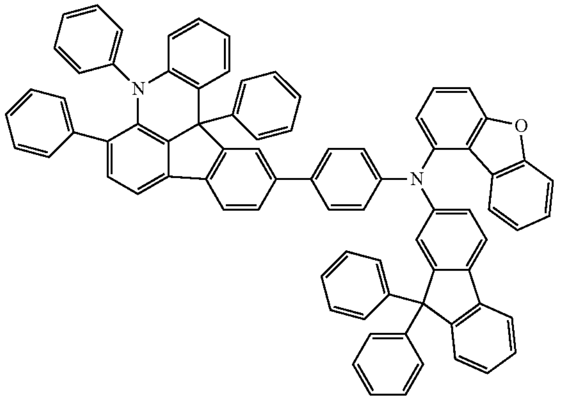
198
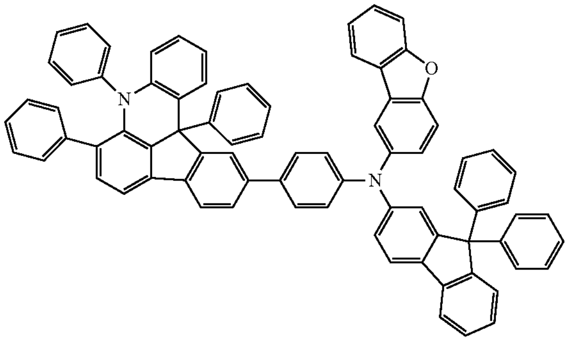
199
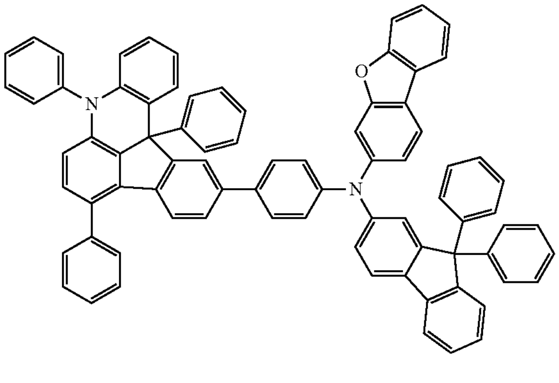
200
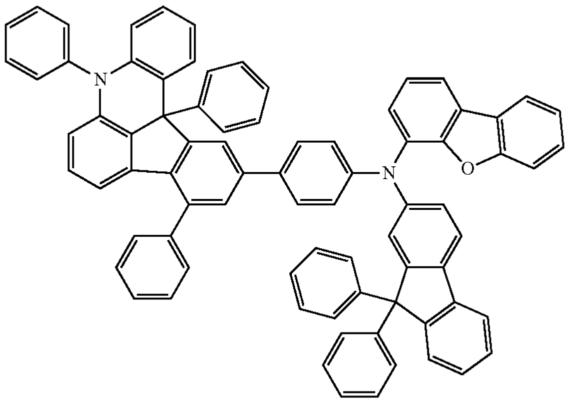

-continued
201
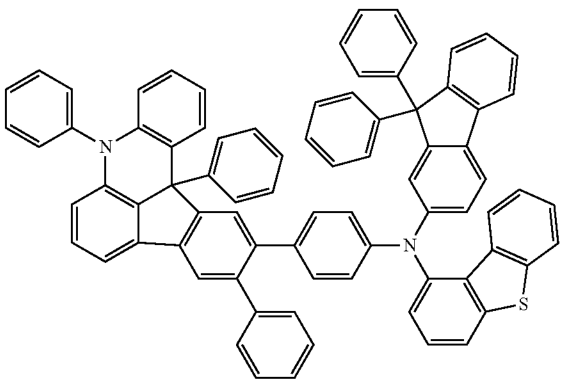
202
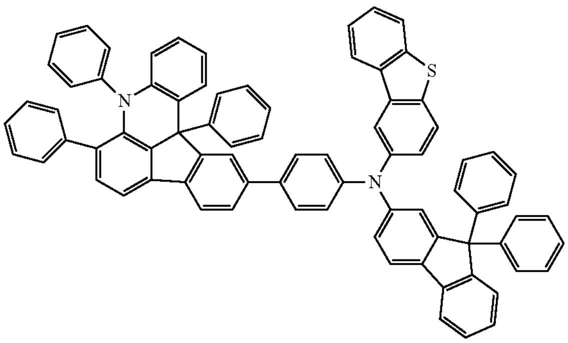
203
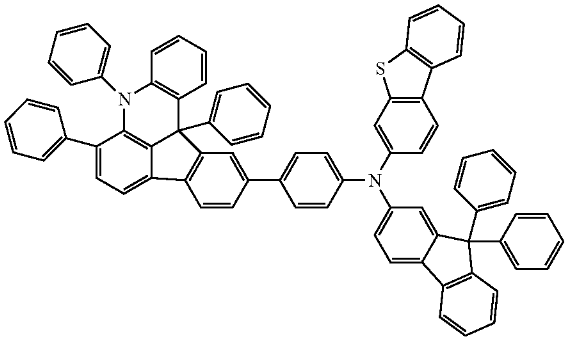
204
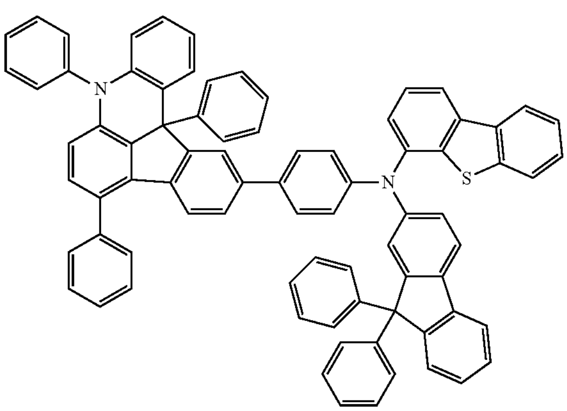
-continued
205
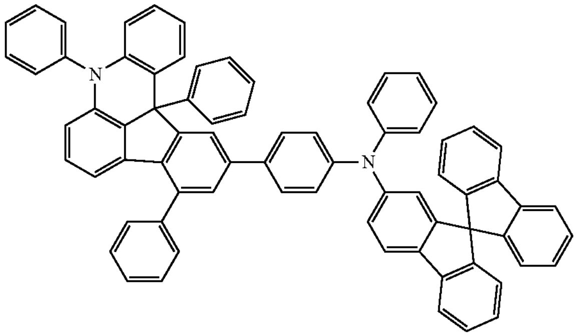
206
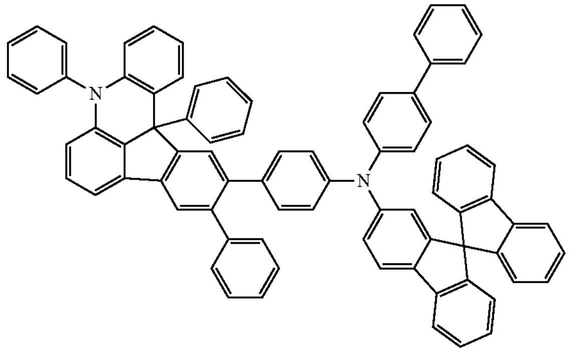
207
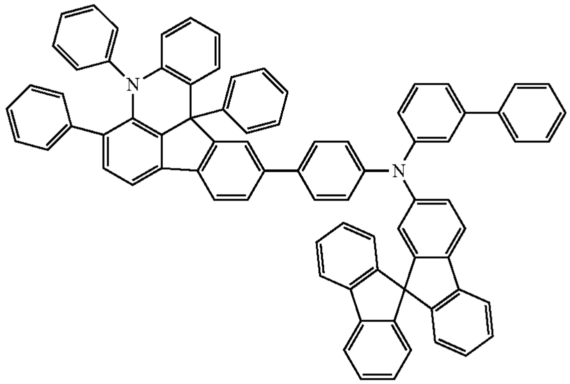
208
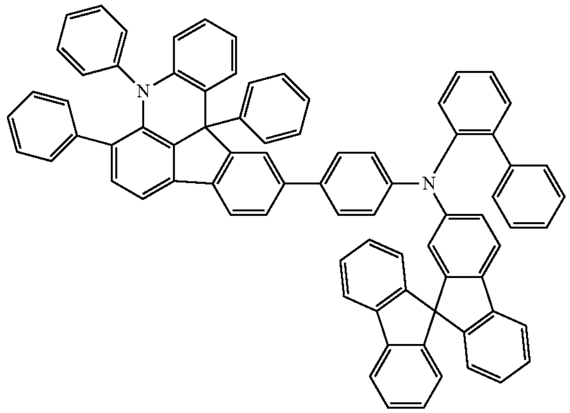

-continued
209
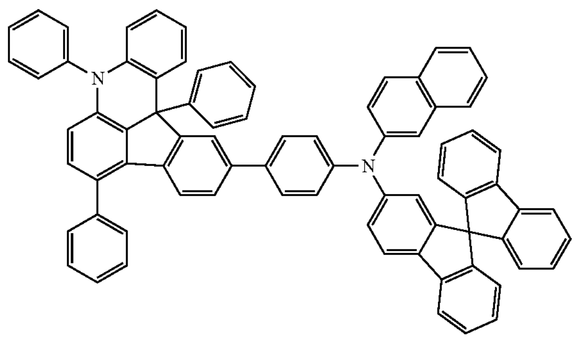
210
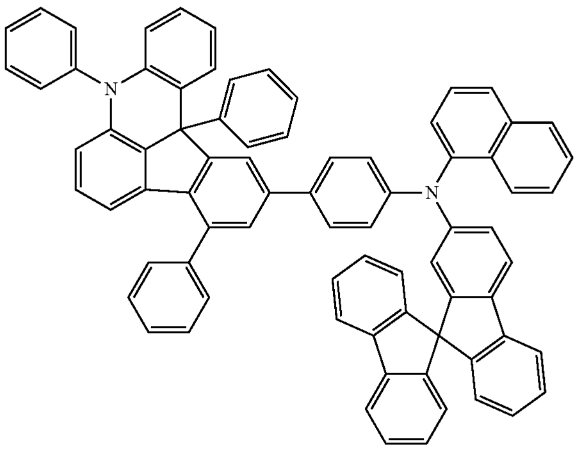
211
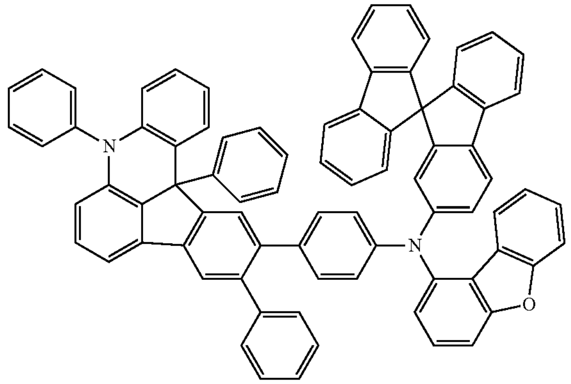
212
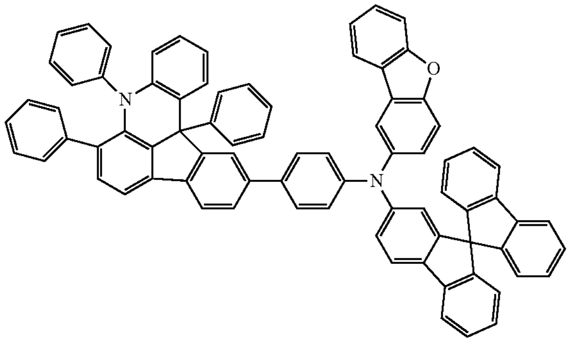
213
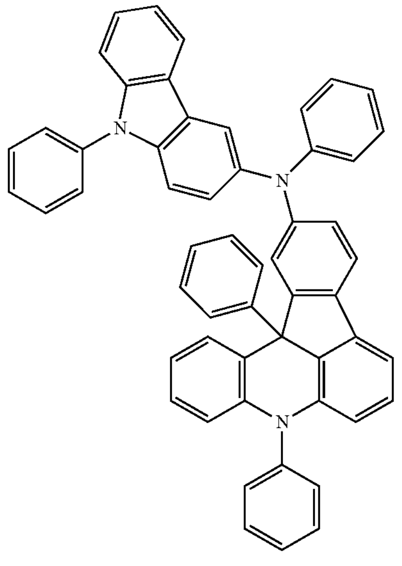
214
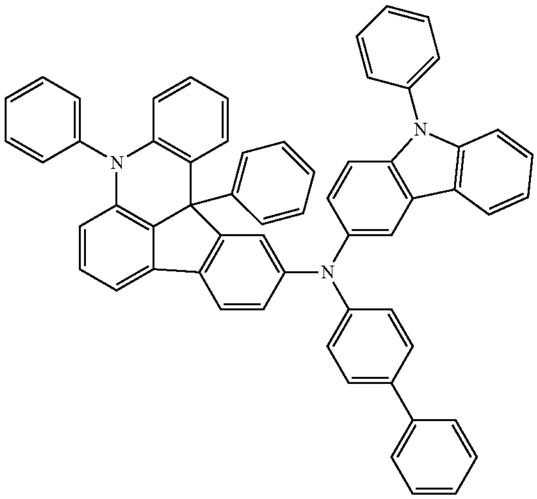

-continued
215
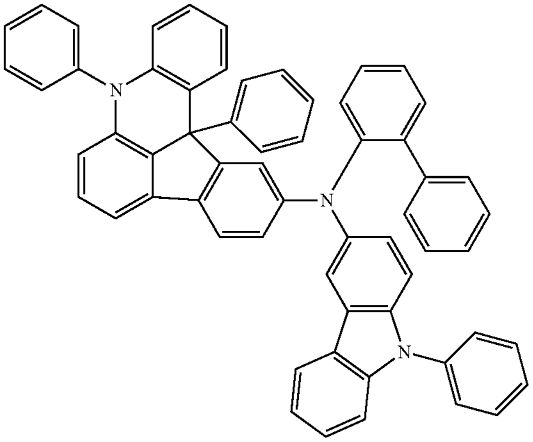
216
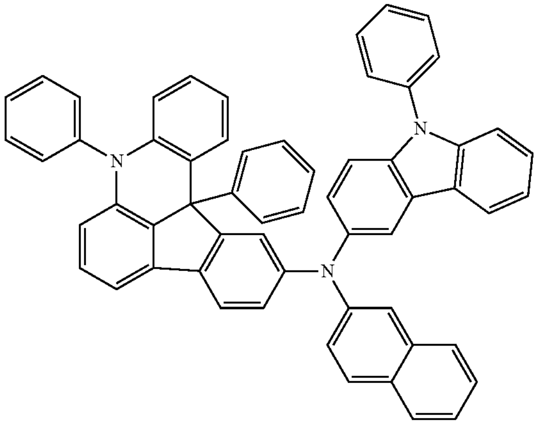
217
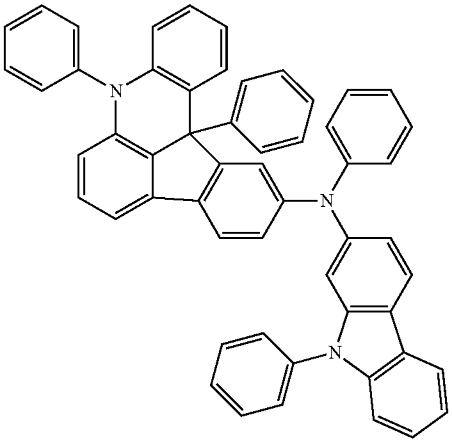
218
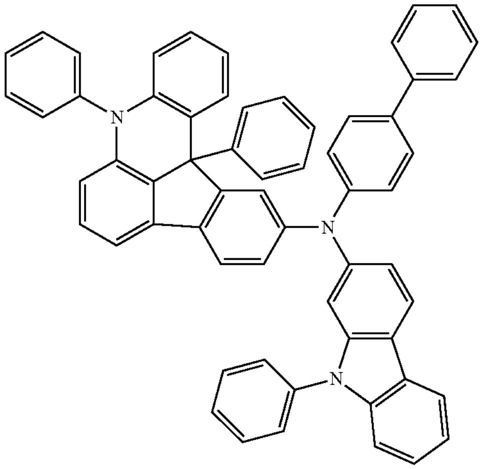
219
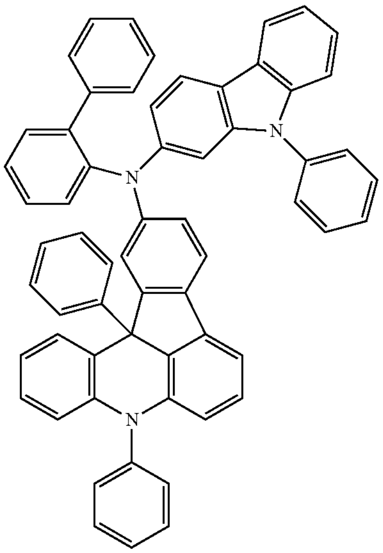
220
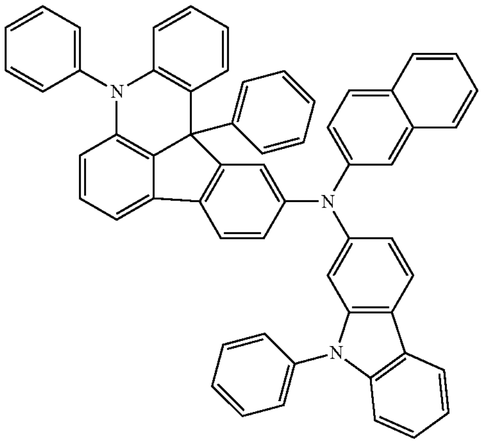

-continued
221
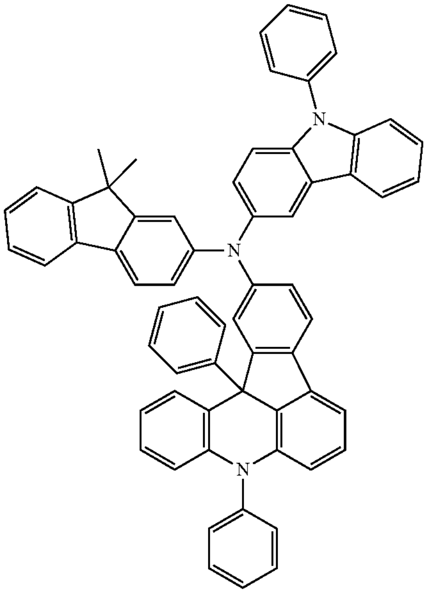
222
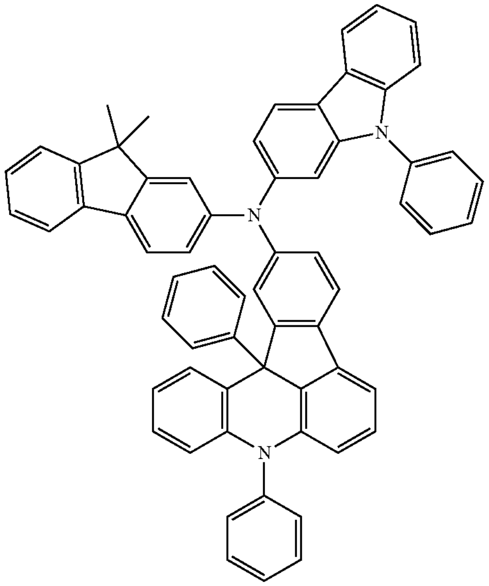
223
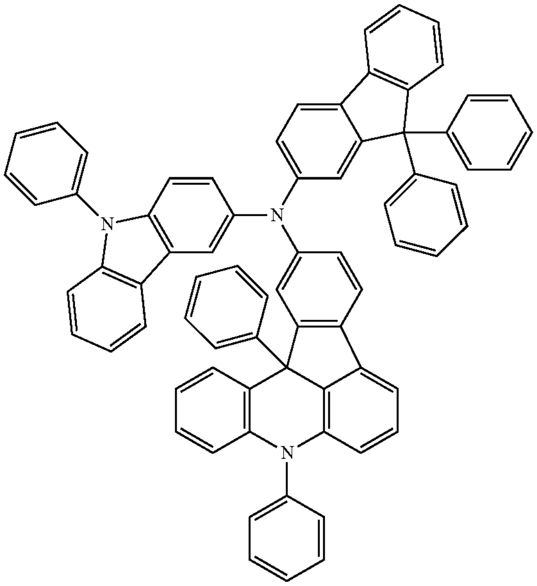
224
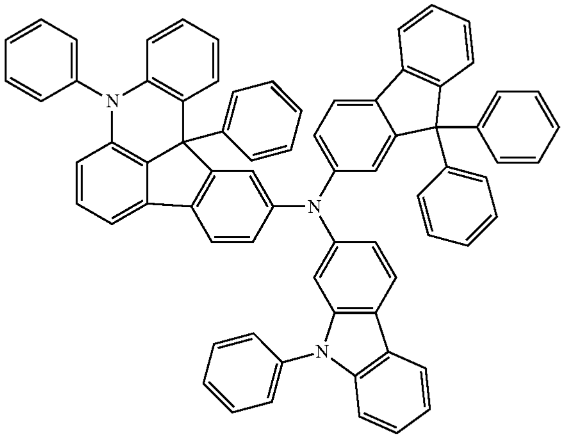

-continued
225
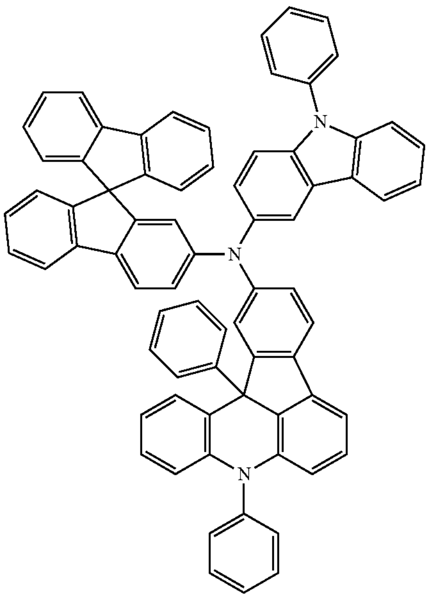
226
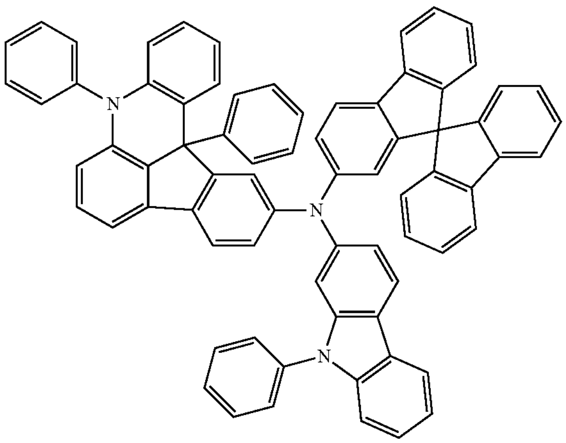
227
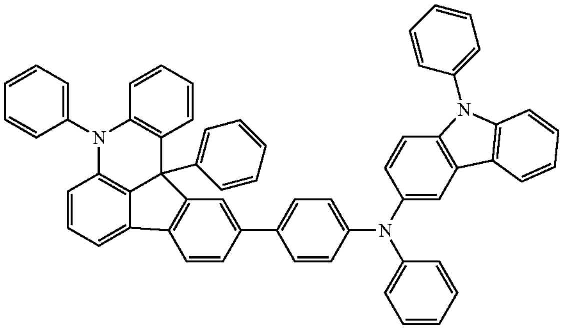
228
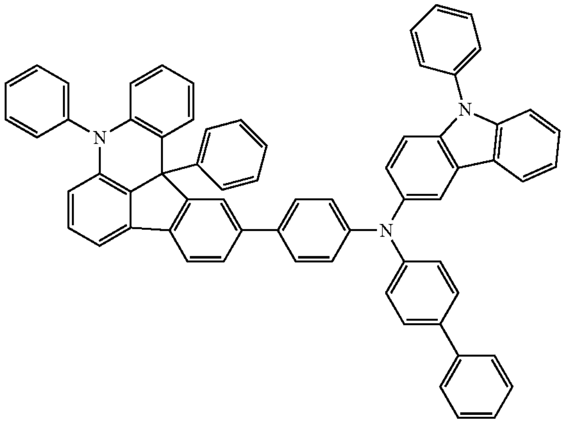
229
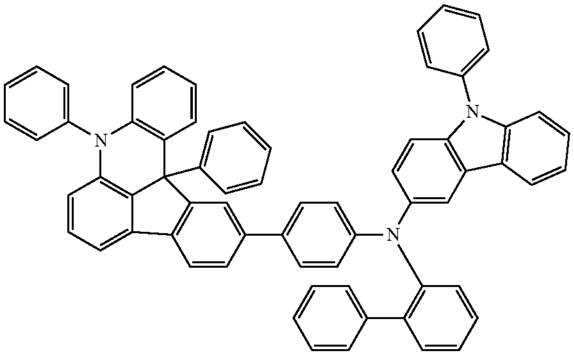
230
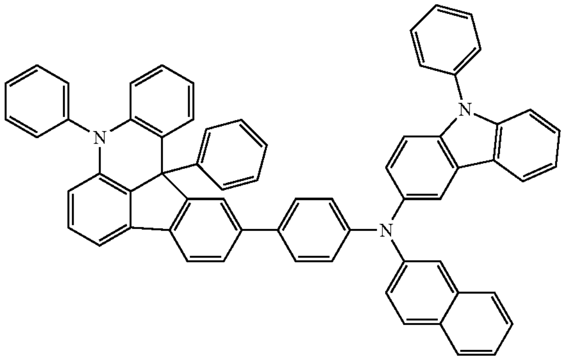

-continued
231
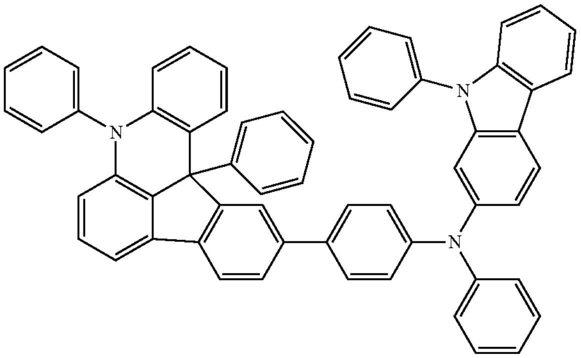
232
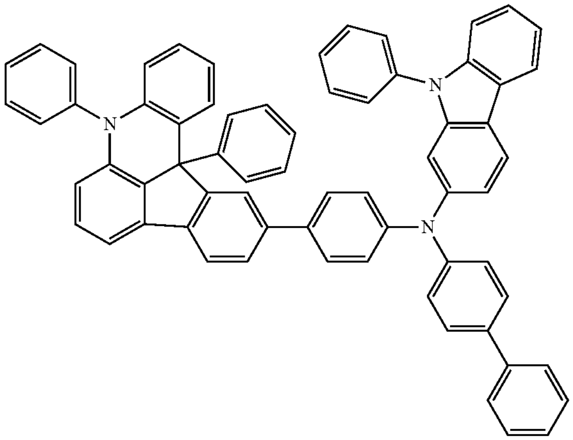
233
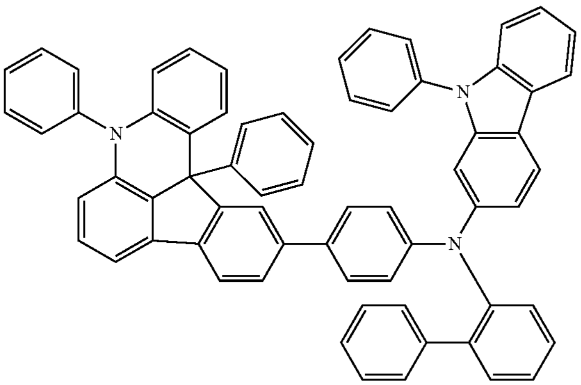
234
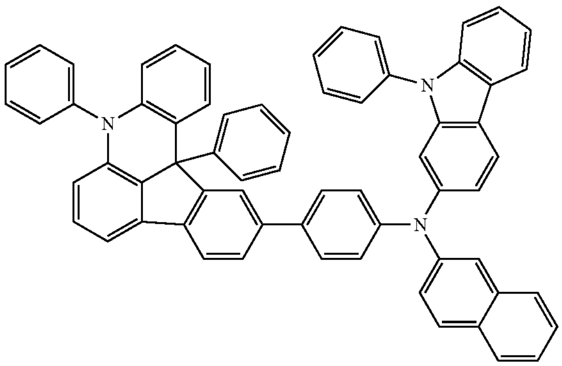
235
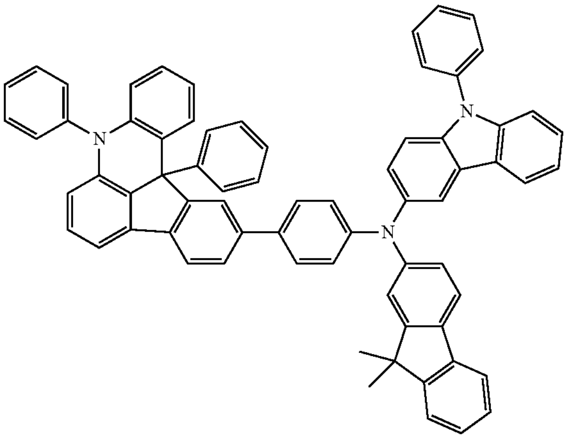
236
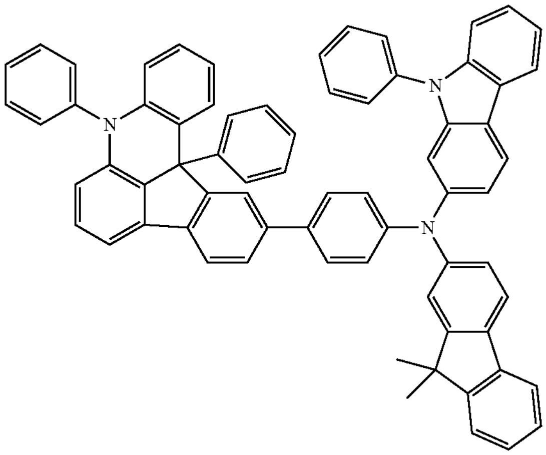

-continued
237
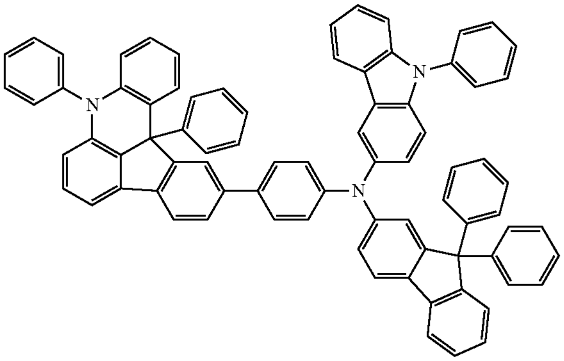
238
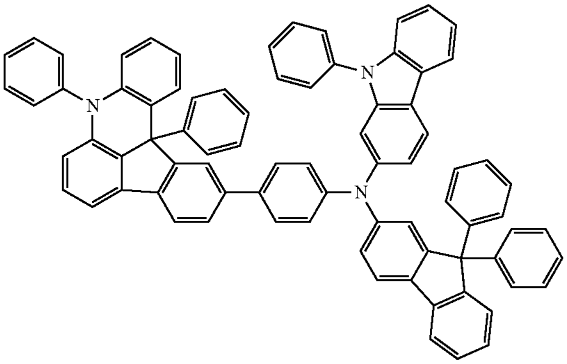
239
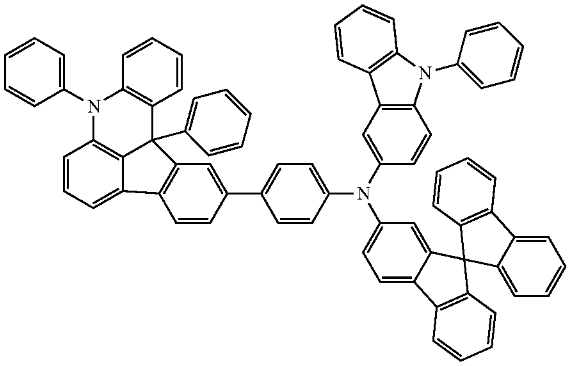
240
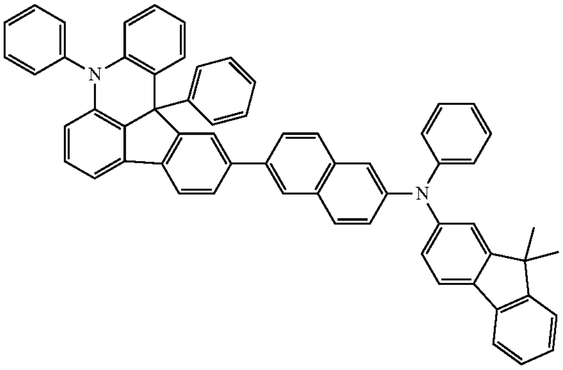
241
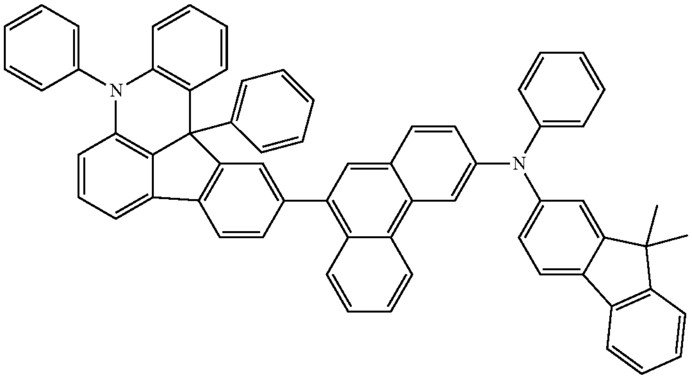
242
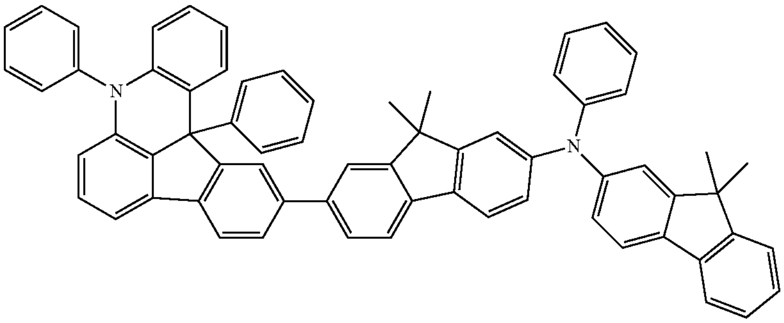

-continued
243
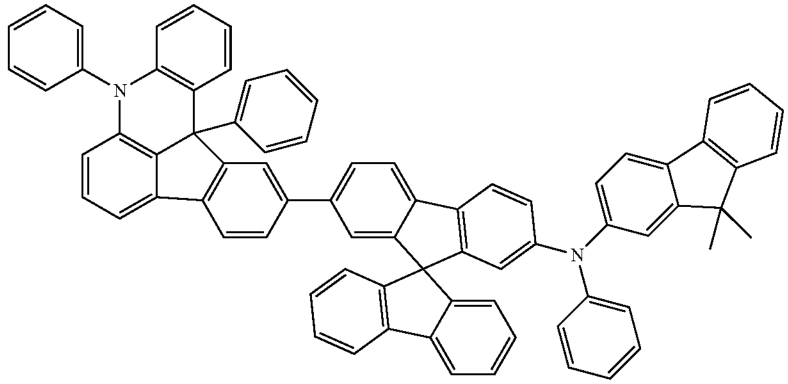
244
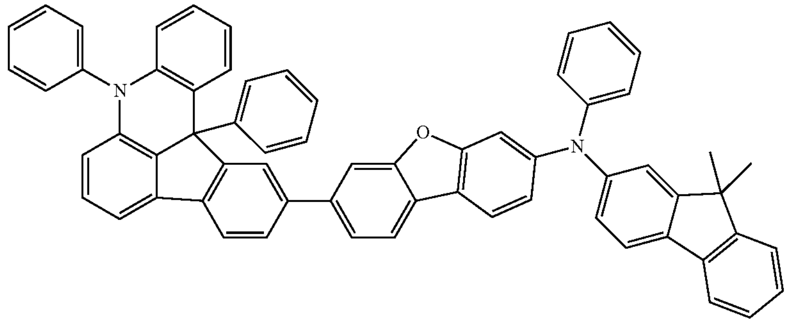
245
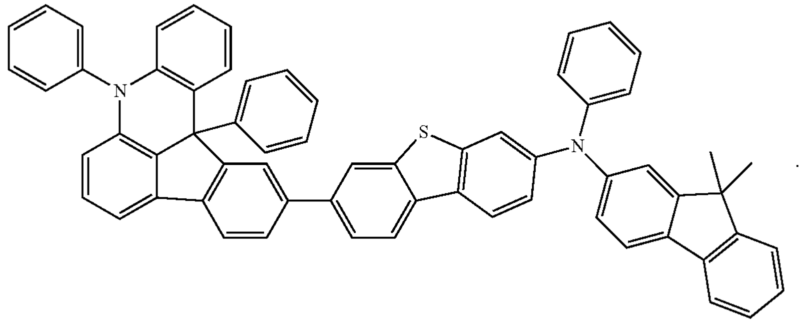
* * * * *